United States Patent
Dixon et al.

(10) Patent No.: US 10,040,767 B2
(45) Date of Patent: Aug. 7, 2018

(54) BENZIMIDAZOLE DERIVATIVES AND USES THEREOF

(71) Applicant: Peloton Therapeutics, Inc., Dallas, TX (US)

(72) Inventors: Darryl David Dixon, Somerset, NJ (US); Jonas Grina, Coppell, TX (US); John A. Josey, Dallas, TX (US); James P. Rizzi, Irving, TX (US); Stephen T. Schlachter, Dallas, TX (US); Eli M. Wallace, Richardson, TX (US); Bin Wang, Dallas, TX (US); Paul Wehn, Dallas, TX (US); Hanbiao Yang, Coppell, TX (US)

(73) Assignee: Peloton Therapeutics, Inc., Dallas, TX (US)

( * ) Notice: Subject to any disclaimer, the term of this patent is extended or adjusted under 35 U.S.C. 154(b) by 0 days.

(21) Appl. No.: 15/310,429

(22) PCT Filed: May 14, 2015

(86) PCT No.: PCT/US2015/030907
§ 371 (c)(1),
(2) Date: Nov. 10, 2016

(87) PCT Pub. No.: WO2015/175845
PCT Pub. Date: Nov. 19, 2015

(65) Prior Publication Data
US 2017/0088523 A1    Mar. 30, 2017

Related U.S. Application Data

(60) Provisional application No. 61/993,831, filed on May 15, 2014, provisional application No. 62/160,783, filed on May 13, 2015.

(51) Int. Cl.
| | | |
|---|---|---|
| C07D 487/04 | (2006.01) |
| C07D 235/12 | (2006.01) |
| C07D 401/06 | (2006.01) |
| C07D 403/12 | (2006.01) |
| A61K 31/4184 | (2006.01) |
| A61K 31/4188 | (2006.01) |
| A61P 35/00 | (2006.01) |

(52) U.S. Cl.
CPC ........ *C07D 235/12* (2013.01); *A61K 31/4184* (2013.01); *A61K 31/4188* (2013.01); *C07D 401/06* (2013.01); *C07D 403/12* (2013.01); *C07D 487/04* (2013.01)

(58) Field of Classification Search
CPC .. C07D 487/04; C07D 235/06; C07D 235/08; C07D 247/02; C07D 401/04; C07D 403/04; A61K 31/4184; A61K 31/437; A61K 31/5025

USPC ........ 544/236; 546/118; 548/304.4; 514/248, 514/303, 394

See application file for complete search history.

(56) References Cited

U.S. PATENT DOCUMENTS

| | | | |
|---|---|---|---|
| 4,992,445 A | 2/1991 | Lawter et al. | |
| 5,001,139 A | 3/1991 | Lawter et al. | |
| 5,023,252 A | 6/1991 | Hseih | |
| 6,291,502 B1 | 9/2001 | Weichert et al. | |
| 7,361,678 B2 * | 4/2008 | Mjalli ................. | C07D 233/64 514/397 |
| 2010/0069452 A1 | 3/2010 | Brandish et al. | |
| 2010/0105749 A1 | 4/2010 | Collins et al. | |
| 2013/0296377 A1 | 11/2013 | Adams et al. | |

FOREIGN PATENT DOCUMENTS

| | | |
|---|---|---|
| WO | WO-2011103018 A1 | 8/2011 |
| WO | WO-2015175845 A1 | 11/2015 |

OTHER PUBLICATIONS

Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Cancer Drug Design and Discovery Neidle, Stephen, ed. (Elsevier/Academic Press, 2008) pp. 427-431.*
Bistrzycki et al. Berichte der Deutschen Chemischen Gesellschaft (1913), 45, 3483-95; CA 7:16463,1913. Caplus Abstract provided.*
Berner et al. CH 560696, Apr. 15, 1975; CA 83:79243,1975. Caplus Abstract provided.*
Soskic et al. Journal of the Serbian Chemical Society (1997), 62(9), 769-775; CA 127: 314407, 1997. Caplus Abstract provided.*
International Search Report dated Jul. 28, 2015 for International Application No. PCT/US2015/030907.
Comerford, et al., Acetate dependence of tumors. Cell. Dec. 18, 2014; 159(7): 1591-1602.

* cited by examiner

*Primary Examiner* — Venkataraman Balasubramanian
(74) *Attorney, Agent, or Firm* — Wilson Sonsini Goodrich & Rosati

(57) ABSTRACT

Benzimidazole derivatives of Formula I, that modulate the activity of ACSS2 are disclosed for therapeutic use. The fused imidazole ring of the compounds disclosed has a diarylmethyl or diarylmethanol moiety attached at the 2-position and the as compounds have at least one other substituent at the 5 or 6 position of the benzimidazole. Also disclosed are methods of using the benzimidazole compounds for the treatment of diseases or disorders, such as cancer.

23 Claims, 1 Drawing Sheet

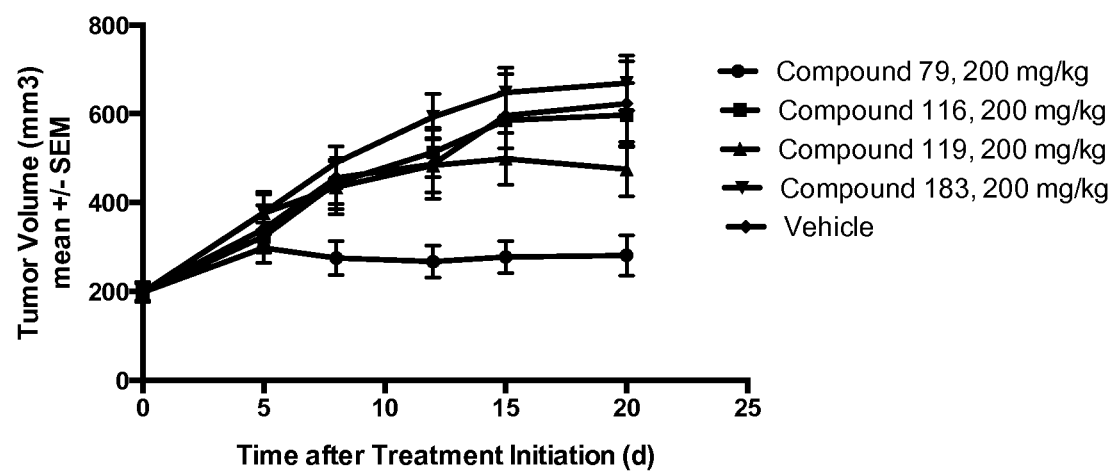

BENZIMIDAZOLE DERIVATIVES AND USES THEREOF

CROSS REFERENCE TO RELATED APPLICATION

This application is a National Stage Entry of PCT/US2015/030907, filed May 14, 2015, which claims the benefit of U.S. Provisional Patent Application No. 61/993,831, filed on May 15, 2014, and U.S. Provisional Patent Application No. 62/160,783, filed on May 13, 2015, each incorporated herein by reference in its entirety.

BACKGROUND OF THE INVENTION

This invention was in part funded by a grant from Cancer Prevention Research Institute of Texas (Grant number R1009).

Normal cells rely on oxidative phosphorylation for energy production when oxygen is plentiful and anaerobic glycolysis when oxygen is limiting. In contrast, Otto Warburg demonstrated more than 80 years ago that cancer cells have rewired metabolic pathways whereby they primarily rely upon aerobic glycolysis even when oxygen is readily available (the "Warburg Effect"). While research in subsequent years has confirmed and expanded upon Warburg's initial findings, it was largely ignored by cancer researchers. However, the last decade or so has witnessed resurgence in the field of cancer metabolism as it has been recognized as a potential Achilles heel of oncogenesis that may lead to new chemotherapeutics.

The central hypothesis of cancer metabolism is that the seminal oncogenic hallmark of rapid, uncontrolled cellular proliferation requires increased production of energy and biomass in the form of ATP production and lipid synthesis. The increased energy requirements of cancer cells are illustrated by the use of Positron Emission Topography (PET) with $^{18}$F-fluorodeoxyglucose (FDG) in cancer patients. Many types of cancer are successfully identified by this FDA-approved technique, which arguably provides some of the strongest support for the central hypothesis that cancer cells have a higher glycolytic demand than normal cells. While many chemotherapeutic agents reduce FDG PET positivity of tumors with some correlation to clinical benefit, the observed reduction in glycolytic flux most likely is secondary to inhibition of cellular proliferation and not a result of directly targeting glycolysis. Researchers have been unsuccessful in directly targeting glycolysis because, even though cancer cells have an acute reliance on this pathway, normal cells also have an absolute requirement for glucose.

At first glance the increased demand for glucose and aerobic glycolysis in cancer cells seems inconsistent because oxidative phosphorylation is a much more efficient use of glucose to produce energy. However, interpreting cancer metabolism only by the quantity of ATP produced is simplistic and may overlook the importance of increased synthesis of macromolecules required for cell division and the links between altered metabolic pathways and oncogenic mutations. Just as cancer cells require more energy to rapidly proliferate, they also require increased biomass. One approach to attack cancer metabolism is to focus on the key cytosolic regulator of lipid, cholesterol and amino acid synthesis, acetyl-CoA. Acetyl-CoA's central role in macromolecule synthesis has been well established, making it an attractive target to disrupt biomass production. Additionally, recent research has shown that acetyl-CoA levels play a pivotal role in acetylation of histones and proteins in yeast and mammalian cells, linking it to epigenetic control of cell growth and proliferation. A novel approach to disrupt acetyl-CoA production is by targeting Acetyl-CoA Synthetase Short Chain 2 (ACSS2). As a primary enzyme responsible for acetyl-CoA generation from acetate, ACSS2 is an ATP-dependent enzyme that catalyzes the transfer of acetate to CoA forming cytosolic acetyl-CoA, which is then converted to lipids, cholesterol and amino acids.

The dependence on acetate by cancer cells can be further demonstrated by $^{11}$C-acetate PET imaging. In a manner analogous to FDG PET imaging, $^{11}$C-acetate PET has been used successfully to image several tumors in the clinic, thereby demonstrating cancer cells have an increased dependence on acetate. Furthermore, reports have shown a differential preference of acetate or glucose uptake in patient tumors leading to the hypothesis that some cancers preferentially depend on acetate metabolism while others depend on glycolysis.

SUMMARY OF THE INVENTION

Therefore, there is a need to develop small molecules that modulate the activity of ACSS2 for the treatment of cancer and other diseases. This application addresses this need and others.

In one aspect, the present disclosure provides a compound of Formula I:

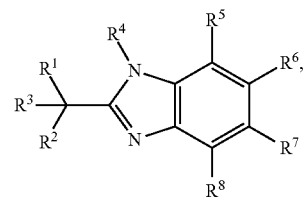

Formula I or a pharmaceutically acceptable salt thereof,
wherein:
$R^1$ and $R^2$ are independently aryl or heteroaryl;
$R^3$ is selected from the group consisting of hydrogen, hydroxy and —CH$_2$OH;
$R^4$ is selected from the group consisting of hydrogen, alkyl, cycloalkyl, heterocycloalkyl and aryl;
$R^5$ and $R^8$ are independently hydrogen, halo, alkoxy, cyano, or alkyl;
$R^6$ and $R^7$ are independently hydrogen, halo, cyano, alkyl, cycloalkyl, alkoxy, aryl, heteroaryl, —NR$^9$C(=O)R$^{10}$, —C(=O)OR$^9$, —C(=O)NR$^{10}$R$^{11}$, —S(=O)$_2$R$^{12}$, or —S(=O)$_2$NR$^{10}$R$^{11}$;
each of said $R^9$, $R^{10}$, and $R^{11}$ is independently selected from the group consisting of hydrogen, alkyl, cycloalkyl, aryl, heteroaryl and heterocycloalkyl;
$R^{12}$ is selected from the group consisting of alkyl, cycloalkyl, alkenyl, alkynyl, aryl, heteroaryl and heterocycloalkyl; and
$R^{10}$, $R^{11}$ and the atom(s) they are attached to may optionally form a 4-8 membered ring containing 0-2 heteroatoms selected from the group consisting of O, N and S. In some embodiments, at least one of $R^6$ and $R^7$ is not hydrogen.

In some embodiments of compounds of Formula I, $R^6$ is alkyl, cycloalkyl, alkoxy, aryl, heteroaryl, —NR$^9$C(=O) R$^{10}$, —C(=O)NR$^{10}$R$^{11}$, —S(=O)$_2$R$^{12}$, or —S(=O)$_2$ NR$^{20}$R$^{11}$, and $R^7$ is hydrogen, halo, or alkyl. In other embodiments, $R^6$ is hydrogen, halo, or alkyl, and $R^7$ is alkyl, alkoxy, aryl, heteroaryl, —NR$^9$C(=O)R$^{10}$, —C(=O) NR$^{10}$R$^{11}$, —S(=O)$_2$R$^{12}$, or —S(=O)$_2$NR$^{10}$R$^{11}$. In still other embodiments, $R^1$ and $R^2$ are independently phenyl or pyridyl, optionally substituted with one or more substituents selected from the group consisting of halo, alkyl, cyano or alkoxy. In another embodiment, R³ is hydroxy. In a further embodiment, R¹, R², and R³ in combination is

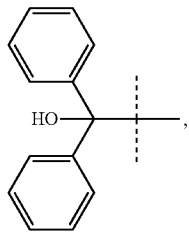

wherein each phenyl is optionally and independently substituted with one or more substituents selected from the group consisting of halo, alkyl, cyano, or alkoxy. In other embodiments, R⁴ is alkyl.

In another aspect, the present disclosure provides a pharmaceutical composition comprising a compound described herein and a pharmaceutically acceptable carrier or excipient. The compound may exist in an amorphous form, a crystalline form, or as a salt, solvate or hydrate.

In another aspect, the present disclosure provides a method of treating cancer by administrating a therapeutically effective amount of a compound described herein or a pharmaceutical composition thereof to a subject in need of such treatment. In some embodiments, the subject is a human.

In another aspect, the present disclosure provides a method of inhibiting the activities of ACSS2 in a cell, comprising contacting the cell with an effective amount of a compound described herein.

In another aspect, the present disclosure provides a kit comprising a pharmaceutical composition comprising a compound described herein and a pharmaceutically acceptable carrier or excipient and an instruction for using the composition to treat a subject suffering from cancer.

In one aspect, the invention provides a compound of Formula II:

Formula II

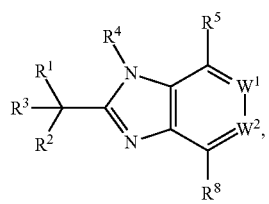

or a pharmaceutically acceptable salt thereof, wherein:

R¹ and R² are independently aryl or heteroaryl; or R¹ and R² together with the atom to which they are attached form a 13- to 16-membered tricyclic ring;

R³ is hydrogen, —OR¹⁴, or —CH₂OR¹⁴;

R⁴ is selected from hydrogen, alkyl, cycloalkyl, heterocycloalkyl, and aryl;

R⁵ and R⁸ are independently selected from hydrogen, halo, cyano, alkoxy, and alkyl;

W¹ is CR⁶ or N;

W² is CR⁷ or N;

R⁶ and R⁷ are independently selected from hydrogen, halo, alkyl, cycloalkyl, heteroalkyl, heterocycloalkyl, alkoxy, aryl, heteroaryl, cyano, —(CH₂)ₜNR⁹C(=O)R¹⁰, —C(=O)OR⁹, —C(=O)NR¹⁰R¹¹, —S(=O)₂R¹², and —S(=O)₂NR¹⁰R¹¹, wherein if W¹ is CR⁶ and W² is CR⁷, at least one of R⁶ and R⁷ is not hydrogen;

t is 0, 1, or 2;

R⁹ is selected from hydrogen, alkyl, cycloalkyl, alkenyl, alkynyl, aryl, heteroaryl, and heterocycloalkyl;

R¹⁰ and R¹¹ are independently selected from hydrogen, alkyl, cycloalkyl, alkenyl, alkynyl, aryl, heteroaryl, and heterocycloalkyl, or R¹⁰ and R¹¹ together with the atom to which they are attached form a 4- to 8-membered ring containing 0-2 heteroatoms;

R¹² is selected from alkyl, cycloalkyl, and heterocycloalkyl; and

R¹⁴ is selected from hydrogen, C₁-C₄ alkyl, and C₁-C₄ acyl.

In some embodiments of compounds of Formula II, R⁶ is alkyl, cycloalkyl, heteroalkyl, heterocycloalkyl, alkoxy, aryl, heteroaryl, cyano, —(CH₂)ₜNR⁹C(=O)R¹⁰, —C(=O)OR⁹, —C(=O)NR¹⁰R¹¹, —S(=O)₂R¹², or —S(=O)₂NR¹⁰R¹¹, and R⁷ is hydrogen, halo, or alkyl. In other embodiments, R⁶ is hydrogen, halo, or alkyl, and R⁷ is alkyl, cycloalkyl, heteroalkyl, heterocycloalkyl, alkoxy, aryl, heteroaryl, cyano, —(CH₂)ₜNR⁹C(=O)R¹⁰, C(=O)OR⁹, —C(=O)NR¹⁰R¹¹, —S(=O)₂R¹², or —S(=O)₂NR¹⁰R¹¹.

In still other embodiments of compounds of Formula II, R¹ and R² are independently selected from phenyl and pyridyl, and each of R¹ and R² is optionally substituted with one or more substituents selected from halo, alkyl, cyano, and alkoxy. In other embodiments, R¹ is phenyl, optionally substituted with one or more substituents selected from halo, alkyl, cyano and alkoxy. In still other embodiments, R² is phenyl, optionally substituted with one or more substituents selected from halo, alkyl, cyano and alkoxy. In a further embodiment, R³ is hydroxy.

In another embodiment of compounds of Formula II, R¹ and R² are each phenyl; R³ is hydroxy; R⁴ is C₁-C₄ alkyl; R⁵ and R⁸ are each hydrogen; W¹ is CR⁶; W² is CR⁷; R⁶ is —C(=O)NR¹⁰R¹¹; R⁷ and R¹⁰ are each hydrogen; and R¹¹ is C₁-C₆ alkyl, aryl or heteroaryl. In other embodiments, R¹¹ is C₁-C₆ alkyl optionally substituted with 1, 2, or 3 fluoro groups. In still other embodiments, R¹¹ is C₁-C₆ alkyl optionally substituted with 1, 2, or 3 hydroxy groups. In a further embodiment, R¹¹ is CH₂CH(OH)CH₃. In another embodiment, R¹ is substituted with 1 or 2 halo groups. In yet another embodiment, R¹ is substituted with 1 or 2 fluoro groups. In some embodiments, R² is substituted with 1 or 2 halo groups. In other embodiments, R² is substituted with 1 or 2 fluoro groups.

In another aspect, the invention provides a compound of Formula II-A:

Formula II-A

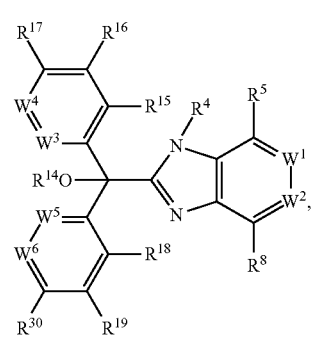

or a pharmaceutically acceptable salt thereof, wherein:

R$^4$ is selected from hydrogen, alkyl, cycloalkyl, heterocycloalkyl, and aryl;

R$^5$ and R$^8$ are independently selected from hydrogen, halo, cyano, alkoxy, and alkyl;

W$^1$ is CR$^6$ or N;

W$^2$ is CR$^7$ or N;

R$^6$ and R$^7$ are independently selected from hydrogen, halo, alkyl, cycloalkyl, heteroalkyl, heterocycloalkyl, alkoxy, aryl, heteroaryl, cyano, —(CH$_2$)$_t$NR$^9$C(=O)R$^{10}$, —C(=O)OR$^9$, —C(=O)NR$^{10}$R$^{11}$, —S(=O)$^2$R$^{12}$, and —S(=O)$_2$NR$^{10}$R$^{11}$, wherein if W$^1$ is CR$^6$ and W$^2$ is CR$^7$, at least one of R$^6$ and R$^7$ is not hydrogen;

t is 0, 1, or 2;

R$^9$ is selected from hydrogen, alkyl, cycloalkyl, alkenyl, alkynyl, aryl, heteroaryl, and heterocycloalkyl;

R$^{10}$ and R$^{11}$ are independently selected from hydrogen, alkyl, cycloalkyl, alkenyl, alkynyl, aryl, heteroaryl, and heterocycloalkyl, or R$^{10}$ and R$^{11}$ together with the atom to which they are attached form a 4- to 8-membered ring containing 0-2 heteroatoms;

R$^{12}$ is selected from alkyl, cycloalkyl, and heterocycloalkyl;

W$^3$ and W$^5$ are independently CR$^{31}$ or N;

W$^4$ and W$^6$ are independently CR$^{22}$ or N;

R$^{14}$ is selected from hydrogen, C$_1$-C$_4$ alkyl, and C$_1$-C$_4$ acyl;

each of R$^{15}$, R$^{18}$, R$^{19}$, R$^{30}$, E$^{31}$, and R$^{22}$ is independently selected from hydrogen, halo, hydroxy, alkyl, alkoxy, cyano, —C(=O)NR$^{23}$R$^{24}$, aryl, and heteroaryl;

R$^{16}$ and R$^{17}$ are independently selected from hydrogen, halo, hydroxy, alkyl, alkoxy, cyano, —C(=O)NR$^{23}$R$^{24}$, aryl, and heteroaryl, or R$^{16}$ and R$^{17}$ together with the atoms to which they are attached form a 5- to 8-membered ring containing 0-2 heteroatoms;

R$^{23}$ and R$^{24}$ are independently selected from hydrogen, C$_1$-C$_6$ alkyl, and —(CH$_2$)$_m$OR$^{25}$;

m is 1, 2, 3, or 4; and

R$^{25}$ is selected from hydrogen, C$_1$-C$_4$ alkyl, and C$_1$-C$_4$ acyl.

In some embodiments of compounds of Formula II-A, W$^3$ is CR$^{31}$, and R$^{31}$ is hydrogen, halo, or C$_1$-C$_4$ alkyl. In other embodiments, W$^4$ is CR$^{22}$, and R$^{22}$ is hydrogen, halo, or C$_1$-C$_4$ alkyl. In still other embodiments, W$^5$ is CR$^{31}$, and R$^{31}$ is hydrogen, halo, or C$_1$-C$_4$ alkyl. In yet another embodiment, W$^6$ is CR$^{22}$, and R$^{22}$ is hydrogen, halo, or C$_1$-C$_4$ alkyl.

In other embodiments of compounds of Formula II-A, R$^{15}$ and R$^{18}$ are independently selected from hydrogen and halo. In some embodiments, R$^{16}$ and R$^{19}$ are independently selected from hydrogen, halo, heteroaryl, —C(=O)NHR$^{24}$, and C$_1$-C$_4$ alkyl. In other embodiments, R$^{17}$ and R$^{30}$ are independently selected from hydrogen, halo, and methyl.

In some embodiments of compounds of Formula II or Formula II-A, R$^{14}$ is hydrogen. In other embodiments, R$^4$ is C$_1$-C$_6$ alkyl. In a further embodiment, R$^4$ is substituted with one or more substituents selected from hydroxy and fluoro. In another embodiment, R$^5$ and R$^8$ are independently selected from hydrogen, halo, and methyl. In still another embodiment, R$^5$ and R$^8$ are each hydrogen.

In other embodiments of compounds of Formula II or Formula II-A, W$^1$ is CR$^6$, R$^6$ is —C(=O)NR$^{10}$R$^{11}$ or —S(=O)$_2$NR$^{10}$R$^{11}$, W$^2$ is CR$^7$, and R$^7$ is hydrogen, halo, or alkyl. In a further embodiment, R$^6$ is —C(=O)NR$^{10}$R$^{11}$. In another embodiment, R$^{11}$ is selected from:

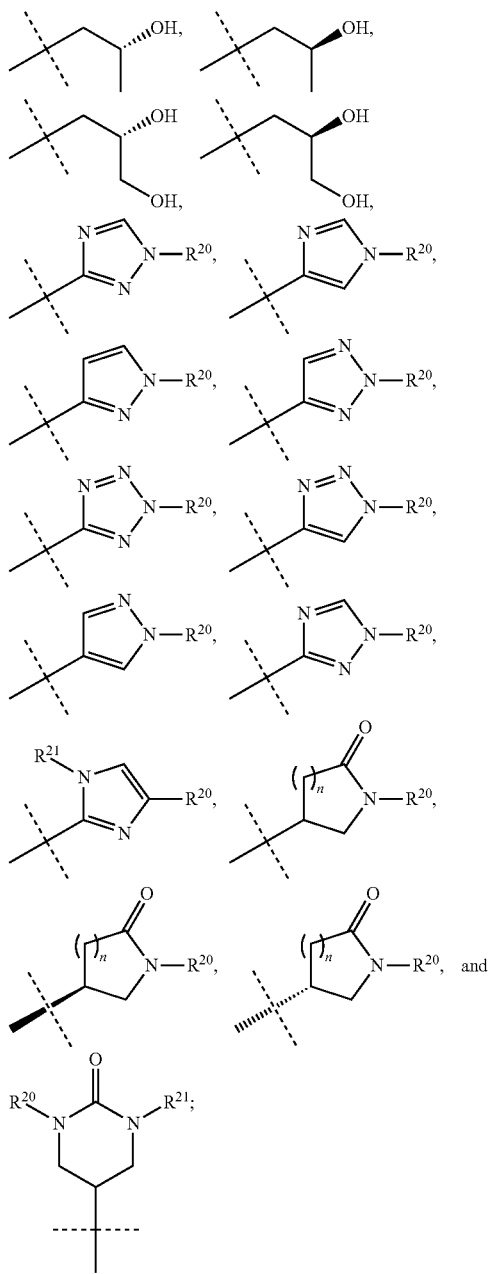

wherein n is 1, 2, 3, or 4, and R$^{20}$ and R$^{21}$ are independently selected from hydrogen, alkyl, cycloalkyl, and heterocycloalkyl. In a further embodiment, R$^{20}$ is C$_1$-C$_4$ alkyl. In yet another embodiment, R$^{20}$ is substituted with one or more hydroxy substituents.

In still other embodiments of compounds of Formula II or Formula II-A, R$^{11}$ is aryl, heteroaryl, or C$_1$-C$_6$ alkyl. In a further embodiment, R$^{11}$ is C$_1$-C$_6$ alkyl optionally substituted with 1, 2, or 3 hydroxy groups. In still another embodiment, R$^{11}$ is C$_1$-C$_6$ alkyl optionally substituted with 1, 2, or 3 fluoro groups. In other embodiments, R$^{11}$ is —CH$_2$CH(OH)CH$_3$. In some embodiments, R$^9$ is hydrogen. In other embodiments, R$^{12}$ is C$_1$-C$_4$ alkyl. In some other embodiments, W$^1$ is CR$^6$ and R$^6$ is —S(=O)$_2$NH$_2$.

In yet other embodiments of compounds of Formula II or Formula II-A, W$^1$ is CR$^6$, R$^6$ is —(CH$_2$)$_p$OH and p is 1, 2, 3, or 4. In a further embodiment, p is 3. In another embodiment, $R^7$ is hydrogen or fluoro. In still other embodiments, $R^6$ and $R^7$ are independently selected from hydrogen, —$(CR^{26}R^{27})_zY$, —$O(CR^{26}R^{27})_zY$, and —$C(=O)NR^{11}$ $(CR^{26}R^{27})_zY$; Y is hydrogen, halo, methyl, cyano, $OR^{28}$, or $NR^{28}R^{29}$; z is 1, 2, 3, 4, 5, or 6; $R^{26}$ and $R^{27}$ are, at each occurrence, independently selected from hydrogen, hydroxy, halo, and $C_1$-$C_4$ alkyl, or $R^{26}$ and $R^{27}$ in combination may form oxo; $R^{26}$ and $R^{27}$ together with the carbon(s) to which they are attached optionally form a 3- to 8-membered ring containing 0-2 heteroatoms; and $R^{28}$ and $R^{29}$ are independently selected from hydrogen, $C_1$-$C_4$ alkyl, and acetyl.

In still another aspect, the invention provides a compound of Formula II-B:

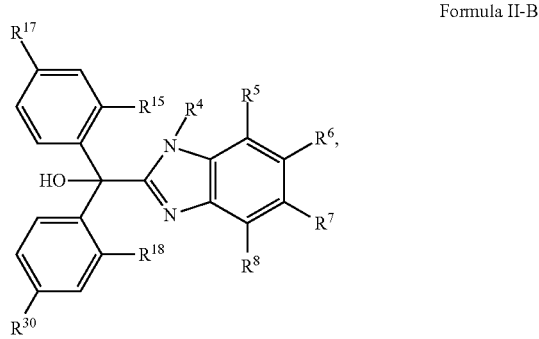

Formula II-B or a pharmaceutically acceptable salt thereof, wherein:

$R^4$ is selected from hydrogen, alkyl, cycloalkyl, heterocycloalkyl, and aryl;

$R^5$ and $R^8$ are independently selected from hydrogen, halo, cyano, alkoxy, and alkyl;

$R^6$ and $R^7$ are independently selected from hydrogen, halo, alkyl, cycloalkyl, heteroalkyl, heterocycloalkyl, alkoxy, aryl, heteroaryl, cyano, —$(CH_2)_tNR^9C(=O)R^{10}$, —$C(=O)OR^9$, —$C(=O)NR^{10}R^{11}$, —$S(O)_2R^{12}$, and —$S(O)_2NR^{10}R^{11}$;

t is 0, 1, or 2;

$R^9$ is selected from hydrogen, alkyl, cycloalkyl, alkenyl, alkynyl, aryl, heteroaryl, and heterocycloalkyl;

$R^{10}$ and $R^{11}$ are independently selected from hydrogen, alkyl, cycloalkyl, alkenyl, alkynyl, aryl, heteroaryl, and heterocycloalkyl, or $R^{10}$ and $R^{11}$ together with the atom to which they are attached form a 4- to 8-membered ring containing 0-2 heteroatoms;

$R^{12}$ is selected from alkyl, cycloalkyl, and heterocycloalkyl; and each of $R^{15}$, $R^{17}$, $R^{18}$, and $R^{30}$ is independently selected from hydrogen, halo, hydroxy, alkyl, alkoxy, and cyano.

In yet another aspect, the present invention provides a pharmaceutical composition comprising a compound disclosed herein and a pharmaceutically acceptable carrier.

In still yet another aspect, the present invention provides a method for inhibiting ACSS2 enzymatic activity, comprising contacting ACSS2 with an effective amount of a compound disclosed herein.

In another aspect, the present invention provides a method for inhibiting ACSS2, comprising contacting ACSS2 with an effective amount of a compound disclosed herein, wherein inhibition of ACSS2 may be evidenced by a reduction of one or more biological effects selected from the group consisting of production of acetyl-CoA, acetate incorporation into lipids, acetate incorporation into histones, and utilization of acetate in tumor cells.

In practicing any of the methods described herein, the step of contacting may further comprise contacting a cell that expresses ACSS2. In some other embodiments, the method further comprises administering a second therapeutic agent to the cell. In other embodiments, the contacting step of the method may take place in vivo. In another embodiment, the contacting step of the method may take place in vitro.

In some other aspects, the present invention provides a method for treating a condition associated with ACSS2, comprising administering to a subject in need thereof a therapeutically effective amount of a compound disclosed herein. In some embodiments, the present invention provides a method for treating a neoplastic condition in a subject, comprising administering to said subject a therapeutically effective amount of a pharmaceutical composition of a compound disclosed herein. In a further embodiment, said subject may be a human.

In still another aspect, the present invention provides a kit comprising a pharmaceutical composition of a compound disclosed herein and instructions for using the composition to treat a subject suffering from a neoplastic condition.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

FIG. 1 shows growth inhibition curves of 786-O xenograft bearing mice treated with compounds 79, 116, 119, 183 and vehicle respectively.

DETAILED DESCRIPTION OF THE INVENTION

The present invention relates to benzimidazole derivatives or pharmaceutically acceptable salts thereof and methods of using benzimidazole derivatives or pharmaceutically acceptable salts thereof for treating a disease or a disorder of a subject. In one embodiment, the disease or disorder is cancer.

While preferred embodiments of the present invention have been shown and described herein, it will be obvious to those skilled in the art that such embodiments are provided by way of example only. Numerous variations, changes and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

Unless defined otherwise, all technical and scientific terms used herein have the same meaning as is commonly understood by one of skill in the art to which this invention belongs. All patents and publications referred to herein are incorporated by reference.

The term "subject" includes, but is not limited to, humans of any age group, e.g., a pediatric subject (e.g., infant, child or adolescent) or adult subject (e.g., young adult, middle-aged adult or senior adult) and/or other primates (e.g., cynomolgus monkeys or rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, the terms "treatment", "treating", "palliating" and "ameliorating" are used interchangeably herein. These terms refer to an approach for obtaining beneficial or desired results including, but are not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compositions can be administered to a patient at risk of developing a particular disease, or to a patient reporting one or more of the physiological symptoms of a disease, even though a diagnosis of this disease may not have been made.

The term "alkyl" refers to a straight or branched hydrocarbon chain radical consisting of carbon and hydrogen atoms, containing no unsaturation, having from one to ten carbon atoms (i.e., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, n-propyl, isopropyl, n-butyl, isobutyl, sec-butyl, tert-butyl, pentyl, isopentyl, neopentyl, hexyl, septyl, and the like. The alkyl is attached to the rest of the molecule by a single bond. Unless stated otherwise specifically in the specification, an alkyl group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)R$^a$, —N(R$^a$)S(=O)$_t$R$^a$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The term "aromatic" or "aryl" refers to an aromatic radical with six to ten ring atoms (i.e., $C_6$-$C_{10}$ aromatic or $C_6$-$C_{10}$ aryl) which has at least one ring having a conjugated pi electron system which is carbocyclic (e.g., phenyl, fluorenyl, and naphthyl). Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently: alkyl, heteroalkyl, alkenyl, allynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)R$^a$, —N(R$^a$)S(=O)$_t$R$^a$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The term "heteroaryl" or, alternatively, "heteroaromatic" refers to a 5- to 18-membered aromatic radical (i.e., $C_5$-$C_{18}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical, e.g., nitrogen or sulfur, is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-c]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —SR$^a$, —OC(=O)—R$^a$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)R$^a$, —N(R$^a$)S(=O)$_t$R$^a$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cyclolalkyl, heterocycloalkyl, aryl or heteroaryl. Examples of monocylic heteroaryls include, but are not limited to, imidazolyl, pyridinyl, pyrrolyl, pyrazinyl, pyrimidinyl, thiazolyl, furanyl and thienyl.

The term "acyl" refers to a —C(=O)R radical, wherein "R" is alkyl, cycloalkyl, aryl, heteroaryl, heteroalkyl, or heterocycloalkyl, which are as described herein. The R group is joined to the carbonyl through a carbon-carbon single bond. In some embodiments, it is a $C_1$-$C_{10}$ acyl radical which refers to the total number of chain or ring atoms of the alkyl, cycloalkyl, aryl, heteroalkyl, heteroaryl or heterocycloalkyl portion of the acyl group plus the carbonyl carbon of acyl, i.e. ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyl group is optionally substituted by one or more substituents which independently are: alkyl, heteroalkyl, alkenyl, alkynyl, cycloalkyl, heterocycloalkyl, aryl, heteroaryl, hydroxy, halo, cyano, trifluoromethyl, trifluoromethoxy, nitro, trimethylsilanyl, —OR$^a$, —SR$^a$, —OC(=O)—R$^a$, —N(R$^a$)$_2$, —C(=O)R$^a$, —C(=O)OR$^a$, —OC(=O)N(R$^a$)$_2$, —C(=O)N(R$^a$)$_2$, —N(R$^a$)C(=O)OR$^a$, —N(R$^a$)C(O)R$^a$, —N(R$^a$)C(=O)N(R$^a$)$_2$, N(R$^a$)C(=NR$^a$)N(R$^a$)$_2$, —N(R$^a$)S(=O)$_t$R$^a$ (where t is 1 or 2), —S(=O)$_t$R$^a$ (where t is 1 or 2), —S(=O)$_t$N(R$^a$)$_2$ (where t is 1 or 2), or P(=O)(OR$^a$)$_2$, wherein each R$^a$ is independently hydrogen, alkyl, heteroalkyl, cycloalkyl, heterocycloalkyl, aryl or heteroaryl.

The term "halo", "halide", or alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. The terms "fluoroalkyl" and "fluoroalkoxy" include haloalkyl and haloalkoxy groups, respectively, in which the halo is fluorine. Examples of fluoroalkyl include, but are not limited to, —CH$_2$F, —CHF$_2$, —CF$_3$, —CF$_2$CH$_3$, —CH$_2$CF$_3$, and —CF$_2$CF$_3$.

The term "cyano" refers to a —CN radical.

The term "alkoxy" refers to an —O-alkyl radical, wherein alkyl is as described herein and contains 1 to 10 carbons (i.e., $C_1$-$C_{10}$ alkoxy). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms. In some embodiments, it is a $C_1$-$C_4$ alkoxy group. Unless stated otherwise specifically in the specification, an alkoxy moiety may be substituted by one or more of the substituents described as suitable substituents for an alkyl radical.

The term "cycloalkyl" refers to a monocyclic or polycyclic non-aromatic radical that contains carbon and hydrogen, and may be saturated, or partially unsaturated. Cycloalkyl groups include groups having from 3 to 10 ring atoms (i.e., $C_3$-$C_{10}$ cycloalkyl). Whenever it appears herein, a numerical range such as "3 to 10" refers to each integer in the given range; e.g., "3 to 10 carbon atoms" means that the cycloalkyl group may consist of 3 carbon ring atoms, etc., up to and including 10 carbon ring atoms. In some embodiments, it is a $C_3$-$C_5$ cycloalkyl radical. Illustrative examples of cycloalkyl groups include, but are not limited to, the following moieties: cyclopropyl, cyclobutyl, cyclopentyl, cyclohexyl, cycloseptyl, cyclooctyl, cyclononyl, cyclodecyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —N(R$^a$)$_2$, —C(=O)R$^a$, —C(=O)OR$^a$, —C(=O)N(R$^a$)$_2$, —N(R$^a$)C(=O)R$^a$, —N(R$^a$)C(=O)R$^a$, —N(R$^a$)S(=O)$_t$R$^a$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The term "heterocyclyl" or "heterocycloalkyl" refers to a stable and not fully aromatic 3- to 18-membered ring (i.e., $C_3$-$C_{18}$ heterocycloalkyl) radical that comprises two to twelve ring carbon atoms and from one to six ring heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. Unless stated otherwise specifically in the specification, the heterocycloalkyl radical may be a monocyclic, bicyclic, tricyclic or tetracyclic ring system, which may include fused or bridged ring systems. The heteroatoms in the heterocycloalkyl radical may be optionally oxidized. One or more nitrogen atoms, if present, may optionally be quaternized. The heterocycloalkyl radical may be partially or fully saturated. The heterocycloalkyl may be attached to the rest of the molecule through any atom of the ring(s). Examples of such heterocycloalkyl radicals include, but are not limited to, 6,7-dihydro-5H-cyclopenta[b]pyridine, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)R$^a$, —N(R$^a$), —C(=O)R$^a$, —C(=O)OR$^a$, —C(=O)N(R$^a$)$_2$, —N(R$^a$)C(=O)OR$^a$, —N(R$^a$)C(=O)R$^a$, —N(R$^a$)S(=O)$_t$R$^a$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The terms "heteroalkyl", "heteroalkenyl" and "heteroalkynyl" include optionally substituted alkyl, alkenyl and alkynyl radicals, which respectively have one or more skeletal chain atoms selected from an atom other than carbon, e.g., oxygen, nitrogen, sulfur, phosphorus or combinations thereof. A numerical range, which refers to the chain length in total, may be given. For example, $C_3$-$C_4$ heteroalkyl has a chain length of 3-4 atoms. For example, a —$CH_2OCH_2CH_3$ radical is referred to as a "$C_4$ heteroalkyl", which includes the heteroatom in the atom chain length description. Connection to the rest of the molecule is through a carbon in the heteroalkyl chain. A heteroalkyl may be a substituted alkyl. The same definition applies to heteroalkenyl or heteroalkynyl. Unless otherwise stated in the specification, a heteroalkyl group may be substituted with one or more substituents which independently are: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —$OR^a$, —$SR^a$, —$OC(=O)$—$R^a$, —$N(R^a)_2$, —$C(=O)R^a$, —$C(=O)OR^a$, —$C(=O)N(R^a)_2$, —$N(R^a)C(=O)OR^a$, —$N(R^a)C(=O)R^a$, —$N(R^a)S(=O)_tR_a$ (where t is 1 or 2), —$S(=O)_tR^a$ (where t is 1 or 2), —$S(=O)_tN(R^a)_2$ (where t is 1 or 2), —$OPO_3WY$ (where W and Y are hydrogen, methyl, ethyl, alkyl, lithium, sodium or potassium) or —$OPO_3Z$ (where Z is calcium, magnesium or iron), wherein each $R^a$ is independently hydrogen, alkyl, heteroalkyl, cycloalkyl, heterocycloalkyl, aryl or heteroaryl.

The term "amino" or "amine" refers to a —$NH_2$ radical group,

The term "alkenyl" refers to a straight or branched hydrocarbon chain radical group consisting of carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group may consist of 2 carbon atoms, 3 carbon atoms, etc., up to and including 10 carbon atoms. In certain embodiments, an alkenyl comprises two to eight carbon atoms (i.e., $C_2$-$C_8$ alkenyl). In other embodiments, an alkenyl comprises two to five carbon atoms (i.e., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —$OR^a$, —$SR^a$, —$OC(=O)$—$R^a$, —$N(R^a)_2$, —$C(=O)R^a$, —$C(=O)OR^a$, —$C(=O)N(R^a)_2$, —$N(R^a)C(=O)R^a$, —$N(R^a)C(=O)OR^a$, —$N(R^a)S(=O)_tR^a$ (where t is 1 or 2), —$S(=O)_tR^a$ (where t is 1 or 2), —$S(=O)_tN(R^a)_2$ (where t is 1 or 2), —$OPO_3WY$ (where W and Y are independently hydrogen, methyl, ethyl, alkyl, lithium, sodium or potassium) or —$OPO_3Z$ (where Z is calcium, magnesium or iron), wherein each $R^a$ is independently hydrogen, alkyl, heteroalkyl, cycloalkyl, heterocycloalkyl, aryl or heteroaryl.

The term "alkynyl" refers to a straight or branched hydrocarbon chain radical group consisting of carbon and hydrogen atoms, containing at least one triple bond, having from two to ten carbon atoms (i.e., $C_2$-$C_{10}$ alkynyl). In some embodiments, an alkynyl group may contain one or more double bonds. Whenever it appears herein, a numerical range such as "2 to 10" refers to each integer in the given range; e.g., "2 to 10 carbon atoms" means that the alkynyl group may consist of 2 carbon atoms, 3 carbon atoms, etc., up to and including 10 carbon atoms. In certain embodiments, an alkynyl comprises two to eight carbon atoms (i.e., $C_2$-$C_8$ alkynyl). In other embodiments, an alkynyl has two to five carbon atoms (i.e., $C_2$-$C_5$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —$OR^a$, —$SR^a$, —$OC(=O)$—$R^a$, —$N(R^a)_2$, —$C(=O)R^a$, —$C(=O)OR^a$, —$C(=O)N(R^a)_2$, —$N(R^a)C(=O)OR^a$, —$N(R^a)C(=O)R^a$, —$N(R^a)S(=O)_tR^a$ (where t is 1 or 2), —$S(=O)_tR^a$ (where t is 1 or 2), —$S(=O)_tN(R^a)_2$ (where t is 1 or 2), —$OPO_3WY$ (where W and Y are independently hydrogen, methyl, ethyl, alkyl, lithium, sodium or potassium) or —$OPO_3Z$ (where Z is calcium, magnesium or iron), wherein each $R^a$ is independently hydrogen, alkyl, heteroalkyl, cycloalkyl, heterocycloalkyl, aryl or heteroaryl.

The term "alkylamino" refers to a chemical moiety with formula —$N(R^a)_2$, wherein each $R^a$ is independently hydrogen, alkyl, heteroalkyl, cycloalkyl, or heterocycloalkyl, and at least one $R^a$ is not hydrogen. Two $R^a$s may optionally form a 3-8 membered ring.

The term "amide" or "amido" refers to a chemical moiety with formula —$C(=O)N(R^a)_2$ or —$NR^aC(=O)R^a$, wherein each $R^a$ is independently selected from the group consisting of hydrogen, alkyl, cycloalkyl, aryl, heteroaryl (bonded through a ring carbon) and heterocycloalkyl. Two $R^a$s, together with the atoms they are attached to, can optionally form a 5-10 membered ring. In some embodiments, it is a $C_1$-$C_4$ amido or amide radical, which includes the amide carbonyl in the total number of carbons in the radical. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound described herein, thereby forming a prodrug. The procedures and specific groups to make such amides are known to those of skilled in the art and can readily be found in reference sources such as Greene and Wuts, *Protective Groups in Organic Synthesis*, 3rd Ed., John Wiley & Sons, New York, N.Y., 1999.

"Ester" refers to a chemical radical of formula —$C(=O)OR$, where R is selected from the group consisting of alkyl, cycloalkyl, aryl, heteroaryl (bonded through a ring carbon) and heteroalkyl (bonded through a ring carbon). Any hydroxy or carboxyl side chain on the compounds described herein can be esterified. The procedures and specific groups to make such esters are known to those of skill in the art and can readily be found in reference sources such as Greene and Wuts, *Protective Groups in Organic Synthesis*, 3rd Ed., John Wiley & Sons, New York, N.Y., 1999. Unless stated otherwise specifically in the specification, an ester group is optionally substituted by one or more substituents which independently are: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —$OR^a$, —$SR^a$, —$OC(=O)$—$R^a$, —$N(R^a)_2$, —$C(=O)R^a$, —$C(=O)OR^a$, —$C(=O)N(R^a)_2$, —$N(R^a)C(=O)OR^a$, —$N(R^a)C(=O)R^a$, —$N(R^a)S(O)_tR^a$ (where t is 1 or 2), —$S(=O)_tOR^a$ (where t is 1 or 2), —$S(=O)_tN(R^a)_2$ (where t is 1 or 2), —$OPO_3WY$ (where W and Y are independently hydrogen, methyl, ethyl, alkyl, lithium, sodium or potassium) or —$OPO_3Z$ (where Z is calcium, magnesium or iron), wherein each $R^a$ is independently hydrogen, alkyl, heteroalkyl, cycloalkyl, heterocycloalkyl, aryl, or heteroaryl.

"Moiety" refers to a specific segment or functional group of a molecule. Chemical moieties are often recognized chemical entities embedded in or appended to a molecule.

"Hydroxy" refers to a —OH radical.
"Oxa" refers to a —O— radical.
"Oxo" refers to a =O radical.
"Nitro" refers to a —NO$_2$ radical.
"Thiocyanato" refers to a —CNS radical.
"Thioxo" refers to a =S radical.

"Substituted" means that the referenced group may be substituted with one or more additional group(s) individually and independently selected from acyl, alkyl, amide, heteroalkyl, cycloalkyl, heterocycloalkyl, aryl, heteroaryl, hydroxy, alkoxy, mercapto, alkylthio, arylthio, cyano, halo, carbonyl, ester, thiocarbonyl, isocyanato, thiocyanato, isothiocyanato, nitro, perhaloalkyl, perfluoroalkyl, phosphate, silyl, sulfinyl, sulfonyl, sulfonamide, sulfoximinyl, alkylamino, arylamino, amino, and the like. The substituents themselves may be substituted, for example, a cycloalkyl substituent may have a halide substituted at one or more ring carbons, and the like. The protecting groups that may form the protective derivatives of the above substituents are known to those of skill in the art and may be found in references such as Greene and Wuts cited herein.

The term "optional" or "optionally" means that the subsequently described event or circumstance may or may not occur, and includes instances where the event or circumstance occurs and instances in which it does not. For example, "alkyl optionally substituted with" encompasses both "alkyl" and "alkyl" substituted with groups as defined herein. It will be understood by those skilled in the art, with respect to any group containing one or more substituents, that such groups are not intended to introduce any substitution or substitution patterns which would be deemed unacceptable by one of ordinary skill in the art.

The methods and formulations described herein include the use of N-oxides, crystalline forms (also known as polymorphs), or pharmaceutically acceptable salts of compounds having the structure of formulae described herein, as well as active metabolites of these compounds having the same type of activity. In addition, the compounds described herein can exist in unsolvated as well as solvated forms with pharmaceutically acceptable solvents such as water, ethanol, and the like. The solvated forms of the compounds presented herein are also considered to be disclosed herein.

Compounds or formulae described herein also include their prodrugs. The term prodrug means a precursor of a drug which undergoes transformation in the body of a treated subject to form a therapeutically active ingredient. In some embodiments, the therapeutically active ingredient is a compound or a compound having a formula described herein.

Compounds or formulae described herein may exhibit their natural isotopic abundance, or one or more of the atoms may be artificially enriched in a particular isotope having the same atomic number, but an atomic mass or mass number different from the atomic mass or mass number predominantly found in nature. The present invention is meant to include all suitable isotopic variations of the compounds described herein. For example, hydrogen has three naturally occurring isotopes, denoted $^1$H (protium), $^2$H (deuterium), and $^3$H (tritium). Protium is the most abundant isotope in nature. Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art or by processes analogous to those described in the Schemes and Examples herein using appropriate isotopically-enriched reagents and/or intermediates. See Pleiss and Voger, *Synthesis and Applications of Isotopically Labeled Compounds*, Vol. 7, Wiley, ISBN-10: 0471495018, published on Mar. 14, 2001.

Unless otherwise specified, compounds or formulae described herein may include, but are not limited to, when possible, their optical isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if needed, can be accomplished, for example, by conventional methods such as crystallization in the presence of a resolving agent, or chromatography, using, for example, a chiral high-pressure liquid chromatography (HPLC) column. In addition, chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well. For example, structure A1 and A2 shown below are tautomeric forms of each other and are considered equivalent in certain embodiments of the present disclosure. It will be appreciated by one of skilled in the art that the equilibrium could be shifted to either direction depending upon factors, for example, pH and concentration.

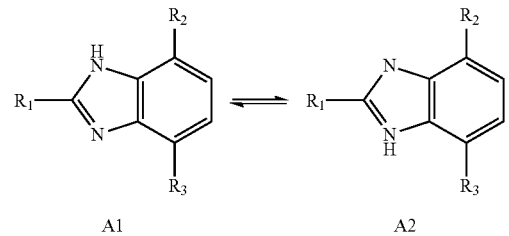

A1          A2

The term "pharmaceutically acceptable" means that a chemical entity, such as a compound, a carrier, an additive or a salt, is acceptable for being administrated to a subject.

The term "pharmaceutically acceptable salts" refers to salts prepared from pharmaceutically acceptable bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts derived from pharmaceutically acceptable organic bases may be selected, for example, from salts of primary, secondary, and tertiary amines, substituted amines including naturally occurring substituted amines, cyclic amines, and basic ion exchange resins, such as arginine, betaine, caffeine, choline, N,N'- dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When chemical entities disclosed herein are basic, salts may be prepared using at least one pharmaceutically acceptable acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, trifluoroacetic acid, and p-toluenesulfonic acids. In some embodiments, such acid may be selected, for example, from citric, hydrobromic, hydrochloric, maleic, phosphoric, sulfuric, fumaric, and tartaric acids.

The term "pharmaceutically acceptable carrier" as used herein means a diluent, excipient, encapsulating material or formulation auxiliary, which may be non-toxic, and inert, which may not have undesirable effect on a subject, preferably a mammal, more preferably a human, or which may be suitable for delivering an active agent to the target site without affecting the activity of the agent.

The term "effective amount" or "therapeutically effective amount" refers to an amount of a compound or pharmaceutical composition described herein that is sufficient to effect the intended application including, but not limited to, disease treatment, as illustrated below. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The specific dose will vary depending on, for example, the particular compounds chosen, the dosing regimen to be followed, whether it is administered in combination with other agents, timing of administration, the tissue to which it is administered, and the physical delivery system in which it is carried.

In cases of a solid dosage form, examples of dosages of the compounds described herein which can be used are an effective amount within the dosage range of about 0.001 mg to about 10 mg per kilogram of body weight, about 0.001 mg to about 20 mg per kilogram of body weight, about 0.001 mg to about 50 mg per kilogram of body weight, about 0.001 mg to about 100 mg per kilogram of body weight, about 0.001 mg to about 200 mg per kilogram of body weight or about 0.001 mg to about 300 mg per kilogram of body weight. When administered orally or by inhalation, examples of dosages are an effective amount within the dosage range of about 0.1 mg to about 10 mg, or about 0.1 mg to about 20 mg, or about 0.1 mg to about 30 mg, or about 0.1 mg to about 40 mg, or about 0.1 mg to about 50 mg, or about 0.1 mg to about 60 mg, or about 0.1 mg to about 70 mg, or about 0.1 mg to about 80 mg, or about 0.1 mg to about 90 mg, or about 0.1 mg to about 100 mg, or about 0.1 mg to about 200 mg, or about 0.1 mg to about 300 mg, or about 0.1 mg to about 400 mg, or about 0.1 mg to about 500 mg, or about 0.1 mg to about 600 mg, or about 0.1 mg to about 700 mg, or about 0.1 mg to about 800 mg, or about 0.1 mg to about 900 mg, or about 0.1 mg to about 1 g. Preferred fixed doses include about 1 mg, about 2 mg, about 3 mg, about 4 mg, about 5 mg, about 6 mg, about 7 mg, about 8 mg, about 9 mg, about 10 mg, about 12 mg, about 15 mg, about 18 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, or about 1 g, independently of body weight. However, it is understood that pediatric patients may require smaller dosages, and depending on the severity of the disease and condition of the patient, dosages may vary. The compound will preferably be administered once daily, but may be administered two, three or four times daily, or every other day, or once or twice per week.

The term "about" refers to ±10% of a stated number or value.

The following abbreviations and terms have the indicated meanings throughout:
DAST=Diethylaminosulfur trifluoride
DCM=Dichloromethane
MTBE=Methyl t-butyl ether
HATU=O-(7-azabenzotriazol-1-yl)-N,N,N',N'-tetramethyluronium hexafluorophosphate
NBS=N-Bromosuccinimide
NMP=N-Methyl-2-pyrrolidone
TEA=Triethylamine
TBAF=Tetrabutylammonium fluoride
CDI=Carbonyldiimidazole
DIEA=N,N-Diisopropylethylamine
TFA=Trifluoroacetic acid
PPTS=Pyridinium p-toluenesulfonate
DMAP=4-Dimethylaminopyridine
DMF=N,N-Dimethylformamide In one aspect, the present disclosure provides a method of modulating the activity of Acetyl-CoA Synthetase Short Chain 2 (ACSS2) in cells by treating the cells with a compound described herein or a pharmaceutically acceptable salt thereof. In one embodiment, the present disclosure provides a method of inhibiting the activity of Acetyl-CoA Synthetase Short Chain 2 (ACSS2) in cells by treating the cells with a compound described herein or a pharmaceutically acceptable salt thereof. In some embodiments, the compound or a pharmaceutically acceptable salt thereof has an $IC_{50}$ of less than 10 µM, less than 5 µM, less than 3 µM, less than 1 µM, or less than 500 nM as determined by human ACSS2 enzymatic assay. In a further embodiment, the compound or a pharmaceutically acceptable salt thereof has an $IC_{50}$ of less than 500 nM. In some other embodiments, the compound or a pharmaceutically acceptable salt thereof has an $EC_{50}$ of less than 10 µM, less than 5 µM, less than 3 µM, less than 1 µM, or less than 500 nM as determined by $^{14}C$-acetate uptake assay in HCT116 or HELA cells. In a further embodiment, the compound or a pharmaceutically acceptable salt thereof has an $EC_{50}$ of less than 500 nM.

In another aspect, the present disclosure provides a method of treating cancer of a subject with a compound described herein or a pharmaceutically acceptable salt thereof. The subject may be a human. In some embodiments, the subject may have up-regulated ACSS2 expression and/or ACSS2 activity in a tissue comparing to that of the same tissue from a normal or healthy subject. Without being bound to theory, the anti-cancer effect may be partially or soley due to ACSS2 inhibition. The cancer may include but are not limited to the following: tumor of the bladder, breast, colorectal, colon, kidney, liver, lung, head and neck, esophagus, bladder, gall bladder, ovary, pancreas, stomach, cervix, thyroid, prostate, and skin, including squamous cell carcinoma; leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma and Burkett's lymphoma; chronic lymphocytic leukemia ("CLL"), acute and chronic myelogenous leukemia, myelodysplastic syndrome and promyelocyte leukemia; fibrosarcoma, rhabdomyosarcoma; mantle cell lymphoma, myeloma; astrocytoma, neuroblastoma, glioma, glioblastoma, malignant glial tumors, astrocytoma, hepatocellular carcinoma, gastrointestinal stromal tumors ("GIST") and schwannomas; melanoma, multiple myeloma, seminoma, teratocarcinoma, osteosarcoma, xenoderma pigmentosum, keratoctanthoma, thyroid follicular cancer, endometrial cancer, gastrointestinal tract cancer and Kaposi's sarcoma. The tissue may be a solid tumor.

As used herein, "agent" or "biologically active agent" refers to a biological, pharmaceutical, or chemical compound. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oliopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

The term "cell proliferation" refers to a phenomenon by which the cell number has changed as a result of division. This term also encompasses cell growth by which the cell morphology has changed (e.g., increased in size) consistent with a proliferative signal.

The terms "co-administration," "administered in combination with," and their grammatical equivalents, encompass administration of two or more agents to an animal so that both agents and/or their metabolites are present in the animal at the same time. Co-administration includes simultaneous administration in separate compositions, administration at different times in separate compositions, or administration in a composition in which both agents are present.

A "therapeutic effect," as used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "selective inhibition" or "selectively inhibit" as applied to a biologically active agent refers to the agent's ability to selectively reduce the target signaling activity as compared to off-target signaling activity, via direct or indirect interaction with the target.

"Radiation therapy" or "radiation treatment" means exposing a patient, using routine methods and compositions known to the practitioner, to radiation emitters such as alpha-particle emitting radionucleotides (e.g., actinium and thorium radionuclides), low linear energy transfer (LET) radiation emitters (e.g., beta emitters), conversion electron emitters (e.g., strontium-89 and samarium-153-EDTMP), or high-energy radiation, including without limitation x-rays, gamma rays, and neutrons.

The term "in vivo" refers to an event that takes place in a subject's body.

The term "in vitro" refers to an event that takes place outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

The term "ACSS2" refers to acetyl-CoA synthetase short chain 2, an ATP-dependent enzyme that catalyzes the synthesis of acetyl-CoA from acetate. ACSS2 is responsible for acetate utilization in cells, including the uptake of acetate into lipids and histones.

"ACSS2 activity" as used herein has its ordinary meaning in the art. ACSS2 activity, for example, includes activation of acetate for use in energy production and lipid synthesis, synthesis of acetyl-CoA, incorporation of cellular acetate into lipids and histones and activation of acetylation-dependent pathways.

The term "inhibiting ACSS2 activity", as used herein, refers to slowing, reducing, altering, as well as completely eliminating and/or preventing ACSS2 activity.

"Aralkyl" or "arylalkyl" refers to an (aryl)alkyl-moiety wherein the arylalkyl moiety is attached via the alkyl portion of the moiety. Aryl and alkyl are as disclosed herein and are optionally substituted by one or more of the substituents described as suitable substituents for aryl and alkyl, respectively.

The term "sp$^3$ hybridized carbon" refers to a carbon atom that is bonded to four other atoms. sp$^3$ hybridization results from the combination of the s orbital and all three p orbitals in the second energy level of carbon. It results in four equivalent orbitals and the geometric arrangement of those four orbitals is tetrahedral.

The term "sulfonyl" refers to a —S(=O)$_2$R$^a$ moiety, wherein R$^a$ is selected from the group consisting of alkyl, amino, cycloalkyl, aryl, heteroalkyl, heteroaryl (bonded through a ring carbon) and heterocycloalkyl (bonded through a ring carbon). Unless stated otherwise specifically in the specification, the R$^a$ group may be substituted by one or more of the substituents described as suitable substituents for an alkyl, an aryl or a heteroaryl moiety.

The term "sulfoximinyl" refers to a —S(=O)(=NR$^a$)R$^b$ moiety, wherein R$^a$ is selected from the group consisting of hydrogen, alkyl, cycloalkyl, aryl, cyano, carbamoyl, acyl, heteroaryl (bonded through a ring carbon) and heterocycloalkyl (bonded through a ring carbon) and R$^b$ is independently selected from the group consisting of alkyl, cycloalkyl, aryl, heteroalkyl, heteroaryl (bonded through a ring carbon) and heterocycloalkyl (bonded through a ring carbon). Unless stated otherwise specifically in the specification, the R$^a$ and R$^b$ groups may be substituted by one or more of the substituents described as suitable substituents for an alkyl, an aryl or a heteroaryl moiety.

"Sulfonamide," "sulfonamidyl" or "sulfonamido" refers to a —S(=O)$_2$N(R$^a$)$_2$ moiety, wherein each R$^a$ is selected independently from the group consisting of hydrogen, alkyl, heteroalkyl, cycloalkyl, aryl, heteroaryl and heterocycloalkyl. The $R^a$ groups in —N($R^a$)$_2$ of the —S(=O)$_2$—N($R^a$)$_2$ moiety may be taken together with the nitrogen to which it is attached to form a 4-, 5-, 6-, or 7-membered ring. In some embodiments, it is a $C_1$-$C_{10}$ sulfonamido, wherein each $R^a$ in sulfonamido contains 1 carbon, 2 carbons, 3 carbons or 4 carbons total. A sulfonamido group is optionally substituted by one or more of the substituents described for alkyl, cycloalkyl, aryl and heteroaryl, respectively.

The term "fluoroalkylsulfonyl" refers to a —S(=O)$_2$$R^a$ moiety, wherein $R^a$ is fluoroalkyl. In some embodiments, $R^a$ is $C_1$-$C_4$ alkyl, substituted with one or more fluorines.

The term "acyloxy" refers to a RC(=O)O— moiety wherein R is alkyl, cycloalkyl, aryl, heteroalkyl, heteroaryl or heterocycloalkyl, which are as described herein. In some embodiments, it is a $C_1$-$C_4$ acyloxy moiety, which refers to the total number of chain or ring atoms of the alkyl, cycloalkyl, aryl, heteroalkyl, heteroaryl or heterocycloalkyl portion of the acyloxy group plus the carbonyl carbon of acyl, i.e., the other ring or chain atoms plus carbonyl. If the R group is heteroaryl or heterocycloalkyl, the hetero ring or chain atoms contribute to the total number of chain or ring atoms. Unless stated otherwise specifically in the specification, the "R" of an acyloxy group is optionally substituted by one or more of the following substituents: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, oxo, thioxo, trimethylsilanyl, —O$R^a$, —S$R^a$, —OC(=O)$R^a$, —OC(=O)O$R^a$, —OC(=O)N($R^a$)$_2$, —N($R^a$)$_2$, —C(=O)O$R^a$, —C(=O)$R^a$, —C(=O)N($R^a$)$_2$, —N($R^a$)C(=O)O$R^a$, —N($R^a$)C(=O)N($R^a$)$_2$, —N($R^a$)C(N$R^a$)N($R^a$)$_2$, —N($R^a$)C(=O)$R^a$, —N($R^a$)S(=O)$_t$$R^a$ (where t is 1 or 2), —N($R^a$)S(=O)$_t$N($R^a$)$_2$ (where t is 1 or 2), —S(=O)$_t$$R^a$ (where t is 1 or 2), —S(=O)$_t$N($R^a$)$_2$ (where t is 1 or 2), —PO$_3$($R^a$)$_2$, —OPO$_3$WY (where W and Y are independently hydrogen, methyl, ethyl, alkyl, lithium, sodium or potassium) or —OPO$_3$Z (where Z is calcium, magnesium or iron), wherein each $R^a$ is independently hydrogen, alkyl, fluoroalkyl, heteroalkyl, cycloalkyl, heterocycloalkyl, heterocycloalkylalkyl, aryl, aralkyl, heteroaryl or heteroarylalkyl.

"Carboxaldehyde" refers to a —C(=O)H moiety.

"Carboxyl" refers to a —C(=O)OH moiety.

"Imino" refers to a =N—$R^a$ moiety, wherein $R^a$ is hydrogen, alkyl, heteroalkyl, cycloalkyl, cyano, aryl, heterocycloalkyl or heteroaryl.

"Isocyanato" refers to a —NCO moiety.

"Isothiocyanato" refers to a —NCS moiety.

"Mercaptyl" refers to an —S(alkyl) or —SH moiety.

"Methylene" refers to a =CH$_2$ moiety.

"Oxime" refers to a =N(—OH)R moiety, where R is hydrogen or alkyl.

"Sulfinyl" refers to a —S(=O)R moiety, where R is selected from the group consisting of alkyl, cycloalkyl, aryl, heteroalkyl, heteroaryl (bonded through a ring carbon) and heterocycloalkyl (bonded through a ring carbon). In some embodiments, R is fluoroalkyl.

"Sulfoxyl" refers to a —S(=O)$_2$OH moiety.

"Sulfonate" refers to a —S(=O)$_2$OR moiety, where R is selected from the group consisting of alkyl, cycloalkyl, aryl, heteroalkyl, heteroaryl (bonded through a ring carbon) and heterocycloalkyl (bonded through a ring carbon). The R group is optionally substituted by one or more of the substituents described for alkyl, heteroalkyl, cycloalkyl, heterocycloalkyl, aryl, and heteroaryl, respectively.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

"Isomers" are different compounds that have the same molecular formula. "Stereoisomers" are isomers that differ only in the way the atoms are arranged in space. "Enantiomers" are a pair of stereoisomers that are non superimposable mirror images of each other. A 1:1 mixture of a pair of enantiomers is a "racemic" mixture. The term "(±)" is used to designate a racemic mixture where appropriate. "Diastereoisomers" or "diastereomers" are stereoisomers that have at least two asymmetric atoms but are not mirror images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) in which they rotate plane polarized light at the wavelength of the sodium D line. Certain compounds described herein contain one or more asymmetric centers and can thus give rise to enantiomers, diastereomers, and other stereoisomeric forms that can be defined, in terms of absolute stereochemistry, as (R)- or (S)-.

The term "enantiomeric excess," as used herein, is the percent excess of one enantiomer compared to that of the other enantiomer in a mixture, and can be calculated using the following equation: enantiomeric excess=((R−S)/(R+S))×100=% (R*)−%(5*), wherein R and S are the number of moles of each enantiomer in the mixture, and R* and S* are the respective mole fractions of the enantiomers in the mixture. For example, for a mixture with 87% R enantiomer and 13% S enantiomer, the enantiomeric excess (ee) is 74%.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in Wuts, *Greene's Protective Groups in Organic Synthesis*, 5$^{th}$ Ed., Wiley, New York, N.Y., 2014. For example, a hydroxy protected form is where at least one of the hydroxy groups present in a compound is protected with a hydroxy protecting group. Likewise, amines and other reactive groups may similarly be protected.

"Solvate" refers to a compound in physical association with one or more molecules of a pharmaceutically acceptable solvent. It will be understood that the present chemical entities encompass the present chemical entities and solvates of the compound, as well as mixtures thereof.

"Solvent," "organic solvent," and "inert solvent" each means a solvent inert under the conditions of the reaction being described in conjunction therewith, including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When ranges are used herein for physical properties, such as molecular weight, or chemical properties, such as chemical formulae, all combinations and subcombinations of ranges and specific embodiments therein are intended to be included.

When "`\`" is drawn across a bond, it denotes where a bond attachment or disconnection occurs. For example, in the chemical structure shown below,

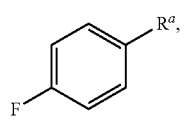

$R^a$ is attached to the para position of a fluorophenyl ring through a single bond. When $R^a$ is phenyl,

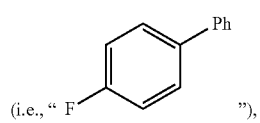

(i.e., "…"), $R^a$ may be drawn as

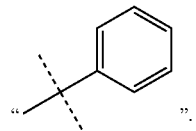

The present invention relates to benzimidazole derivatives or pharmaceutically acceptable salts thereof and methods of using benzimidazole derivatives or pharmaceutically acceptable salts thereof for treating a disease or a disorder of a subject. In one embodiment, the disease or disorder is cancer.

In one aspect, the present disclosure provides a compound of Formula I:

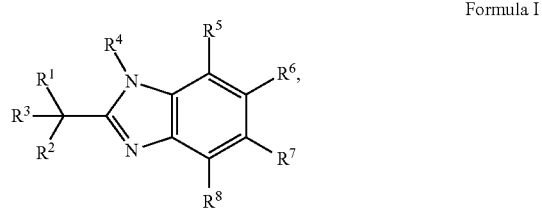

Formula I or a pharmaceutically acceptable salt thereof,
wherein:
$R^1$ and $R^2$ are independently aryl or heteroaryl;
$R^3$ is selected from the group consisting of hydrogen, hydroxy and —$CH_2OH$;
$R^4$ is selected from the group consisting of hydrogen, alkyl, cycloalkyl, heterocycloalkyl, aryl and heteroaryl;
$R^5$ and $R^8$ are independently hydrogen, halo, cyano, alkoxy, or alkyl;
$R^6$ and $R^7$ are independently hydrogen, halo, cyano, alkyl, cycloalkyl, alkoxy, aryl, heteroaryl, —$NR^9C(=O)R^{10}$, —$C(=O)OR^9$, —$C(=O)NR^{10}R^{11}$, —$S(=O)_2R^{12}$, or —$S(=O)_2NR^{10}R^{11}$;
each of said $R^9$, $R^{10}$, and $R^{11}$ is independently selected from the group consisting of hydrogen, alkyl, cycloalkyl, aryl, heteroaryl and heterocycloalkyl;
$R^{12}$ is selected from the group consisting of alkyl, cycloalkyl, alkenyl, alkynyl, aryl, heteroaryl and heterocycloalkyl; and
$R^{10}$, $R^{11}$ and the atom(s) they are attached to may optionally form a 4-8 membered ring containing 0-2 heteroatoms selected from the group consisting of O, N and S.

In some embodiments, $R^1$ and $R^2$ are independently phenyl or pyridyl. In a further embodiment, $R^1$ and $R^2$ are independently phenyl. In a still further embodiment, each of $R^1$ and $R^2$ is optionally substituted with at least one substituent selected from the group consisting of halo, hydroxy, cyano, alkyl, alkoxy, or —$S(=O)_2$-alkyl.

In some embodiments, $R^3$ is hydroxy.

In some embodiments, $R^4$ is alkyl. In some further embodiments, $R^4$ is substituted with one or more halo or hydroxy. In some other further embodiments, $R^4$ is selected from the group consisting of methyl, ethyl, —$CH(CH_3)_2$, —$CH_2CH_2F$, —$CH_2CHF_2$, —$CH_2CF_3$, —$CHFCH_3$, —$CF_2CH_3$ and —$CH_2CH_2OH$.

In some embodiments, $R^5$ and $R^8$ are independently hydrogen, halo, alkoxy, or alkyl. In some further embodiments, $R^5$ and $R^8$ are independently hydrogen or halo. In a further embodiment, $R^5$ and $R^8$ are hydrogen.

In some embodiments, at least one of $R^6$ and $R^7$ is not hydrogen. In some embodiments, $R^6$ is cyano, —$NR^9C(=O)R^{10}$, —$C(=O)OR^9$, —$C(=O)NR^{10}R^{11}$, —$S(=O)_2R^{12}$, or —$S(=O)_2NR^{10}R^{11}$, and $R^7$ is hydrogen, halo, or alkyl. In some further embodiments, $R^7$ is hydrogen or fluoro and $R^6$ is —$C(=O)NR^{10}R^{11}$ or —$S(=O)_2NR^{10}R^{11}$. In a further embodiment, at least one of $R^{10}$ and $R^{11}$ is hydrogen.

In some embodiments, $R^6$ is hydrogen, halo, or alkyl, and $R^7$ is cyano, —$NR^9C(=O)R^{10}$, —$C(=O)OR^{10}$, —$C(=O)NR^{10}R^{11}$, —$S(=O)_2R^{12}$, or —$S(=O)_2NR^{10}R^{11}$. In some further embodiments, $R^6$ is hydrogen or halo, and $R^7$ is —$C(=O)NR^{10}R^{11}$ or —$S(=O)_2R^{12}$. In a further embodiment, at least one of $R^{10}$ and $R^{11}$ is hydrogen.

In some embodiments, $R^1$ and $R^2$ are phenyl and $R^3$ is —OH. In a further embodiment, each phenyl is independently substituted with at least one substituent selected from the group consisting of halo, cyano, alkyl, or alkoxy. In a further embodiment, each phenyl is independently substituted with halo. In another further embodiment, $R^1$, $R^2$ and $R^3$ in combination is

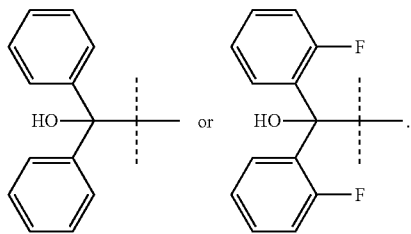

In some embodiments, $R^6$ is —$C(=O)NHR^{13}$, wherein $R^{13}$ is alkyl, cycloalkyl, aryl, or heteroaryl. In a further embodiment, $R^{13}$ is selected from the group consisting of:

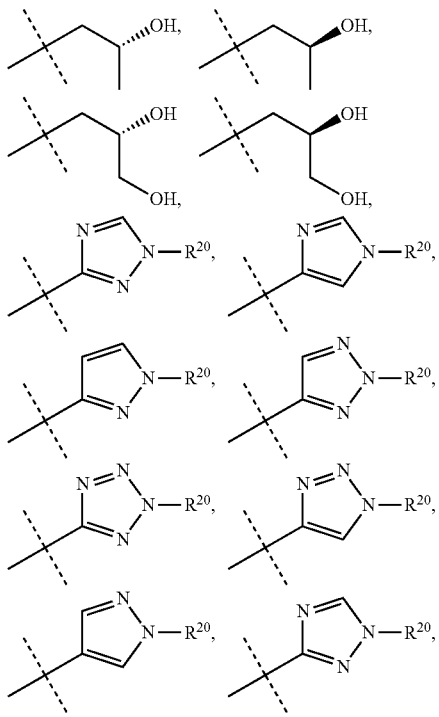

-continued

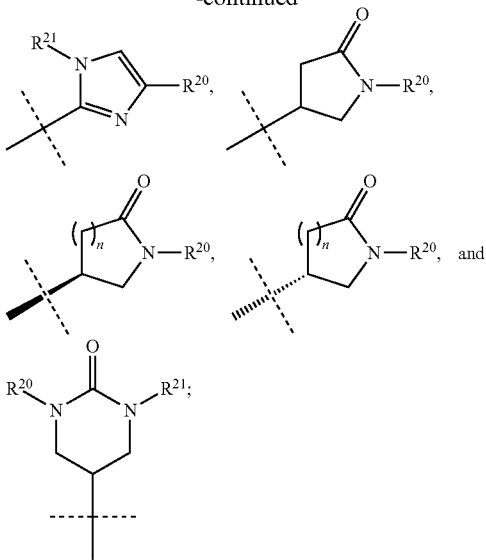

wherein n is 1, 2, 3, or 4; $R^{20}$ and $R^{21}$ are independently selected from the group consisting of hydrogen, alkyl, cycloalkyl or heterocycloalkyl. In a further embodiment, each of $R^{20}$ and $R^{21}$ is independently alkyl.

In some embodiments, $R^6$ is —$S(=O)_2NH_2$. In a further embodiment, $R^7$ is hydrogen or fluoro.

In some embodiments, $R^6$ is —$NR^9C(=O)R^{10}$, —$NR^9S(=O)_2R^{10}$, —$C(=O)NR^{10}R^{11}$, or —$S(=O)_2NR^{10}R^{11}$; $R^7$ is hydrogen, halo, or alkyl; and $R^3$ is hydroxy. In a further embodiment, $R^6$ is —$C(=O)NHR^{13}$ or —$S(=O)_2NH_2$ and $R^7$ is hydrogen or fluoro, wherein $R^{13}$ is alkyl, cycloalkyl, aryl, or heteroaryl.

In some embodiments, $R^7$ is —$NR^9C(=O)R^{10}$, —$NR^9S(=O)_2R^{10}$, —$C(=O)NR^{10}R^{11}$, or —$S(=O)_2NR^{10}R^{11}$, $R^6$ is hydrogen, halo, or alkyl, and $R^3$ is hydroxy. In a further embodiment, $R^7$ is —$C(=O)NHR^{13}$ or —$S(=O)_2NH_2$ and $R^6$ is hydrogen, alkyl, or halo, wherein $R^{13}$ is alkyl, cycloalkyl, aryl, or heteroaryl.

In some embodiments, $R^6$ is —$(CH_2)_nOH$ and $R^7$ is hydrogen, halo, or alkyl, wherein n is 1, 2, 3, or 4. In one further embodiment, n is 3. In another further embodiment, $R^7$ is hydrogen. In a still further embodiment, $R^3$ is hydroxy.

In some embodiments, each of $R^1$ and $R^2$ is independently phenyl; $R^3$ is hydroxy; $R^4$ is alkyl or cycloalkyl; $R^6$ is —$C(=O)NHR^{13}$ or —$S(=O)_2NH_2$, wherein $R^{13}$ is alkyl, cycloalkyl, aryl, or heteroaryl; and $R^7$ is hydrogen or fluoro. In a further embodiment, $R^6$ is —$C(=O)NHR^{13}$ and each of $R^5$ and $R^8$ is hydrogen. In a still further embodiment, $R^{13}$ is selected from the group consisting of:

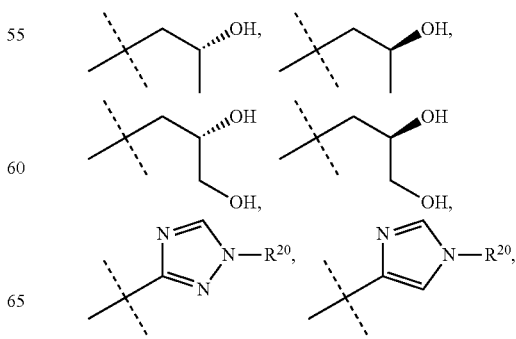

-continued

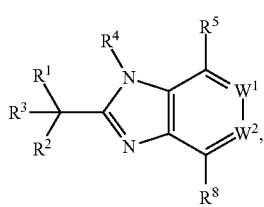

wherein n is 1, 2, 3, or 4; $R^{20}$ and $R^{21}$ are independently selected from the group consisting of hydrogen, alkyl, cycloalkyl, or heterocycloalkyl. In a still further embodiment, each of $R^{20}$ and $R^{21}$ is alkyl.

In some embodiments, $R^1$ and $R^2$ are independently phenyl or pyridyl, optionally substituted with one or more substituents selected from the group consisting of halo, alkyl, cyano, and alkoxy. In another embodiments, $R^1$ and $R^2$ are independently phenyl, optionally substituted with one or more substituents selected from the group consisting of halo, alkyl, cyano, and alkoxy.

In some embodiments, $R^6$ is —C(=O)$NR^{10}R^{11}$ or —S(=O)$_2NR^{10}R^{11}$, and $R^7$ is hydrogen, halo, or alkyl. In some other embodiments, $R^6$ is —(CH$_2$)$_n$OH and n is 1, 2, 3, or 4. In a further embodiment, n is 3. In still another embodiment, $R^7$ is hydrogen or fluoro.

In another aspect, the present invention provides a compound of Formula II:

Formula II or a pharmaceutically acceptable salt thereof, wherein:

$R^1$ and $R^2$ are independently aryl or heteroaryl; or $R^1$ and $R^2$ together with the atom to which they are attached form a 13- to 16-membered tricyclic ring;

$R^3$ is hydrogen, —OR$^{14}$, or —CH$_2$OR$^{14}$;

$R^4$ is selected from hydrogen, alkyl, cycloalkyl, heterocycloalkyl, and aryl;

$R^5$ and $R^8$ are independently selected from hydrogen, halo, cyano, alkoxy, and alkyl;

$W^1$ is CR$^6$ or N;

$W^2$ is CR$^7$ or N;

$R^6$ and $R^7$ are independently selected from hydrogen, halo, alkyl, cycloalkyl, heteroalkyl, heterocycloalkyl, alkoxy, aryl, heteroaryl, cyano, —(CH$_2$)$_t$NR$^9$C(=O)R$^{10}$, —C(=O)OR$^9$, —C(=O)NR$^{10}R^{11}$, —S(O)$_2R^{12}$, and —S(O)$_2NR^{10}R^{11}$, wherein if $W^1$ is CR$^6$ and $W^2$ is CR$^7$, at least one of $R^6$ and $R^7$ is not hydrogen;

t is 0, 1, or 2;

$R^9$ is selected from hydrogen, alkyl, cycloalkyl, alkenyl, alkynyl, aryl, heteroaryl, and heterocycloalkyl;

$R^{10}$ and $R^{11}$ are independently selected from hydrogen, alkyl, cycloalkyl, alkenyl, alkynyl, aryl, heteroaryl, and heterocycloalkyl, or $R^{10}$ and $R^{11}$ together with the atom to which they are attached form a 4- to 8-membered ring containing 0-2 heteroatoms;

$R^{12}$ is selected from alkyl, cycloalkyl, and heterocycloalkyl; and $R^{14}$ is selected from hydrogen, C$_1$-C$_4$ alkyl, and C$_1$-C$_4$ acyl.

In some embodiments, $R^1$ and $R^2$ are independently selected from phenyl and pyridyl, and each of $R^1$ and $R^2$ is optionally substituted with one or more substituents selected from halo, alkyl, cyano, and alkoxy. In other embodiments, each of $R^1$ and $R^2$ is optionally substituted with halo or hydroxy. In some other embodiments, $R^1$ is phenyl, optionally substituted with one or more substituents selected from halo, alkyl, cyano, and alkoxy. In some embodiments, $R^1$ is substituted with 1 or 2 halo groups. In another embodiment, $R^1$ is substituted with 1 or 2 fluoro groups. In still other embodiments, $R^2$ is phenyl, optionally substituted with one or more substituents selected from halo, alkyl, cyano, and alkoxy. In other embodiments, $R^2$ is substituted with 1 or 2 halo groups. In still another embodiment, $R^2$ is substituted with 1 or 2 fluoro groups.

In some embodiments, $R^1$ and $R^2$ are independently aryl, heteroaryl, or CH$_2$OR$^{33}$. In some embodiments, $R^1$ is CH$_2$OR$^{33}$ and $R^2$ is phenyl or pyridyl. In some embodiments, $R^{33}$ is selected from hydrogen, C$_1$-C$_4$ alkyl, and C$_1$-C$_4$ acyl.

In some embodiments, $R^1$, $R^2$, and $R^3$ in combination form:

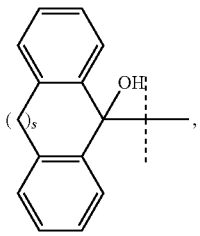

optionally substituted with one or more substituents selected from halo or alkyl. In a further embodiment, s is 0, 1, 2, or 3.

In some embodiments, $R^3$ is hydroxy. In yet another embodiment, $R^{14}$ is hydrogen.

In some embodiments, $R^4$ is $C_1$-$C_6$ alkyl. In some further embodiments, $R^4$ is substituted with one or more substituents selected from hydroxy and fluoro. In some embodiments, $R^4$ is substituted with hydroxy or alkoxy, including, for example, methoxy. In still other embodiments, $R^4$ is substituted with amino or dimethylamino. In another embodiment, $R^4$ is $C_1$-$C_4$ alkyl. In still another embodiment, $R^4$ is methyl. In yet another embodiment, $R^4$ is ethyl. In some other embodiments, $R^4$ is fluoroalkyl. In some embodiments, $R^4$ is $C_1$-$C_6$ alkyl substituted with one or more hydroxy or fluoro groups. In some embodiments, $R^4$ is alkenyl or alkynyl.

In some embodiments, $R^5$ and $R^8$ are independently selected from hydrogen, halo, and methyl. In some other embodiments, $R^5$ and $R^8$ are each hydrogen. In some embodiments, $R^5$ is hydrogen. In another embodiment, $R^8$ is hydrogen.

In some embodiments, $R^6$ is alkyl, cycloalkyl, heteroalkyl, heterocycloalkyl, alkoxy, aryl, heteroaryl, cyano, —$(CH_2)_t NR^9C(=O)R^{10}$, —$C(=O)OR^9$, —$C(=O)NR^{10}R^{11}$, —$S(=O)_2R^{12}$, or —$S(=O)_2NR^{10}R^{11}$, and $R^7$ is hydrogen, halo, or alkyl. In some further embodiments, $R^6$ is hydrogen, halo, or alkyl, and $R^7$ is alkyl, cycloalkyl, heteroalkyl, heterocycloalkyl, alkoxy, aryl, heteroaryl, cyano, —$(CH_2)_t NR^9C(=O)R^{10}$, —$C(=O)OR^9$, —$C(=O)NR^{10}R^{11}$, —$S(O)_2R^{12}$, or —$S(O)_2NR^{10}R^{11}$.

In some embodiments, $R^6$ is alkyl, alkoxy, heteroalkyl or heterocycloalkyl. In some other embodiments, $R^6$ is alkyl, cycloalkyl, heteroalkyl, or heterocycloalkyl, optionally substituted with hydroxy or halo. In other embodiments, $R^6$ is —$C(=O)NR^{10}R^{11}$. In another embodiment, $R^6$—$S(=O)_2NH_2$. In some embodiments, $W^1$ is $CR^6$, $R^6$ is —$C(=O)NR^{10}R^{11}$, is $CR^7$, and $R^7$ is hydrogen. In some embodiments, $R^6$ is $OR^{50}$, and $R^{50}$ is hydrogen, alkyl, cycloalkyl, heteroalkyl, heterocycloalkyl, aryl, or heteroaryl. In some embodiments, $W^1$ is $CR^6$, $R^6$ is —$C(=O)NR^{10}R^{11}$ or —$S(O)_2NR^{10}R^{11}$, $W^2$ is $CR^7$, and $R^7$ is hydrogen, halo, or alkyl. In some embodiments, $W^2$ is $CR^7$, $R^7$ is —$C(=O)NR^{10}R^{11}$, $W^1$ is $CR^6$, and $R^6$ is hydrogen.

In some embodiments, $W^1$ is N and $W^2$ is $CR^7$. In other embodiments, $W^1$ is $CR^6$ and $W^2$ is N. In still other embodiments, $W^1$ and $W^2$ are each N. In yet another embodiment, $W^1$ is $CR^6$, $R^6$ is —$C(=O)NR^{10}R^{11}$, and $W^2$ is N.

In some embodiments, $R^6$ and $R^7$ are independently selected from hydrogen, $(CR^{26}R^{27})_zY$, —$O(CR^{26}R^{27})_zY$, and —$C(=O)NR^{11}(CR^{26}R^{27})_zY$; Y is hydrogen, halo, methyl, cyano, $OR^{28}$, or $NR^{28}R^{29}$; z is 1, 2, 3, 4, 5, or 6; $R^{26}$ and $R^{27}$ are, at each occurrence, independently selected from hydrogen, hydroxy, halo, and $C_1$-$C_4$ alkyl, or $R^{26}$ and $R^{27}$ in combination may form oxo; $R^{26}$ and $R^{27}$ together with the carbon(s) to which they are attached optionally form a 3- to 8-membered ring containing 0-2 heteroatoms; and $R^{28}$ and $R^{29}$ are independently selected from hydrogen, $C_1$-$C_4$ alkyl, and acetyl. In some embodiments, $R^{26}$ and $R^{27}$ are, at each occurrence, optionally selected from hydrogen, hydroxy, fluoro, and methyl.

In some embodiments, $W^1$ is $CR^6$ and $R^6$ is —$S(=O)_2NH_2$. In a further embodiment, $W^1$ is $CR^6$, $R^6$ is —$(CH_2)_p$OH and p is 1, 2, 3, or 4. In yet another embodiment, p is 3.

In some embodiments, $R^7$ is hydrogen or fluoro.

In some embodiments, $R^9$ is hydrogen. In other embodiments, $R^9$ is alkyl. In a further embodiment, $R^9$ is $C_1$-$C_4$ alkyl.

In some embodiments, $R^{10}$ is hydrogen. In some embodiments, $R^{10}$ is $C_1$-$C_4$ alkyl.

In some embodiments, $R^{11}$ is selected from:

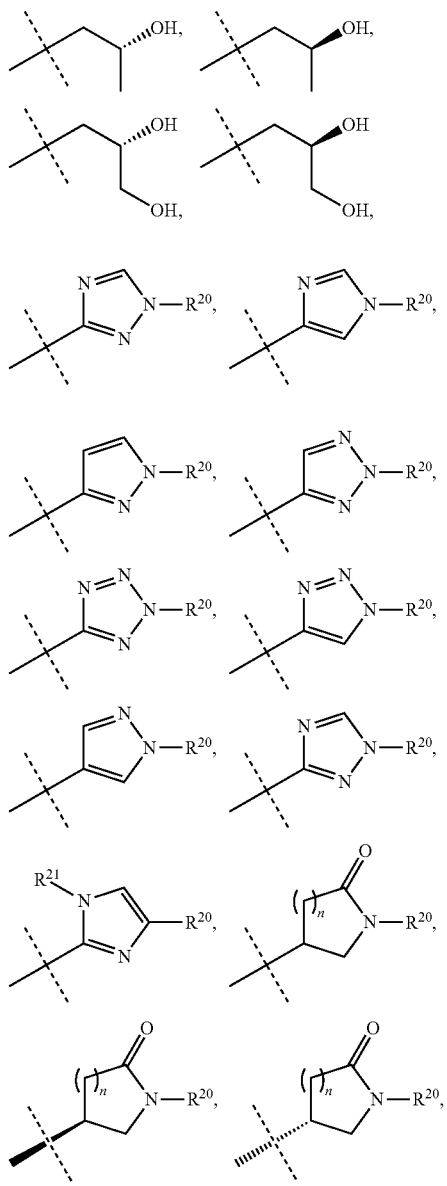

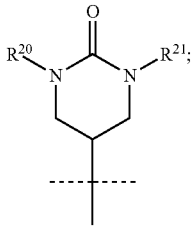

wherein n is 1, 2, 3, or 4, and $R^{20}$ and $R^{21}$ are independently selected from hydrogen, alkyl, cycloalkyl, and heterocycloalkyl. In some further embodiments, $R^{20}$ is $C_1$-$C_4$ alkyl. In still other embodiments, $R^{20}$ is substituted with one or more hydroxy substituents.

In some embodiments, $R^{11}$ is aryl, heteroaryl, or $C_1$-$C_6$ alkyl. In other embodiments, $R^{11}$ is $C_1$-$C_6$ alkyl optionally substituted with 1, 2, or 3 hydroxy groups. In still other embodiments, $R^{11}$ is $C_1$-$C_6$ alkyl optionally substituted with 1, 2, or 3 fluoro groups. In a further embodiment, $R^{11}$ is —CH$_2$CH(OH)CH$_3$. In yet another embodiment, $R^{11}$ is fluoroalkyl.

In some embodiments, $R^{11}$ is —(CR$^{26}$R$^{27}$)$_z$Y; Y is hydrogen, halo, methyl, cyano, OR$^{28}$, or NR$^{28}$R$^{29}$; z is 1, 2, 3, 4, 5, or 6; $R^{26}$ and $R^{27}$ are, at each occurrence, independently selected from hydrogen, hydroxy, halo, and $C_1$-$C_4$ alkyl, or $R^{26}$ and $R^{27}$ in combination may form oxo; $R^{26}$ and $R^{27}$ together with the carbon(s) to which they are attached optionally form a 3- to 8-membered ring containing 0-2 heteroatoms; and $R^{28}$ and $R^{29}$ are independently selected from hydrogen, $C_1$-$C_4$ alkyl, and acetyl. In some embodiments, $R^{26}$ and $R^{27}$ are, at each occurrence, optionally substituted with one or more hydroxy or halo groups.

In some embodiments, $R^{12}$ is $C_1$-$C_4$ alkyl.

In some embodiments, $R^1$ and $R^2$ are each phenyl; $R^3$ is hydroxy; $R^4$ is $C_1$-$C_4$ alkyl; $R^5$ and $R^8$ are each hydrogen; $W^1$ is CR$^6$; $W^2$ is CR$^7$; $R^6$ is —C(=O)NR$^{10}$R$^{11}$; $R^7$ and $R^{10}$ are each hydrogen; and $R^{11}$ is $C_1$-$C_6$ alkyl, aryl or heteroaryl.

In some embodiments, $R^1$ and $R^2$ are each phenyl; $R^3$ is hydroxy; $R^4$ is methyl or ethyl; and $R^5$ and $R^8$ are each hydrogen. In other embodiments, $W^1$ is CR$^6$; $W^2$ is CR$^7$; $R^6$ is —C(=O)NR$^{10}$R$^{11}$; and $R^7$ and $R^{10}$ are each hydrogen. In still other embodiments, $R^1$ and $R^2$ are each phenyl; $W^1$ is CR$^6$; and $R^6$ is —C(=O)NR$^{10}$R$^{11}$. In yet another embodiment, $R^1$ and $R^2$ are each phenyl; $W^2$ is CR$^7$; and $R^7$ is —C(=O)NR$^{10}$R$^{11}$. In some embodiments, $R^1$ is o-fluorophenyl, $R^3$ is hydroxy, and $R^4$ is $C_1$-$C_4$ alkyl. In still other embodiments, $R^1$ is o-fluorophenyl; $R^3$ is hydroxy; $W^1$ is CR$^6$; $R^6$ is —C(=O)NR$^{10}$R$^{11}$; and $R^{11}$ is —CH$_2$CH(OH)CH$_3$. In still other embodiments, $R^1$ and $R^2$ are each phenyl, and each of $R^1$ and $R^2$ is optionally substituted with one or more halo groups; one of $R^6$ and $R^7$ is —C(=O)NR$^{10}$R$^{11}$; and $R^{11}$ is CH$_2$CH(OH)CH$_3$. In yet another embodiment, $R^1$ and $R^2$ are each phenyl; $R^3$ is —OR$^{14}$; and $R^4$ is hydrogen or $C_1$-$C_6$ alkyl.

In yet another aspect, the present invention provides a compound of Formula II-A:

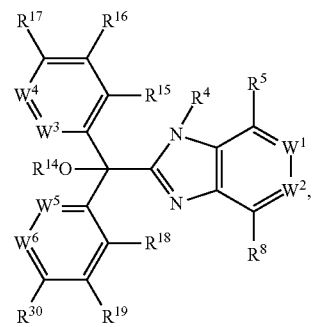

Formula II-A or a pharmaceutically acceptable salt thereof, wherein:

$R^4$ is selected from hydrogen, alkyl, cycloalkyl, heterocycloalkyl, and aryl;

$R^5$ and $R^8$ are independently selected from hydrogen, halo, cyano, alkoxy, and alkyl;

$W^1$ is CR$^6$ or N;

$W^2$ is CR$^7$ or N;

$R^6$ and $R^7$ are independently selected from hydrogen, halo, alkyl, cycloalkyl, heteroalkyl, heterocycloalkyl, alkoxy, aryl, heteroaryl, cyano, —(CH$_2$)$_t$NR$^9$C(=O)R$^{10}$, —C(=O)OR$^9$, —C(=O)NR$^{10}$R$^{11}$, —S(=O)$^2$R$^{12}$, and —S(=O)$_2$NR$^{10}$R$^{11}$, wherein if $W^1$ is CR$^6$ and $W^2$ is CR$^7$, at least one of $R^6$ and $R^7$ is not hydrogen;

t is 0, 1, or 2;

$R^9$ is selected from hydrogen, alkyl, cycloalkyl, alkenyl, alkynyl, aryl, heteroaryl, and heterocycloalkyl;

$R^{10}$ and $R^{11}$ are independently selected from hydrogen, alkyl, cycloalkyl, alkenyl, alkynyl, aryl, heteroaryl, and heterocycloalkyl, or $R^{10}$ and $R^1$ together with the atom to which they are attached form a 4- to 8-membered ring containing 0-2 heteroatoms;

$R^{12}$ is selected from alkyl, cycloalkyl, and heterocycloalkyl;

$W^3$ and $W^5$ are independently CR$^{31}$ or N;

$W^4$ and $W^6$ are independently CR$^{22}$ or N;

$R^{14}$ is selected from hydrogen, $C_1$-$C_4$ alkyl, and $C_1$-$C_4$ acyl;

each of $R^{15}$, $R^{18}$, $R^{19}$, $R^{30}$, $R^{31}$, and $R^{22}$ is independently selected from hydrogen, halo, hydroxy, alkyl, alkoxy, cyano, —C(=O)NR$^{23}$R$^{24}$, aryl, and heteroaryl;

$R^{16}$ and $R^{17}$ are independently selected from hydrogen, halo, hydroxy, alkyl, alkoxy, cyano, —C(=O)NR$^{23}$R$^{24}$, aryl, and heteroaryl, or $R^{16}$ and $R^{17}$ together with the atoms to which they are attached form a 5- to 8-membered ring containing 0-2 heteroatoms;

$R^{23}$ and $R^{24}$ are independently selected from hydrogen, $C_1$-$C_6$ alkyl, and —(CH$_2$)$_m$OR$^{25}$;

m is 1, 2, 3, or 4; and $R^{25}$ is selected from hydrogen, $C_1$-$C_4$ alkyl, and $C_1$-$C_4$ acyl.

In some embodiments, $R^4$ is $C_1$-$C_6$ alkyl. In some further embodiments, $R^4$ is substituted with one or more substituents selected from hydroxy and fluoro. In some embodiments, $R^4$ is substituted with hydroxy or alkoxy, including, for example, methoxy. In still other embodiments, $R^4$ is substituted with amino or dimethylamino. In another embodiment, $R^4$ is $C_1$-$C_4$ alkyl. In still another embodiment, $R^4$ is methyl. In yet another embodiment, $R^4$ is ethyl. In some other embodiments, $R^4$ is fluoroalkyl. In some embodiments, $R^4$ is $C_1$-$C_6$ alkyl substituted with one or more hydroxy or fluoro groups.

In some embodiments, $R^5$ and $R^8$ are independently selected from hydrogen, halo, and methyl. In some other embodiments, $R^5$ and $R^8$ are each hydrogen. In some embodiments, $R^5$ is hydrogen. In another embodiment, $R^8$ is hydrogen.

In some embodiments, $R^6$ is alkyl, cycloalkyl, heteroalkyl, heterocycloalkyl, alkoxy, aryl, heteroaryl, cyano, —(CH$_2$)$_t$NR$^9$C(=O)R$^{10}$, —C(=O)OR$^9$, —C(=O)NR$^{10}$R$^{11}$, —S(=O)$_2$R$^{12}$, or —S(=O)$_2$NR$^{10}$R$^{11}$, and $R^7$ is hydrogen, halo, or alkyl. In some further embodiments, $R^6$ is hydrogen, halo, or alkyl, and $R^7$ is alkyl, cycloalkyl, heteroalkyl, heterocycloalkyl, alkoxy, aryl, heteroaryl, cyano, —(CH$_2$)$_t$NR$^9$C(=O)R$^{10}$, —C(=O)OR$^9$, —C(=O)NR$^{10}$R$^{11}$, —S(O)$_2$R$^{12}$, or —S(O)$_2$NR$^{10}$R$^{11}$.

In some embodiments, $R^6$ is alkyl, alkoxy, heteroalkyl or heterocycloalkyl. In some other embodiments, $R^6$ is alkyl, cycloalkyl, heteroalkyl, or heterocycloalkyl, optionally substituted with hydroxy or halo. In other embodiments, $R^6$ is —C(=O)NR$^{10}$R$^{11}$. In another embodiment, $R^6$—S(=O)$_2$NH$_2$. In some embodiments, $W^1$ is CR$^6$, $R^6$ is —C(=O)NR$^{10}$R$^{11}$, $W^2$ is CR$^7$, and $R^7$ is hydrogen. In some embodiments, $R^6$ is OR$^{50}$, and $R^{50}$ is hydrogen, alkyl, cycloalkyl, heteroalkyl, heterocycloalkyl, aryl, or heteroaryl. In some embodiments, $W^1$ is CR$^6$, $R^6$ is —C(=O)NR$^{10}$R$^{11}$ or —S(O)$_2$NR$^{10}$R$^{11}$, $W^2$ is CR$^7$, and $R^7$ is hydrogen, halo, or alkyl. In some embodiments, $W^2$ is CR$^7$, $R^7$ is —C(=O)NR$^{10}$R$^{11}$, $W^1$ is CR$^6$, and $R^6$ is hydrogen.

In some embodiments, $W^1$ is N and $W^2$ is CR$^7$. In other embodiments, $W^1$ is CR$^6$ and $W^2$ is N. In still other embodiments, $W^1$ and $W^2$ are each N. In yet another embodiment, $W^1$ is CR$^6$, $R^6$ is —C(=O)NR$^{10}$R$^{11}$, and $W^2$ is N.

In some embodiments, $R^6$ and $R^7$ are independently selected from hydrogen, —(CR$^{26}$R$^{27}$)$_z$Y, —O(CR$^{26}$R$^{27}$)$_z$Y, and —C(=O)NR$^{11}$(CR$^{26}$R$^{27}$)$_z$Y; Y is hydrogen, halo, methyl, cyano, OR$^{28}$, or NR$^{28}$R$^{29}$; z is 1, 2, 3, 4, 5, or 6; $R^{26}$ and $R^{27}$ are, at each occurrence, independently selected from hydrogen, hydroxy, halo, and C$_1$-C$_4$ alkyl, or $R^{26}$ and $R^{27}$ in combination may form oxo; $R^{26}$ and $R^{27}$ together with the carbon(s) to which they are attached optionally form a 3- to 8-membered ring containing 0-2 heteroatoms; and $R^{28}$ and $R^{29}$ are independently selected from hydrogen, C$_1$-C$_4$ alkyl, and acetyl. In some embodiments, $R^{26}$ and $R^{27}$ are, at each occurrence, optionally selected from hydrogen, hydroxy, fluoro and methyl.

In some embodiments, $W^1$ is CR$^6$ and $R^6$ is —S(=O)$_2$NH$_2$. In a further embodiment, $W^1$ is CR$^6$, $R^6$ is —(CH$_2$)$_p$OH and p is 1, 2, 3, or 4. In yet another embodiment, p is 3.

In some embodiments, $R^7$ is hydrogen or fluoro.

In some embodiments, $R^9$ is hydrogen. In other embodiments, $R^9$ is alkyl. In a further embodiment, $R^9$ is C$_1$-C$_4$ alkyl.

In some embodiments, $R^{10}$ is hydrogen. In some embodiments, $R^{10}$ is C$_1$-C$_4$ alkyl.

In some embodiments, $R^{11}$ is selected from:

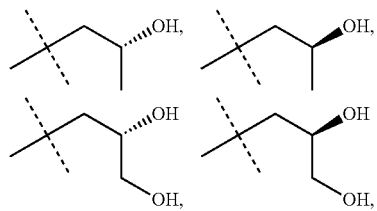

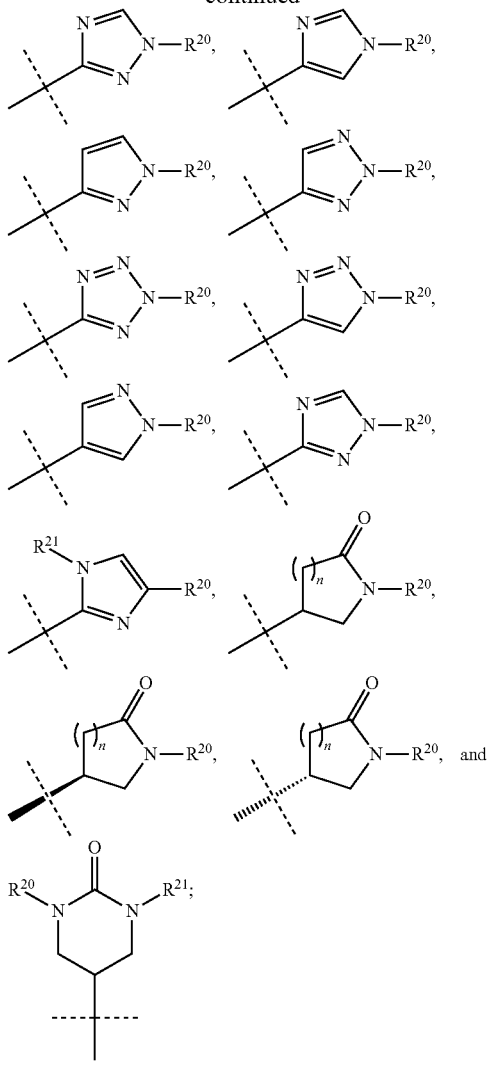

wherein n is 1, 2, 3, or 4, and $R^{20}$ and $R^{21}$ are independently selected from hydrogen, alkyl, cycloalkyl, and heterocycloalkyl. In some further embodiments, $R^{20}$ is C$_1$-C$_4$ alkyl. In still other embodiments, $R^{20}$ is substituted with one or more hydroxy substituents.

In some embodiments, $R^{11}$ is aryl, heteroaryl, or C$_1$-C$_6$ alkyl. In other embodiments, $R^{11}$ is C$_1$-C$_6$ alkyl optionally substituted with 1, 2, or 3 hydroxy groups. In still other embodiments, $R^{11}$ is C$_1$-C$_6$ alkyl optionally substituted with 1, 2, or 3 fluoro groups. In a further embodiment, $R^{11}$ is —CH$_2$CH(OH)CH$_3$. In yet another embodiment, $R^{11}$ is fluoroalkyl.

In some embodiments, $R^{11}$ is (CR$^{26}$R$^{27}$)$_z$Y; Y is hydrogen, halo, methyl, cyano, OR$^{28}$, or NR$^{28}$R$^{29}$; z is 1, 2, 3, 4, 5, or 6; $R^{26}$ and $R^{27}$ are, at each occurrence, independently selected from hydrogen, hydroxy, halo, and C$_1$-C$_4$ alkyl, or $R^{26}$ and $R^{27}$ in combination may form oxo; $R^{26}$ and $R^{27}$ together with the carbon(s) to which they are attached optionally form a 3- to 8-membered ring containing 0-2 heteroatoms; and $R^{28}$ and $R^{29}$ are independently selected from hydrogen, C$_1$-C$_4$ alkyl, and acetyl. In some embodiments, $R^{26}$ and $R^{27}$ are, at each occurrence, optionally substituted with one or more hydroxy or halo groups.

In some embodiments, $R^{12}$ is $C_1$-$C_4$ alkyl.

In some embodiments, $W^3$ is $CR^{31}$, and $R^{31}$ is hydrogen, halo, or $C_1$-$C_4$ alkyl. In other embodiments, $W^4$ is $CR^{22}$, and $R^{22}$ is hydrogen, halo, or $C_1$-$C_4$ alkyl. In still other embodiments, $W^5$ is $CR^{31}$, and $R^{31}$ is hydrogen, halo, or $C_1$-$C_4$ alkyl. In yet other embodiments, $W^6$ is $CR^{22}$, and $R^{22}$ is hydrogen, halo, or $C_1$-$C_4$ alkyl. In some embodiments, $W^3$ is N. In still other embodiments, $W^5$ is N.

In some embodiments, $R^{15}$ and $R^{18}$ are independently selected from hydrogen and halo. In some embodiments, $R^{15}$ is fluoro. In some embodiments, $R^{18}$ is fluoro. In another embodiment, $R^{15}$ and $R^{18}$ are each fluoro. In other embodiments, $R^{16}$ and $R^{19}$ are independently selected from hydrogen, halo, heteroaryl, —C(=O)NHR$^{24}$, and $C_1$-$C_4$ alkyl. In yet another embodiment, $R^{16}$ is —C(=O)NHR$^{24}$. In another embodiment, $R^{19}$ is hydrogen. In still other embodiments, $R^{17}$ and $R^{30}$ are independently selected from hydrogen, halo, and methyl. In some other embodiments, $R^{17}$ is fluoro. In still another embodiment, $R^{30}$ is fluoro. In a further embodiment, $R^{15}$ is fluoro, and $R^{16}$, $R^{17}$, $R^{19}$, and $R^{30}$ are each hydrogen.

In some embodiments, $R^{23}$ is hydrogen and $R^{24}$ is $C_1$-$C_6$ alkyl. In some embodiments, $R^{24}$ is —(CH$_2$)$_m$OR$^{25}$, and $R^{25}$ is hydrogen, acetyl or methyl. In other embodiments, $R^{24}$ is methyl, ethyl, propyl, isopropyl, or butyl.

In some embodiments, $W^3$ and $W^5$ are each $CR^{31}$; $W^4$ and $W^6$ are each $CR^{22}$; and $R^{31}$ and $R^{22}$ are each hydrogen. In a further embodiment, $W^3$ and $W^5$ are each $CR^{31}$; $W^4$ and $W^6$ are each $CR^{22}$; $R^{16}$, $R^{19}$, $R^{31}$, and $R^{22}$ are each hydrogen; and $R^{15}$ is halo.

In some embodiments, $W^3$ and $W^5$ are each carbon atoms and are connected by a bond, a $C_1$-$C_3$ alkyl group, a $C_1$-$C_3$ heteroalkyl group, or a $C_2$-$C_3$ alkenyl group, such that a 13- to 16-membered tricyclic ring is formed. Representative compounds with the tricyclic ring include, but are not limited to, the following:

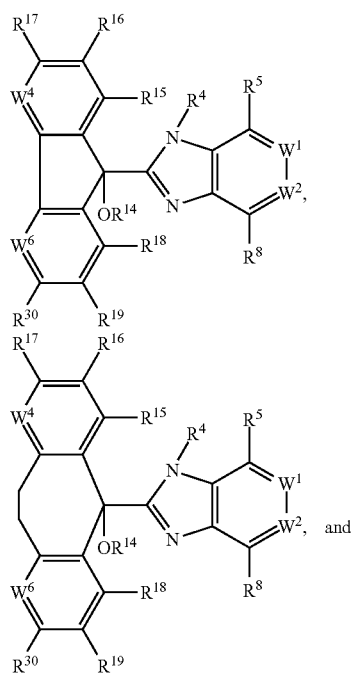

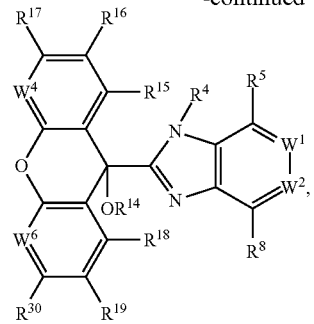

wherein the ring formed by linking $W^3$ and $W^5$ may be optionally substituted with one or more of halo, hydroxy, oxo, alkyl, or heteroalkyl.

In some embodiments, $R^4$ is $C_1$-$C_4$ alkyl; $R^5$ and $R^8$ are each hydrogen; $W^1$ is $CR^6$; $W^2$ is $CR^7$; $R^6$ is —C(=O)NR$^{10}$R$^{11}$; and $R^7$ and $R^{10}$ are each hydrogen. In some other embodiments, $R^4$ is methyl or ethyl, and $R^5$ and $R^8$ are each hydrogen. In other embodiments, $W^1$ is $CR^6$; $W^2$ is $CR^7$; $R^6$ is —C(=O)NR$^{10}$R$^{11}$; and $R^7$ and $R^{10}$ are each hydrogen. In still other embodiments, $R^{15}$ is halo; $W^1$ is $CR^6$; and $R^6$ is —C(=O)NR$^{10}$R$^{11}$. In yet another embodiment, $R^{15}$ is halo; $W^2$ is $CR^7$; and $R^7$ is —C(=O)NR$^{10}$R$^{11}$. In some embodiments, $R^{15}$ and $R^{18}$ are independently selected from hydrogen and halo and $R^4$ is $C_1$-$C_4$ alkyl. In still other embodiments, $R^{15}$ and $R^{18}$ are independently selected from hydrogen and halo; $W^1$ is $CR^6$; $R^6$ is —C(=O)NR$^{10}$R$^{11}$; and $R^{11}$ is —CH$_2$CH(OH)CH$_3$. In still other embodiments, at least one of $R^{15}$ and $R^{18}$ is fluoro; and one of $R^6$ and $R^7$ is —C(=O)NR$^{10}$R$^{11}$. In some embodiments, $W^3$ and $W^5$ are each $CR^{31}$; $W^4$ and $W^6$ are each $CR^{22}$; $R^{16}$, $R^{19}$, $R^{31}$, and $R^{22}$ are each hydrogen; each of $R^{15}$, $R^{17}$, $R^{18}$, and $R^{30}$ is independently selected from hydrogen, halo, hydroxy, alkoxy, and $C_1$-$C_3$ alkyl; $R^4$ is $C_1$-$C_4$ alkyl; $R^5$ and $R^8$ are each hydrogen; and one of $R^6$ and $R^7$ is hydrogen or halo.

In still another aspect, the invention provides a compound of Formula II-B:

Formula II-B

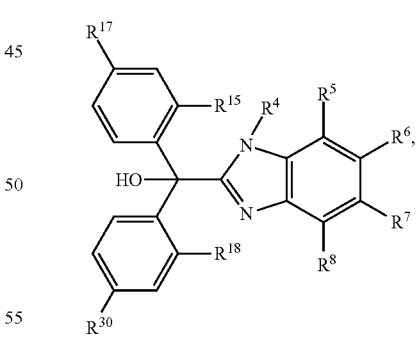

or a pharmaceutically acceptable salt thereof, wherein:

$R^4$ is selected from hydrogen, alkyl, cycloalkyl, heterocycloalkyl, and aryl;

$R^5$ and $R^8$ are independently selected from hydrogen, halo, cyano, alkoxy, and alkyl;

$R^6$ and $R^7$ are independently selected from hydrogen, halo, alkyl, cycloalkyl, heteroalkyl, heterocycloalkyl, alkoxy, aryl, heteroaryl, cyano, —(CH$_2$)$_t$NR$^9$C(=O)R$^{10}$, —C(=O)OR$^9$, —C(=O)NR$^{10}$R$^{11}$, —S(O)$_2$R$^{12}$, and —S(O)$_2$NR$^{10}$R$^{11}$;

t is 0, 1, or 2;

$R^9$ is selected from hydrogen, alkyl, cycloalkyl, alkenyl, alkynyl, aryl, heteroaryl, and heterocycloalkyl;

$R^{10}$ and $R^{11}$ are independently selected from hydrogen, alkyl, cycloalkyl, alkenyl, alkynyl, aryl, heteroaryl, and heterocycloalkyl, or $R^{10}$ and $R^{11}$ together with the atom to which they are attached form a 4- to 8-membered ring containing 0-2 heteroatoms;

$R^{12}$ is selected from alkyl, cycloalkyl, and heterocycloalkyl; and each of $R^{15}$, $R^{17}$, $R^{18}$, and $R^{30}$ is independently selected from hydrogen, halo, hydroxy, alkyl, alkoxy, and cyano.

In some embodiments, $R^4$ is $C_1$-$C_6$ alkyl. In some further embodiments, $R^4$ is substituted with one or more substituents selected from hydroxy and fluoro. In some embodiments, $R^4$ is substituted with hydroxy or alkoxy, including, for example, methoxy. In still other embodiments, $R^4$ is substituted with amino or dimethylamino. In another embodiment, $R^4$ is $C_1$-$C_4$ alkyl. In still another embodiment, $R^4$ is methyl. In yet another embodiment, $R^4$ is ethyl. In some other embodiments, $R^4$ is fluoroalkyl. In some embodiments, $R^4$ is $C_1$-$C_6$ alkyl substituted with one or more hydroxy or fluoro groups.

In some embodiments, $R^5$ and $R^8$ are independently selected from hydrogen, halo, and methyl. In some other embodiments, $R^5$ and $R^8$ are each hydrogen. In some embodiments, $R^5$ is hydrogen. In another embodiment, $R^8$ is hydrogen.

In some embodiments, $R^6$ is alkyl, cycloalkyl, heteroalkyl, heterocycloalkyl, alkoxy, aryl, heteroaryl, cyano, —(CH$_2$)$_t$NR$^9$C(=O)R$^{10}$, —C(=O)OR$^9$, —C(=O)NR$^{10}$R$^{11}$, —S(=O)$_2$R$^{12}$, or —S(=O)$_2$NR$^{10}$R$^{11}$, and $R^7$ is hydrogen, halo, or alkyl. In some further embodiments, $R^6$ is hydrogen, halo, or alkyl, and $R^7$ is alkyl, cycloalkyl, heteroalkyl, heterocycloalkyl, alkoxy, aryl, heteroaryl, cyano, —(CH$_2$)$_t$NR$^9$C(=O)R$^{10}$, —C(=O)OR$^9$, —C(=O)NR$^{10}$R$^{11}$, —S(O)$_2$R$^{12}$, or —S(O)$_2$NR$^{10}$R$^{11}$.

In some embodiments, $R^6$ is alkyl, alkoxy, heteroalkyl or heterocycloalkyl. In some other embodiments, $R^6$ is alkyl, cycloalkyl, heteroalkyl, or heterocycloalkyl, optionally substituted with hydroxy or halo. In other embodiments, $R^6$ is —C(=O)NR$^{10}$R$^{11}$. In another embodiment, $R^6$—S(=O)$_2$NH$_2$. In some embodiments, $R_6$ is —C(=O)NR$^{10}$R$^{11}$ and $R^7$ is hydrogen. In some embodiments, $R^6$ is OR$^{50}$, and R$^{50}$ is hydrogen, alkyl, cycloalkyl, heteroalkyl, heterocycloalkyl, aryl, or heteroaryl. In some embodiments, $R^6$ is —C(=O)NR$^{10}$R$^{11}$ or —S(=O)$_2$NR$^{10}$R$^{11}$ and $R^7$ is hydrogen, halo, or alkyl. In some embodiments, $R^7$ is —C(=O)NR$^{10}$R$^{11}$ and $R^6$ is hydrogen.

In some embodiments, $R^6$ and $R^7$ are independently selected from hydrogen, (CR$^{26}$R$^{27}$)$_z$Y, —O(CR$^{26}$R$^{27}$)$_z$Y, and —C(=O)NR$^{11}$(CR$^{26}$R$^{27}$)$_z$Y; Y is hydrogen, halo, methyl, cyano, OR$^{28}$, or NR$^{28}$R$^{29}$; z is 1, 2, 3, 4, 5, or 6; $R^{26}$ and $R^{27}$ are, at each occurrence, independently selected from hydrogen, hydroxy, halo, and $C_1$-$C_4$ alkyl, or $R^{26}$ and $R^{27}$ in combination may form oxo; $R^{26}$ and $R^{27}$ together with the carbon(s) to which they are attached optionally form a 3- to 8-membered ring containing 0-2 heteroatoms; and $R^{28}$ and $R^{29}$ are independently selected from hydrogen, $C_1$-$C_4$ alkyl, and acetyl. In some embodiments, $R^{26}$ and $R^{27}$ are, at each occurrence, optionally selected from hydrogen, hydroxy, fluoro and methyl.

In some embodiments, $R^6$ is —S(=O)$_2$NH$_2$. In a further embodiment, $R^6$ is —(CH$_2$)$_p$OH and p is 1, 2, 3, or 4. In yet another embodiment, p is 3.

In some embodiments, $R^7$ is hydrogen or fluoro.

In some embodiments, $R^9$ is hydrogen. In other embodiments, $R^9$ is alkyl. In a further embodiment, $R^9$ is $C_1$-$C_4$ alkyl.

In some embodiments, $R^{10}$ is hydrogen. In some embodiments, $R^{10}$ is $C_1$-$C_4$ alkyl.

In some embodiments, $R^{11}$ is selected from:

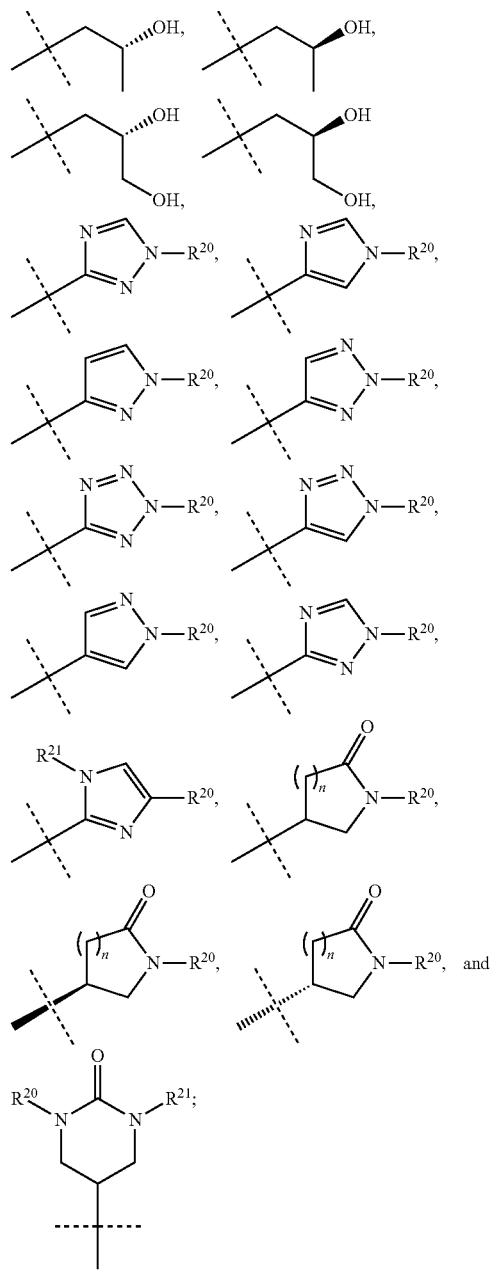

wherein n is 1, 2, 3, or 4, and $R^{20}$ and $R^{21}$ are independently selected from hydrogen, alkyl, cycloalkyl, and heterocycloalkyl. In some further embodiments, $R^{20}$ is $C_1$-$C_4$ alkyl. In still other embodiments, $R^{20}$ is substituted with one or more hydroxy substituents.

In some embodiments, $R^{11}$ is aryl, heteroaryl, or $C_1$-$C_6$ alkyl. In other embodiments, $R^{11}$ is $C_1$-$C_6$ alkyl optionally substituted with 1, 2, or 3 hydroxy groups. In still other embodiments, $R^{11}$ is $C_1$-$C_6$ alkyl optionally substituted with 1, 2, or 3 fluoro groups. In a further embodiment, $R^{11}$ is —$CH_2CH(OH)CH_3$. In yet another embodiment, $R^{11}$ is fluoroalkyl.

In some embodiments, $R^{11}$ is —$(CR^{26}R^{27})_zY$; Y is hydrogen, halo, methyl, cyano, $OR^{28}$, or $NR^{28}R^{29}$; z is 1, 2, 3, 4, 5, or 6; $R^{26}$ and $R^{27}$ are, at each occurrence, independently selected from hydrogen, hydroxy, halo, and $C_1$-$C_4$ alkyl, or $R^{26}$ and $R^{27}$ in combination may form oxo; $R^{26}$ and $R^{27}$ together with the carbon(s) to which they are attached optionally form a 3- to 8-membered ring containing 0-2 heteroatoms; and $R^{28}$ and $R^{29}$ are independently selected from hydrogen, $C_1$-$C_4$ alkyl, and acetyl. In some embodiments, $R^{26}$ and $R^{27}$ are, at each occurrence, optionally substituted with one or more hydroxy or halo groups.

In some embodiments, $R^{12}$ is $C_1$-$C_4$ alkyl.

In some embodiments, $R^{15}$ and $R^{18}$ are independently selected from hydrogen and halo. In some embodiments, $R^{15}$ is fluoro. In some embodiments, $R^{18}$ is fluoro. In another embodiment, $R^{15}$ and $R^{18}$ are each fluoro. In still other embodiments, $R^{17}$ and $R^{30}$ are independently selected from hydrogen, halo, and methyl. In some other embodiments, $R^{17}$ is fluoro. In still another embodiment, $R^{30}$ is fluoro. In a further embodiment, $R^{15}$ is fluoro, and $R^{17}$ and $R^{30}$ are each hydrogen.

In some embodiments, $R^4$ is $C_1$-$C_4$ alkyl; $R^5$ and $R^8$ are each hydrogen; $R^6$ is —$C(=O)NR^{10}R^{11}$; and $R^7$ and $R^{10}$ are each hydrogen. In some other embodiments, $R^4$ is methyl or ethyl and $R^5$ and $R^8$ are each hydrogen. In other embodiments, $R^6$ is —$C(=O)NR^{10}R^{11}$ and $R^7$ and $R^{10}$ are each hydrogen. In still other embodiments, $R^{15}$ is halo and $R^6$ is —$C(=O)NR^{10}R^{11}$. In yet another embodiment, $R^{15}$ is halo and $R^7$ is —$C(=O)NR^{10}R^{11}$. In some embodiments, $R^{15}$ and $R^{18}$ are independently selected from hydrogen and halo and $R^4$ is $C_1$-$C_4$ alkyl. In still other embodiments, $R^{15}$ and $R^{18}$ are independently selected from hydrogen and halo; $R^6$ is —$C(=O)NR^{10}R^{11}$; and $R^{11}$ is —$CH_2CH(OH)CH_3$. In still other embodiments, at least one of $R^{15}$ and $R^{18}$ is fluoro; one of $R^6$ and $R^7$ is —$C(=O)NR^{10}R^{11}$; and $R^{11}$ is —$CH_2CH(OH)CH_3$. In some embodiments, each of $R^{15}$, $R^{17}$, $R^{18}$, and $R^{30}$ is independently selected from hydrogen, halo, hydroxy, alkoxy, and $C_1$-$C_3$ alkyl; $R^4$ is $C_1$-$C_4$ alkyl; $R^5$ and $R^8$ are each hydrogen; and one of $R^6$ and $R^7$ is hydrogen or halo.

In another aspect, the present disclosure provides a compound or pharmaceutically acceptable salt or prodrug thereof, selected from the group consisting of the compounds given in Table 1.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1-5, the steps in some cases may be performed in a different order than the order shown in Schemes 1-5. Various modifications to these synthetic reaction schemes may be made and will be suggested to one skilled in the art having referred to the disclosure contained in this Application. Numberings or R groups in each scheme do not necessarily correspond to that of the claims or other schemes or tables herein.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In general, compounds of the invention may be prepared by the following reaction schemes:

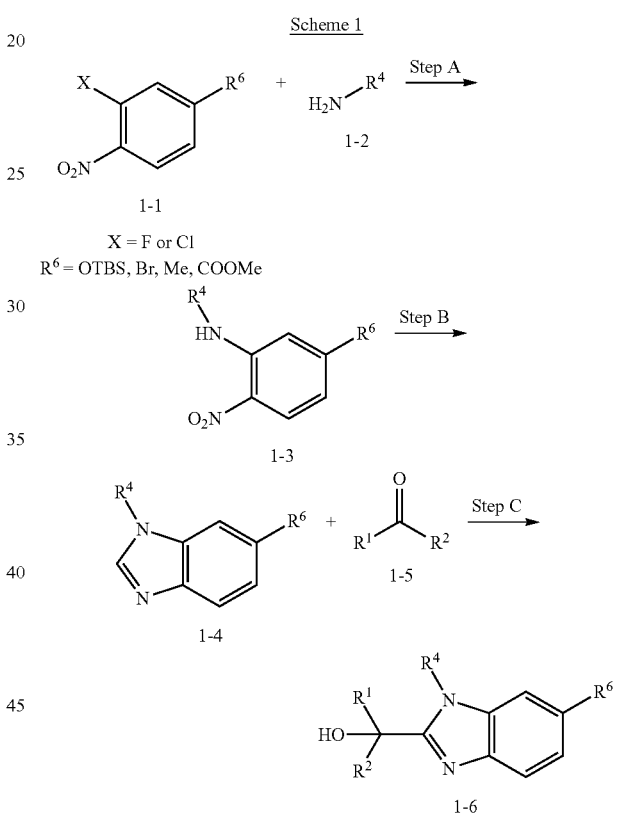

In some embodiments, a compound of Formula 1-6 may be prepared according to steps outlined in Scheme 1. For example, a nitroaniline of Formula 1-3 is prepared by reacting aryl halide 1-1 with a suitably substituted amine (1-2) in the presence of a base (e.g., triethyl amine, $K_2CO_3$, $K_3PO_4$) and a solvent (e.g., ethanol, acetonitrile, NMP). In some embodiments, a cyclization to benzimidazole 1-4 is performed using any method known in the art, including, for example, the addition of iron powder, formic acid and $NH_4Cl$, optionally in isopropanol at reflux. Alternatively, the same transformation may be accomplished using palladium on carbon and trimethylorthoformate in methanol in the presence of $H_2$. In other embodiments, Step C comprises the addition of a base (e.g., n-BuLi, t-BuLi, LiHMDS) in a suitable solvent (e.g., THF) at an appropriate temperature (e.g., −78° C., 0° C., r.t.) to form benzimidazole 1-6.

Scheme 2

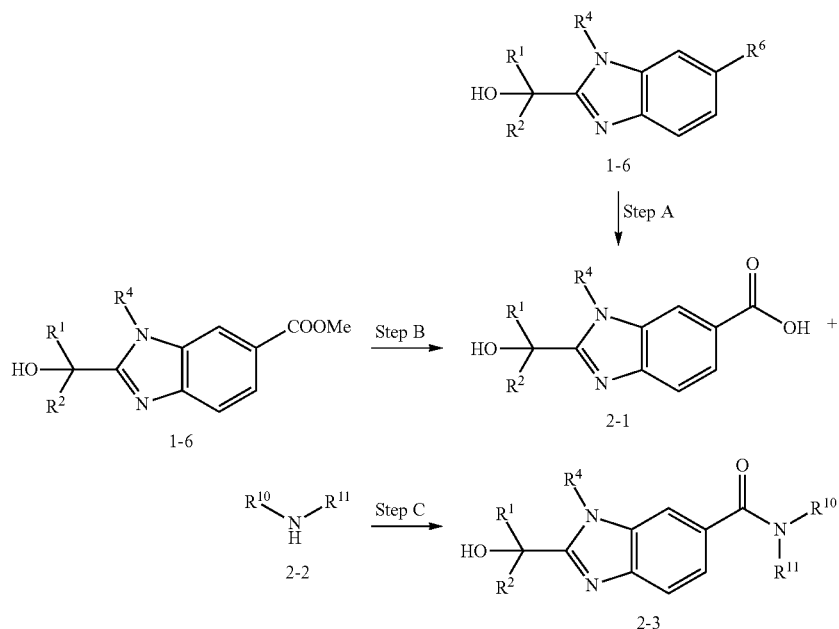

In some additional embodiments, a compound of Formula 2-3 is prepared from a compound of Formula 1-6 according to steps outlined in Scheme 2. For example, when $R^6$ is methyl, oxidation to a carboxylic acid of Formula 2-1 may be completed using $KMnO_4$ in t-BuOH and water at reflux, or by any other method generally known in the art. In some embodiments, $R^6$ is a methyl ester and is converted to an acid of Formula 2-1 by a hydrolysis reaction (e.g., LiOH, THF/$H_2O$, r.t.). In some other embodiments, a compound of Formula 2-3 is prepared using any suitable peptide coupling conditions (e.g., HATU, $iPr_2NEt$, DMF, r.t.; HATU, pyridine, 80° C.).

Scheme 3

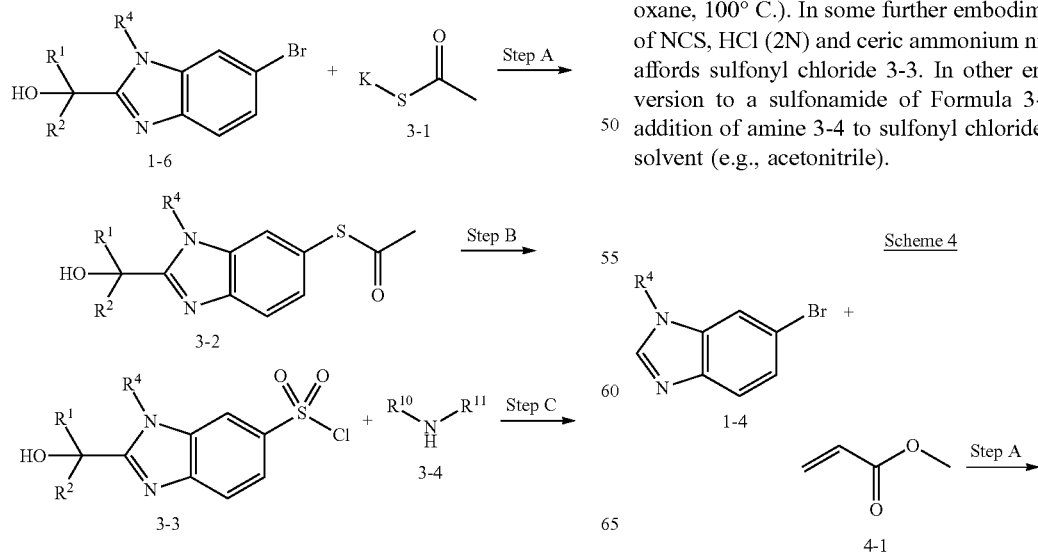

-continued

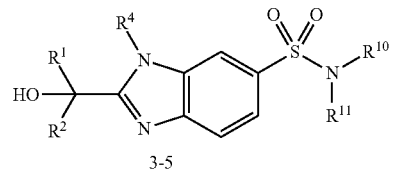

In some other embodiments, a compound of Formula 3-5 may be prepared according to steps outlined in Scheme 3. In some embodiments, aryl halide 1-6 is coupled to potassium thioacetate (3-1) (e.g., using $Pd_2(dba)_3$, Xantphos, 1,4-dioxane, 100° C.). In some further embodiments, the addition of NCS, HCl (2N) and ceric ammonium nitrate at 10-20° C. affords sulfonyl chloride 3-3. In other embodiments, conversion to a sulfonamide of Formula 3-5 may occur by addition of amine 3-4 to sulfonyl chloride 3-3 in a suitable solvent (e.g., acetonitrile).

Scheme 4

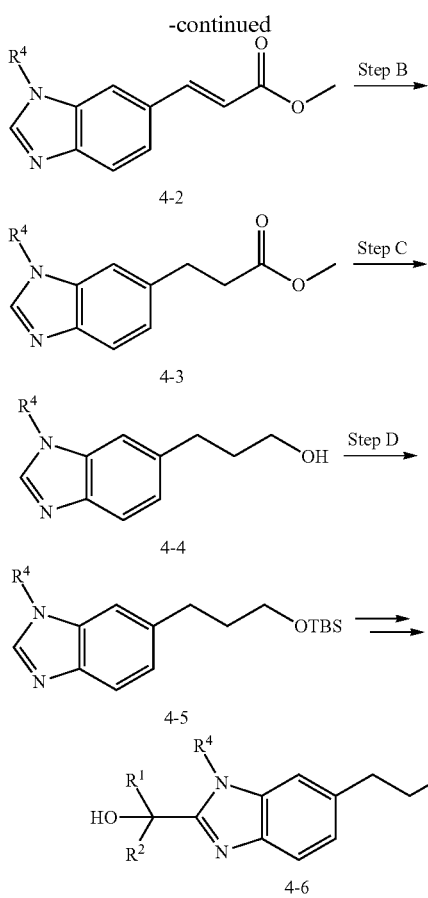

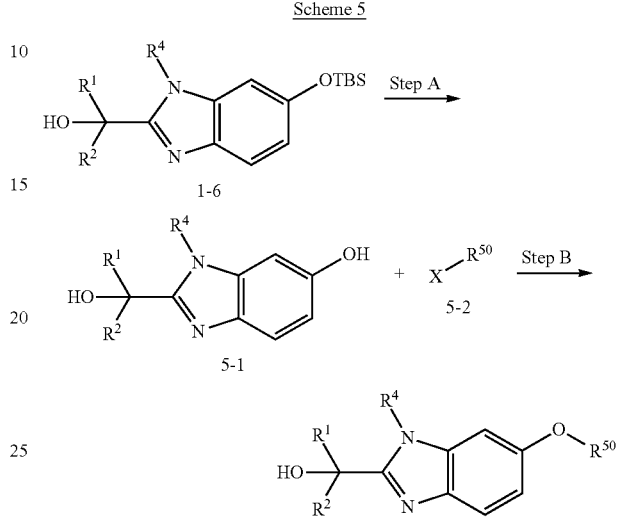

compound 4-3. In other embodiments, reduction to alcohol 4-4 may proceed by the addition of $CaCl_2$, $NaBH_4$ in methanol at r.t. In another embodiment, the alcohol is protected as a silyl ether (4-5), then converted to a compound of Formula 4-6 as generally described in Scheme 1.

In still further embodiments, a compound of Formula 4-6 may be prepared according to steps outlined in Scheme 4. For example, the addition of unsaturated ester 4-1 to aryl bromide 1-4 may give a compound of Formula 4-2 (e.g., using $PdCl_2(DPPF)$, $Et_3N$, DMF, 110° C.). In some embodiments, reduction of 4-2 may proceed using palladium on carbon in methanol under 1 atmosphere of $H_2$ to afford In other embodiments, a compound of Formula 5-3 may be prepared according to steps outlined in Scheme 5. For example, deprotection to reveal phenol 5-1 may be effected by the addition of TBAF in THF at r.t. In some embodiments, aryl ether 5-3 is formed by coupling phenol 5-1 to halide 5-2, using a suitable base (e.g., $K_2CO_3$, NaH) and solvent (e.g., DMF).

In some other embodiments, a compound of a formula given in Table 1 is synthesized according to one of the general routes outlined in Schemes 1-5, Examples 1-82 or by methods generally known in the art.

TABLE 1

| No. | Structure | Mass Characterization | $^1$H NMR Data |
|---|---|---|---|
| 1 | 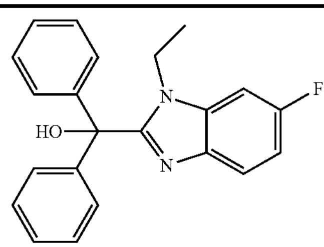 | 347 (M + H) | (400 MHz, $CDCl_3$): δ 7.69 (dd, 1H), 7.29-7.37 (m, 10H), 6.96-7.03 (m, 2H), 4.83 (s, 1H), 3.96 (q, 2H), 0.71 (t, 3H) |
| 2 | 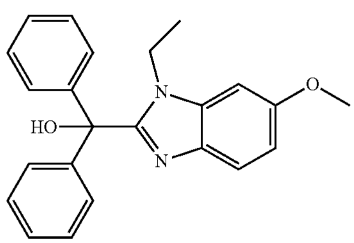 [SMILES: CCn1c(C(O)(c2ccccc2)c2ccccc2)nc2ccc(OC)cc21] | 359 (M + H) | (400 MHz, $CDCl_3$): δ 7.67 (d, 1H), 7.30-7.38 (m, 10H), 6.92 (dd, 1H), 6.76 (d, 1H), 5.09 (s, 1H), 3.95 (q, 2H), 3.87 (s, 3H), 0.68 (t, 3H) |

TABLE 1-continued
| No. | Structure | Mass Characterization | ¹H NMR Data |
|---|---|---|---|
| 3 | 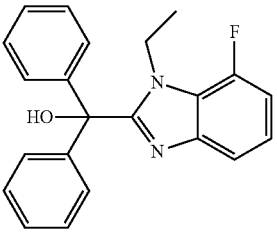 [SMILES: CCn1c(C(O)(c2ccccc2)c2ccccc2)nc2cccc(F)c21] | 347 (M + H) | (400 MHz, CDCl$_3$): δ 7.56 (d, 1H), 7.32-7.39 (m, 10H), 7.17 (td, 1H), 6.98 (dd, 1H), 4.99 (s, 1H), 4.12 (q, 2H), 0.73 (t, 3H) |
| 4 | 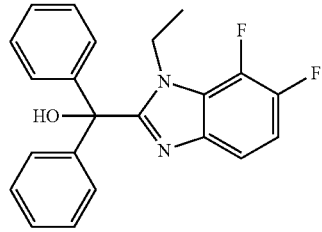 [SMILES: CCn1c(C(O)(c2ccccc2)c2ccccc2)nc2ccc(F)c(F)c21] | 365 (M + H) | (400 MHz, CDCl$_3$): δ 7.45 (dd, 1H), 7.32-7.40 (m, 10H), 7.07 (dt, 1H), 4.64 (s, 1H), 4.13 (q, 2H), 0.80 (t, 3H) |
| 5 | 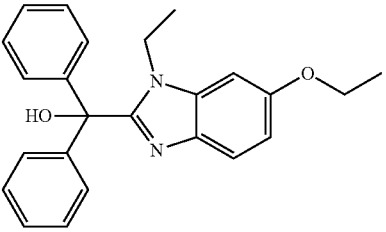 [SMILES: CCOc1ccc2nc(C(O)(c3ccccc3)c3ccccc3)n(CC)c2c1] | 373 (M + H) | (400 MHz, CDCl$_3$): δ 7.66 (d, 1H), 7.30-7.37 (m, 10H), 6.92 (dd, 1H), 6.76 (d, 1H), 5.09 (s, 1H), 4.09 (q, 2H), 3.94 (q, 2H), 1.45 (t, 3H), 0.68 (t, 3H) |
| 6 | 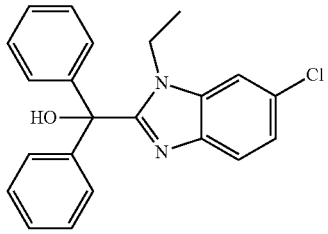 [SMILES: CCn1c(C(O)(c2ccccc2)c2ccccc2)nc2ccc(Cl)cc21] | 363 (M + H) | (400 MHz, CDCl$_3$): δ 7.71 (d, 1H), 7.31-7.40 (m, 10H), 7.28 (s, 1H), 7.25 (dd, 1H), 4.83 (s, 1H), 4.00 (q, 2H), 0.76 (t, 3H) |
| 7 | 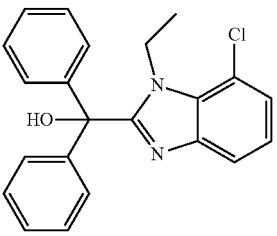 [SMILES: CCn1c(C(O)(c2ccccc2)c2ccccc2)nc2cccc(Cl)c21] | 363 (M + H) | (400 MHz, CDCl$_3$): δ 7.70 (dd, 1H), 7.32-7.40 (m, 10H), 7.25 (d, 1H), 7.18 (t, 1H), 5.10 (s, 1H), 4.32 (q, 2H), 0.70 (t, 3H) |
| 8 | 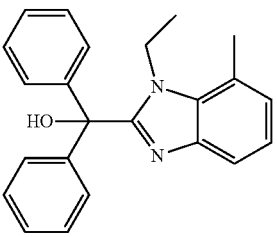 [SMILES: CCn1c(C(O)(c2ccccc2)c2ccccc2)nc2cccc(C)c21] | 343 (M + H) | (400 MHz, CDCl$_3$): δ 7.65 (d, 1H), 7.31-7.37 (m, 10H), 7.17 (t, 1H), 7.03 (d, 1H), 5.45 (s, 1H), 4.16 (q, 2H), 2.68 (s, 3H), 0.59 (t, 3H) |

TABLE 1-continued

| No. | Structure | Mass Characterization | $^1$H NMR Data |
|---|---|---|---|
| 9 | 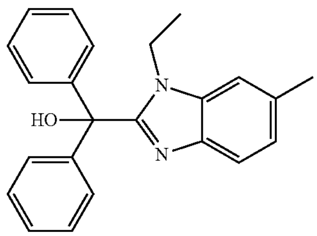 [SMILES: CCn1c(C(O)(c2ccccc2)c2ccccc2)nc2ccc(C)cc21] | 343 (M + H) | (400 MHz, CDCl$_3$): δ 7.68 (d, 1H), 7.31-7.38 (m, 10H), 7.12-7.13 (m, 2H), 5.23 (s, 1H), 3.96 (q, 2H), 2.51 (s, 3H), 0.69 (t, 3H) |
| 10 | 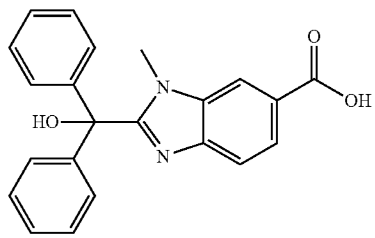 [SMILES: Cn1c(C(O)(c2ccccc2)c2ccccc2)nc2ccc(C(=O)O)cc21] | 359 (M + H) | |
| 11 | 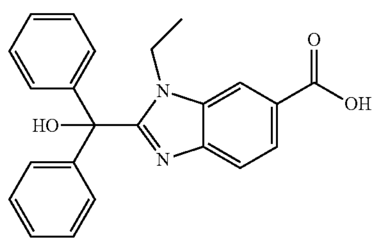 [SMILES: CCn1c(C(O)(c2ccccc2)c2ccccc2)nc2ccc(C(=O)O)cc21] | 373 (M + H) | (400 MHz, d$^6$-DMSO): δ 8.07 (s, 1H), 7.79 (d, 1H), 7.64 (d, 1H), 7.24-7.34 (m, 10H), 7.22 (s, 1H), 4.25 (q, 2H), 1.01 (t, 3H) |
| 12 | 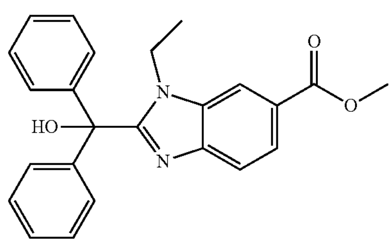 [SMILES: CCn1c(C(O)(c2ccccc2)c2ccccc2)nc2ccc(C(=O)OC)cc21] | 387 (M + H) | (400 MHz, CDCl$_3$): δ 8.08 (s, 1H), 7.99 (d, 1H), 7.79 (d, 1H), 7.31-7.35 (m, 10H), 4.90 (s, 1H), 4.08 (q, 2H), 3.95 (s, 3H), 0.78 (t, 3H) |
| 13 | 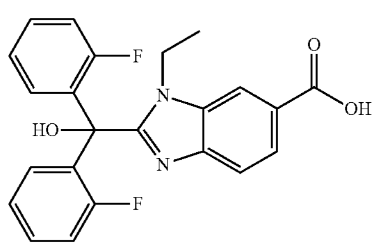 [SMILES: CCn1c(C(O)(c2ccccc2F)c2ccccc2F)nc2ccc(C(=O)O)cc21] | 409 (M + H) | |
| 14 | 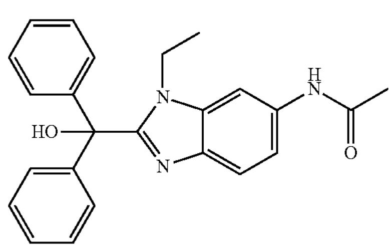 [SMILES: CCn1c(C(O)(c2ccccc2)c2ccccc2)nc2ccc(NC(C)=O)cc21] | 386 (M + H) | (400 MHz, d$^6$-DMSO): δ 9.97 (s, 1H), 7.92 (s, 1H), 7.47 (d, 1H), 7.23-7.33 (m, 10H), 7.16 (dd, 1H), 7.10 (s, 1H), 4.19 (q, 2H), 2.03 (s, 3H), 0.97 (t, 3H) |

TABLE 1-continued

| No. | Structure | Mass Characterization | ¹H NMR Data |
|---|---|---|---|
| 15 | 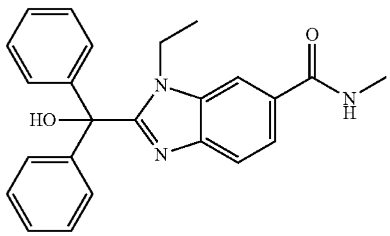 [SMILES: CCn1c(C(O)(c2ccccc2)c2ccccc2)nc2ccc(C(=O)NC)cc21] | 386 (M + H) | (400 MHz, CDCl$_3$): δ 7.98 (s, 1H), 7.79 (d, 1H), 7.55 (dd, 1H), 7.32-7.40 (m, 10H), 6.15-6.31 (brs, 1H), 4.93 (s, 1H), 4.08 (q, 2H), 3.06 (d, 3H), 0.78 (t, 3H) |
| 16 | 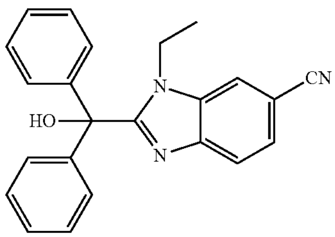 [SMILES: CCn1c(C(O)(c2ccccc2)c2ccccc2)nc2ccc(C#N)cc21] | 354 (M + H) | (400 MHz, CDCl$_3$): δ 7.85 (d, 1H), 7.66 (s, 1H), 7.54 (d, 1H), 7.31-7.39 (m, 10H), 4.48 (s, 1H), 4.11 (q, 2H), 0.85 (t, 3H) |
| 17 | 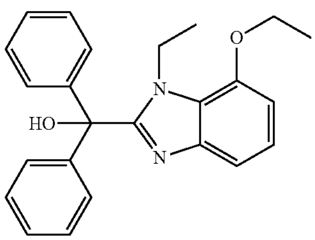 [SMILES: CCOc1cccc2nc(C(O)(c3ccccc3)c3ccccc3)n(CC)c12] | 373 (M + H) | (400 MHz, CDCl$_3$): δ 7.36 (d, 1H), 7.26-7.35 (m, 10H), 7.14 (t, 1H), 6.68 (d, 1H), 5.52 (s, 1H), 4.13 (q, 4H), 1.41 (t, 3H), 0.59 (t, 3H) |
| 18 | 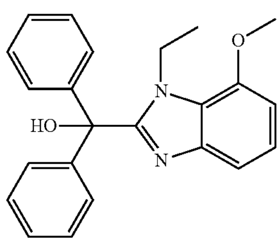 [SMILES: CCn1c(C(O)(c2ccccc2)c2ccccc2)nc2cccc(OC)c21] | 359 (M + H) | (400 MHz, CDCl$_3$): δ 7.43 (d, 1H), 7.32-7.40 (m, 10H), 7.20 (t, 1H), 6.74 (d, 1H), 5.57 (s, 1H), 4.16 (q, 2H), 3.94 (s, 3H), 0.60 (t, 3H) |
| 19 | 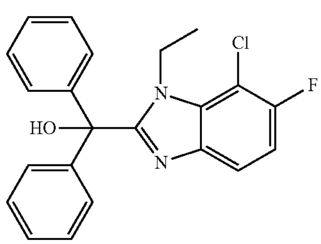 [SMILES: CCn1c(C(O)(c2ccccc2)c2ccccc2)nc2ccc(F)c(Cl)c21] | 381 (M + H) | (400 MHz, CDCl$_3$): δ 7.61 (dd, 1H), 7.31-7.40 (m, 10H), 7.10 (t, 1H), 4.76 (s, 1H), 4.33 (q, 2H), 0.78 (t, 3H) |
| 20 | 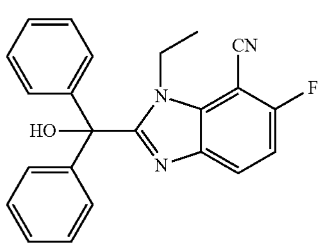 [SMILES: CCn1c(C(O)(c2ccccc2)c2ccccc2)nc2ccc(F)c(C#N)c21] | 372 (M + H) | (400 MHz, d$^6$-DMSO): δ 8.01 (dd, 1H), 7.26-7.36 (m, 12H), 4.38 (q, 2H), 1.03 (t, 3H) |

TABLE 1-continued

| No. | Structure | Mass Characterization | 1H NMR Data |
|---|---|---|---|
| 21 | 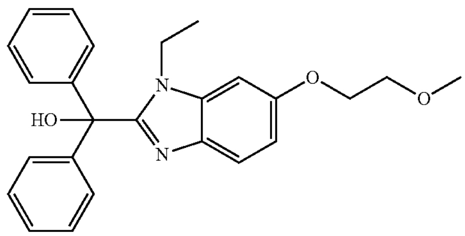 [SMILES: CCn1c(C(O)(c2ccccc2)c2ccccc2)nc2ccc(OCCOC)cc21] | 403 (M + H) | (400 MHz, CDCl3): δ 7.67 (d, 1H), 7.30-7.37 (m, 10H), 6.95 (d, 1H), 6.82 (s, 1H), 5.08 (s, 1H), 4.18 (t, 2H), 3.94 (q, 2H), 3.79 (t, 2H), 3.47 (s, 3H), 0.68 (t, 3H) |
| 22 | 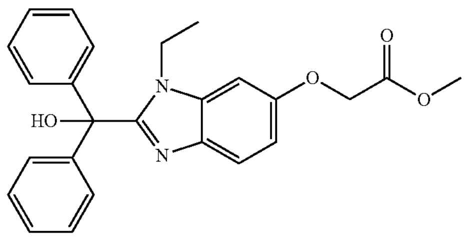 [SMILES: CCn1c(C(O)(c2ccccc2)c2ccccc2)nc2ccc(OCC(=O)OC)cc21] | 417 (M + H) | (400 MHz, CDCl3): δ 7.69 (d, 1H), 7.29-7.38 (m, 10H), 6.93 (dd, 1H), 6.82 (d, 1H), 4.97-5.01 (brs, 1H), 4.70 (s, 2H), 3.95 (q, 2H), 3.82 (s, 3H), 0.69 (t, 3H) |
| 23 | 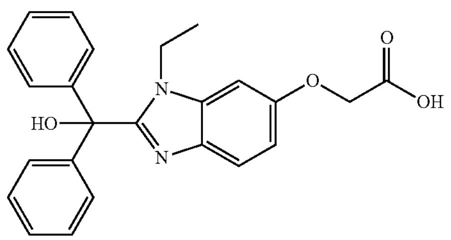 [SMILES: CCn1c(C(O)(c2ccccc2)c2ccccc2)nc2ccc(OCC(=O)O)cc21] | 403 (M + H) | (400 MHz, d6-DMSO): δ 7.45 (d, 1H), 7.21-7.33 (m, 10H), 7.06 (s, 1H), 6.96 (s, 1H), 6.78 (d, 1H), 4.70 (s, 2H), 4.10 (q, 2H), 0.96 (t, 3H) |
| 24 | 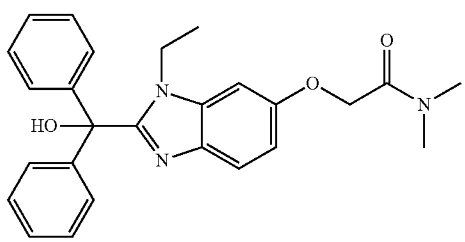 [SMILES: CCn1c(C(O)(c2ccccc2)c2ccccc2)nc2ccc(OCC(=O)N(C)C)cc21] | 430 (M + H) | (400 MHz, CDCl$_3$): δ 7.65 (d, 1H), 7.28-7.37 (m, 10H), 6.89-6.93 (m, 2H), 5.05 (s, 1H), 4.73 (s, 2H), 3.92 (q, 2H), 3.10 (s, 3H), 2.95 (s, 3H), 0.66 (t, 3H) |
| 25 | 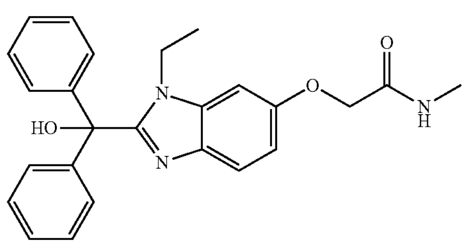 [SMILES: CCn1c(C(O)(c2ccccc2)c2ccccc2)nc2ccc(OCC(=O)NC)cc21] | 416 (M + H) | (400 MHz, CDCl$_3$): δ 7.72 (d, 1H), 7.33-7.40 (m, 10H), 6.94 (dd, 1H), 6.78 (d, 1H), 6.62-6.71 (brs, 1H), 4.94 (s, 1H), 4.58 (s, 2H), 3.99 (q, 2H), 2.94 (d, 3H), 0.73 (t, 3H) |
| 26 | 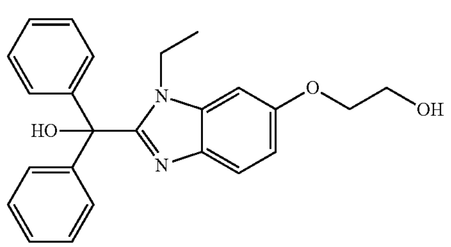 [SMILES: CCn1c(C(O)(c2ccccc2)c2ccccc2)nc2ccc(OCCO)cc21] | 389 (M + H) | (400 MHz, CDCl$_3$): δ 7.68 (d, 1H), 7.30-7.37 (m, 10H), 6.94 (dd, 1H), 6.80 (d, 1H), 5.02 (s, 1H), 4.15 (t, 2H), 4.00 (t, 2H), 3.95 (q, 2H), 2.04 (t, 1H), 0.70 (t, 3H) |

TABLE 1-continued

| No. | Structure | Mass Characterization | ¹H NMR Data |
|---|---|---|---|
| 27 | 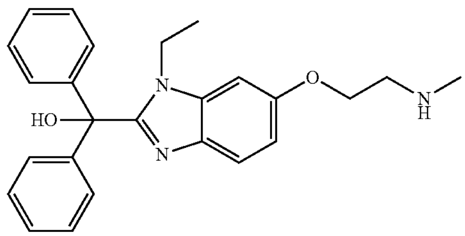 [SMILES: CCn1c(C(O)(c2ccccc2)c2ccccc2)nc2ccc(OCCNC)cc21] | 402 (M + H) | (400 MHz, CDCl₃): δ 7.64 (d, 1H), 7.27-7.38 (m, 10H), 6.91 (d, 1H), 6.81 (s, 1H), 4.20 (t, 2H), 3.94 (q, 2H), 3.34-3.57 (brs, 2H), 3.09 (t, 2H), 2.57 (s, 3H), 0.69 (t, 3H) |
| 28 | 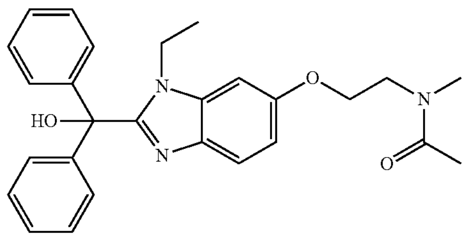 [SMILES: CCn1c(C(O)(c2ccccc2)c2ccccc2)nc2ccc(OCCN(C)C(C)=O)cc21] | 444 (M + H) | (400 MHz, d⁶-DMSO): δ 7.44 (dd, 1H), 7.23-7.32 (m, 10H), 7.05 (d, 1H), 7.02 (s, 1H), 6.77 (d, 1H), 4.07-4.18 (m, 4H), 3.69 (t, 1H), 3.63 (t, 1H), 3.06 (s, 1.5H), 2.86 (s, 1.5H), 2.06 (s, 1.5H), 1.98 (s, 1.5H), 0.95-1.00 (m, 3H) |
| 29 | 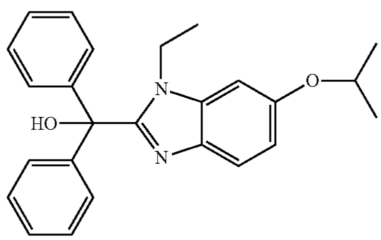 [SMILES: CCn1c(C(O)(c2ccccc2)c2ccccc2)nc2ccc(OC(C)C)cc21] | 387 (M + H) | (400 MHz, CDCl₃): δ 7.66 (d, 1H), 7.30-7.37 (m, 10H), 6.90 (dd, 1H), 6.78 (s, 1H), 5.12 (s, 1H), 4.57 (m, 1H), 3.93 (q, 2H), 1.37 (d, 6H), 0.68 (t, 3H) |
| 30 | 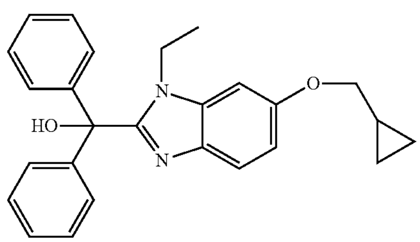 [SMILES: CCn1c(C(O)(c2ccccc2)c2ccccc2)nc2ccc(OCC3CC3)cc21] | 399 (M + H) | (400 MHz, CDCl₃): δ 7.66 (d, 1H), 7.29-7.37 (m, 10H), 6.93 (dd, 1H), 6.76 (d, 1H), 5.11 (s, 1H), 3.93 (q, 2H), 3.85 (d, 2H), 1.27-1.34 (m, 1H), 0.64-0.69 (m, 5H), 0.35-0.39 (m, 2H) |
| 31 | 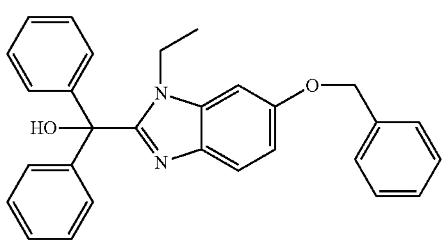 [SMILES: CCn1c(C(O)(c2ccccc2)c2ccccc2)nc2ccc(OCc3ccccc3)cc21] | 435 (M + H) | (400 MHz, CDCl₃): δ 7.68 (d, 1H), 7.47 (d, 2H), 7.39 (t, 2H), 7.30-7.38 (m, 11H), 7.00 (dd, 1H), 6.84 (d, 1H), 5.13 (s, 2H), 5.06 (s, 1H), 3.94 (q, 2H), 0.67 (t, 3H) |
| 32 | 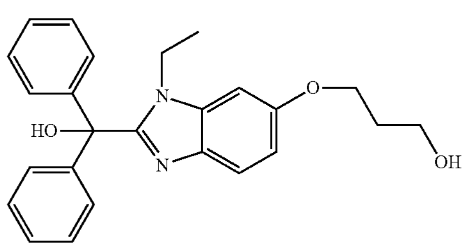 [SMILES: CCn1c(C(O)(c2ccccc2)c2ccccc2)nc2ccc(OCCCO)cc21] | 403 (M + H) | (400 MHz, d⁶-DMSO): δ 7.43 (d, 1H), 7.23-7.33 (m, 10H), 7.05 (s, 1H), 6.97 (d, 1H), 6.76 (dd, 1H), 4.52 (t, 1H), 4.01 (q, 2H), 4.06 (t, 2H), 3.56 (q, 2H), 1.87 (m, 2H), 0.97 (t, 3H) |

TABLE 1-continued

| No. | Structure | Mass Characterization | ¹H NMR Data |
|---|---|---|---|
| 33 | 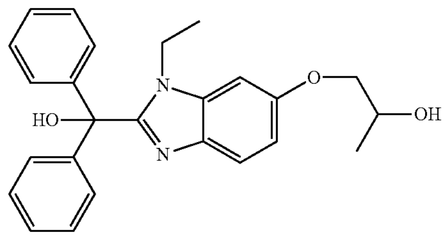 [SMILES: CCn1c(C(O)(c2ccccc2)c2ccccc2)nc2ccc(OCC(C)O)cc21] | 403 (M + H) | (400 MHz, CDCl$_3$): δ 7.66 (d, 1H), 7.30-7.37 (m, 10H), 6.92 (dd, 1H), 6.78 (d, 1H), 5.02 (s, 1H), 4.16-4.27 (m, 1H), 3.98 (dd, 1H), 3.95 (q, 2H), 3.85 (dd, 1H), 2.37 (s, 1H), 1.30 (d, 3H), 0.39 (t, 3H) |
| 34 | 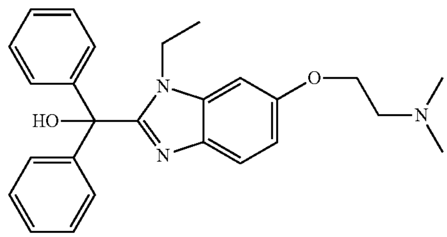 [SMILES: CCn1c(C(O)(c2ccccc2)c2ccccc2)nc2ccc(OCCN(C)C)cc21] | 416 (M + H) | (400 MHz, d$^6$-DMSO): δ 7.43 (d, 1H), 7.22-7.32 (m, 10H), 7.05 (s, 1H), 7.00 (d, 1H), 6.77 (dd, 1H), 4.08-4.13 (m, 4H), 2.72 (t, 2H), 2.28 (s, 6H), 0.97 (t, 3H) |
| 35 | 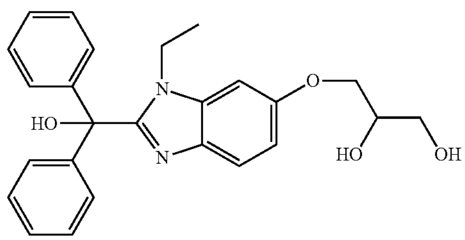 [SMILES: CCn1c(C(O)(c2ccccc2)c2ccccc2)nc2ccc(OCC(O)CO)cc21] | 419 (M + H) | (400 MHz, d$^6$-DMSO): δ 7.43 (d, 1H), 7.21-7.35 (m, 10H), 7.01-7.07 (brs, 1H), 6.97 (d, 1H), 6.77 (dd, 1H), 4.91 (d, 1H), 4.64 (t, 1H), 4.10 (q, 2H), 4.01 (dd, 1H), 3.89 (dd, 1H), 3.77-3.83 (m, 1H), 3.44 (t, 2H), 0.97 (t, 3H) |
| 36 | 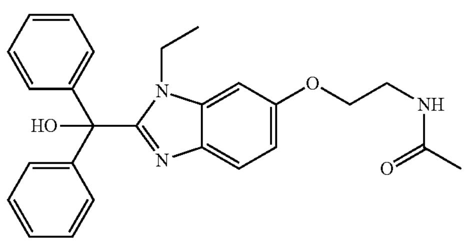 [SMILES: CCn1c(C(O)(c2ccccc2)c2ccccc2)nc2ccc(OCCNC(C)=O)cc21] | 430 (M + H) | (400 MHz, d$^6$-DMSO): δ 8.10 (t, 1H), 7.46 (d, 1H), 7.24-7.34 (m, 10H), 7.07 (s, 1H), 7.03 (d, 1H), 6.79 (dd, 1H), 4.12 (q, 2H), 4.02 (t, 2H), 3.42 (q, 2H), 1.82 (s, 3H), 0.98 (t, 3H) |
| 37 | 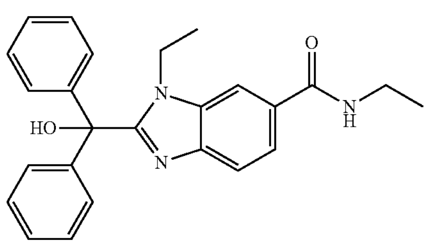 [SMILES: CCNC(=O)c1ccc2nc(C(O)(c3ccccc3)c3ccccc3)n(CC)c2c1] | 400 (M + H) | (400 MHz, d$^6$-DMSO): δ 8.45 (t, 1H), 7.99 (s, 1H), 7.69 (dd, 1H), 7.25-7.35 (m, 10H), 7.20 (s, 1H), 4.22 (q, 2H), 3.27-3.34 (m, 2H), 1.31 (t, 3H), 1.04 (t, 3H) |
| 38 | 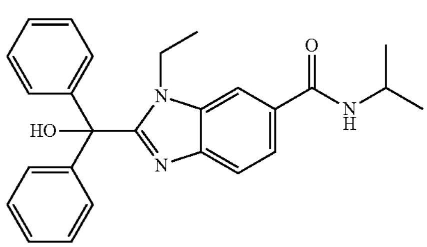 [SMILES: CCn1c(C(O)(c2ccccc2)c2ccccc2)nc2ccc(C(=O)NC(C)C)cc21] | 414 (M + H) | (400 MHz, CDCl$_3$): δ 7.93 (s, 1H), 7.76 (d, 1H), 7.52 (dd, 1H), 7.29-7.37 (m, 10H), 5.97 (d, 1H), 4.90 (s, 1H), 4.26-4.35 (m, 1H), 4.05 (q, 2H), 1.27 (d, 6H), 0.75 (t, 3H) |

| No. | Structure | Mass Characterization | ¹H NMR Data |
|---|---|---|---|
| 39 | 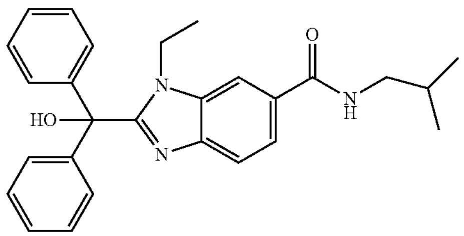 [SMILES: CCn1c(C(O)(c2ccccc2)c2ccccc2)nc2ccc(C(=O)NCC(C)C)cc21] | 428 (M + H) | (400 MHz, CDCl₃): δ 7.97 (s, 1H), 7.79 (d, 1H), 7.55 (dd, 1H), 7.31-7.39 (m, 10H), 6.24 (s, 1H), 4.92 (s, 1H), 4.07 (q, 2H), 3.34 (t, 2H), 1.85-2.01 (m, 1H), 1.00 (d, 6H), 0.77 (t, 3H) |
| 40 | 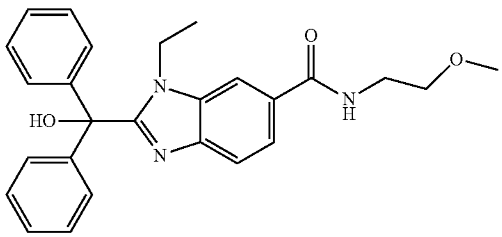 [SMILES: CCn1c(C(O)(c2ccccc2)c2ccccc2)nc2ccc(C(=O)NCCOC)cc21] | 430 (M + H) | (400 MHz, CDCl₃): δ 7.95 (s, 1H), 7.78 (d, 1H), 7.58 (d, 1H), 7.27-7.42 (m, 10H), 6.62 (s, 1H), 4.90-5.03 (brs, 1H), 4.07 (q, 2H), 3.68 (t, 2H), 3.58 (t, 2H), 3.39 (s, 3H), 0.77 (t, 3H) |
| 41 | 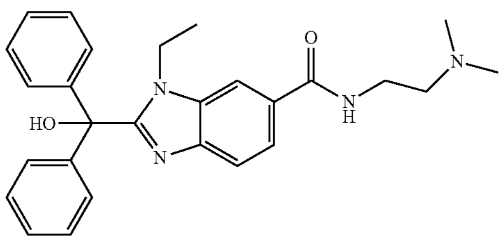 [SMILES: CCn1c(C(O)(c2ccccc2)c2ccccc2)nc2ccc(C(=O)NCCN(C)C)cc21] | 443 (M + H) | (400 MHz, CDCl₃): δ 7.97 (s, 1H), 7.78 (d, 1H), 7.59 (d, 1H), 7.31-7.38 (m, 10H), 6.96 (t, 1H), 4.65-5.28 (brs, 1H), 4.46 (q, 2H), 3.56 (q, 2H), 2.56 (q, 2H), 2.28 (s, 6H), 0.75 (t, 3H) |
| 42 | 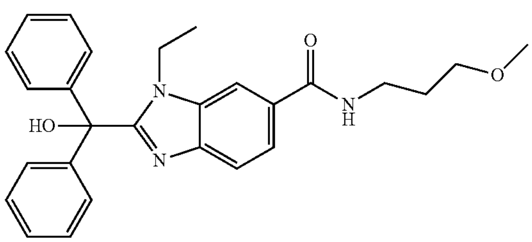 [SMILES: CCn1c(C(O)(c2ccccc2)c2ccccc2)nc2ccc(C(=O)NCCCOC)cc21] | 444 (M + H) | (400 MHz, CDCl₃): δ 7.95 (d, 1H), 7.78 (d, 1H), 7.55 (dd, 1H), 7.31-7.39 (m, 10H), 6.96-7.04 (brs, 1H), 4.95 (s, 1H), 4.07 (q, 2H), 3.57-3.64 (m, 4H), 3.40 (s, 3H), 1.69-1.95 (m, 2H), 0.76 (t, 3H) |
| 43 | 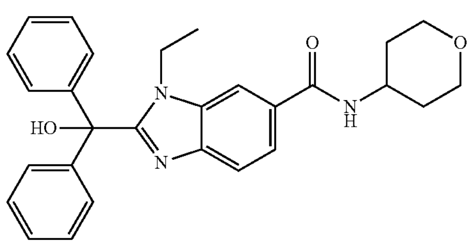 [SMILES: CCn1c(C(O)(c2ccccc2)c2ccccc2)nc2ccc(C(=O)NC3CCOCC3)cc21] | 456 (M + H) | (400 MHz, CDCl₃): δ 7.94 (s, 1H), 7.79 (d, 1H), 7.55 (d, 1H), 7.28-7.41 (m, 10H), 6.05 (d, 1H), 4.87 (s, 1H), 4.17-4.30 (m, 1H), 4.08 (q, 2H), 4.02 (d, 2H), 3.56 (t, 2H), 2.04 (d, 2H), 1.57-1.65 (m, 2H), 0.78 (t, 3H) |
| 44 | 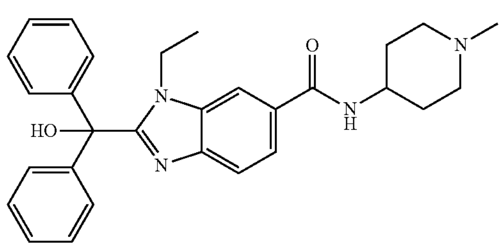 [SMILES: CCn1c(C(O)(c2ccccc2)c2ccccc2)nc2ccc(C(=O)NC3CCN(C)CC3)cc21] | 469 (M + H) | (400 MHz, CDCl₃): δ 7.93 (s, 1H), 7.79 (d, 1H), 7.54 (d, 1H), 7.27-7.43 (m, 10H), 6.04 (d, 1H), 4.88-5.14 (brs, 1H), 4.02-4.09 (m, 3H), 2.85 (d, 2H), 2.32 (s, 3H), 2.19 (t, 2H), 2.06 (d, 2H), 1.52-1.64 (m, 2H), 0.79 (t, 3H) |

TABLE 1-continued

| No. | Structure | Mass Characterization | ¹H NMR Data |
|---|---|---|---|
| 45 | 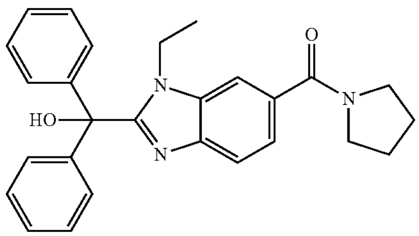 [SMILES: CCn1c(C(O)(c2ccccc2)c2ccccc2)nc2ccc(C(=O)N3CCCC3)cc21] | 426 (M + H) | (400 MHz, CDCl$_3$): δ 7.77 (d, 1H), 7.59 (d, 1H), 7.43 (dd, 1H), 7.31-7.39 (m, 10H), 5.04 (s, 1H), 4.03 (q, 2H), 3.68 (t, 2H), 3.51 (t, 2H), 1.95-2.00 (m, 2H), 1.87-1.90 (m, 2H), 0.74 (t, 2H) |
| 46 | 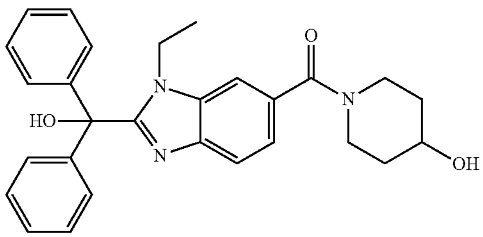 [SMILES: CCn1c(C(O)(c2ccccc2)c2ccccc2)nc2ccc(C(=O)N3CCC(O)CC3)cc21] | 456 (M + H) | (400 MHz, CDCl$_3$): δ 7.80 (d, 1H), 7.48 (s, 1H), 7.30-7.38 (m, 11H), 4.99 (s, 1H), 3.65-4.40 (m, 5H), 3.26-3.43 (m, 2H), 1.78-2.09 (m, 2H), 1.42-1.71 (m, 2H), 0.76 (t, 3H) |
| 47 | 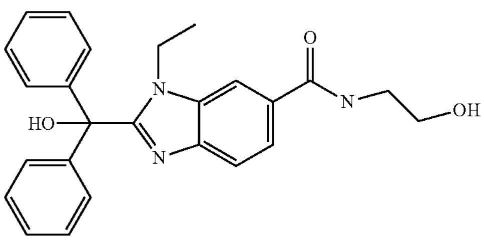 [SMILES: CCn1c(C(O)(c2ccccc2)c2ccccc2)nc2ccc(C(=O)NCCO)cc21] | 416 (M + H) | (400 MHz, CDCl$_3$): δ 7.96 (d, 1H), 7.80 (d, 1H), 7.59 (dd, 1H), 7.30-7.39 (m, 10H), 6.68 (t, 1H), 4.88 (s, 1H), 4.08 (q, 2H), 3.85-3.89 (m, 2H), 3.66-3.69 (m, 2H), 2.62 (t, 1H), 0.78 (t, 3H) |
| 48 | 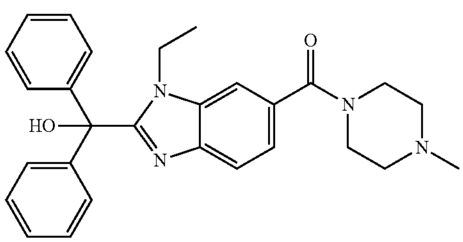 [SMILES: CCn1c(C(O)(c2ccccc2)c2ccccc2)nc2ccc(C(=O)N3CCN(C)CC3)cc21] | 455 (M + H) | (400 MHz, d$^6$-DMSO): δ 7.61 (d, 1H), 7.52 (s, 1H), 7.25-7.34 (m, 10H), 7.17 (d, 1H), 7.15 (s, 1H), 4.21 (q, 2H), 3.28-3.65 (m, 4H), 2.23-2.39 (m, 4H), 2.18 (s, 3H), 0.98 (t, 3H) |
| 49 | 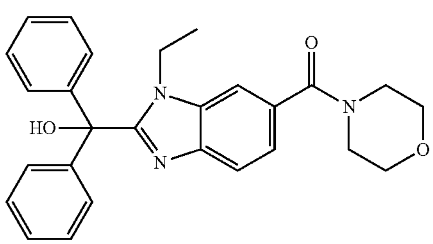 [SMILES: CCn1c(C(O)(c2ccccc2)c2ccccc2)nc2ccc(C(=O)N3CCOCC3)cc21] | 442 (M + H) | (400 MHz, d$^6$-DMSO): δ 7.62 (d, 1H), 7.56 (s, 1H), 7.25-7.35 (m, 10H), 7.20 (dd, 1H), 7.16 (s, 1H), 4.21 (q, 2H), 3.40-3.66 (m, 8H), 0.96 (t, 3H) |
| 50 | 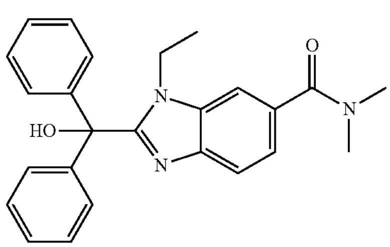 [SMILES: CCn1c(C(O)(c2ccccc2)c2ccccc2)nc2ccc(C(=O)N(C)C)cc21] | 400 (M + H) | (400 MHz, CDCl$_3$): δ 7.77 (d, 1H), 7.48 (s, 1H), 7.30-7.37 (m, 11H), 5.04 (s, 1H), 4.02 (q, 2H), 3.09 (s, 6H), 0.74 (t, 3H) |

TABLE 1-continued

| No. | Structure | Mass Characterization | ¹H NMR Data |
|---|---|---|---|
| 51 | 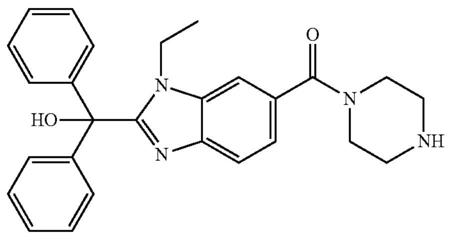 [SMILES: CCn1c(C(O)(c2ccccc2)c2ccccc2)nc2ccc(C(=O)N3CCNCC3)cc21] | 442 (M + H) | (400 MHz, d⁶-DMSO): δ 7.61 (d, 1H), 7.52 (s, 1H), 7.26-7.34 (m, 10H), 7.16 (d, 1H), 7.15 (s, 1H), 4.21 (q, 2H), 3.01-3.49 (m, 4H), 2.58-2.85 (m, 4H), 0.98 (t, 3H) |
| 52 | 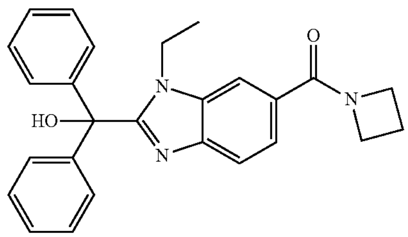 [SMILES: CCn1c(C(O)(c2ccccc2)c2ccccc2)nc2ccc(C(=O)N3CCC3)cc21] | 412 (M + H) | (400 MHz, d⁶-DMSO): δ 7.74 (s, 1H), 7.63 (d, 1H), 7.44 (dd, 1H), 7.26-7.36 (m, 10H), 7.20 (s, 1H), 4.34 (t, 2H), 4.25 (q, 2H), 4.06 (t, 2H), 2.22-2.30 (m, 2H), 0.99 (t, 3H) |
| 53 | 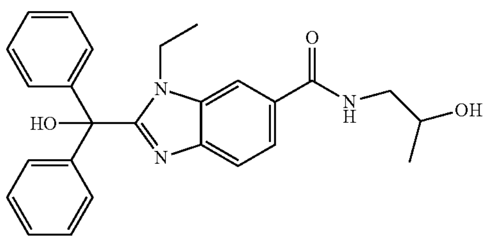 | 430 (M + H) | (400 MHz, d⁶-DMSO): δ 8.39 (t, 1H), 8.02 (s, 1H), 7.70 (d, 1H), 7.60 (d, 1H), 7.28-7.34 (m, 10H), 7.19 (s, 1H), 4.73 (d, 1H), 4.21 (q, 2H), 3.17-3.24 (m, 2H), 1.02-1.07 (m, 6H) |
| 54 | 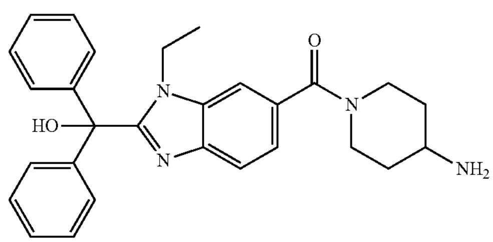 [SMILES: CCn1c(C(O)(c2ccccc2)c2ccccc2)nc2ccc(C(=O)N3CCC(N)CC3)cc21] | 455 (M + H) | (400 MHz, d⁶-DMSO): δ 7.59 (d, 1H), 7.48 (s, 1H), 7.24-7.33 (m, 10H), 7.14 (s, 1H), 7.13 (d, 1H), 4.19 (q, 2H), 3.45-3.69 (m, 2H), 2.86-3.09 (m, 2H), 2.73-2.96 (m, 1H), 1.55-1.83 (m, 2H), 1.08-1.39 (m, 4H), 0.96 (t, 3H) |
| 55 | 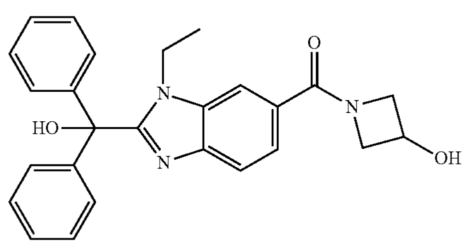 [SMILES: CCn1c(C(O)(c2ccccc2)c2ccccc2)nc2ccc(C(=O)N3CC(O)C3)cc21] | 428 (M + H) | (400 MHz, d⁶-DMSO): δ 7.74 (s, 1H), 7.63 (d, 1H), 7.44 (d, 1H), 7.26-7.38 (m, 10H), 7.20 (s, 1H), 5.72 (d, 1H), 4.37-4.58 (m, 2H), 4.20-4.34 (m, 3H), 3.96-4.09 (m, 1H), 3.76-3.85 (m, 1H), 1.00 (t, 3H) |
| 56 | 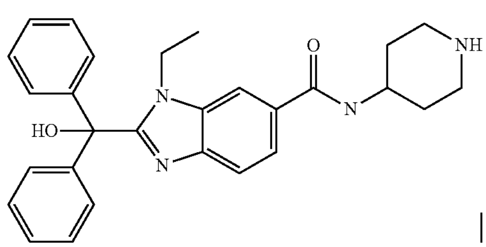 [SMILES: CCn1c(C(O)(c2ccccc2)c2ccccc2)nc2ccc(C(=O)NC3CCNCC3)cc21] | 455 (M + H) | (400 MHz, d⁶-DMSO): δ 7.94 (s, 1H), 7.79 (d, 1H), 7.53 (d, 1H), 7.31-7.37 (m, 10H), 5.03 (d, 1H), 3.90-4.16 (m, 3H), 3.10 (d, 2H), 2.75 (t, 2H), 2.05 (d, 2H), 1.36-1.46 (m, 2H), 0.79 (t, 3H) |

TABLE 1-continued

| No. | Structure | Mass Characterization | ¹H NMR Data |
|---|---|---|---|
| 57 | 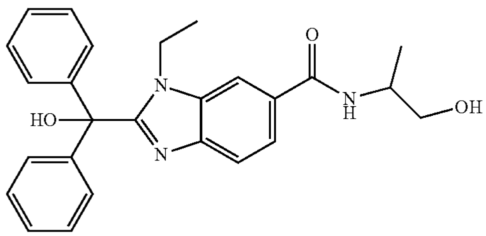 [SMILES: CCn1c(C(O)(c2ccccc2)c2ccccc2)nc2ccc(C(=O)NC(C)CO)cc21] | 430 (M + H) | (400 MHz, CDCl₃): δ 7.97 (s, 1H), 7.82 (d, 1H), 7.59 (d, 1H), 7.32-7.41 (m, 10H), 6.37 (d, 1H), 4.89 (s, 1H), 4.31-4.39 (m, 1H), 4.09 (q, 2H), 3.81-3.85 (m, 1H), 3.68-3.73 (m, 1H), 2.77 (t, 1H), 1.34 (d, 3H), 0.80 (t, 3H) |
| 58 | 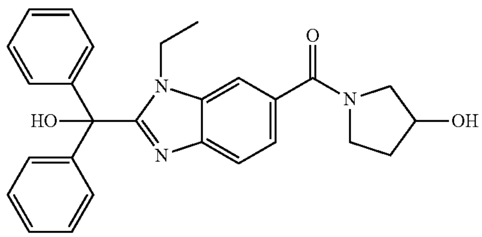 [SMILES: CCn1c(C(O)(c2ccccc2)c2ccccc2)nc2ccc(C(=O)N3CCC(O)C3)cc21] | 442 (M + H) | (400 MHz, CDCl₃): δ 7.77 (d, 1H), 7.60 (s, 1H), 7.31-7.47 (m, 11H), 5.01 (s, 1H), 4.56-4.68 (m, 0.5H), 4.42-4.52 (m, 0.5H), 4.03 (q, 2H), 3.51-3.86 (m, 4H), 1.77-2.14 (m, 3H), 0.75 (t, 3H) |
| 59 | 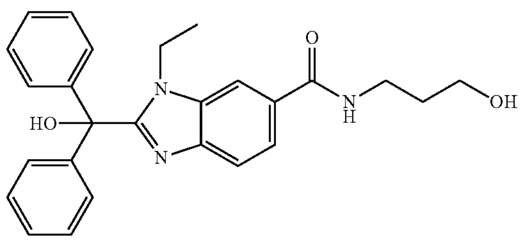 [SMILES: CCn1c(C(O)(c2ccccc2)c2ccccc2)nc2ccc(C(=O)NCCCO)cc21] | 430 (M + H) | (400 MHz, CDCl₃): δ 7.97 (s, 1H), 7.79 (d, 1H), 7.56 (dd, 1H), 7.31-7.39 (m, 10H), 6.69 (t, 1H), 4.87 (s, 1H), 4.08 (q, 2H), 3.67-3.74 (m, 4H), 3.14 (t, 1H), 1.80-1.84 (m, 2H), 0.78 (t, 3H) |
| 60 | 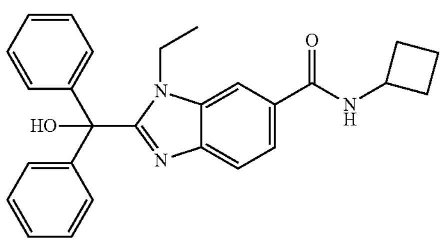 [SMILES: CCn1c(C(O)(c2ccccc2)c2ccccc2)nc2ccc(C(=O)NC3CCC3)cc21] | 426 (M + H) | (400 MHz, CDCl₃): δ 7.95 (s, 1H), 7.79 (d, 1H), 7.56 (d, 1H), 7.32-7.40 (m, 10H), 6.32 (d, 1H), 4.92 (s, 1H), 4.64 (q, 1H), 4.08 (q, 2H), 2.45-2.52 (m, 2H), 1.95-2.06 (m, 2H), 1.78-1.84 (m, 2H), 0.79 (t, 3H) |
| 61 | 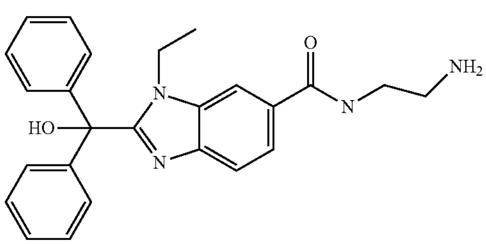 [SMILES: CCn1c(C(O)(c2ccccc2)c2ccccc2)nc2ccc(C(=O)NCCN)cc21] | 415 (M + H) | (400 MHz, d⁶-DMSO): δ 8.55 (s, 1H), 8.01 (s, 1H), 7.70 (d, 1H), 7.61 (d, 1H), 7.23-7.32 (m, 10H), 7.18 (s, 1H), 5.90-6.90 (brs, 2H), 4.20 (q, 2H), 3.42 (q, 2H), 2.88 (t, 2H), 1.03 (t, 3H) |
| 62 | 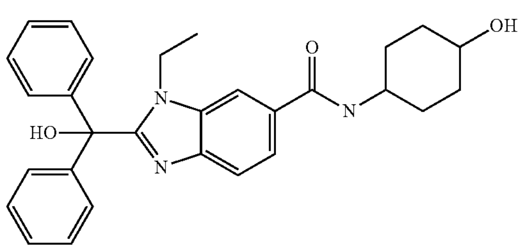 [SMILES: CCn1c(C(O)(c2ccccc2)c2ccccc2)nc2ccc(C(=O)NC3CCC(O)CC3)cc21] | 470 (M + H) | (400 MHz, CDCl₃): δ 7.94 (s, 1H), 7.78 (d, 1H), 7.52 (d, 1H), 7.30-7.38 (m, 10H), 5.96 (d, 1H), 4.88 (s, 1H), 4.07 (q, 2H), 3.95-4.05 (m, 1H), 3.62-3.73 (m, 1H), 2.16 (d, 2H), 2.05 (d, 2H), 1.29-1.53 (m, 4H), 0.77 (t, 3H) |

TABLE 1-continued

| No. | Structure | Mass Characterization | ¹H NMR Data |
|---|---|---|---|
| 63 | 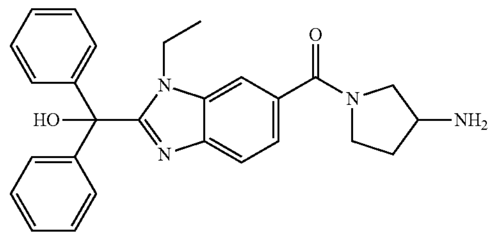 [SMILES: CCn1c(C(O)(c2ccccc2)c2ccccc2)nc2ccc(C(=O)N3CCC(N)C3)cc21] | 441 (M + H) | (400 MHz, CDCl$_3$): δ 7.75 (d, 1H), 7.58 (s, 1H), 7.31-7.45 (m, 11H), 4.02 (q, 2H), 3.68-3.88 (m, 3H), 3.23-3.58 (m, 2H), 1.99-2.25 (m, 1H), 1.52-1.85 (m, 3H), 0.73 (t, 3H) |
| 64 | 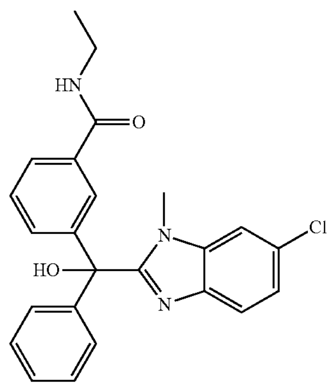 [SMILES: CCNC(=O)c1cccc(C(O)(c2ccccc2)c2nc3ccc(Cl)cc3n2C)c1] | 420 (M + H) | (400 MHz, d6-DMSO): δ 8.42 (t, 1H), 7.83 (s, 1H), 7.71 (d, 1H), 7.64 (d, 1H), 7.57 (d, 1H), 7.23-7.38 (m, 8H), 7.17 (dd, 1H), 3.51 (s, 3H), 3.18-3.25 (m, 2H), 1.06 (t, 3H) |
| 65 | 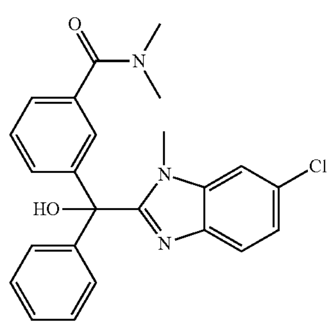 [SMILES: CN(C)C(=O)c1cccc(C(O)(c2ccccc2)c2nc3ccc(Cl)cc3n2C)c1] | 420 (M + H) | (400 MHz, d$^6$-DMSO): δ 7.68 (d, 1H), 7.60 (d, 1H), 7.26-7.42 (m, 10H), 7.20 (dd, 1H), 3.56 (s, 3H), 2.93 (s, 3H), 2.86 (s, 3H) |
| 66 | 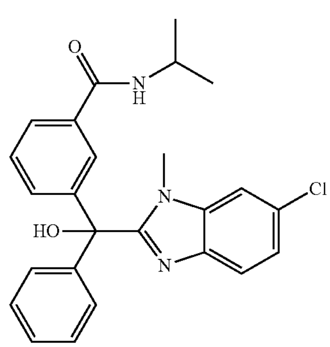 [SMILES: CC(C)NC(=O)c1cccc(C(O)(c2ccccc2)c2nc3ccc(Cl)cc3n2C)c1] | 434 (M + H) | (400 MHz, d$^6$-DMSO): δ 8.17 (d, 1H), 7.84 (s, 1H), 7.73 (d, 1H), 7.64 (d, 1H), 7.57 (d, 1H), 7.22-7.37 (m, 8H), 7.17 (dd, 1H), 3.98-4.07 (m, 1H), 3.51 (s, 3H), 1.10 (d, 6H) |

TABLE 1-continued

| No. | Structure | Mass Characterization | ¹H NMR Data |
|---|---|---|---|
| 67 | 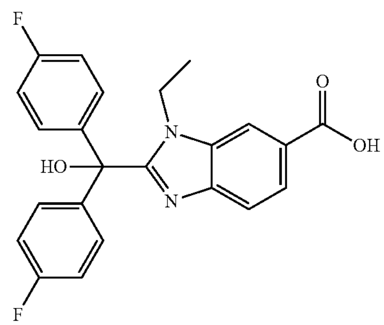 [SMILES: CCn1c(C(O)(c2ccc(F)cc2)c2ccc(F)cc2)nc2ccc(C(=O)O)cc21] | 409 (M + H) | (400 MHz, d6-DMSO): δ 12.66-12.95 (brs, 1H), 8.09 (s, 1H), 7.79 (d, 1H), 7.65 (d, 1H), 7.36 (s, 1H), 7.31 (dd, 4H), 7.16 (t, 4H), 4.26 (q, 2H), 1.04 (t, 3H) |
| 68 | 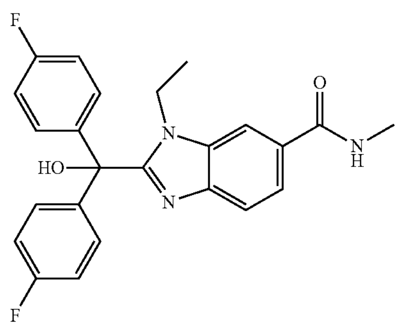 [SMILES: CCn1c(C(O)(c2ccc(F)cc2)c2ccc(F)cc2)nc2ccc(C(=O)NC)cc21] | 422 (M + H) | (400 MHz, CDCl$_3$): δ 7.98 (d, 1H), 7.80 (d, 1H), 7.57 (dd, 1H), 7.30 (dd, 4H), 7.07 (t, 4H), 6.18-6.25 (brs, 1H), 4.70 (s, 1H), 4.10 (q, 2H), 3.08 (d, 3H), 0.88 (t, 3H) |
| 69 | 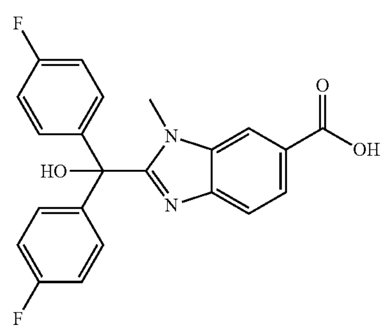 [SMILES: Cn1c(C(O)(c2ccc(F)cc2)c2ccc(F)cc2)nc2ccc(C(=O)O)cc21] | 395 (M + H) | (400 MHz, d6-DMSO): δ 12.65-12.90 (brs, 1H), 8.09 (d, 1H), 7.78 (dd, 1H), 7.62 (d, 1H), 7.36 (s, 1H), 7.24-7.28 (m, 4H), 7.14 (t, 4H), 3.61 (s, 3H) |
| 70 | 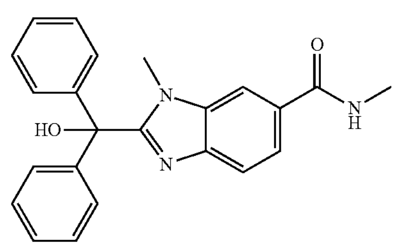 [SMILES: CNC(=O)c1ccc2nc(C(O)(c3ccccc3)c3ccccc3)n(C)c2c1] | 372 (M + H) | (400 MHz, d⁶-DMSO): δ 8.37 (q, 1H), 8.00 (d, 1H), 7.68 (dd, 1H), 7.60 (d, 1H), 7.24-7.34 (m, 10H), 7.19 (s, 1H), 3.58 (s, 3H), 2.79 (d, 3H) |
| 71 | 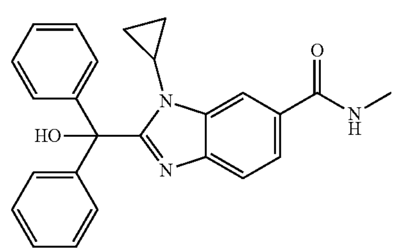 [SMILES: CNC(=O)c1ccc2nc(C(O)(c3ccccc3)c3ccccc3)n(C3CC3)c2c1] | 398 (M + H) | (400 MHz, d⁶-DMSO): δ 8.45 (q, 1H), 8.06 (s, 1H), 7.67 (dd, 1H), 7.60 (d, 1H), 7.26-7.39 (m, 10H), 7.00 (s, 1H), 3.14-3.20 (m, 1H), 2.80 (d, 3H), 0.78-0.83 (m, 2H), 0.60-0.65 (m, 2H) |

TABLE 1-continued

| No. | Structure | Mass Characterization | ¹H NMR Data |
|---|---|---|---|
| 72 | 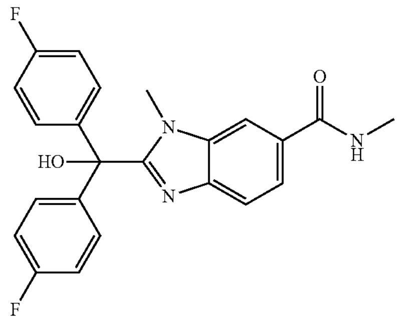 [SMILES: CNC(=O)c1ccc2nc(C(O)(c3ccc(F)cc3)c3ccc(F)cc3)n(C)c2c1] | 408 (M + H) | (400 MHz, CDCl$_3$): δ 7.95 (s, 1H), 7.79 (d, 1H), 7.57 (d, 1H), 7.30 (dd, 4H), 7.07 (t, 4H), 6.15-6.27 (brs, 1H), 4.60 (s, 1H), 3.49 (s, 3H), 3.07 (d, 3H) |
| 73 | 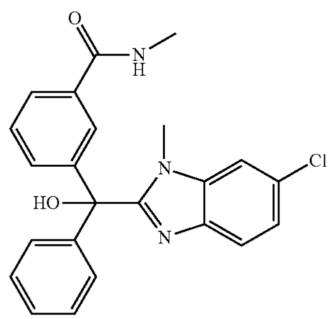 [SMILES: CNC(=O)c1cccc(C(O)(c2ccccc2)c2nc3ccc(Cl)cc3n2C)c1] | 406 (M + H) | (400 MHz, d$^6$-DMSO): δ 8.38 (s, 1H), 7.83 (s, 1H), 7.71 (dd, 1H), 7.66 (s, 1H), 7.58 (dd, 1H), 7.26-7.39 (m, 8H), 7.18 (d, 1H), 3.52 (s, 3H), 2.73 (d, 3H) |
| 74 | 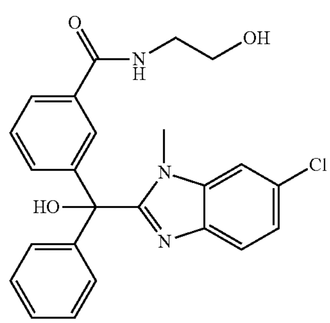 [SMILES: Cn1c(C(O)(c2ccccc2)c2cccc(C(=O)NCCO)c2)nc2ccc(Cl)cc21] | 436 (M + H) | (400 MHz, d$^6$-DMSO): δ 8.37 (t, 1H), 7.85 (s, 1H), 7.73 (d, 1H), 7.83 (s, 1H), 7.57 (d, 1H), 7.23-7.36 (m, 8H), 7.16 (dd, 1H), 4.62-4.71 (brs, 1H), 3.51 (s, 3H), 3.45 (t, 2H), 3.27 (t, 2H) |
| 75 | 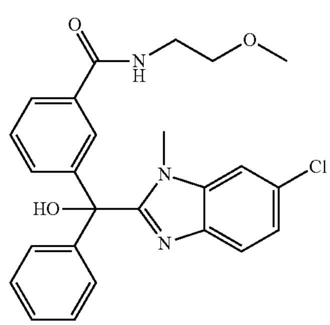 [SMILES: COCCNC(=O)c1cccc(C(O)(c2ccccc2)c2nc3ccc(Cl)cc3n2C)c1] | 450 (M + H) | (400 MHz, d$^6$-DMSO): δ 8.50 (t, 1H), 7.87 (s, 1H), 7.76 (d, 1H), 7.67 (d, 1H), 7.60 (d, 1H), 7.27-7.42 (m, 8H), 7.20 (dd, 1H), 3.54 (s, 3H), 3.78-3.43 (m, 4H), 3.24 (s, 3H) |
| 76 | 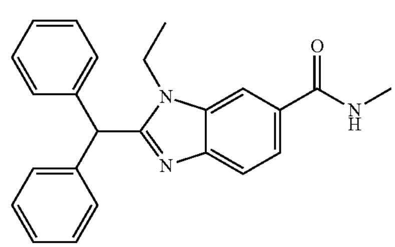 [SMILES: CCn1c(C(c2ccccc2)c2ccccc2)nc2ccc(C(=O)NC)cc21] | 370 (M + H) | (400 MHz, CDCl$_3$): δ 7.96 (d, 1H), 7.76 (d, 1H), 7.48 (dd, 1H), 7.26-7.35 (m, 10H), 6.16-6.23 (brs, 1H), 5.71 (s, 1H), 4.19 (q, 2H), 3.05 (d, 3H), 1.19 (t, 3H) |

TABLE 1-continued

| No. | Structure | Mass Characterization | ¹H NMR Data |
|---|---|---|---|
| 77 | 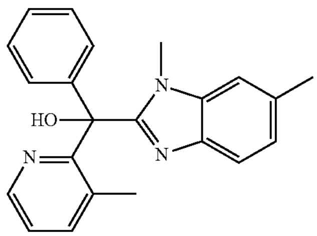 [SMILES: Cc1ccc2nc(C(O)(c3ccccc3)c3ncccc3C)n(C)c2c1] | 344 (M + H) | |
| 78 | 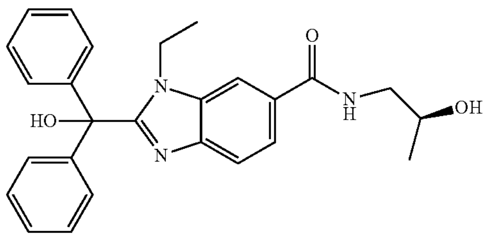 [SMILES: CCn1c(C(O)(c2ccccc2)c2ccccc2)nc2ccc(C(=O)NC[C@H](C)O)cc21] | 430 (M + H) | (400 MHz, CDCl₃): δ 7.94 (s, 1H), 7.79 (d, 1H), 7.59 (d, 1H), 7.26-7.38 (m, 10H), 6.65 (bs, 1H), 4.86 (s, 1H), 4.08 (m, 3H), 3.69 (m, 1H), 3.37 (m, 1H), 2.57 (bs, 1H), 1.27 (d, 3H), 0.78 (t, 3H) |
| 79 | 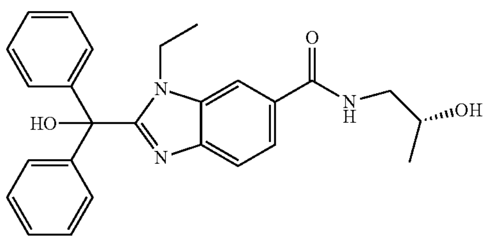 [SMILES: CCn1c(C(O)(c2ccccc2)c2ccccc2)nc2ccc(C(=O)NC[C@@H](C)O)cc21] | 430 (M + H) | (400 MHz, CDCl₃): δ 7.96 (s, 1H), 7.79 (d, 1H), 7.59 (d, 1H), 7.26-7.38 (m, 10H), 6.67 (bs, 1H), 4.86 (s, 1H), 4.08 (m, 3H), 3.69 (m, 1H), 3.37 (m, 1H), 2.59 (bs, 1H), 1.27 (d, 3H), 0.78 (t, 3H) |
| 80 | 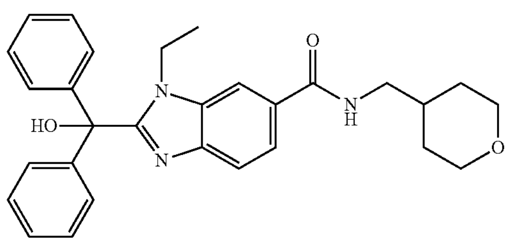 [SMILES: CCn1c(C(O)(c2ccccc2)c2ccccc2)nc2ccc(C(=O)NCC3CCOCC3)cc21] | 470 (M + H) | (400 MHz, d⁶-DMSO): δ 8.45 (t, 1H), 7.99 (s, 1H), 7.69 (dd, 1H), 7.60 (d, 1H), 7.24-7.36 (m, 10H), 7.19 (s, 1H), 4.21 (q, 2H), 3.83 (d, 2H), 3.22 (dd, 2H), 3.17 (t, 2H), 1.74-1.85 (m, 1H), 1.58 (d, 2H), 1.14-1.24 (m, 2H), 1.04 (t, 3H) |
| 81 | 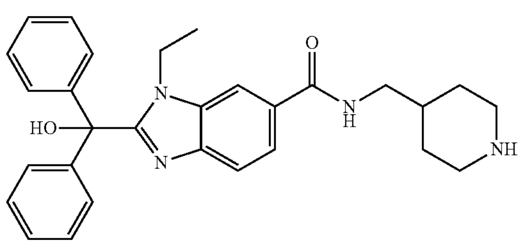 [SMILES: CCn1c(C(O)(c2ccccc2)c2ccccc2)nc2ccc(C(=O)NCC3CCNCC3)cc21] | 469 (M + H) | (400 MHz, d⁶-DMSO): δ 8.51-8.88 (m, 3H), 8.06-8.18 (m, 1H), 7.75-7.83 (m, 1H), 7.66-7.69 (m, 1H), 7.31-7.42 (m, 10H), 4.27 (q, 2H), 3.19-3.26 (m, 4H), 2.81 (q, 2H), 1.78-1.89 (m, 3H), 1.30-1.44 (m, 2H), 1.04 (t, 3H) |
| 82 | 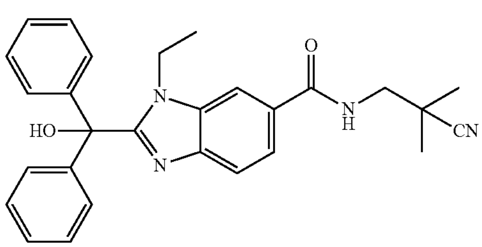 [SMILES: CCn1c(C(O)(c2ccccc2)c2ccccc2)nc2ccc(C(=O)NCC(C)(C)C#N)cc21] | 453 (M + H) | (400 MHz, CDCl₃): δ 7.95 (s, 1H), 7.82 (d, 1H), 7.63 (d, 1H), 7.31-7.40 (m, 10H), 6.60 (t, 1H), 4.84 (s, 1H), 4.09 (q, 2H), 3.66 (d, 2H), 1.44 (s, 6H), 0.80 (t, 3H) |

TABLE 1-continued

| No. | Structure | Mass Characterization | ¹H NMR Data |
|---|---|---|---|
| 83 | 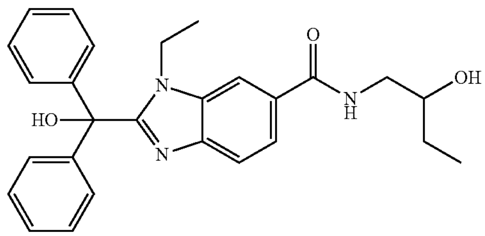 [SMILES: CCC(O)CNC(=O)c1ccc2nc(C(O)(c3ccccc3)c3ccccc3)n(CC)c2c1] | 444 (M + H) | |
| 84 | 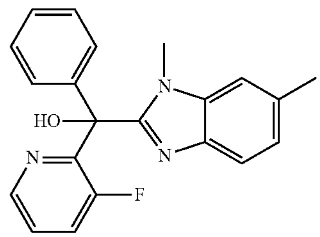 | 348 (M + H) | |
| 85 | 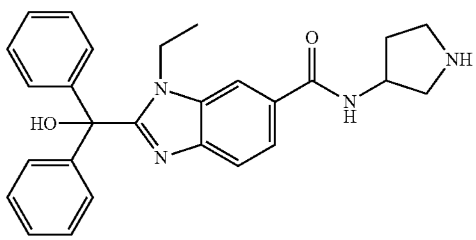 [SMILES: CCn1c(C(O)(c2ccccc2)c2ccccc2)nc2ccc(C(=O)NC3CCNC3)cc21] | 441 (M + H) | (400 MHz, d⁶-DMSO): δ 9.29-9.37 (brs, 1H), 9.02-9.14 (brs, 1H), 8.82-8.82 (brs, 1H), 8.23 (bs, 1H), 7.84 (d, 1H), 7.69 (d, 1H), 7.31-7.39 (m, 9H), 4.55-4.62 (m, 1H), 4.30 (q, 2H), 3.23-3.42 (m, 4H), 2.18-2.26 (m, 1H), 1.99-2.08 (m, 1H), 1.07 (t, 3H) |
| 86 | 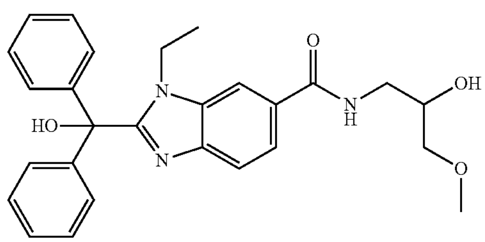 [SMILES: CCn1c(C(O)(c2ccccc2)c2ccccc2)nc2ccc(C(=O)NCC(O)COC)cc21] | 460 (M + H) | (400 MHz, CDCl₃): δ 7.96 (s, 1H), 7.80 (dd, 1H), 7.60 (d, 1H), 7.32-7.39 (m, 10H), 6.74 (t, 1H), 4.90 (s, 1H), 4.08 (q, 2H), 3.99-4.05 (m, 1H), 3.76-3.83 (m, 1H), 3.47-3.57 (m, 2H), 3.40-3.46 (m, 4H), 3.16 (m, 1H), 0.78 (t, 3H) |
| 87 | 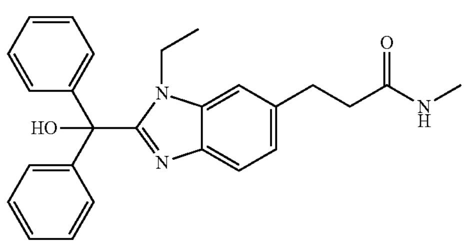 [SMILES: CCn1c(C(O)(c2ccccc2)c2ccccc2)nc2ccc(CCC(=O)NC)cc21] | 414 (M + H) | (400 MHz, d⁶-DMSO): δ 7.72 (d, 1H), 7.45 (d, 1H), 7.26-7.32 (m, 10H), 7.08 (s, 1H), 6.99 (d, 1H), 4.12 (q, 2H), 2.91 (t, 2H), 2.53 (d, 3H), 2.39 (t, 2H), 0.97 (t, 3H) |
| 88 | 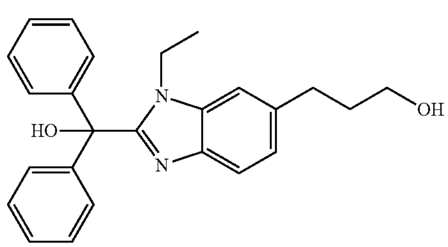 [SMILES: CCn1c(C(O)(c2ccccc2)c2ccccc2)nc2ccc(CCCO)cc21] | 387 (M + H) | (400 MHz, CDCl₃): δ 7.70 (d, 1H), 7.31-7.37 (m, 10H), 7.13-7.15 (m, 2H), 5.21 (s, 1H), 3.97 (q, 2H), 3.72 (t, 2H), 2.84 (t, 2H), 1.93-2.00 (m, 2H), 0.68 (t, 3H) |

TABLE 1-continued

| No. | Structure | Mass Characterization | ¹H NMR Data |
|---|---|---|---|
| 89 | 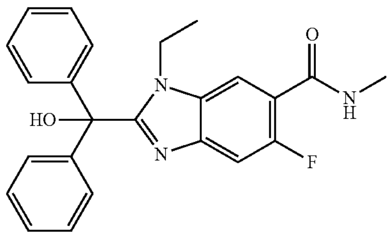 [SMILES: CCn1c(C(O)(c2ccccc2)c2ccccc2)nc2cc(F)c(C(=O)NC)cc21] | 404 (M + H) | (400 MHz, CDCl₃): δ 8.15 (d, 1H), 7.48 (d, 1H), 7.29-7.38 (m, 10H), 6.89-6.99 (brs, 1H), 4.69 (s, 1H), 4.08 (q, 2H), 3.06 (d, 1H), 0.80 (t, 3H) |
| 90 | 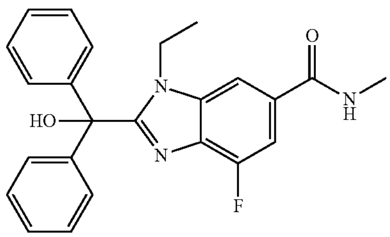 [SMILES: CCn1c(C(O)(c2ccccc2)c2ccccc2)nc2c(F)cc(C(=O)NC)cc21] | 404 (M + H) | (400 MHz, CDCl₃): δ 7.72 (d, 1H), 7.32-7.43 (m, 10H), 7.29 (d, 1H), 6.24 (s, 1H), 5.01 (s, 1H), 4.06 (q, 2H), 3.04 (d, 3H), 0.75 (t, 3H) |
| 91 | 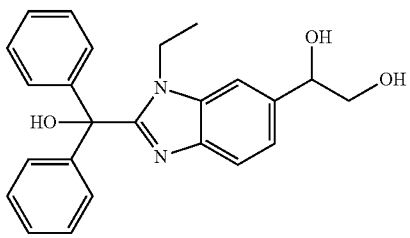 [SMILES: CCn1c(C(O)(c2ccccc2)c2ccccc2)nc2ccc(C(O)CO)cc21] | 389 (M + H) | (400 MHz, d⁶-DMSO): δ 7.47 (d, 1H), 7.40 (s, 1H), 7.23-7.33 (m, 10H), 7.12 (d, 1H), 7.08 (s, 1H), 5.20 (d, 1H), 4.61-4.68 (m, 2H), 4.14 (q, 2H), 3.43-3.46 (m, 2H), 0.96 (t, 3H) |
| 92 | 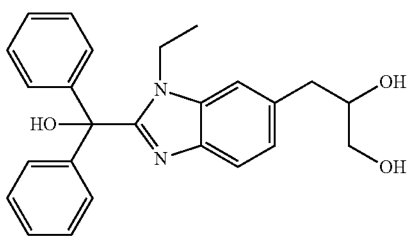 [SMILES: CCn1c(C(O)(c2ccccc2)c2ccccc2)nc2ccc(CC(O)CO)cc21] | 403 (M + H) | (400 MHz, CDCl₃): δ 7.74 (d, 1H), 7.31-7.39 (m, 10H), 7.19 (s, 1H), 7.15 (dd, 1H), 5.12 (s, 1H), 3.97-4.03 (m, 3H), 3.75 (dd, 1H), 3.57 (dd, 1H), 2.96 (dd, 1H), 2.88 (dd, 1H), 0.71 (t, 3H) |
| 93 | 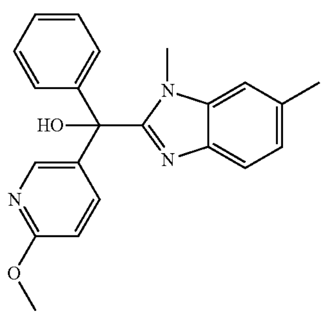 [SMILES: COc1ccc(C(O)(c2ccccc2)c2nc3ccc(C)cc3n2C)cn1] | 360 (M + H) | |
| 94 | 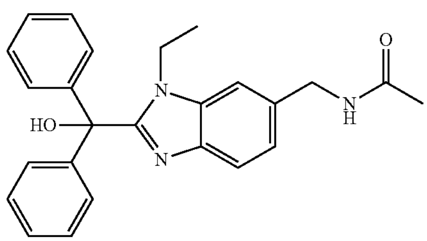 [SMILES: CCn1c(C(O)(c2ccccc2)c2ccccc2)nc2ccc(CNC(C)=O)cc21] | 400 (M + H) | (400 MHz, CDCl₃): δ 7.75 (d, 1H), 7.32-7.41 (m, 10H), 7.28 (s, 1H), 7.21 (d, 1H), 5.72-5.83 (brs, 1H), 5.07 (s, 1H), 4.56 (d, 2H), 4.01 (q, 2H), 2.03 (s, 3H), 0.72 (t, 3H) |

TABLE 1-continued

| No. | Structure | Mass Characterization | $^1$H NMR Data |
|-----|-----------|----------------------|----------------|
| 95 | 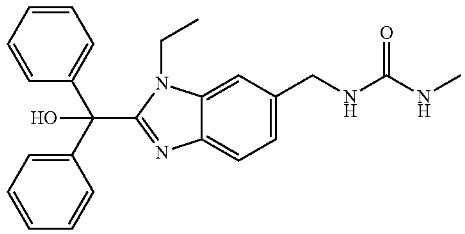 [SMILES: CCn1c(C(O)(c2ccccc2)c2ccccc2)nc2ccc(CNC(=O)NC)cc21] | 415 (M + H) | (400 MHz, CDCl$_3$): δ 7.71 (d, 1H), 7.30-7.37 (m, 10H), 7.28 (s, 1H), 7.18 (dd, 1H), 5.08 (t, 1H), 4.69 (t, 1H), 4.48 (d, 2H), 4.26-4.35 (brs, 1H), 3.99 (q, 2H), 2.76 (d, 3H), 0.70 (t, 3H) |
| 96 | 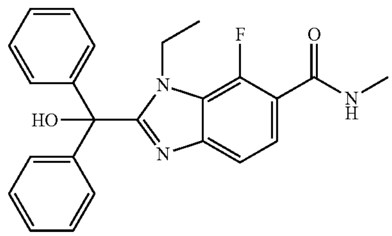 [SMILES: CCn1c(C(O)(c2ccccc2)c2ccccc2)nc2ccc(C(=O)NC)c(F)c21] | 404 (M + H) | (400 MHz, CDCl$_3$): δ 7.92 (dd, 1H), 7.60 (d, 1H), 7.31-7.45 (m, 10H), 6.54-6.64 (brs, 1H), 4.65 (s, 1H), 4.20 (q, 2H), 3.07 (d, 3H), 0.84 (t, 3H) |
| 97 | 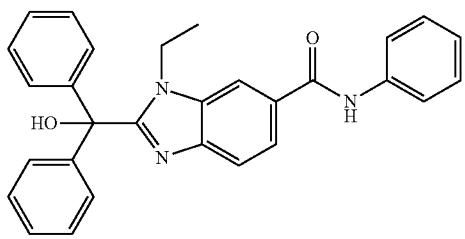 [SMILES: CCn1c(C(O)(c2ccccc2)c2ccccc2)nc2ccc(C(=O)Nc3ccccc3)cc21] | 448 (M + H) | (400 MHz, CDCl$_3$): δ 8.03 (s, 1H), 7.93 (s, 1H), 7.84 (d, 1H), 7.68 (t, 2H), 7.32-7.41 (m, 13H), 7.16 (t, 1H), 4.83 (s, 1H), 4.10 (q, 2H), 0.80 (t, 3H) |
| 98 | 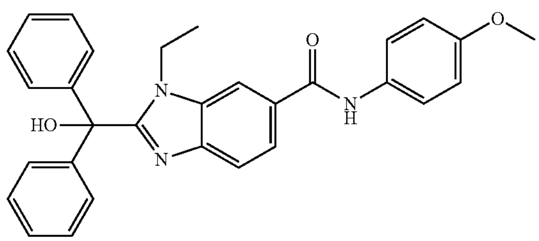 [SMILES: CCn1c(C(O)(c2ccccc2)c2ccccc2)nc2ccc(C(=O)Nc3ccc(OC)cc3)cc21] | 478 (M + H) | (400 MHz, CDCl$_3$): δ 8.02 (d, 1H), 7.83 (d, 1H), 7.82 (s, 1H), 7.68 (dd, 1H), 7.56 (d, 2H), 7.31-7.39 (m, 10H), 6.92 (d, 2H), 4.84 (s, 1H), 4.09 (q, 2H), 3.82 (s, 3H), 0.79 (t, 3H) |
| 99 | 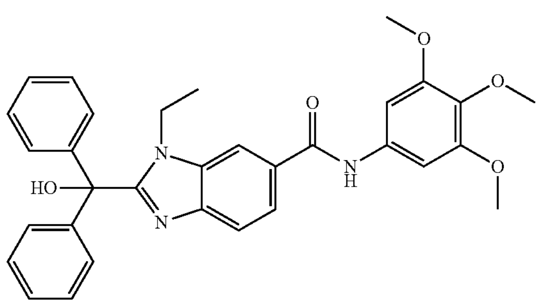 [SMILES: CCn1c(C(O)(c2ccccc2)c2ccccc2)nc2ccc(C(=O)Nc3cc(OC)c(OC)c(OC)c3)cc21] | 538 (M + H) | (400 MHz, CDCl$_3$): δ 8.05 (s, 1H), 7.86 (s, 1H), 7.85 (d, 1H), 7.68 (dd, 1H), 7.32-7.40 (m, 10H), 7.01 (s, 2H), 4.76 (s, 1H), 4.11 (q, 2H), 3.90 (s, 6H), 3.85 (s, 3H), 0.81 (t, 3H) |
| 100 | 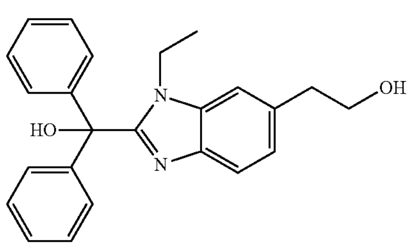 [SMILES: CCn1c(C(O)(c2ccccc2)c2ccccc2)nc2ccc(CCO)cc21] | 373 (M + H) | (400 MHz, CDCl$_3$): δ 7.74 (d, 1H), 7.30-7.37 (m, 10H), 7.18 (s, 1H), 7.16 (dd, 1H), 5.17 (s, 1H), 3.98 (q, 2H), 3.92 (q, 2H), 3.00 (t, 2H), 1.40 (t, 1H), 0.69 (t, 3H) |

TABLE 1-continued
| No. | Structure | Mass Characterization | ¹H NMR Data |
|---|---|---|---|
| 101 | 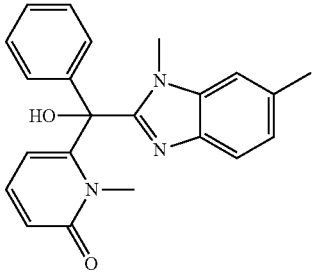 [SMILES: Cc1ccc2nc(C(O)(c3ccccc3)c3cccc(=O)n3C)n(C)c2c1] | 360 (M + H) | (400 MHz, CDCl$_3$): δ 7.62 (d, 1H), 7.61 (t, 1H), 7.29-7.32 (m, 5H), 7.11 (s, 1H), 7.06 (d, 1H), 6.97 (d, 1H), 6.71 (d, 1H), 6.70 (s, 1H), 3.95 (s, 3H), 3.59 (s, 3H), 2.50 (s, 3H) |
| 102 | 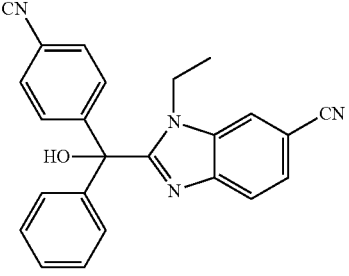 | 374 (M + H) | |
| 103 | 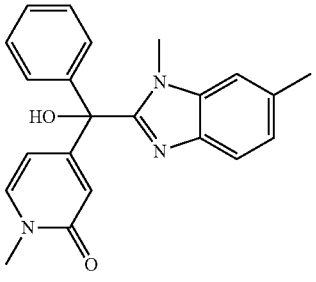 [SMILES: Cc1ccc2nc(C(O)(c3ccccc3)c3ccn(C)c(=O)c3)n(C)c2c1] | 360 (M + H) | (400 MHz, d$^6$-DMSO): δ 7.55 (d, 1H), 7.50 (d, 1H), 7.31-7.39 (m, 4H), 7.23-7.27 (m, 3H), 7.03 (dd, 1H), 6.22 (d, 1H), 6.19 (dd, 1H), 3.54 (s, 3H), 3.38 (s, 3H), 2.44 (s, 3H) |
| 104 | 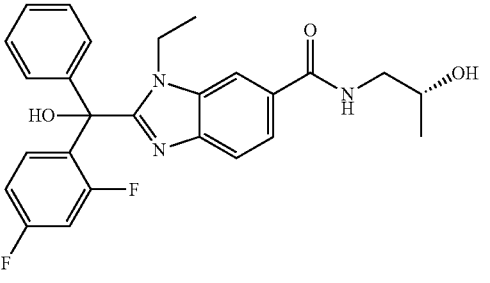 [SMILES: CCn1c(C(O)(c2ccccc2)c2ccc(F)cc2F)nc2ccc(C(=O)NC[C@@H](C)O)cc21] | 466 (M + H) | (400 MHz, CDCl$_3$): δ 7.96 (s, 1H), 7.76 (d, 1H), 7.56 (dd, 1H), 7.33-7.40 (m, 5H), 6.89-6.95 (m, 1H), 6.74-6.78 (m, 1H), 6.61-6.67 (m, 2H), 4.32-4.37 (brs, 1H), 4.03-4.31 (m, 3H), 3.66-3.73 (m, 1H), 3.32-3.39 (m, 1H), 2.80 (s, 1H), 1.27 (d, 3H), 1.04 (t, 3H) |
| 105 | 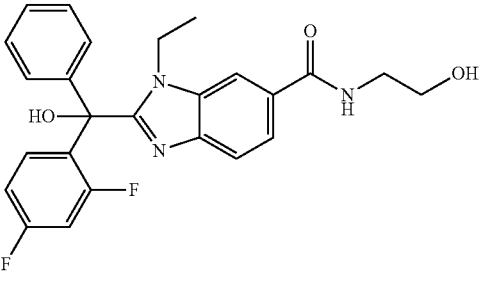 [SMILES: CCn1c(C(O)(c2ccccc2)c2ccc(F)cc2F)nc2ccc(C(=O)NCCO)cc21] | 452 (M + H) | (400 MHz, CDCl$_3$): δ 7.94 (d, 1H), 7.73 (d, 1H), 7.53 (dd, 1H), 7.33-7.40 (m, 5H), 6.88-6.94 (m, 1H), 6.74-6.78 (m, 1H), 6.63-6.71 (m, 2H), 4.33-4.40 (brs. 1H), 4.10-4.30 (m, 2H), 3.83 (t, 2H), 3.65 (q, 2H), 1.03 (t, 3H) |

TABLE 1-continued

| No. | Structure | Mass Characterization | ¹H NMR Data |
|---|---|---|---|
| 106 | 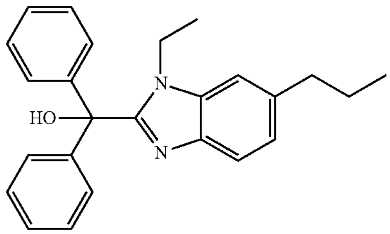 [SMILES: CCCc1ccc2nc(C(O)(c3ccccc3)c3ccccc3)n(CC)c2c1] | 371 (M + H) | (400 MHz, CDCl₃): δ 7.70 (d, 1H), 7.31-7.38 (m, 10H), 7.11-7.14 (m, 2H), 5.20-5.40 (brs, 1H), 3.97 (q, 2H), 2.73 (t, 2H), 1.67-1.76 (m, 2H), 0.99 (t, 3H), 0.68 (t, 3H) |
| 107 | 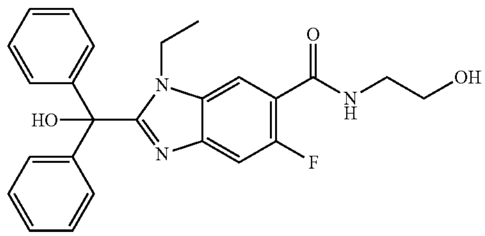 [SMILES: CCn1c(C(O)(c2ccccc2)c2ccccc2)nc2cc(F)c(C(=O)NCCO)cc21] | 434 (M + H) | (400 MHz, CDCl₃): δ 8.14 (d, 1H), 7.49 (d, 1H), 7.30-7.37 (m, 10H), 4.64 (s, 1H), 4.08 (q, 2H), 3.85 (t, 2H), 3.68 (q, 2H), 2.54-2.78 (brs, 1H), 0.80 (t, 3H) |
| 108 | 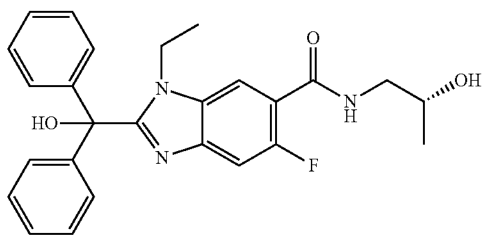 [SMILES: CCn1c(C(O)(c2ccccc2)c2ccccc2)nc2cc(F)c(C(=O)NC[C@@H](C)O)cc21] | 448 (M + H) | (400 MHz, d⁶-DMSO): δ 8.10-8.14 (brs, 1H), 7.77 (d, 1H), 7.50 (d, 1H), 7.25-7.36 (m, 11H), 4.77 (d, 1H), 4.22 (q, 2H), 3.76-3.82 (m, 1H), 3.20-3.26 (m, 2H), 1.09 (d, 3H), 1.03 (t, 3H) |
| 109 | 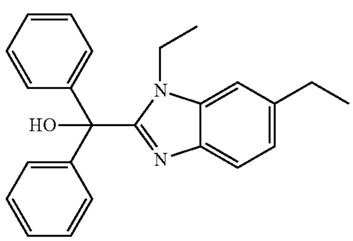 [SMILES: CCc1ccc2nc(C(O)(c3ccccc3)c3ccccc3)n(CC)c2c1] | 357 (M + H) | (400 MHz, CDCl₃): δ 7.70 (d, 1H), 7.31-7.37 (m, 10H), 7.15 (d, 1H), 7.13 (s, 1H), 5.27 (s, 1H), 3.97 (q, 2H), 2.80 (q, 2H), 1.31 (t, 3H), 0.68 (t, 3H) |
| 110 | 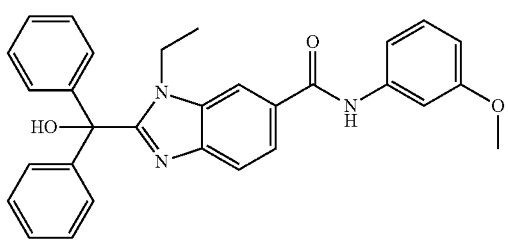 [SMILES: CCn1c(C(O)(c2ccccc2)c2ccccc2)nc2ccc(C(=O)Nc3cccc(OC)c3)cc21] | 478 (M + H) | |
| 111 | 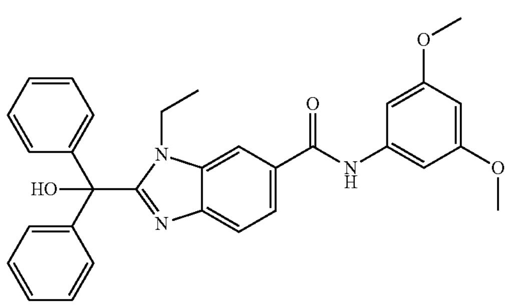 [SMILES: CCn1c(C(O)(c2ccccc2)c2ccccc2)nc2ccc(C(=O)Nc3cc(OC)cc(OC)c3)cc21] | 508 (M + H) | |

TABLE 1-continued

| No. | Structure | Mass Characterization | ¹H NMR Data |
|-----|-----------|----------------------|-------------|
| 112 | 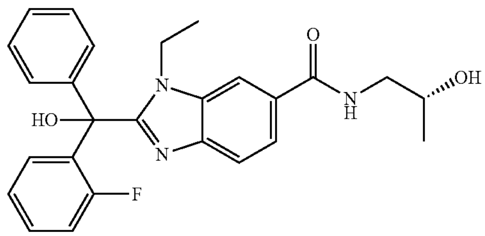 [SMILES: CCn1c(C(O)(c2ccccc2)c2ccccc2F)nc2ccc(C(=O)NC[C@@H](C)O)cc21] | 448 (M + H) | |
| 113 | 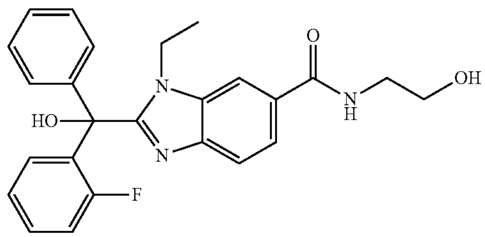 [SMILES: CCn1c(C(O)(c2ccccc2)c2ccccc2F)nc2ccc(C(=O)NCCO)cc21] | 434 (M + H) | |
| 114 | 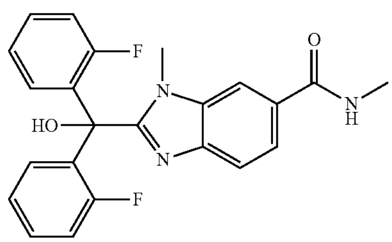 [SMILES: CNC(=O)c1ccc2nc(C(O)(c3ccccc3F)c3ccccc3F)n(C)c2c1] | 408 (M + H) | |
| 115 | 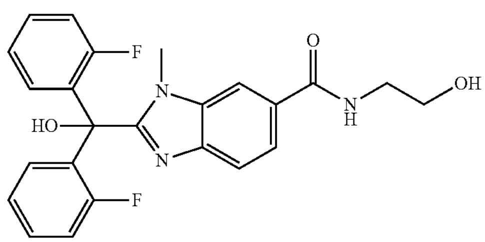 [SMILES: Cn1c(C(O)(c2ccccc2F)c2ccccc2F)nc2ccc(C(=O)NCCO)cc21] | 438 (M + H) | |
| 116 | 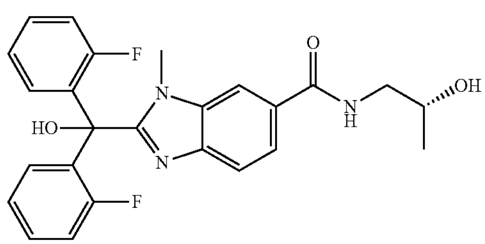 [SMILES: C[C@@H](O)CNC(=O)c1ccc2nc(C(O)(c3ccccc3F)c3ccccc3F)n(C)c2c1] | 452 (M + H) | |
| 117 | 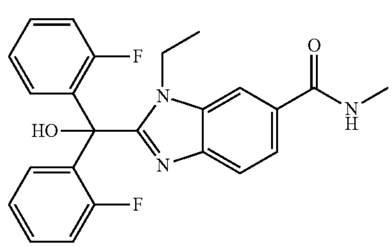 [SMILES: CCn1c(C(O)(c2ccccc2F)c2ccccc2F)nc2ccc(C(=O)NC)cc21] | 422 (M + H) | |

TABLE 1-continued

| No. | Structure | Mass Characterization | ¹H NMR Data |
|---|---|---|---|
| 118 | 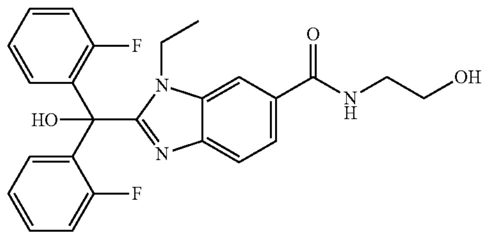 [SMILES: CCn1c(C(O)(c2ccccc2F)c2ccccc2F)nc2ccc(C(=O)NCCO)cc21] | 452 (M + H) | |
| 119 | 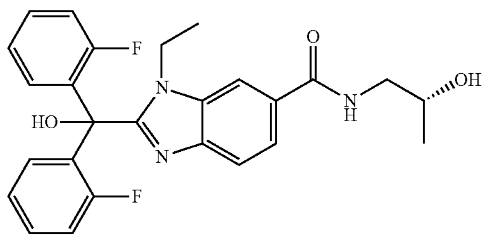 [SMILES: CCn1c(C(O)(c2ccccc2F)c2ccccc2F)nc2ccc(C(=O)NC[C@@H](C)O)cc21] | 466 (M + H) | |
| 120 | 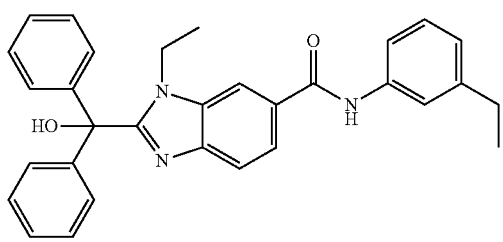 [SMILES: CCc1cccc(NC(=O)c2ccc3nc(C(O)(c4ccccc4)c4ccccc4)n(CC)c3c2)c1] | 476 (M + H) | |
| 121 | 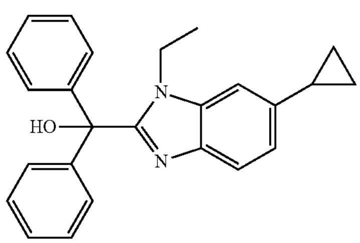 [SMILES: CCn1c(C(O)(c2ccccc2)c2ccccc2)nc2ccc(C3CC3)cc21] | 369 (M + H) | |
| 122 | 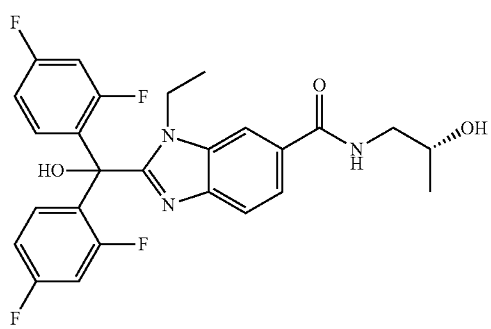 [SMILES: CCn1c(C(O)(c2ccc(F)cc2F)c2ccc(F)cc2F)nc2ccc(C(=O)NC[C@@H](C)O)cc21] | 502 (M + H) | |

TABLE 1-continued

| No. | Structure | Mass Characterization | ¹H NMR Data |
|---|---|---|---|
| 123 | 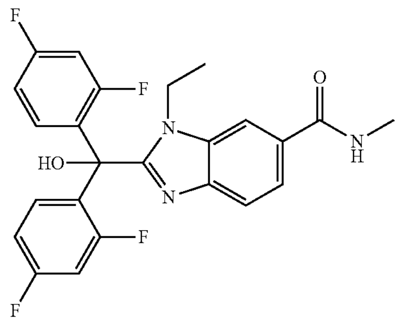 [SMILES: CCn1c(C(O)(c2ccc(F)cc2F)c2ccc(F)cc2F)nc2ccc(C(=O)NC)cc21] | 458 (M + H) | |
| 124 | 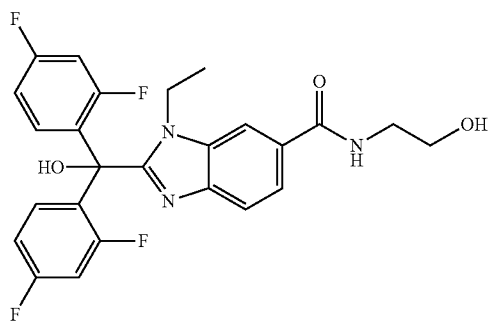 [SMILES: CCn1c(C(O)(c2ccc(F)cc2F)c2ccc(F)cc2F)nc2ccc(C(=O)NCCO)cc21] | 488 (M + H) | |
| 125 | 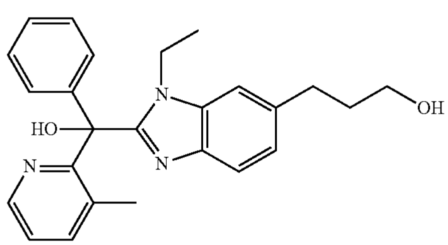 | 406 (M + H) | |
| 126 | 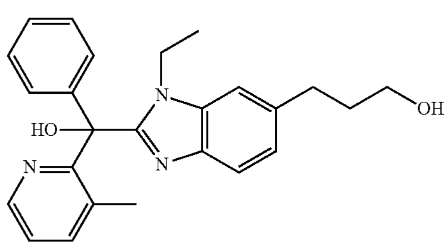 [SMILES: CCn1c(C(O)(c2ccccc2)c2ncccc2C)nc2ccc(CCCO)cc21] | 402 (M + H) | |
| 127 | 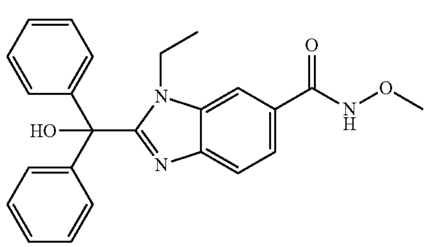 | 402 (M + H) | |

TABLE 1-continued

| No. | Structure | Mass Characterization | ¹H NMR Data |
|---|---|---|---|
| 128 | 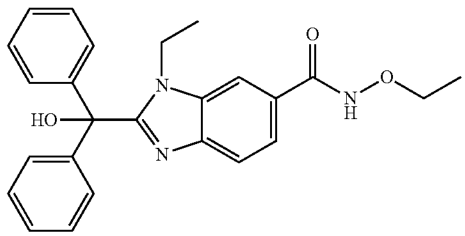 [SMILES: CCONC(=O)c1ccc2nc(C(O)(c3ccccc3)c3ccccc3)n(CC)c2c1] | 416 (M + H) | |
| 129 | 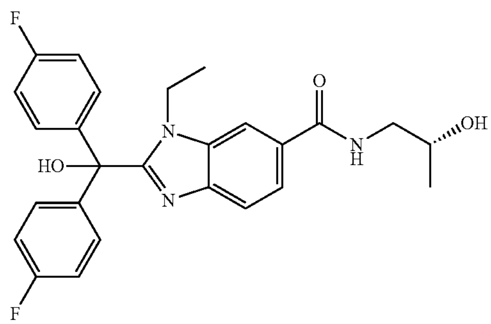 [SMILES: CCn1c(C(O)(c2ccc(F)cc2)c2ccc(F)cc2)nc2ccc(C(=O)NC[C@@H](C)O)cc21] | 466 (M + H) | |
| 130 | 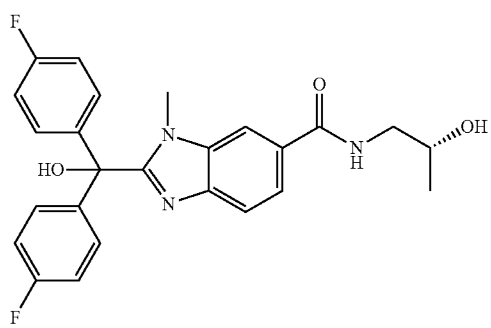 [SMILES: C[C@@H](O)CNC(=O)c1ccc2nc(C(O)(c3ccc(F)cc3)c3ccc(F)cc3)n(C)c2c1] | 452 (M + H) | |
| 131 | 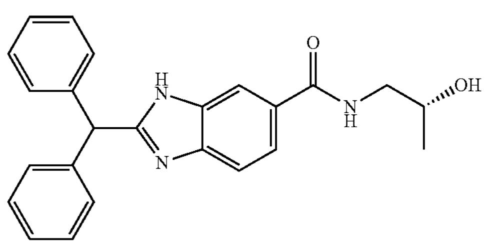 [SMILES: C[C@@H](O)CNC(=O)c1ccc2nc(C(c3ccccc3)c3ccccc3)[nH]c2c1] | 386 (M + H) | |
| 132 | 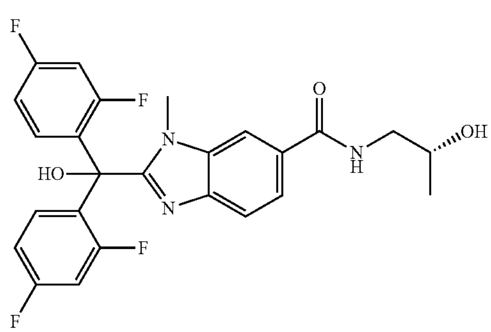 [SMILES: C[C@@H](O)CNC(=O)c1ccc2nc(C(O)(c3ccc(F)cc3F)c3ccc(F)cc3F)n(C)c2c1] | 488 (M + H) | |

TABLE 1-continued

| No. | Structure | Mass Characterization | ¹H NMR Data |
|---|---|---|---|
| 133 | 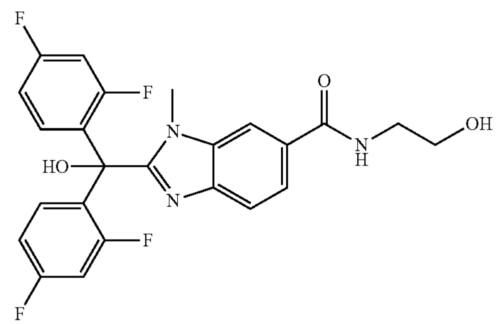 [SMILES: Cn1c(C(O)(c2ccc(F)cc2F)c2ccc(F)cc2F)nc2ccc(C(=O)NCCO)cc21] | 474 (M + H) | |
| 134 | 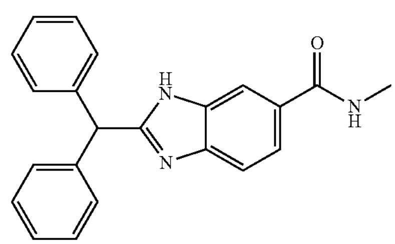 [SMILES: CNC(=O)c1ccc2nc(C(c3ccccc3)c3ccccc3)[nH]c2c1] | 342 (M + H) | |
| 135 | 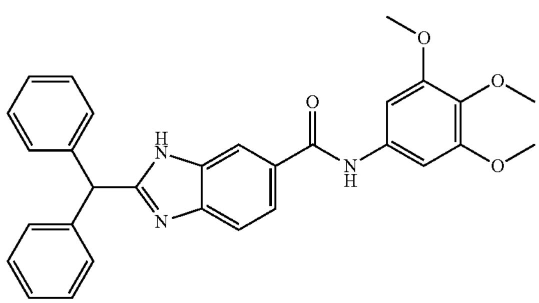 [SMILES: COc1cc(NC(=O)c2ccc3nc(C(c4ccccc4)c4ccccc4)[nH]c3c2)cc(OC)c1OC] | 494 (M + H) | |
| 136 | 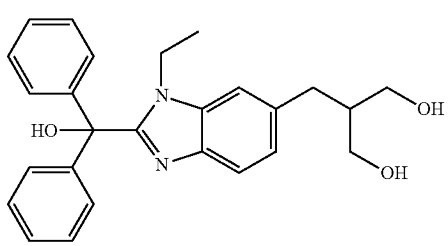 [SMILES: CCn1c(C(O)(c2ccccc2)c2ccccc2)nc2ccc(CC(CO)CO)cc21] | 417 (M + H) | |
| 137 | 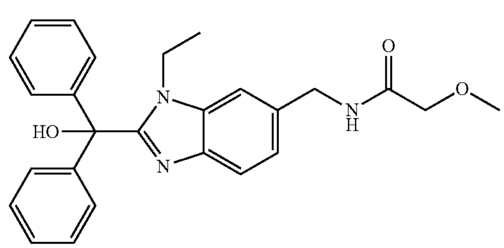 [SMILES: CCn1c(C(O)(c2ccccc2)c2ccccc2)nc2ccc(CNC(=O)COC)cc21] | 430 (M + H) | |

TABLE 1-continued

| No. | Structure | Mass Characterization | ¹H NMR Data |
|---|---|---|---|
| 138 | 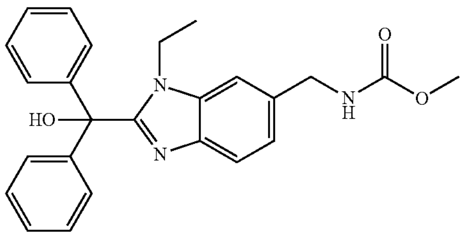 [SMILES: CCn1c(C(O)(c2ccccc2)c2ccccc2)nc2ccc(CNC(=O)OC)cc21] | 416 (M + H) | |
| 139 | 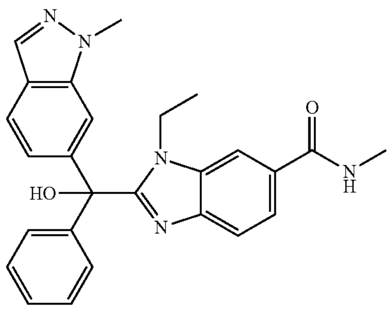 [SMILES: CCn1c(C(O)(c2ccccc2)c2ccc3cnn(C)c3c2)nc2ccc(C(=O)NC)cc21] | 440 (M + H) | |
| 140 | 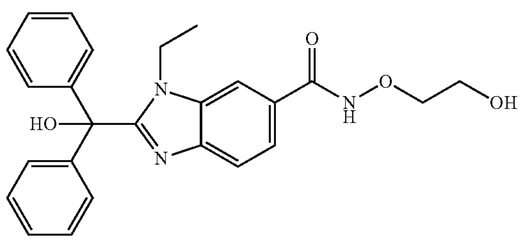 [SMILES: CCn1c(C(O)(c2ccccc2)c2ccccc2)nc2ccc(C(=O)NOCCO)cc21] | 432 (M + H) | |
| 141 | 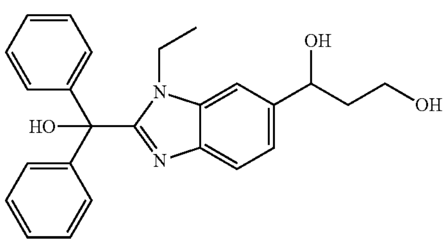 [SMILES: CCn1c(C(O)(c2ccccc2)c2ccccc2)nc2ccc(C(O)CCO)cc21] | 403 (M + H) | |
| 142 | 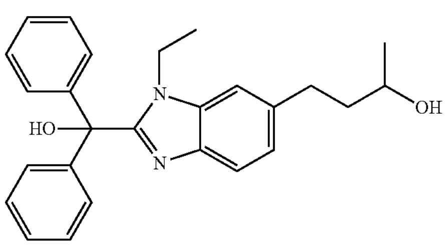 [SMILES: CCn1c(C(O)(c2ccccc2)c2ccccc2)nc2ccc(CCC(C)O)cc21] | 401 (M + H) | |
| 143 | 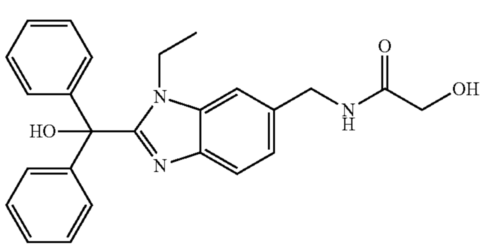 [SMILES: CCn1c(C(O)(c2ccccc2)c2ccccc2)nc2ccc(CNC(=O)CO)cc21] | 416 (M + H) | |

TABLE 1-continued

| No. | Structure | Mass Characterization | ¹H NMR Data |
|---|---|---|---|
| 144 | 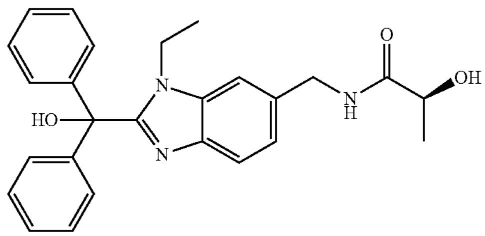 [SMILES: CCn1c(C(O)(c2ccccc2)c2ccccc2)nc2ccc(CNC(=O)[C@H](C)O)cc21] | 430 (M + H) | |
| 145 | 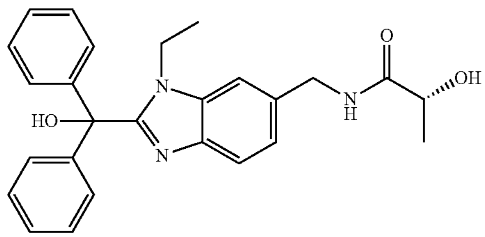 [SMILES: CCn1c(C(O)(c2ccccc2)c2ccccc2)nc2ccc(CNC(=O)[C@@H](C)O)cc21] | 430 (M + H) | |
| 146 | 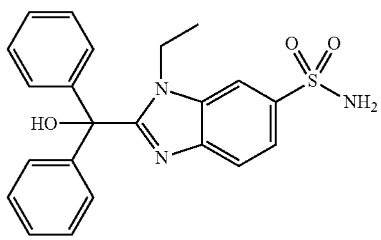 [SMILES: CCn1c(C(O)(c2ccccc2)c2ccccc2)nc2ccc(S(N)(=O)=O)cc21] | 408 (M + H) | |
| 147 | 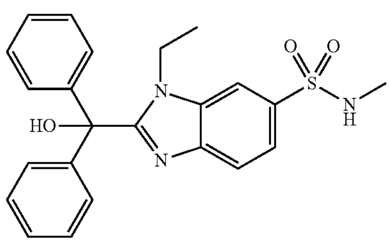 [SMILES: CCn1c(C(O)(c2ccccc2)c2ccccc2)nc2ccc(S(=O)(=O)NC)cc21] | 422 (M + H) | |
| 148 | 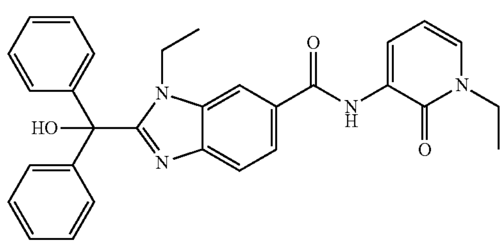 [SMILES: CCn1cccc(NC(=O)c2ccc3nc(C(O)(c4ccccc4)c4ccccc4)n(CC)c3c2)c1=O] | 493 (M + H) | |
| 149 | 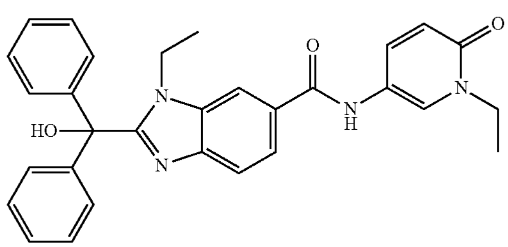 [SMILES: CCn1cc(NC(=O)c2ccc3nc(C(O)(c4ccccc4)c4ccccc4)n(CC)c3c2)ccc1=O] | 493 (M + H) | |

TABLE 1-continued

| No. | Structure | Mass Characterization | ¹H NMR Data |
|---|---|---|---|
| 150 | 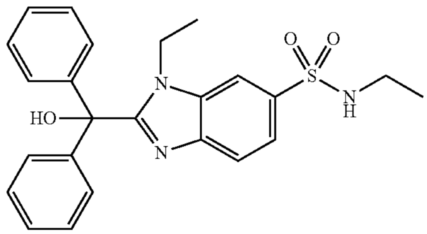 [SMILES: CCNS(=O)(=O)c1ccc2nc(C(O)(c3ccccc3)c3ccccc3)n(CC)c2c1] | 436 (M + H) | |
| 151 | 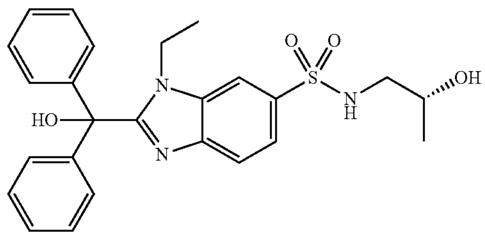 [SMILES: CCn1c(C(O)(c2ccccc2)c2ccccc2)nc2ccc(S(=O)(=O)NC[C@@H](C)O)cc21] | 466 (M + H) | |
| 152 | 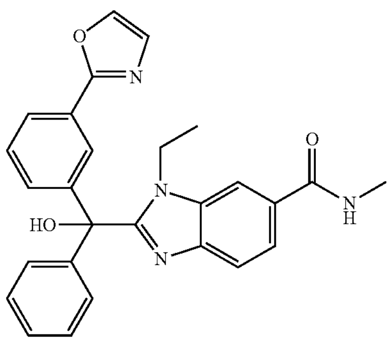 [SMILES: CCn1c(C(O)(c2ccccc2)c2cccc(-c3ncco3)c2)nc2ccc(C(=O)NC)cc21] | 453 (M + H) | |
| 153 | 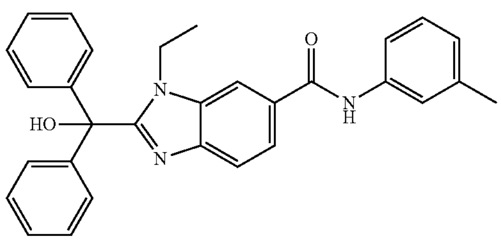 | 562 (M + H) | |
| 154 | 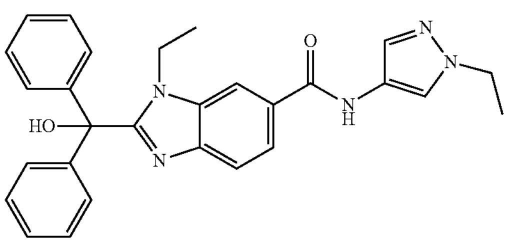 [SMILES: CCn1cc(NC(=O)c2ccc3nc(C(O)(c4ccccc4)c4ccccc4)n(CC)c3c2)cn1] | 466 (M + H) | |
| 155 | 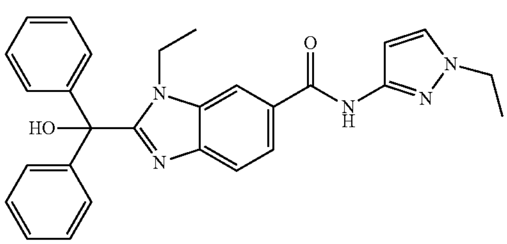 [SMILES: CCn1ccc(NC(=O)c2ccc3nc(C(O)(c4ccccc4)c4ccccc4)n(CC)c3c2)n1] | 466 (M + H) | |

TABLE 1-continued

| No. | Structure | Mass Characterization | ¹H NMR Data |
|---|---|---|---|
| 156 | 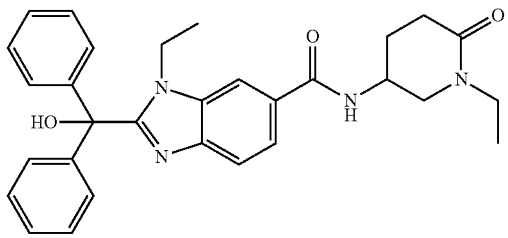 [SMILES: CCN1CC(NC(=O)c2ccc3nc(C(O)(c4ccccc4)c4ccccc4)n(CC)c3c2)CCC1=O] | 497 (M + H) | |
| 157 | 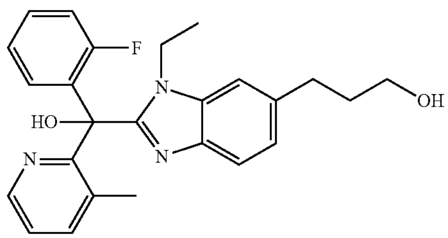 [SMILES: CCn1c(C(O)(c2ccccc2F)c2ncccc2C)nc2ccc(CCCO)cc21] | 420 (M + H) | |
| 158 | 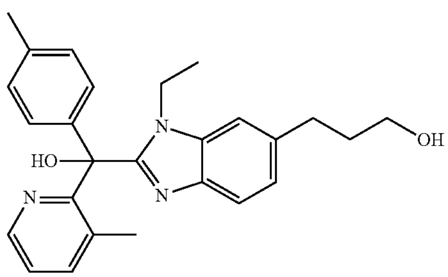 [SMILES: CCn1c(C(O)(c2ccc(C)cc2)c2ncccc2C)nc2ccc(CCCO)cc21] | 416 (M + H) | |
| 159 | 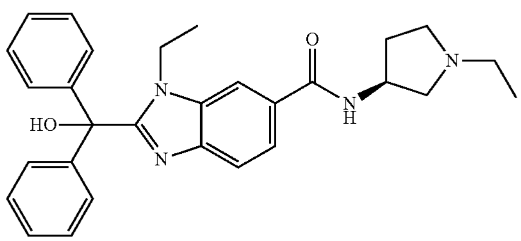 [SMILES: CCN1CC[C@H](NC(=O)c2ccc3nc(C(O)(c4ccccc4)c4ccccc4)n(CC)c3c2)C1] | 469 (M + H) | |
| 160 | 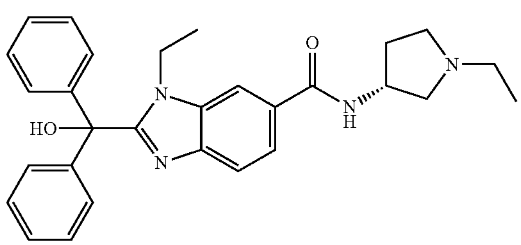 [SMILES: CCN1CC[C@@H](NC(=O)c2ccc3nc(C(O)(c4ccccc4)c4ccccc4)n(CC)c3c2)C1] | 469 (M + H) | |
| 161 | 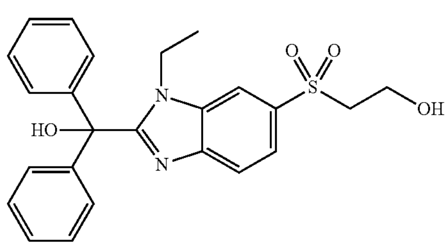 [SMILES: CCn1c(C(O)(c2ccccc2)c2ccccc2)nc2ccc(S(=O)(=O)CCO)cc21] | 437 (M + H) | |

TABLE 1-continued

| No. | Structure | Mass Characterization | ¹H NMR Data |
|---|---|---|---|
| 162 | 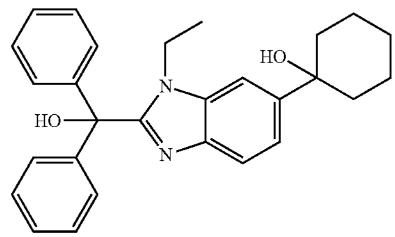 [SMILES: CCn1c(C(O)(c2ccccc2)c2ccccc2)nc2ccc(C3(O)CCCCC3)cc21] | 427 (M + H) | |
| 163 | 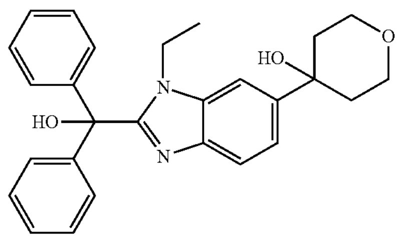 [SMILES: CCn1c(C(O)(c2ccccc2)c2ccccc2)nc2ccc(C3(O)CCOCC3)cc21] | 429 (M + H) | |
| 164 | 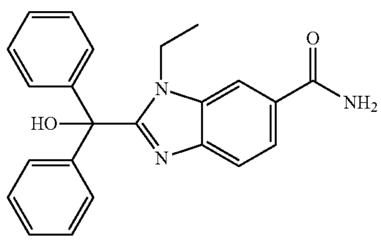 [SMILES: CCn1c(C(O)(c2ccccc2)c2ccccc2)nc2ccc(C(N)=O)cc21] | 372 (M + H) | |
| 165 | 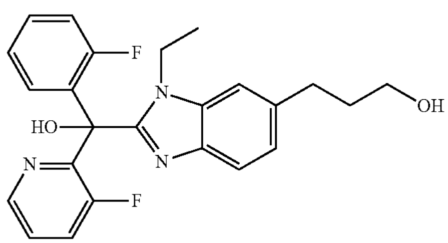 [SMILES: CCn1c(C(O)(c2ccccc2F)c2ncccc2F)nc2ccc(CCCO)cc21] | 424 (M + H) | |
| 166 | 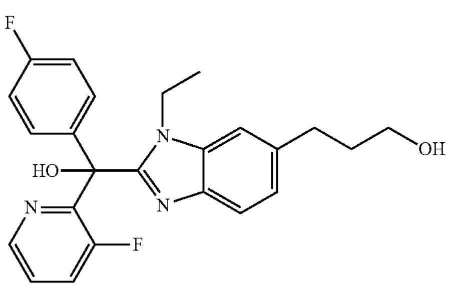 [SMILES: CCn1c(C(O)(c2ccc(F)cc2)c2ncccc2F)nc2ccc(CCCO)cc21] | 424 (M + H) | |
| 167 | 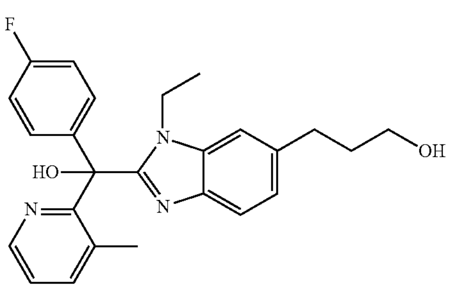 [SMILES: CCn1c(C(O)(c2ccc(F)cc2)c2ncccc2C)nc2ccc(CCCO)cc21] | 420 (M + H) | |

TABLE 1-continued

| No. | Structure | Mass Characterization | ¹H NMR Data |
|---|---|---|---|
| 168 | 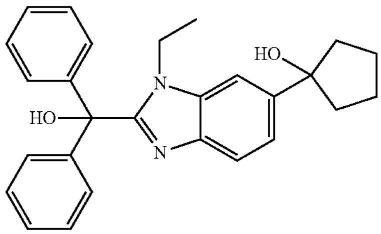 [SMILES: CCn1c(C(O)(c2ccccc2)c2ccccc2)nc2ccc(C3(O)CCCC3)cc21] | 413 (M + H) | |
| 169 | 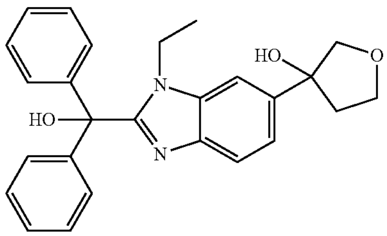 [SMILES: CCn1c(C(O)(c2ccccc2)c2ccccc2)nc2ccc(C3(O)CCOC3)cc21] | 415 (M + H) | |
| 170 | 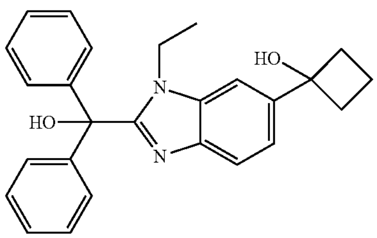 [SMILES: CCn1c(C(O)(c2ccccc2)c2ccccc2)nc2ccc(C3(O)CCC3)cc21] | 399 (M + H) | |
| 171 | 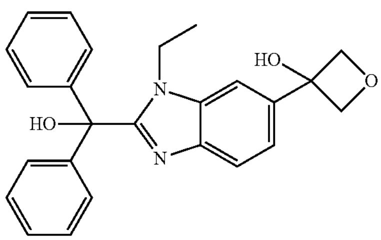 [SMILES: CCn1c(C(O)(c2ccccc2)c2ccccc2)nc2ccc(C3(O)COC3)cc21] | 401 (M + H) | |
| 172 | 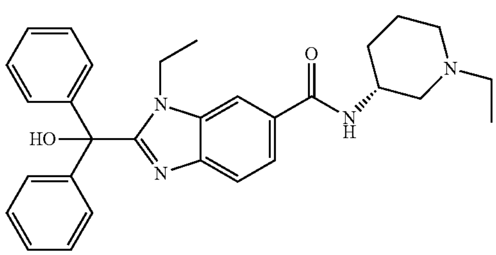 [SMILES: CCN1CCC[C@@H](NC(=O)c2ccc3nc(C(O)(c4ccccc4)c4ccccc4)n(CC)c3c2)C1] | 483 (M + H) | |
| 173 | 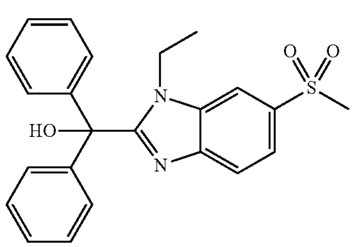 [SMILES: CCn1c(C(O)(c2ccccc2)c2ccccc2)nc2ccc(S(C)(=O)=O)cc21] | 389 (M + H) | |

TABLE 1-continued

| No. | Structure | Mass Characterization | ¹H NMR Data |
|---|---|---|---|
| 174 | 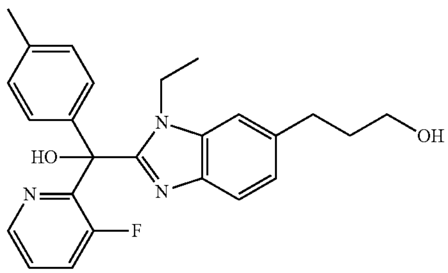 [SMILES: CCn1c(C(O)(c2ccc(C)cc2)c2ncccc2F)nc2ccc(CCCO)cc21] | 420 (M + H) | |
| 175 | 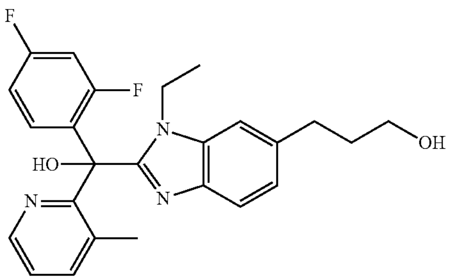 [SMILES: CCn1c(C(O)(c2ccc(F)cc2F)c2ncccc2C)nc2ccc(CCCO)cc21] | 438 (M + H) | |
| 176 | 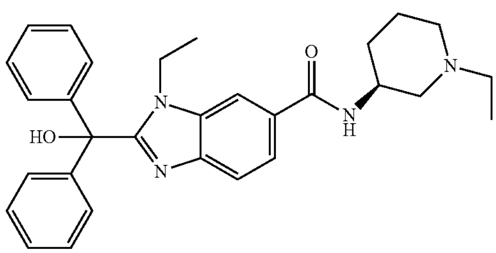 [SMILES: CCN1CCC[C@H](NC(=O)c2ccc3nc(C(O)(c4ccccc4)c4ccccc4)n(CC)c3c2)C1] | 483 (M + H) | |
| 177 | 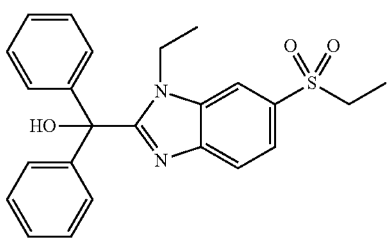 [SMILES: CCn1c(C(O)(c2ccccc2)c2ccccc2)nc2ccc(S(=O)(=O)CC)cc21] | 421 (M + H) | |
| 178 | 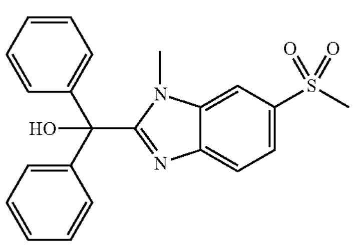 [SMILES: Cn1c(C(O)(c2ccccc2)c2ccccc2)nc2ccc(S(C)(=O)=O)cc21] | 393 (M + H) | |

TABLE 1-continued
| No. | Structure | Mass Characterization | ¹H NMR Data |
|---|---|---|---|
| 179 | 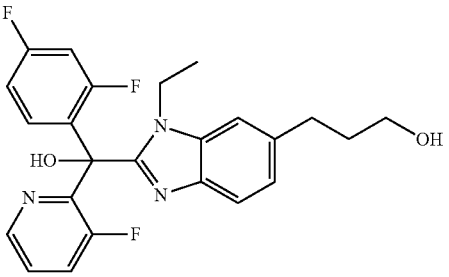 | 420 (M + H) | |
| 180 | 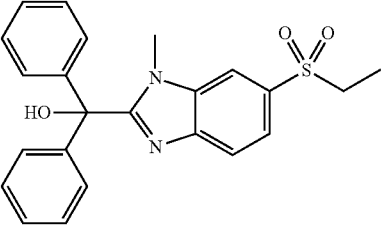 [SMILES: CCS(=O)(=O)c1ccc2nc(C(O)(c3ccccc3)c3ccccc3)n(C)c2c1] | 407 (M + H) | |
| 181 | 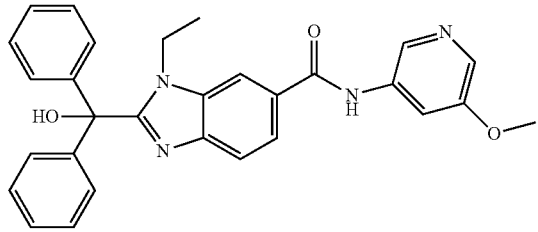 [SMILES: CCn1c(C(O)(c2ccccc2)c2ccccc2)nc2ccc(C(=O)Nc3cncc(OC)c3)cc21] | 479 (M + H) | |
| 182 | 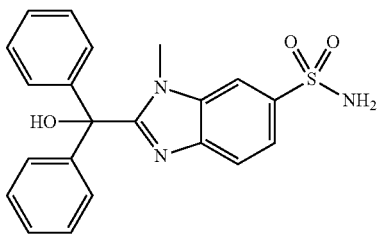 [SMILES: Cn1c(C(O)(c2ccccc2)c2ccccc2)nc2ccc(S(N)(=O)=O)cc21] | 394 (M + H) | |
| 183 | 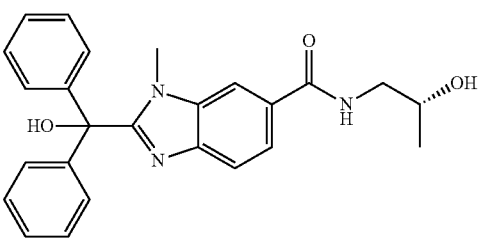 [SMILES: C[C@@H](O)CNC(=O)c1ccc2nc(C(O)(c3ccccc3)c3ccccc3)n(C)c2c1] | 416 (M + H) | |
| 184 | 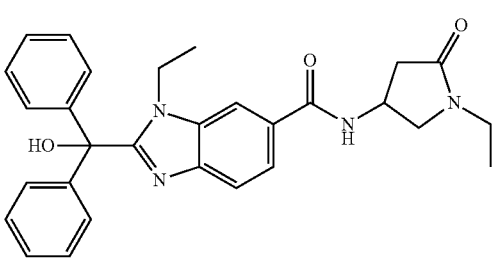 [SMILES: CCN1CC(NC(=O)c2ccc3nc(C(O)(c4ccccc4)c4ccccc4)n(CC)c3c2)CC1=O] | 483 (M + H) | |

TABLE 1-continued

| No. | Structure | Mass Characterization | ¹H NMR Data |
|---|---|---|---|
| 185 | 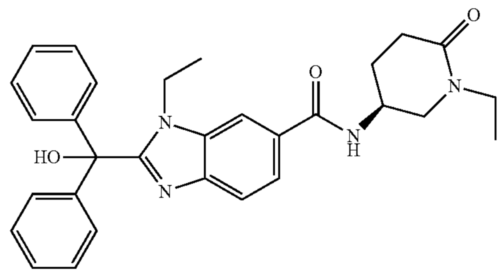 [SMILES: CCN1C[C@@H](NC(=O)c2ccc3nc(C(O)(c4ccccc4)c4ccccc4)n(CC)c3c2)CCC1=O] | 497 (M + H) | |
| 186 | 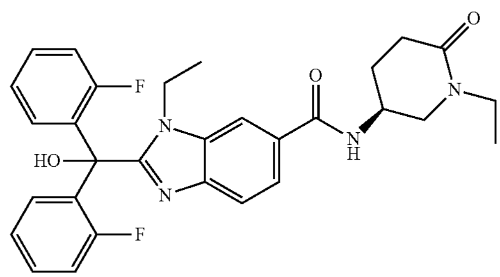 [SMILES: CCN1C[C@@H](NC(=O)c2ccc3nc(C(O)(c4ccccc4F)c4ccccc4F)n(CC)c3c2)CCC1=O] | 533 (M + H) | |
| 187 | 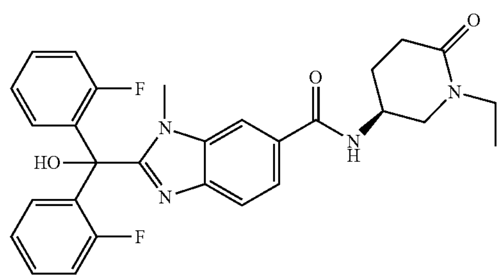 [SMILES: CCN1C[C@@H](NC(=O)c2ccc3nc(C(O)(c4ccccc4F)c4ccccc4F)n(C)c3c2)CCC1=O] | 519 (M + H) | |
| 188 | 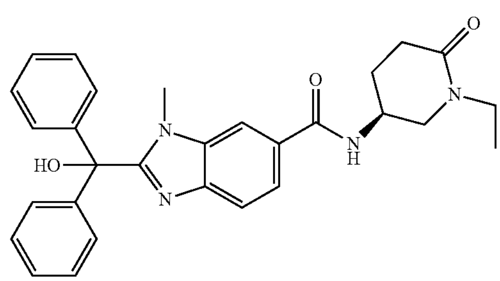 [SMILES: CCN1C[C@@H](NC(=O)c2ccc3nc(C(O)(c4ccccc4)c4ccccc4)n(C)c3c2)CCC1=O] | 483 (M + H) | |
| 189 | 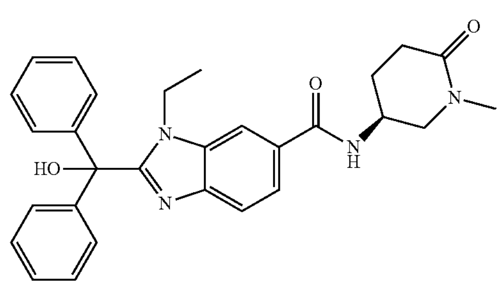 [SMILES: CCn1c(C(O)(c2ccccc2)c2ccccc2)nc2ccc(C(=O)N[C@H]3CCC(=O)N(C)C3)cc21] | 483 (M + H) | |

TABLE 1-continued

| No. | Structure | Mass Characterization | ¹H NMR Data |
|---|---|---|---|
| 190 | 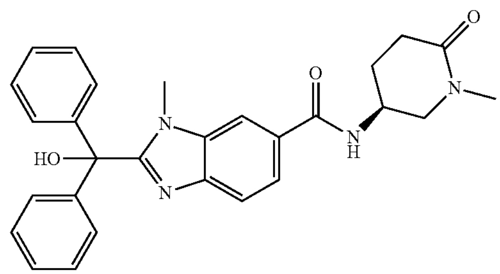 [SMILES: CN1C[C@@H](NC(=O)c2ccc3nc(C(O)(c4ccccc4)c4ccccc4)n(C)c3c2)CCC1=O] | 469 (M + H) | |
| 191 | 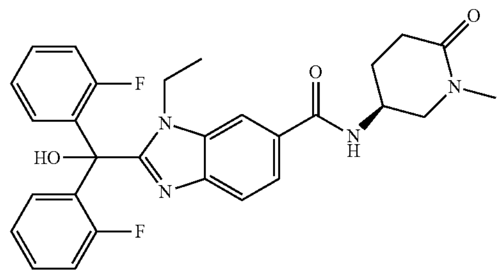 [SMILES: CCn1c(C(O)(c2ccccc2F)c2ccccc2F)nc2ccc(C(=O)N[C@H]3CCC(=O)N(C)C3)cc21] | 519 (M + H) | |
| 192 | 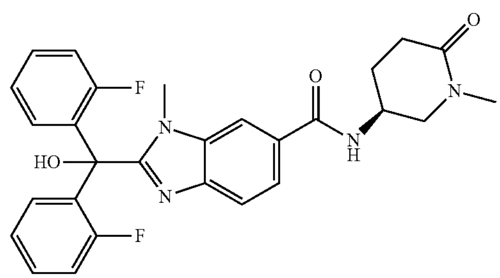 [SMILES: CN1C[C@@H](NC(=O)c2ccc3nc(C(O)(c4ccccc4F)c4ccccc4F)n(C)c3c2)CCC1=O] | 505 (M + H) | |
| 193 | 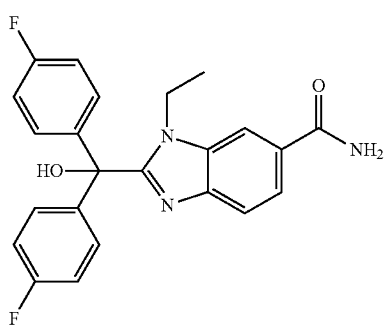 | 394 (M + H) | |
| 194 | 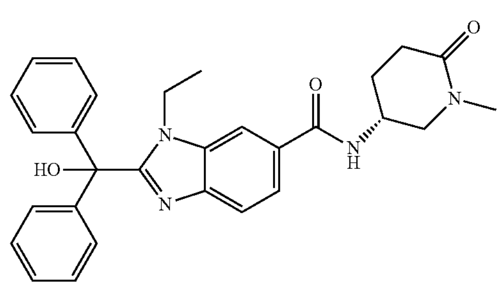 [SMILES: CCn1c(C(O)(c2ccccc2)c2ccccc2)nc2ccc(C(=O)N[C@@H]3CCC(=O)N(C)C3)cc21] | 483 (M + H) | |

TABLE 1-continued

| No. | Structure | Mass Characterization | ¹H NMR Data |
|-----|-----------|----------------------|-------------|
| 195 | 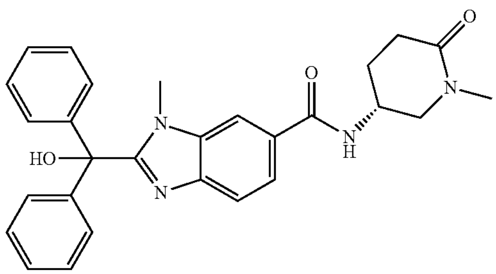 [SMILES: CN1C[C@H](NC(=O)c2ccc3nc(C(O)(c4ccccc4)c4ccccc4)n(C)c3c2)CCC1=O] | 469 (M + H) | |
| 196 | 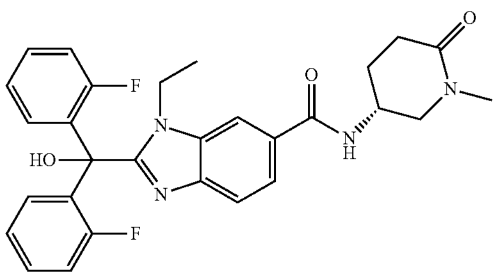 [SMILES: CCn1c(C(O)(c2ccccc2F)c2ccccc2F)nc2ccc(C(=O)N[C@@H]3CCC(=O)N(C)C3)cc21] | 519 (M + H) | |
| 197 | 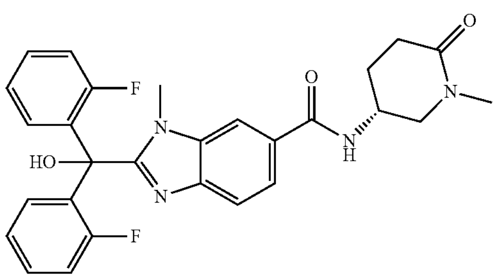 [SMILES: CN1C[C@H](NC(=O)c2ccc3nc(C(O)(c4ccccc4F)c4ccccc4F)n(C)c3c2)CCC1=O] | 505 (M + H) | |
| 198 | 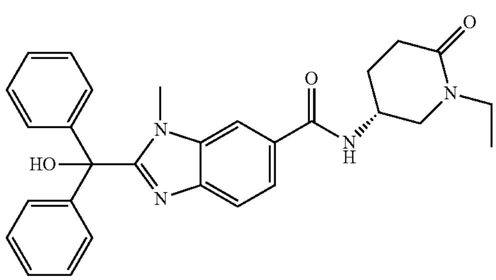 [SMILES: CCN1C[C@H](NC(=O)c2ccc3nc(C(O)(c4ccccc4)c4ccccc4)n(C)c3c2)CCC1=O] | 483 (M + H) | |
| 199 | 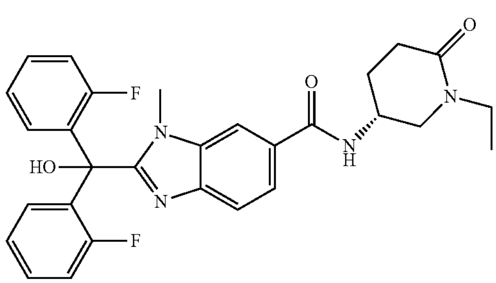 [SMILES: CCN1C[C@H](NC(=O)c2ccc3nc(C(O)(c4ccccc4F)c4ccccc4F)n(C)c3c2)CCC1=O] | 519 (M + H) | |

TABLE 1-continued

| No. | Structure | Mass Characterization | ¹H NMR Data |
|---|---|---|---|
| 200 | 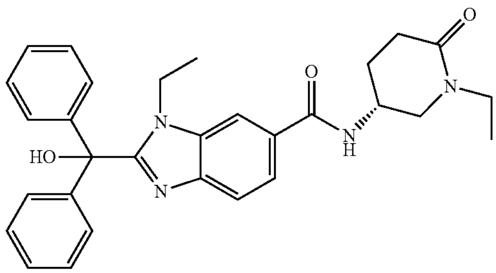 [SMILES: CCN1C[C@H](NC(=O)c2ccc3nc(C(O)(c4ccccc4)c4ccccc4)n(CC)c3c2)CCC1=O] | 497 (M + H) | |
| 201 | 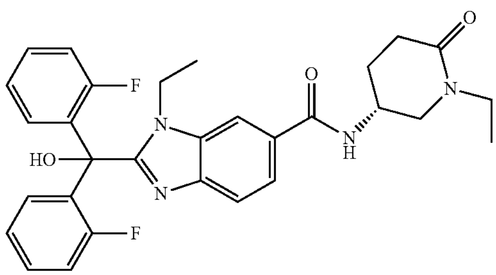 [SMILES: CCN1C[C@H](NC(=O)c2ccc3nc(C(O)(c4ccccc4F)c4ccccc4F)n(CC)c3c2)CCC1=O] | 533 (M + H) | |
| 202 | 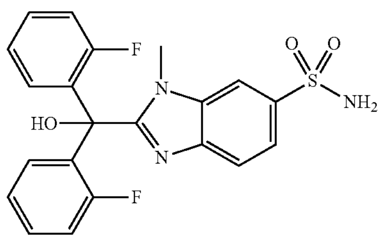 [SMILES: Cn1c(C(O)(c2ccccc2F)c2ccccc2F)nc2ccc(S(N)(=O)=O)cc21] | 430 (M + H) | |
| 203 | 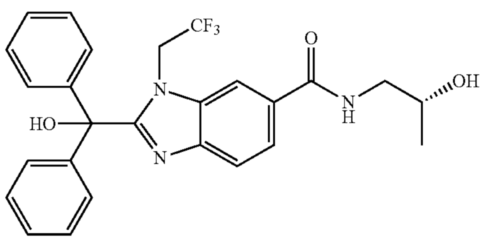 | 397 (M + H) | |
| 204 | 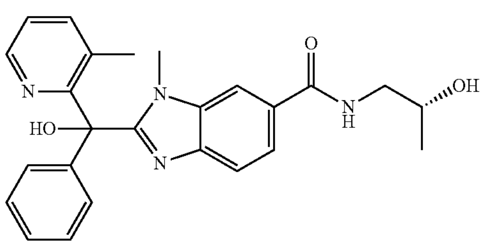 [SMILES: Cc1cccnc1C(O)(c1ccccc1)c1nc2ccc(C(=O)NC[C@@H](C)O)cc2n1C] | 431 (M + H) | |
| 205 | 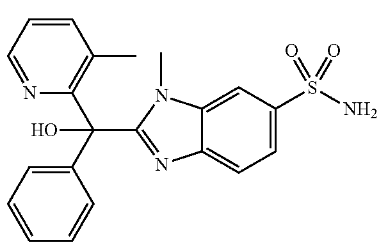 [SMILES: Cc1cccnc1C(O)(c1ccccc1)c1nc2ccc(S(N)(=O)=O)cc2n1C] | 409 (M + H) | |

TABLE 1-continued

| No. | Structure | Mass Characterization | ¹H NMR Data |
|---|---|---|---|
| 206 | 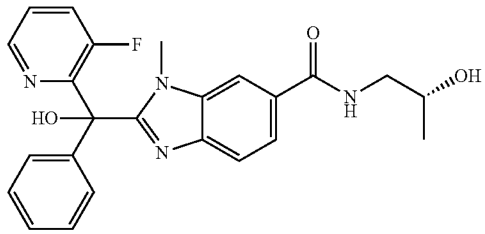 [SMILES: C[C@@H](O)CNC(=O)c1ccc2nc(C(O)(c3ccccc3)c3ncccc3F)n(C)c2c1] | 435 (M + H) | |
| 207 | 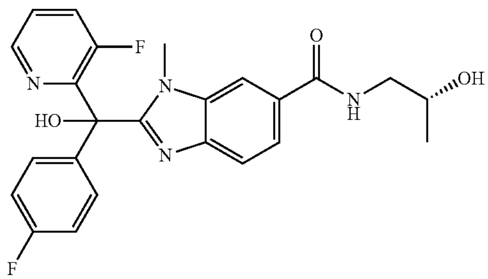 [SMILES: C[C@@H](O)CNC(=O)c1ccc2nc(C(O)(c3ccc(F)cc3)c3ncccc3F)n(C)c2c1] | 453 (M + H) | |
| 208 | 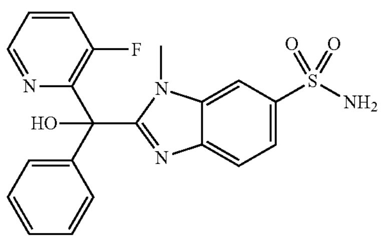 [SMILES: Cn1c(C(O)(c2ccccc2)c2ncccc2F)nc2ccc(S(N)(=O)=O)cc21] | 413 (M + H) | |
| 209 | 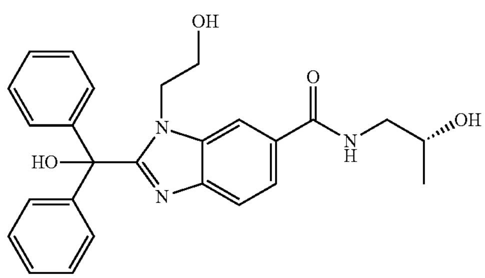 | 403 (M + H) | |
| 210 | 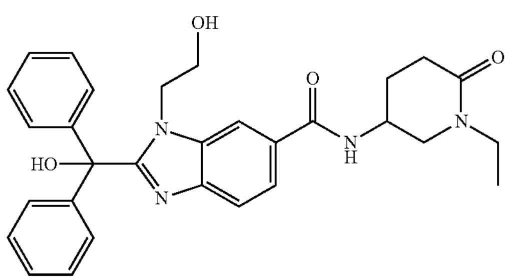 [SMILES: CCN1CC(NC(=O)c2ccc3nc(C(O)(c4ccccc4)c4ccccc4)n(CCO)c3c2)CCC1=O] | 513 (M + H) | |
| 211 | 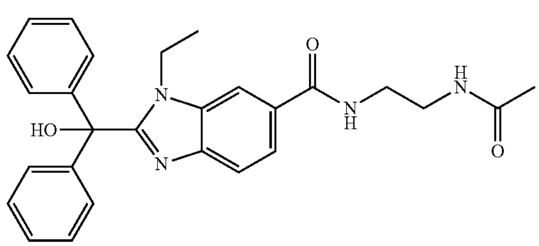 [SMILES: CCn1c(C(O)(c2ccccc2)c2ccccc2)nc2ccc(C(=O)NCCNC(C)=O)cc21] | 457 (M + H) | |

TABLE 1-continued

| No. | Structure | Mass Characterization | ¹H NMR Data |
|---|---|---|---|
| 212 | 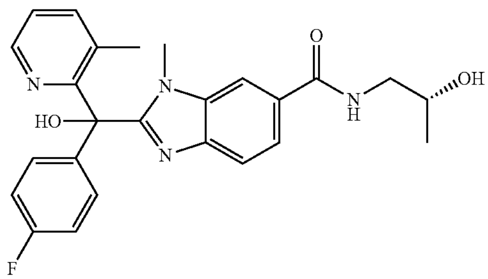 [SMILES: Cc1cccnc1C(O)(c1ccc(F)cc1)c1nc2ccc(C(=O)NC[C@@H](C)O)cc2n1C] | 449 (M + H) | |
| 213 | 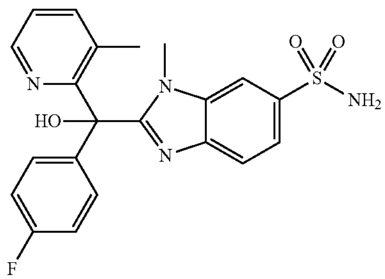 [SMILES: Cc1cccnc1C(O)(c1ccc(F)cc1)c1nc2ccc(S(N)(=O)=O)cc2n1C] | 427 (M + H) | |
| 214 | 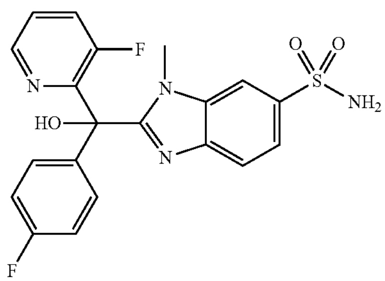 [SMILES: Cn1c(C(O)(c2ccc(F)cc2)c2ncccc2F)nc2ccc(S(N)(=O)=O)cc21] | 431 (M + H) | |
| 215 | 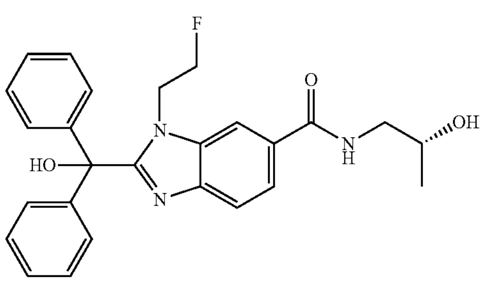 [SMILES: C[C@@H](O)CNC(=O)c1ccc2nc(C(O)(c3ccccc3)c3ccccc3)n(CCF)c2c1] | 448 (M + H) | |
| 216 | 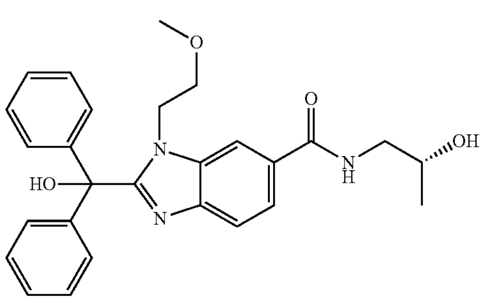 [SMILES: COCCn1c(C(O)(c2ccccc2)c2ccccc2)nc2ccc(C(=O)NC[C@@H](C)O)cc21] | 460 (M + H) | |

TABLE 1-continued

| No. | Structure | Mass Characterization | ¹H NMR Data |
|---|---|---|---|
| 217 | 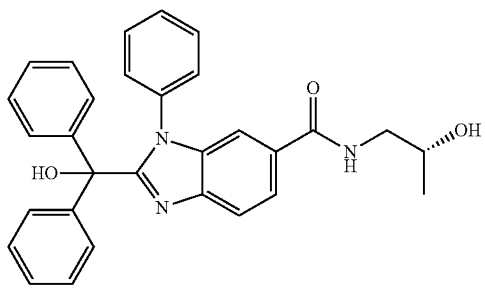 [SMILES: C[C@@H](O)CNC(=O)c1ccc2nc(C(O)(c3ccccc3)c3ccccc3)n(-c3ccccc3)c2c1] | 478 (M + H) | |
| 218 | 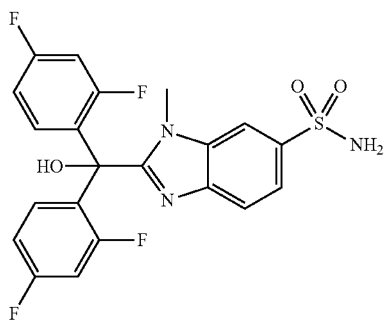 [SMILES: Cn1c(C(O)(c2ccc(F)cc2F)c2ccc(F)cc2F)nc2ccc(S(N)(=O)=O)cc21] | 466 (M + H) | |
| 219 | 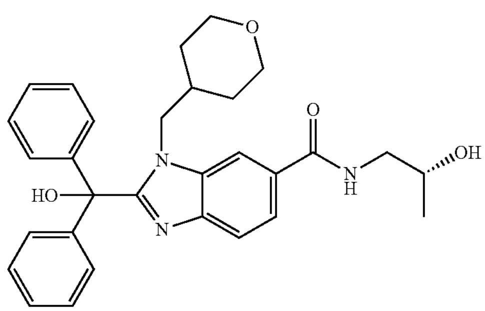 [SMILES: C[C@@H](O)CNC(=O)c1ccc2nc(C(O)(c3ccccc3)c3ccccc3)n(CC3CCOCC3)c2c1] | 500 (M + H) | |
| 220 | 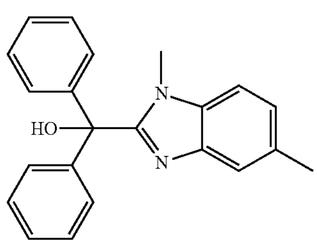 [SMILES: Cc1ccc2c(c1)nc(C(O)(c1ccccc1)c1ccccc1)n2C] | 329 (M + H) | |
| 221 | 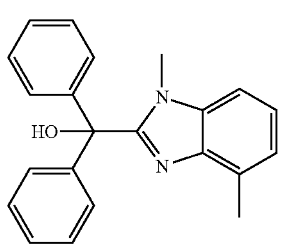 [SMILES: Cc1cccc2c1nc(C(O)(c1ccccc1)c1ccccc1)n2C] | 329 (M + H) | |

TABLE 1-continued

| No. | Structure | Mass Characterization | ¹H NMR Data |
|---|---|---|---|
| 222 | 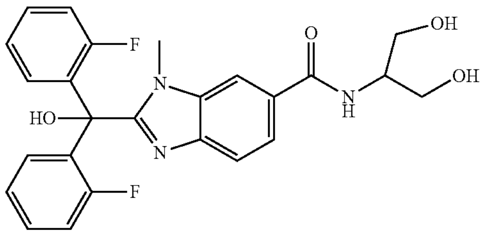 | 512 (M + H) | |
| 223 | 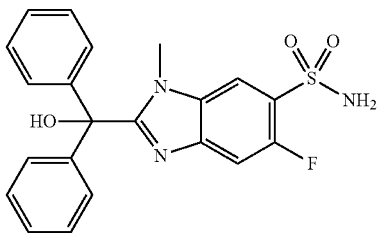 [SMILES: Cn1c(C(O)(c2ccccc2)c2ccccc2)nc2cc(F)c(S(N)(=O)=O)cc21] | 412 (M + H) | |
| 224 | 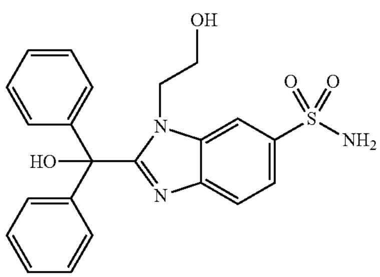 [SMILES: NS(=O)(=O)c1ccc2nc(C(O)(c3ccccc3)c3ccccc3)n(CCO)c2c1] | 424 (M + H) | |
| 225 | 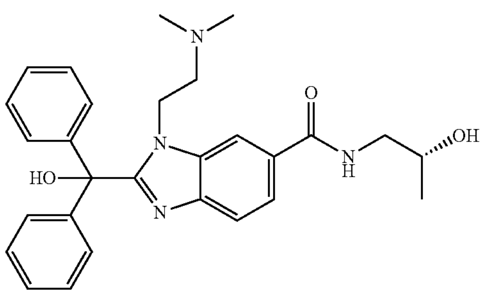 [SMILES: C[C@@H](O)CNC(=O)c1ccc2nc(C(O)(c3ccccc3)c3ccccc3)n(CCN(C)C)c2c1] | 473 (M + H) | |
| 226 | 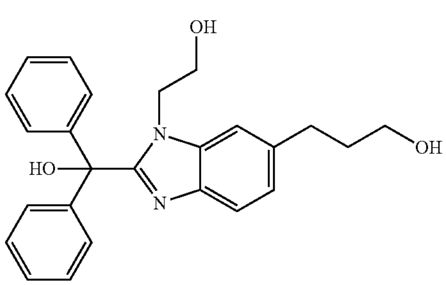 [SMILES: OCCCc1ccc2nc(C(O)(c3ccccc3)c3ccccc3)n(CCO)c2c1] | 403 (M + H) | |

TABLE 1-continued

| No. | Structure | Mass Characterization | ¹H NMR Data |
|---|---|---|---|
| 227 | 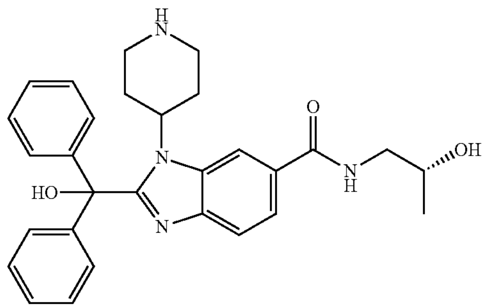 [SMILES: C[C@@H](O)CNC(=O)c1ccc2nc(C(O)(c3ccccc3)c3ccccc3)n(C3CCNCC3)c2c1] | 485 (M + H) | |
| 228 | 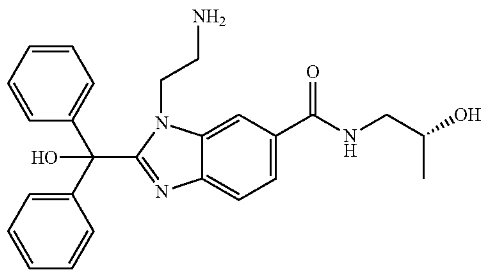 [SMILES: C[C@@H](O)CNC(=O)c1ccc2nc(C(O)(c3ccccc3)c3ccccc3)n(CCN)c2c1] | 445 (M + H) | |
| 229 | 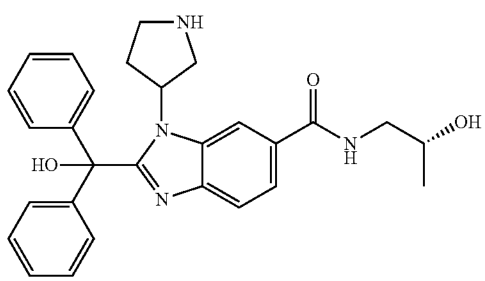 [SMILES: C[C@@H](O)CNC(=O)c1ccc2nc(C(O)(c3ccccc3)c3ccccc3)n(C3CCNC3)c2c1] | 471 (M + H) | |
| 230 | 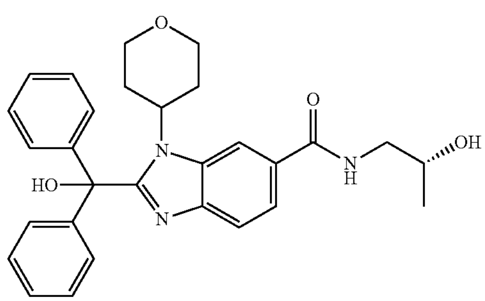 [SMILES: C[C@@H](O)CNC(=O)c1ccc2nc(C(O)(c3ccccc3)c3ccccc3)n(C3CCOCC3)c2c1] | 486 (M + H) | |
| 231 | 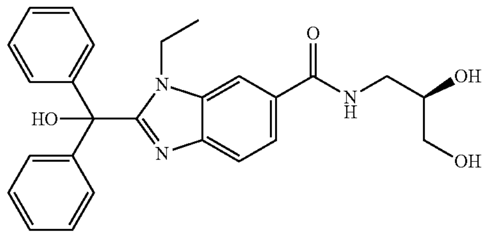 [SMILES: CCn1c(C(O)(c2ccccc2)c2ccccc2)nc2ccc(C(=O)NC[C@@H](O)CO)cc21] | 446 (M + H) | |

TABLE 1-continued

| No. | Structure | Mass Characterization | ¹H NMR Data |
|-----|-----------|----------------------|-------------|
| 232 | 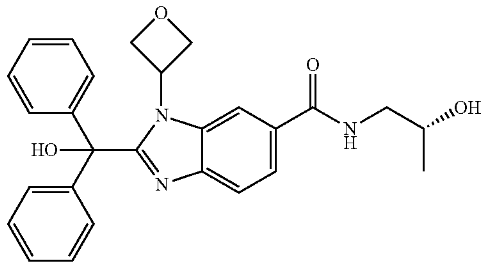 [SMILES: C[C@@H](O)CNC(=O)c1ccc2nc(C(O)(c3ccccc3)c3ccccc3)n(C3COC3)c2c1] | 458 (M + H) | |
| 233 | 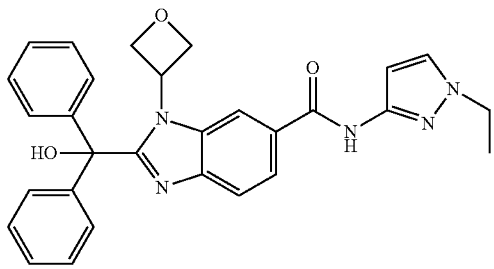 [SMILES: CCn1ccc(NC(=O)c2ccc3nc(C(O)(c4ccccc4)c4ccccc4)n(C4COC4)c3c2)n1] | 494 (M + H) | |
| 234 | 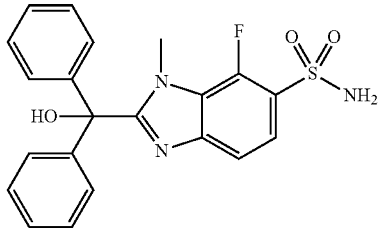 [SMILES: Cn1c(C(O)(c2ccccc2)c2ccccc2)nc2ccc(S(N)(=O)=O)c(F)c21] | 412 (M + H) | |
| 235 | 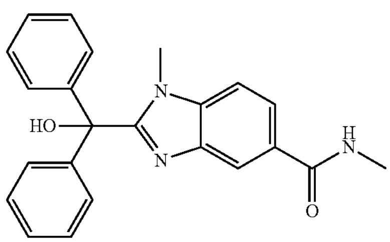 [SMILES: CNC(=O)c1ccc2c(c1)nc(C(O)(c1ccccc1)c1ccccc1)n2C] | 372 (M + H) | |
| 236 | 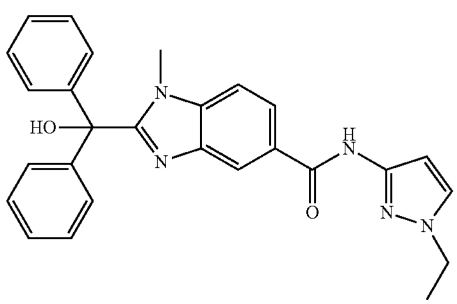 [SMILES: CCn1ccc(NC(=O)c2ccc3c(c2)nc(C(O)(c2ccccc2)c2ccccc2)n3C)n1] | 452 (M + H) | |
| 237 | 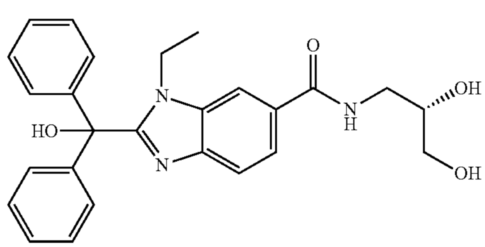 [SMILES: CCn1c(C(O)(c2ccccc2)c2ccccc2)nc2ccc(C(=O)NC[C@H](O)CO)cc21] | 446 (M + H) | |

TABLE 1-continued
| No. | Structure | Mass Characterization | ¹H NMR Data |
|---|---|---|---|
| 238 | 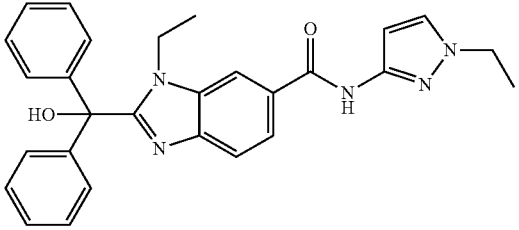 [SMILES: CCn1ccc(NC(=O)c2ccc3nc(C(O)(c4ccccc4)c4ccccc4)n(CC)c3c2)n1] | 466 (M + H) | |
| 239 | 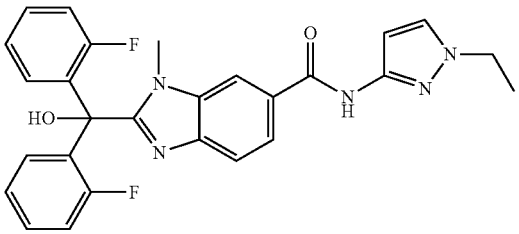 [SMILES: CCn1ccc(NC(=O)c2ccc3nc(C(O)(c4ccccc4F)c4ccccc4F)n(C)c3c2)n1] | 488 (M + H) | |
| 240 | 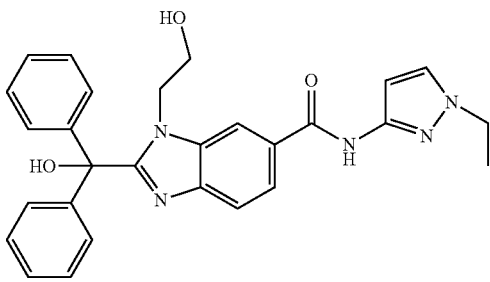 [SMILES: CCn1ccc(NC(=O)c2ccc3nc(C(O)(c4ccccc4)c4ccccc4)n(CCO)c3c2)n1] | 482 (M + H) | |
| 241 | 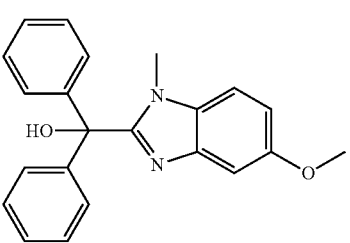 [SMILES: COc1ccc2c(c1)nc(C(O)(c1ccccc1)c1ccccc1)n2C] | 345 (M + H) | |
| 242 | 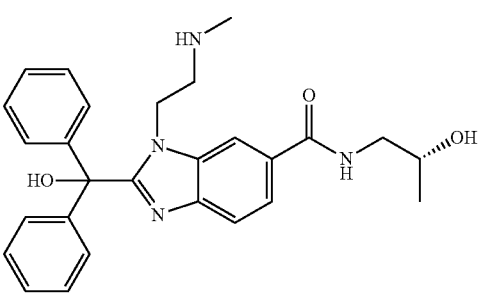 [SMILES: CNCCn1c(C(O)(c2ccccc2)c2ccccc2)nc2ccc(C(=O)NC[C@@H](C)O)cc21] | 459 (M + H) | |

TABLE 1-continued

| No. | Structure | Mass Characterization | $^1$H NMR Data |
|---|---|---|---|
| 243 | 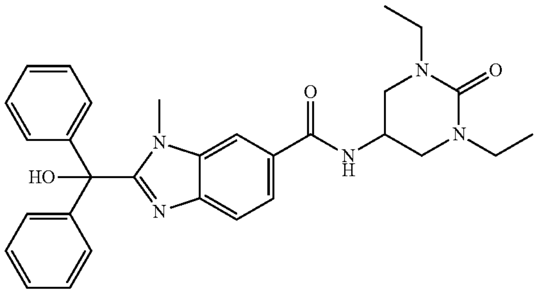 [SMILES: CCN1CC(NC(=O)c2ccc3nc(C(O)(c4ccccc4)c4ccccc4)n(C)c3c2)CN(CC)C1=O] | 512 (M + H) | |
| 244 | 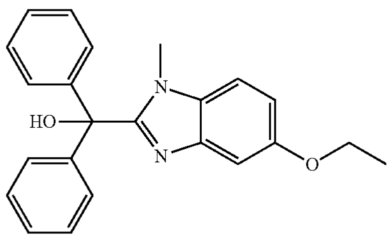 [SMILES: CCOc1ccc2c(c1)nc(C(O)(c1ccccc1)c1ccccc1)n2C] | 359 (M + H) | |
| 245 | 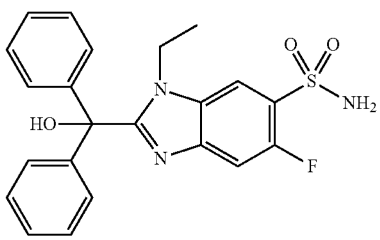 [SMILES: CCn1c(C(O)(c2ccccc2)c2ccccc2)nc2cc(F)c(S(N)(=O)=O)cc21] | 426 (M + H) | |
| 246 | 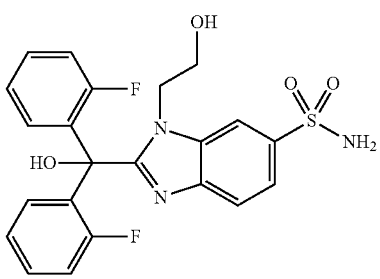 [SMILES: NS(=O)(=O)c1ccc2nc(C(O)(c3ccccc3F)c3ccccc3F)n(CCO)c2c1] | 460 (M + H) | |
| 247 | 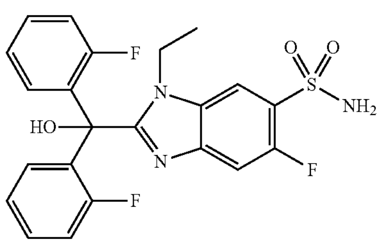 [SMILES: CCn1c(C(O)(c2ccccc2F)c2ccccc2F)nc2cc(F)c(S(N)(=O)=O)cc21] | 462 (M + H) | |
| 248 | 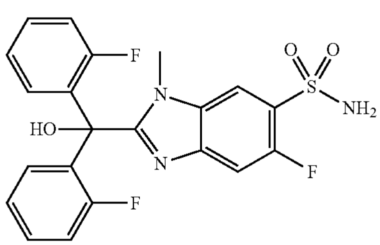 [SMILES: Cn1c(C(O)(c2ccccc2F)c2ccccc2F)nc2cc(F)c(S(N)(=O)=O)cc21] | 448 (M + H) | |

TABLE 1-continued

| No. | Structure | Mass Characterization | 1H NMR Data |
|---|---|---|---|
| 249 | 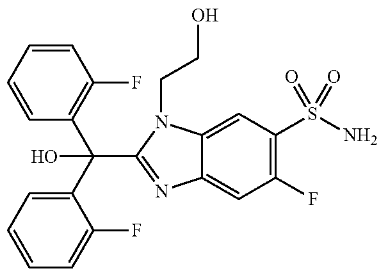 [SMILES: NS(=O)(=O)c1cc2c(cc1F)nc(C(O)(c1ccccc1F)c1ccccc1F)n2CCO] | 478 (M + H) | |
| 250 | 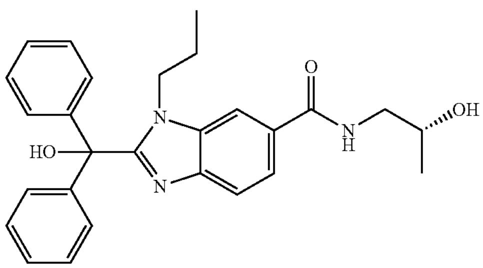 [SMILES: CCCn1c(C(O)(c2ccccc2)c2ccccc2)nc2ccc(C(=O)NC[C@@H](C)O)cc21] | 443 (M + H) | |
| 251 | 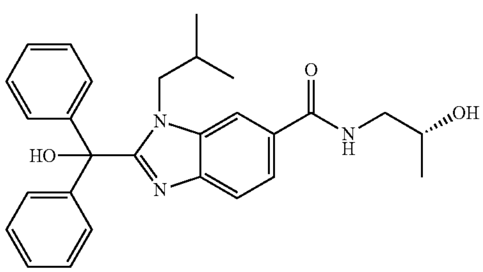 [SMILES: CC(C)Cn1c(C(O)(c2ccccc2)c2ccccc2)nc2ccc(C(=O)NC[C@@H](C)O)cc21] | 458 (M + H) | |
| 252 | 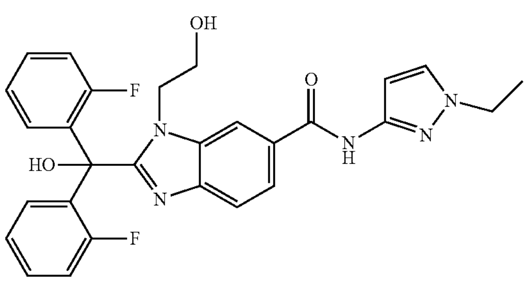 [SMILES: CCn1ccc(NC(=O)c2ccc3nc(C(O)(c4ccccc4F)c4ccccc4F)n(CCO)c3c2)n1] | 518 (M + H) | |
| 253 | 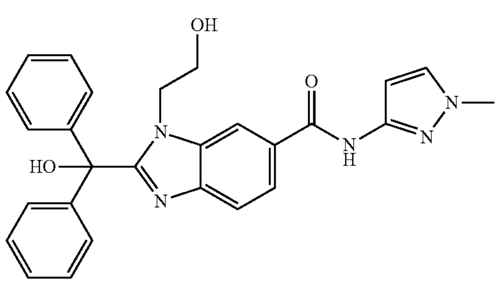 [SMILES: Cn1ccc(NC(=O)c2ccc3nc(C(O)(c4ccccc4)c4ccccc4)n(CCO)c3c2)n1] | 468 (M + H). | |

TABLE 1-continued

| No. | Structure | Mass Characterization | ¹H NMR Data |
|---|---|---|---|
| 254 | 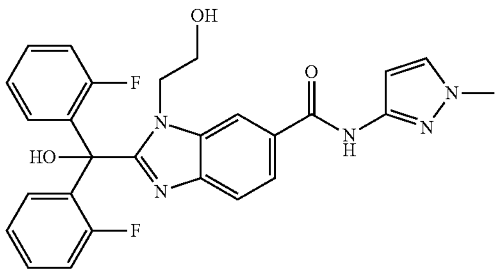 [SMILES: Cn1ccc(NC(=O)c2ccc3nc(C(O)(c4ccccc4F)c4ccccc4F)n(CCO)c3c2)n1] | 504 (M + H) | |
| 255 | 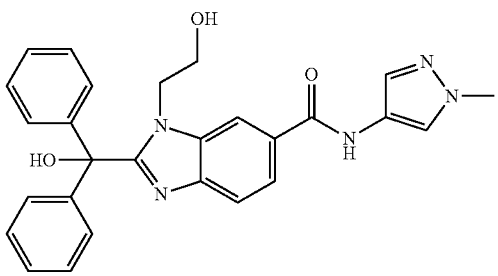 [SMILES: Cn1cc(NC(=O)c2ccc3nc(C(O)(c4ccccc4)c4ccccc4)n(CCO)c3c2)cn1] | 468 (M + H) | |
| 256 | 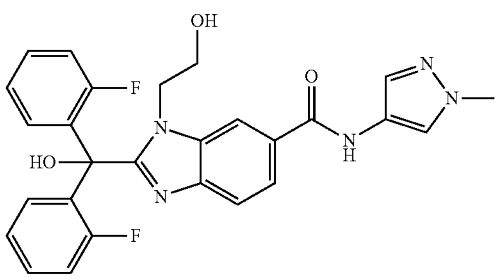 [SMILES: Cn1cc(NC(=O)c2ccc3nc(C(O)(c4ccccc4F)c4ccccc4F)n(CCO)c3c2)cn1] | 504 (M + H) | |
| 257 | 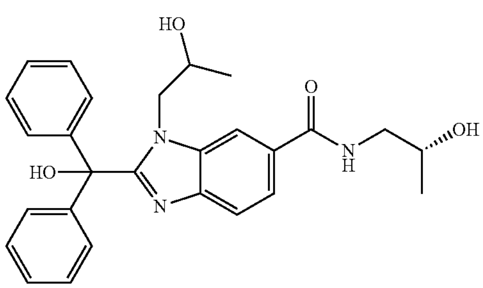 [SMILES: CC(O)Cn1c(C(O)(c2ccccc2)c2ccccc2)nc2ccc(C(=O)NC[C@@H](C)O)cc21] | 460 (M + H) | |
| 258 | 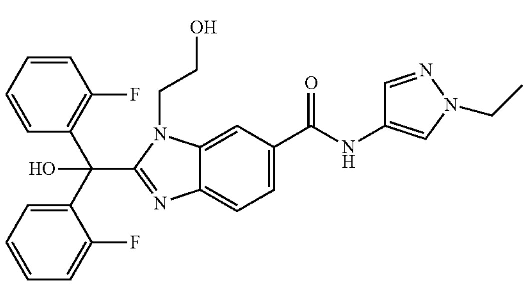 [SMILES: CCn1cc(NC(=O)c2ccc3nc(C(O)(c4ccccc4F)c4ccccc4F)n(CCO)c3c2)cn1] | 518 (M + H) | |

TABLE 1-continued

| No. | Structure | Mass Characterization | ¹H NMR Data |
|---|---|---|---|
| 259 | 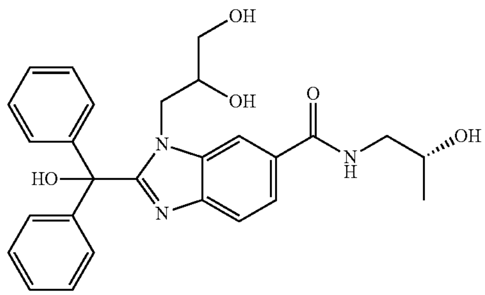 [SMILES: C[C@@H](O)CNC(=O)c1ccc2nc(C(O)(c3ccccc3)c3ccccc3)n(CC(O)CO)c2c1] | 476 (M + H) | |
| 260 | 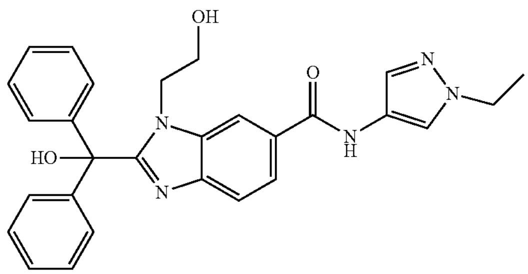 [SMILES: CCn1cc(NC(=O)c2ccc3nc(C(O)(c4ccccc4)c4ccccc4)n(CCO)c3c2)cn1] | 482 (M + H) | |
| 261 | 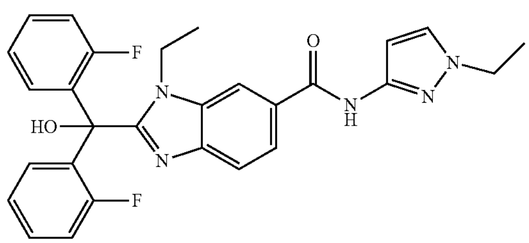 [SMILES: CCn1ccc(NC(=O)c2ccc3nc(C(O)(c4ccccc4F)c4ccccc4F)n(CC)c3c2)n1] | 502 (M + H) | (400 MHz, CDCl$_3$): δ 8.51 (s, 1H), 8.03 (s, 1H), 7.79 (d, 1H), 7.70 (d, 1H), 7.37 (m, 2H), 7.26 (s, 1H), 7.14 (m, 4H), 7.03 (m, 2H), 6.83 (s, 1H), 4.63 (t, 1H), 4.23 (q, 2H), 4.05 (q, 2H), 1.47 (t, 3H), 1.10 (t, 3H) |
| 262 | 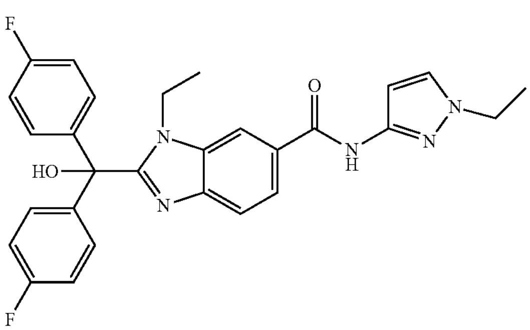 [SMILES: CCn1ccc(NC(=O)c2ccc3nc(C(O)(c4ccc(F)cc4)c4ccc(F)cc4)n(CC)c3c2)n1] | 502 (M + H) | (400 MHz, CDCl$_3$): δ 8.51 (s, 1H), 8.02 (s, 1H), 7.84 (d, 1H), 7.77 (d, 1H), 7.28 (m, 5H), 7.06 (m, 4H), 6.80 (s, 1H), 4.65 (s, 1H), 4.08 (m, 4H), 1.47 (t, 3H), 0.88 (t, 3H) |
| 263 | 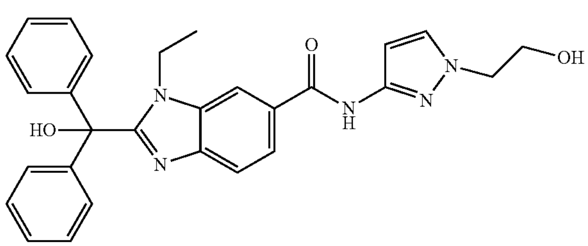 [SMILES: CCn1c(C(O)(c2ccccc2)c2ccccc2)nc2ccc(C(=O)Nc3ccn(CCO)n3)cc21] | 482 (M + H) | |

TABLE 1-continued

| No. | Structure | Mass Characterization | $^1$H NMR Data |
|---|---|---|---|
| 264 | 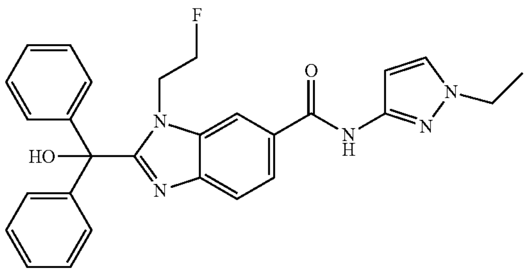 [SMILES: CCn1ccc(NC(=O)c2ccc3nc(C(O)(c4ccccc4)c4ccccc4)n(CCF)c3c2)n1] | 484 (M + H) | (400 MHz, CDCl$_3$): δ 8.50 (s, 1H), 8.06 (s, 1H), 7.83 (d, 1H), 7.77 (d, 1H), 7.35 (m, 5H), 7.28 (m, 5H), 6.82 (s, 1H), 4.42 (m, 1H), 4.37 (m, 1H), 4.21 (m, 1H), 4.16 (m, 1H), 4.08 (m, 3H), 1.46 (t, 3H) |
| 265 | 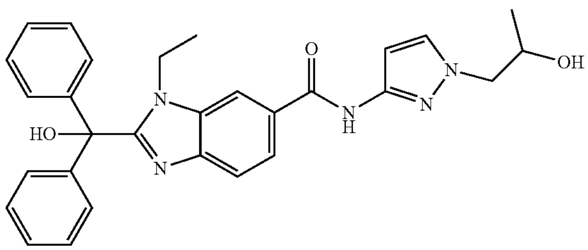 [SMILES: CCn1c(C(O)(c2ccccc2)c2ccccc2)nc2ccc(C(=O)Nc3ccn(CC(C)O)n3)cc21] | 496 (M + H) | |
| 266 | 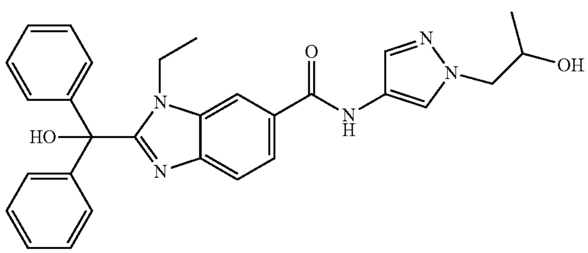 [SMILES: CCn1c(C(O)(c2ccccc2)c2ccccc2)nc2ccc(C(=O)Nc3cnn(CC(C)O)c3)cc21] | 496 (M + H) | |
| 267 | 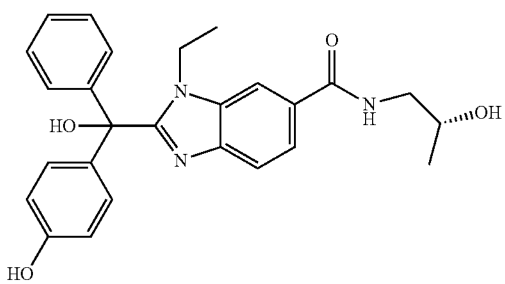 [SMILES: CCn1c(C(O)(c2ccccc2)c2ccc(O)cc2)nc2ccc(C(=O)NC[C@@H](C)O)cc21] | 446 (M + H) | |
| 268 | 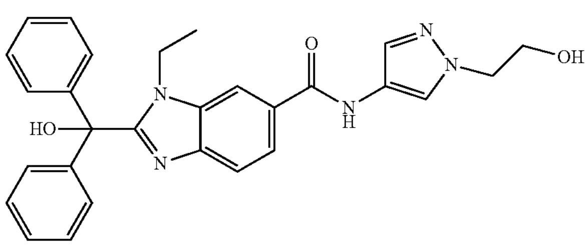 [SMILES: CCn1c(C(O)(c2ccccc2)c2ccccc2)nc2ccc(C(=O)Nc3cnn(CCO)c3)cc21] | 482 (M + H) | |
| 269 | 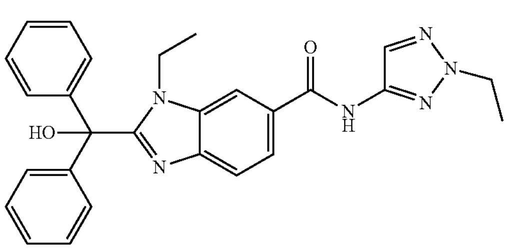 [SMILES: CCn1ncc(NC(=O)c2ccc3nc(C(O)(c4ccccc4)c4ccccc4)n(CC)c3c2)n1] | 467 (M + H) | (400 MHz, CDCl$_3$): δ 8.58 (s, 1H), 8.15 (s, 1H), 8.02 (s, 1H), 7.83 (d, 1H), 7.71 (d, 1H), 7.31-7.37 (m, 10H), 4.79 (s, 1H), 4.40 (q, 2H), 4.12 (q, 2H), 1.47 (t, 3H), 0.8 (t, 3H) |

TABLE 1-continued

| No. | Structure | Mass Characterization | ¹H NMR Data |
|---|---|---|---|
| 270 | 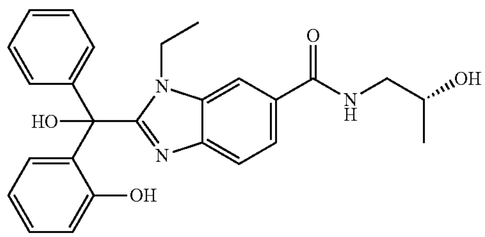 [SMILES: CCn1c(C(O)(c2ccccc2)c2ccccc2O)nc2ccc(C(=O)NC[C@@H](C)O)cc21] | 446 (M + H) | |
| 271 | 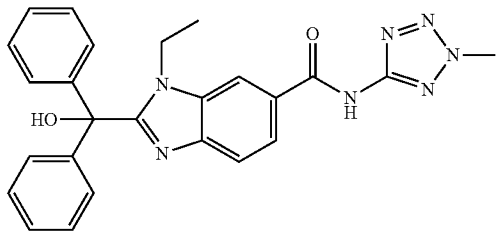 | 482 (M + H) | |
| 272 | 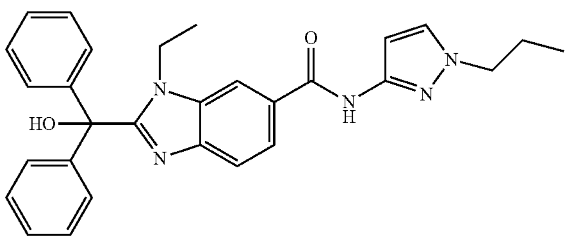 [SMILES: CCCn1ccc(NC(=O)c2ccc3nc(C(O)(c4ccccc4)c4ccccc4)n(CC)c3c2)n1] | 480 (M + H) | |
| 273 | 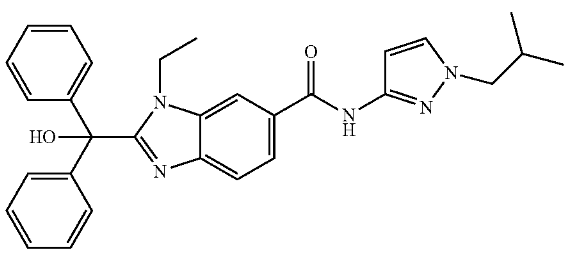 [SMILES: CCn1c(C(O)(c2ccccc2)c2ccccc2)nc2ccc(C(=O)Nc3ccn(CC(C)C)n3)cc21] | 494 (M + H) | |
| 274 | 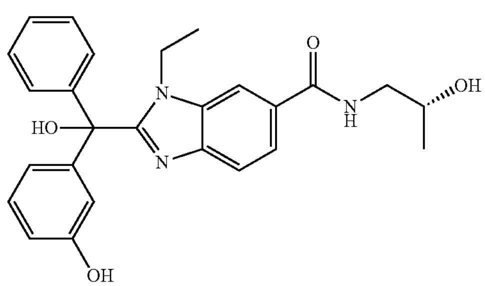 [SMILES: CCn1c(C(O)(c2ccccc2)c2cccc(O)c2)nc2ccc(C(=O)NC[C@@H](C)O)cc21] | 446 (M + H) | |
| 275 | 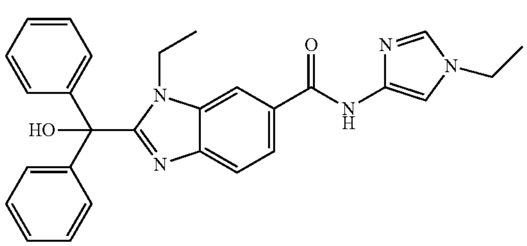 | 466 (M + H) | |

TABLE 1-continued

| No. | Structure | Mass Characterization | ¹H NMR Data |
|---|---|---|---|
| 276 | 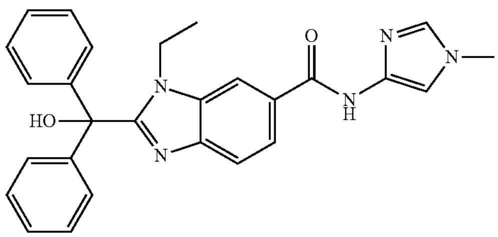 [SMILES: CCn1c(C(O)(c2ccccc2)c2ccccc2)nc2ccc(C(=O)Nc3cn(C)cn3)cc21] | 452 (M + H) | |
| 277 | 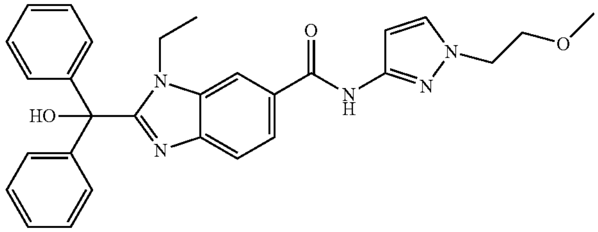 [SMILES: CCn1c(C(O)(c2ccccc2)c2ccccc2)nc2ccc(C(=O)Nc3ccn(CCOC)n3)cc21] | 496 (M + H) | |
| 278 | 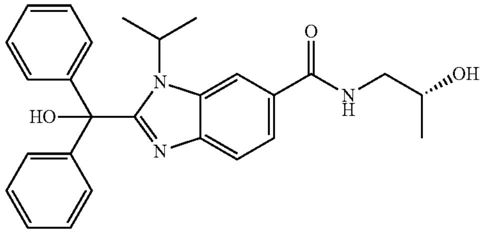 [SMILES: CC(C)n1c(C(O)(c2ccccc2)c2ccccc2)nc2ccc(C(=O)NC[C@@H](C)O)cc21] | 444 (M + H) | |
| 279 | 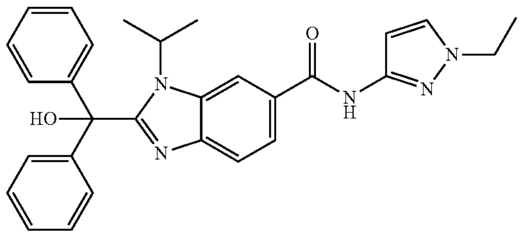 [SMILES: CCn1ccc(NC(=O)c2ccc3nc(C(O)(c4ccccc4)c4ccccc4)n(C(C)C)c3c2)n1] | 480 (M + H) | |
| 280 | 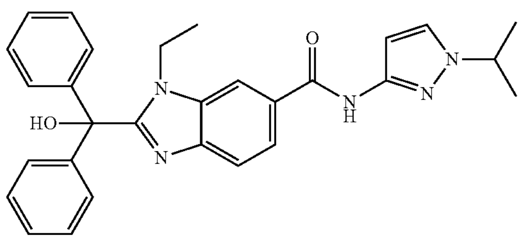 [SMILES: CCn1c(C(O)(c2ccccc2)c2ccccc2)nc2ccc(C(=O)Nc3ccn(C(C)C)n3)cc21] | 480 (M + H) | |
| 281 | 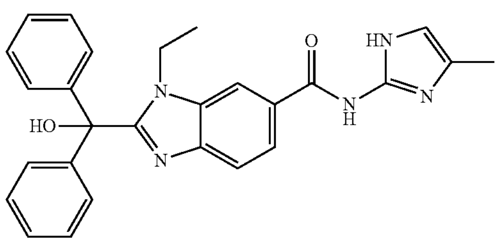 [SMILES: CCn1c(C(O)(c2ccccc2)c2ccccc2)nc2ccc(C(=O)Nc3nc(C)c[nH]3)cc21] | 452 (M + H) | |

TABLE 1-continued

| No. | Structure | Mass Characterization | ¹H NMR Data |
|---|---|---|---|
| 282 | 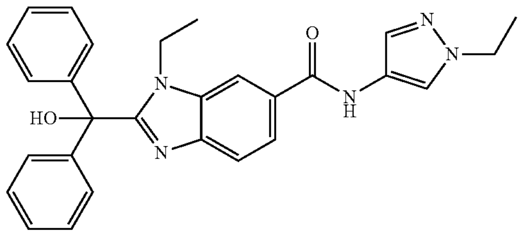 | 423 (M + H) | |
| 283 | 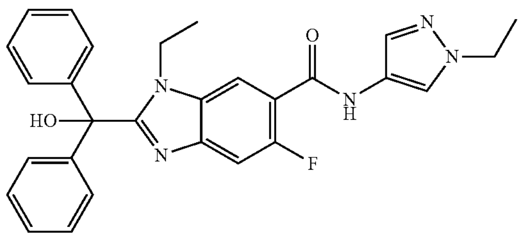 | 441 (M + H) | |
| 284 | 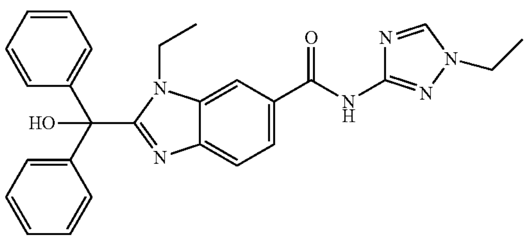 [SMILES: CCn1cnc(NC(=O)c2ccc3nc(C(O)(c4ccccc4)c4ccccc4)n(CC)c3c2)n1] | 467 (M + H) | (400 MHz, CDCl₃): δ 8.59 (s, 1H), 8.04 (s, 1H), 7.90 (s, 1H), 7.83 (d, 1H), 7.78 (d, 1H), 7.31-7.39 (m, 10H), 4.85 (s, 1H), 4.68 (q, 2H), 4.10 (q, 2H), 1.58 (t, 3H), 0.78 (t, 3H) |
| 285 | 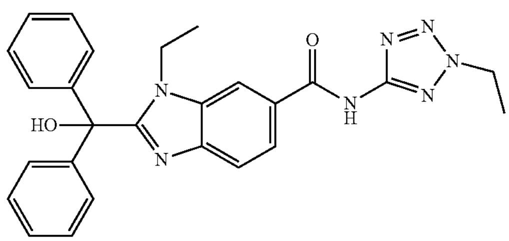 | 468 (M + H) | (400 MHz, CDCl₃): δ 8.89 (s, 1H), 8.06 (s, 1H), 7.86 (d, 1H), 7.79 (d, 1H), 7.32-7.40 (m, 10H), 4.79 (s, 1H), 4.68 (q, 2H), 4.17 (q, 2H), 1.70 (t, 3H), 0.81 (t, 3H) |
| 286 | 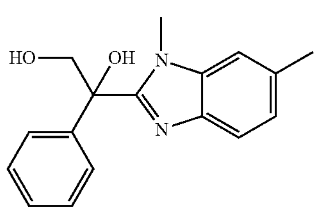 [SMILES: Cc1ccc2nc(C(O)(CO)c3ccccc3)n(C)c2c1] | 283 (M + H) | (400 MHz, CDCl₃): δ 7.64 (d, 1H), 7.37 (m, 5H), 7.14 (d, 1H), 7.12 (s, 1H), 4.63 (m, 1H), 4.41 (m, 1H), 3.85 (s, 1H), 3.58 (t, 1H), 3.39 (s, 3H), 2.48 (s, 3H) |
| 287 | 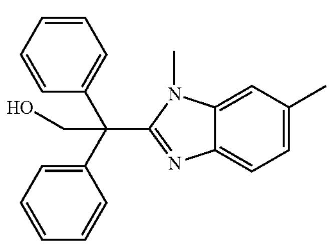 [SMILES: Cc1ccc2nc(C(CO)(c3ccccc3)c3ccccc3)n(C)c2c1] | 343 (M + H) | (400 MHz, CDCl₃): δ 7.67 (d, 1H), 7.52 (m, 4H), 7.41 (m, 2H), 7.33 (d, 1H), 7.22 (m, 3H), 7.13 (m, 2H), 4.37-4.44 (m, 2H), 4.18 (bs, 1H), 3.42 (s, 3H), 2.43 (s, 3H) |

TABLE 1-continued

| No. | Structure | Mass Characterization | ¹H NMR Data |
|---|---|---|---|
| 288 | 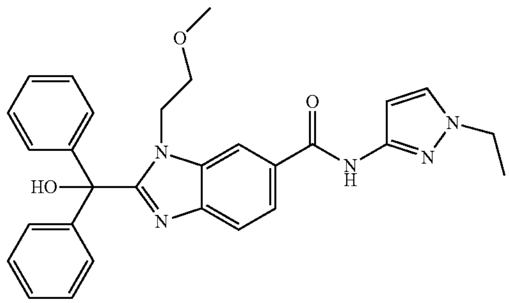 | 496 (M + H) | (400 MHz, CDCl$_3$): δ 8.53 (s, 1H), 8.02 (s, 1H), 7.81 (d, 1H), 7.73 (d, 1H), 7.31-7.40 (m, 10H), 6.83 (s, 1H), 5.53 (s, 1H), 4.25 (t, 2H), 4.08 (q, 2H), 3.45 (t, 2H), 3.20 (s, 3H), 1.47 (t, 3H) |
| 289 | 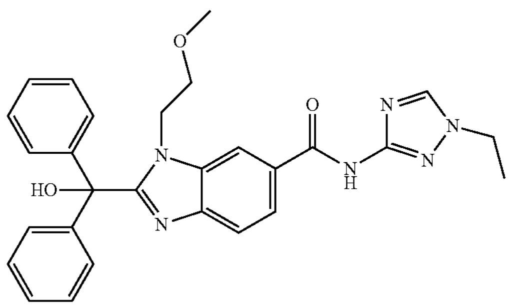 | 497 (M + H) | (400 MHz, CDCl$_3$): δ 8.67 (s, 1H), 8.06 (s, 1H), 7.87 (s, 1H), 7.83 (d, 1H), 7.78 (d, 1H), 7.32-7.40 (m, 10H), 4.50 (s, 1H), 4.35 (t, 2H), 4.20 (q, 2H), 3.22 (t, 2H), 3.21 (s, 3H), 1.57 (t, 3H) |
| 290 | 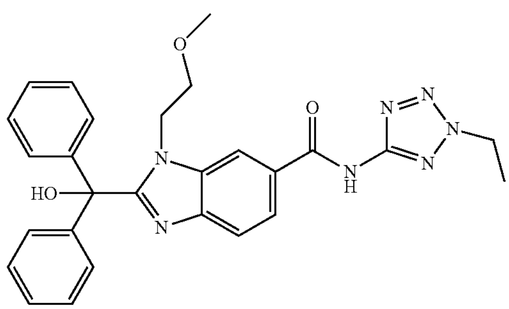 | 498 (M + H) | (400 MHz, CDCl$_3$): δ 8.98 (s, 1H), 8.14 (s, 1H), 7.85 (d, 1H), 7.79 (d, 1H), 7.32-7.38 (m, 10H), 5.19 (s, 1H), 4.65 (q, 2H), 4.37 (t, 2H), 3.40 (t, 2H), 3.22 (s, 3H), 1.65 (t, 3H) |
| 291 | 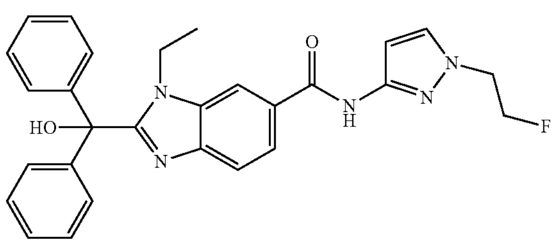 [SMILES: CCn1c(C(O)(c2ccccc2)c2ccccc2)nc2ccc(C(=O)Nc3ccn(CCF)n3)cc21] | 484 (M + H) | |
| 292 | 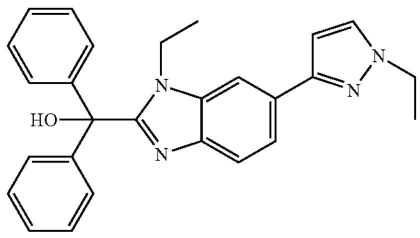 [SMILES: CCn1ccc(-c2ccc3nc(C(O)(c4ccccc4)c4ccccc4)n(CC)c3c2)n1] | 423 (M + H) | |

TABLE 1-continued

| No. | Structure | Mass Characterization | ¹H NMR Data |
|---|---|---|---|
| 293 | 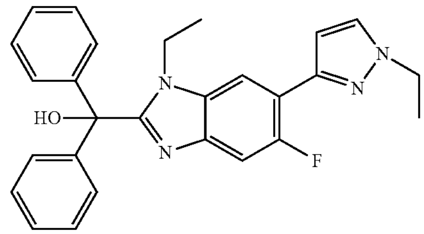 [SMILES: CCn1ccc(-c2cc3c(cc2F)nc(C(O)(c2ccccc2)c2ccccc2)n3CC)n1] | 441 (M + H) | |
| 294 | 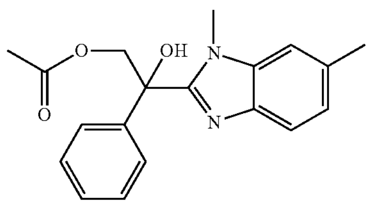 [SMILES: CC(=O)OCC(O)(c1ccccc1)c1nc2ccc(C)cc2n1C] | 325 (M + H) | (400 MHz, CDCl$_3$): δ 7.75 (d, 1H), 7.27-7.38 (m, 5H), 7.11 (d, 1H), 7.06 (s, 1H), 4.20 (d, 1H), 3.68 (d, 1H), 3.91 (s, 1H), 3.49 (s, 3H), 2.50 (s, 3H), 2.03 (s, 3H) |
| 295 | 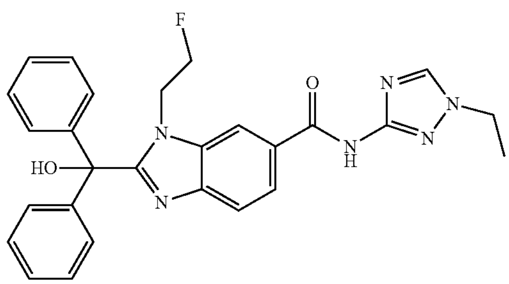 [SMILES: CCn1cnc(NC(=O)c2ccc3nc(C(O)(c4ccccc4)c4ccccc4)n(CCF)c3c2)n1] | 485 (M + H) | (400 MHz, CDCl$_3$): δ 8.58 (s, 1H), 8.07 (s, 1H), 7.88 (s, 1H), 7.81 (d, 1H), 7.79 (d, 1H), 7.26-7.38 (m, 10H), 4.45 (m, 1H), 4.39 (m, 1H), 4.20 (m, 4H), 4.11 (m, 1H), 1.58 (t, 3H) |
| 296 | 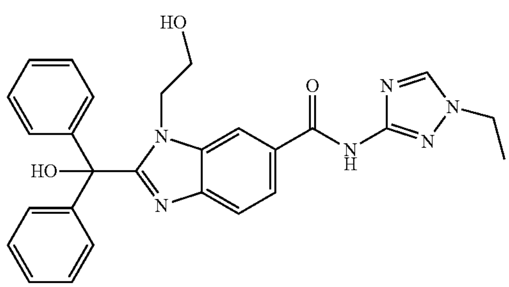 [SMILES: CCn1cnc(NC(=O)c2ccc3nc(C(O)(c4ccccc4)c4ccccc4)n(CCO)c3c2)n1] | 483 (M + H) | (400 MHz, CDCl$_3$): δ 8.97 (s, 1H), 7.92 (s, 1H), 7.84 (s, 1H), 7.59 (m, 2H), 7.25-7.39 (m, 10H), 5.82 (s, 1H), 4.18 (m, 4H), 3.85 (bs, 1H), 3.69 (m, 2H), 1.48 (t, 3H) |
| 297 | 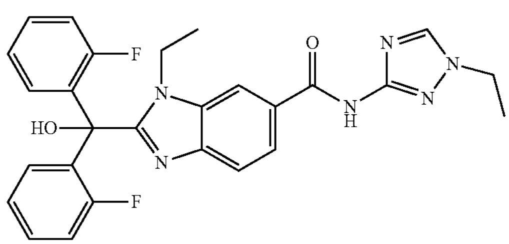 [SMILES: CCn1cnc(NC(=O)c2ccc3nc(C(O)(c4ccccc4F)c4ccccc4F)n(CC)c3c2)n1] | 503 (M + H) | (400 MHz, CDCl$_3$): δ 8.57 (s, 1H), 8.08 (s, 1H), 7.91 (s, 1H), 7.80 (d, 1H), 7.76 (d, 1H), 7.40 (m, 2H), 7.17 (m, 4H), 7.17 (m, 2H), 4.62 (m, 1H), 4.23 (m, 4H), 1.58 (t, 3H), 1.14 (t, 3H) |
| 298 | 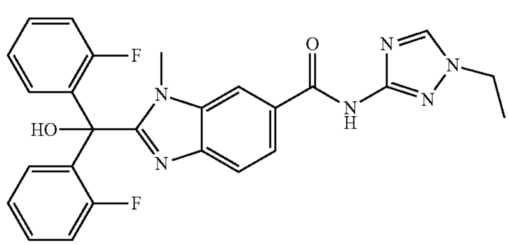 [SMILES: CCn1cnc(NC(=O)c2ccc3nc(C(O)(c4ccccc4F)c4ccccc4F)n(C)c3c2)n1] | 489 (M + H) | (400 MHz, CDCl$_3$): δ 8.86 (s, 1H), 8.07 (s, 1H), 7.85 (s, 1H), 7.78 (d, 1H), 7.76 (d, 1H), 7.38 (m, 2H), 7.05-7.18 (m, 6H), 4.70 (m, 1H), 4.21 (q, 2H), 3.65 (s, 3H), 1.57 (t, 3H) |

TABLE 1-continued

| No. | Structure | Mass Characterization | $^1$H NMR Data |
|---|---|---|---|
| 299 | 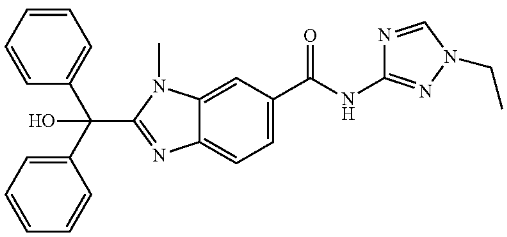 [SMILES: CCn1cnc(NC(=O)c2ccc3nc(C(O)(c4ccccc4)c4ccccc4)n(C)c3c2)n1] | 453 (M + H) | (400 MHz, CDCl$_3$): δ 8.79 (s, 1H), 8.03 (s, 1H), 7.87 (s, 1H), 7.78 (d, 1H), 7.75 (d, 1H), 7.28-7.38 (m, 10H), 4.80 (s, 1H), 4.21 (q, 2H), 3.43 (s, 3H), 1.56 (t, 3H) |
| 300 | 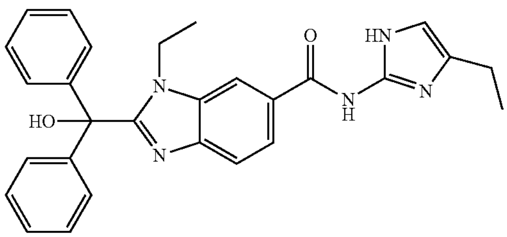 | 423 (M + H) | |
| 301 | 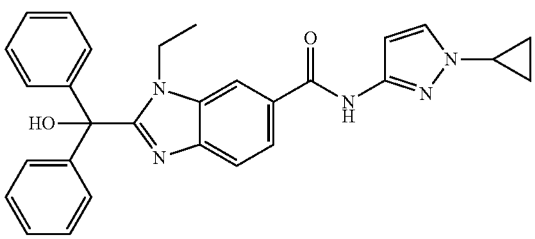 [SMILES: CCn1c(C(O)(c2ccccc2)c2ccccc2)nc2ccc(C(=O)Nc3ccn(C4CC4)n3)cc21] | 478 (M + H) | |
| 302 | 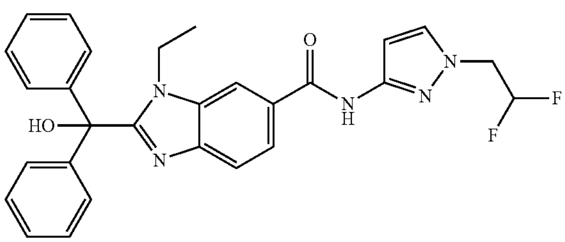 [SMILES: CCn1c(C(O)(c2ccccc2)c2ccccc2)nc2ccc(C(=O)Nc3ccn(CC(F)F)n3)cc21] | 502 (M + H) | |
| 303 | 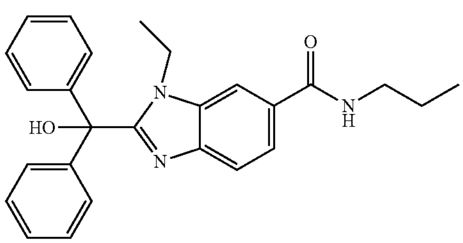 [SMILES: CCCNC(=O)c1ccc2nc(C(O)(c3ccccc3)c3ccccc3)n(CC)c2c1] | 414 (M + H) | |
| 304 | 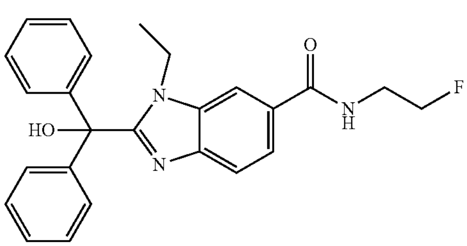 [SMILES: CCn1c(C(O)(c2ccccc2)c2ccccc2)nc2ccc(C(=O)NCCF)cc21] | 418 (M + H) | |

TABLE 1-continued

| No. | Structure | Mass Characterization | ¹H NMR Data |
|---|---|---|---|
| 305 | 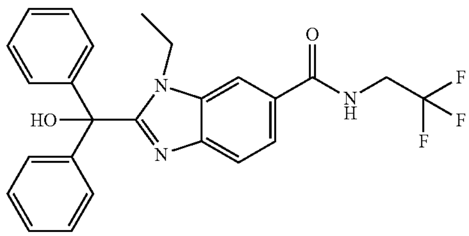 [SMILES: CCn1c(C(O)(c2ccccc2)c2ccccc2)nc2ccc(C(=O)NCC(F)(F)F)cc21] | 454 (M + H) | |
| 306 | 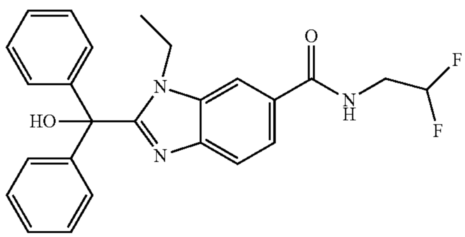 [SMILES: CCn1c(C(O)(c2ccccc2)c2ccccc2)nc2ccc(C(=O)NCC(F)F)cc21] | 436 (M + H) | |
| 307 | 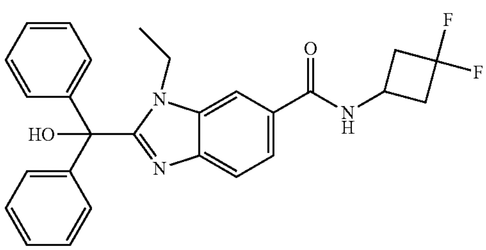 [SMILES: CCn1c(C(O)(c2ccccc2)c2ccccc2)nc2ccc(C(=O)NC3CC(F)(F)C3)cc21] | 462 (M + H) | |
| 308 | 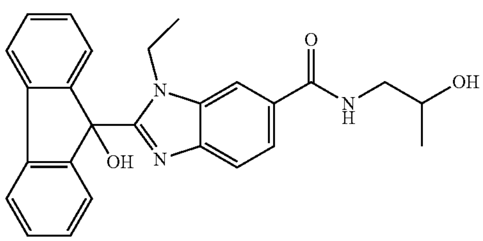 [SMILES: CCn1c(C2(O)c3ccccc3-c3ccccc32)nc2ccc(C(=O)NCC(C)O)cc21] | 428 (M + H) | |
| 309 | 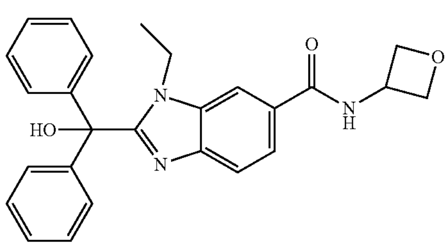 [SMILES: CCn1c(C(O)(c2ccccc2)c2ccccc2)nc2ccc(C(=O)NC3COC3)cc21] | 428 (M + H) | |
| 310 | 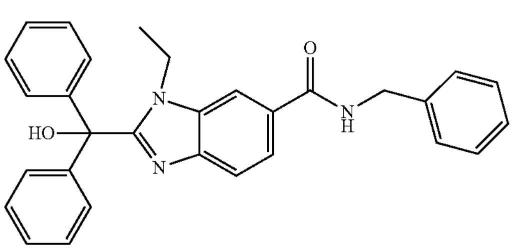 [SMILES: CCn1c(C(O)(c2ccccc2)c2ccccc2)nc2ccc(C(=O)NCc3ccccc3)cc21] | 462 (M + H) | |

TABLE 1-continued

| No. | Structure | Mass Characterization | ¹H NMR Data |
|---|---|---|---|
| 311 | 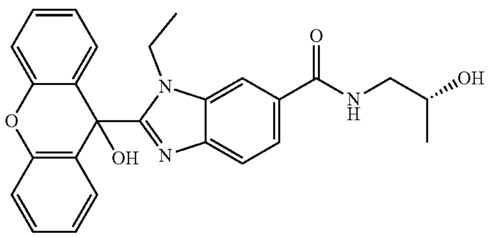 [SMILES: CCn1c(C2(O)c3ccccc3Oc3ccccc32)nc2ccc(C(=O)NC[C@@H](C)O)cc21] | 444 (M + H) | |
| 312 | 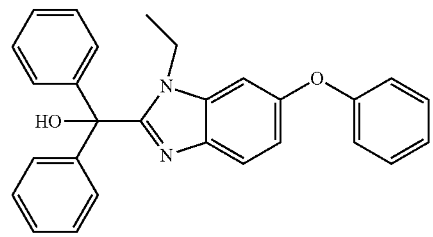 [SMILES: CCn1c(C(O)(c2ccccc2)c2ccccc2)nc2ccc(Oc3ccccc3)cc21] | 421 (M + H) | |
| 313 | 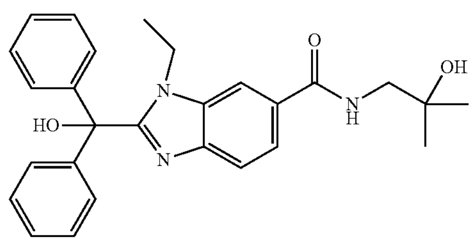 [SMILES: CCn1c(C(O)(c2ccccc2)c2ccccc2)nc2ccc(C(=O)NCC(C)(C)O)cc21] | 444 (M + H) | |
| 314 | 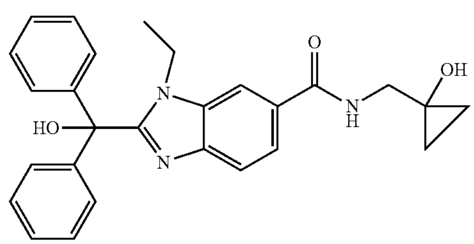 [SMILES: CCn1c(C(O)(c2ccccc2)c2ccccc2)nc2ccc(C(=O)NCC3(O)CC3)cc21] | 442 (M + H) | |
| 315 | 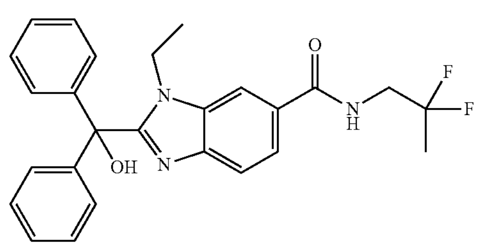 [SMILES: CCn1c(C(O)(c2ccccc2)c2ccccc2)nc2ccc(C(=O)NCC(C)(F)F)cc21] | 450 (M + H) | |
| 316 | 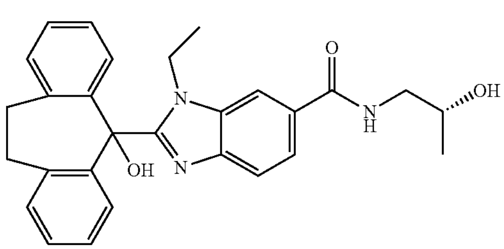 [SMILES: CCn1c(C2(O)c3ccccc3CCc3ccccc32)nc2ccc(C(=O)NC[C@@H](C)O)cc21] | 456 (M + H) | |

TABLE 1-continued

| No. | Structure | Mass Characterization | $^1$H NMR Data |
|-----|-----------|----------------------|----------------|
| 317 | 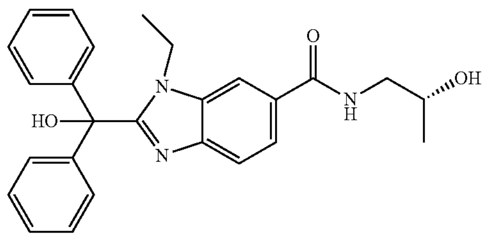 [SMILES: CCn1c(C(O)(c2ccccc2)c2ccccc2)nc2ccc(C(=O)NC[C@@H](C)O)cc21] | 431 (M + H) | |
| 318 | 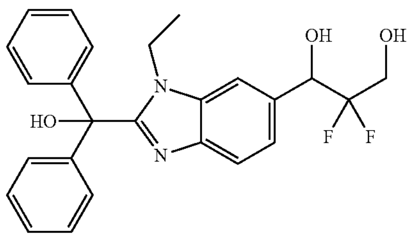 [SMILES: CCn1c(C(O)(c2ccccc2)c2ccccc2)nc2ccc(C(O)C(F)(F)CO)cc21] | 439 (M + H) | |
| 319 | 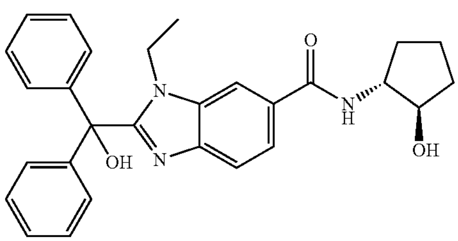 [SMILES: CCn1c(C(O)(c2ccccc2)c2ccccc2)nc2ccc(C(=O)N[C@@H]3CCC[C@H]3O)cc21] | 456 (M + H) | |
| 320 | 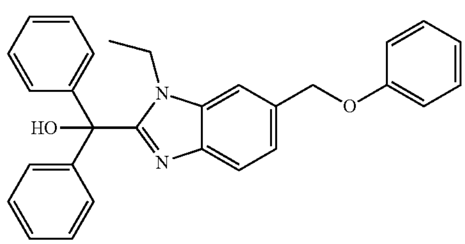 [SMILES: CCn1c(C(O)(c2ccccc2)c2ccccc2)nc2ccc(COc3ccccc3)cc21] | 435 (M + H) | |
| 321 | 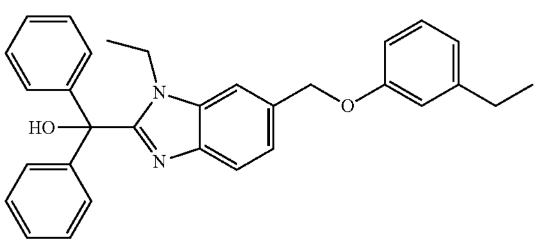 [SMILES: CCc1cccc(OCc2ccc3nc(C(O)(c4ccccc4)c4ccccc4)n(CC)c3c2)c1] | 463 (M + H) | |
| 322 | 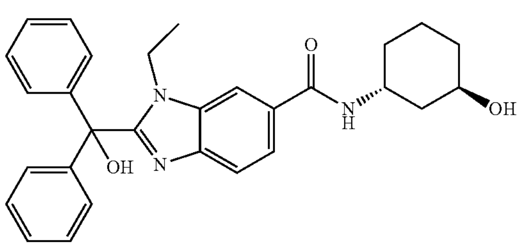 [SMILES: CCn1c(C(O)(c2ccccc2)c2ccccc2)nc2ccc(C(=O)N[C@@H]3CCC[C@@H](O)C3)cc21] | 470 (M + H) | |

TABLE 1-continued

| No. | Structure | Mass Characterization | ¹H NMR Data |
|---|---|---|---|
| 323 | 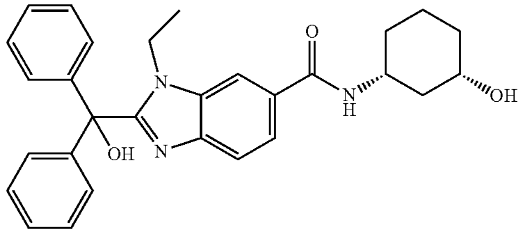 [SMILES: CCn1c(C(O)(c2ccccc2)c2ccccc2)nc2ccc(C(=O)N[C@@H]3CCC[C@H](O)C3)cc21] | 470 (M + H) | |
| 324 | 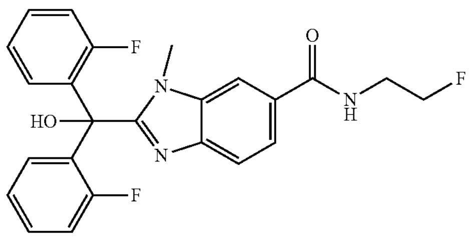 [SMILES: Cn1c(C(O)(c2ccccc2F)c2ccccc2F)nc2ccc(C(=O)NCCF)cc21] | 440 (M + H) | |
| 325 | 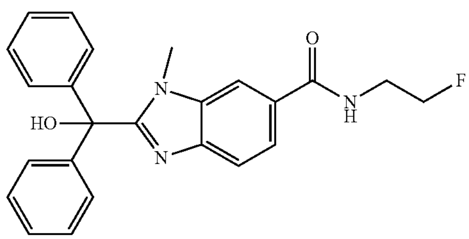 [SMILES: Cn1c(C(O)(c2ccccc2)c2ccccc2)nc2ccc(C(=O)NCCF)cc21] | 404 (M + H) | |
| 326 | 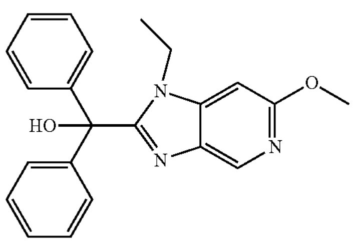 [SMILES: CCn1c(C(O)(c2ccccc2)c2ccccc2)nc2cnc(OC)cc21] | 360 (M + H) | |
| 327 | 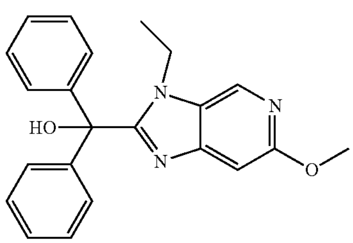 [SMILES: CCn1c(C(O)(c2ccccc2)c2ccccc2)nc2cc(OC)ncc21] | 360 (M + H) | |
| 328 | 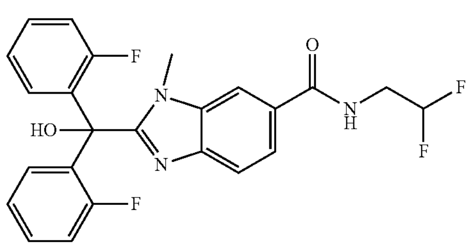 [SMILES: Cn1c(C(O)(c2ccccc2F)c2ccccc2F)nc2ccc(C(=O)NCC(F)F)cc21] | 458 (M + H) | |

TABLE 1-continued

| No. | Structure | Mass Characterization | ¹H NMR Data |
|---|---|---|---|
| 329 | 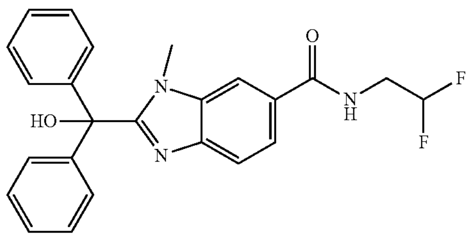 [SMILES: Cn1c(C(O)(c2ccccc2)c2ccccc2)nc2ccc(C(=O)NCC(F)F)cc21] | 422 (M + H) | |
| 330 | 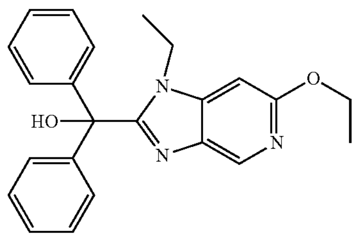 [SMILES: CCOc1cc2c(cn1)nc(C(O)(c1ccccc1)c1ccccc1)n2CC] | 374 (M + H) | |
| 331 | 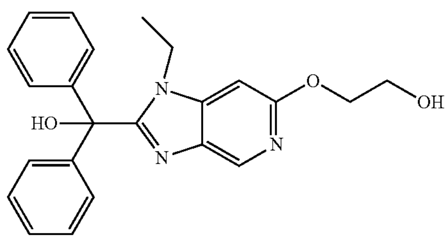 [SMILES: CCn1c(C(O)(c2ccccc2)c2ccccc2)nc2cnc(OCCO)cc21] | 390 (M + H) | |
| 332 | 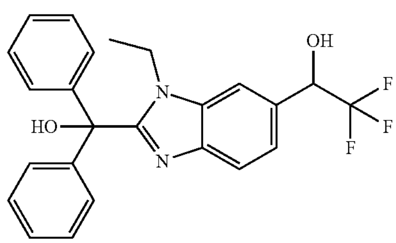 [SMILES: CCn1c(C(O)(c2ccccc2)c2ccccc2)nc2ccc(C(O)C(F)(F)F)cc21] | 427 (M + H) | |
| 333 | 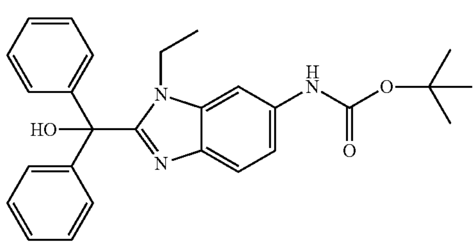 [SMILES: CCn1c(C(O)(c2ccccc2)c2ccccc2)nc2ccc(NC(=O)OC(C)(C)C)cc21] | 444 (M + H) | |
| 334 | 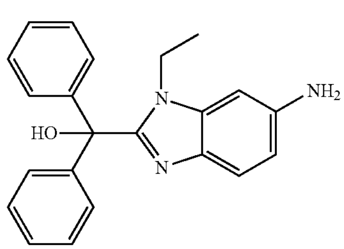 [SMILES: CCn1c(C(O)(c2ccccc2)c2ccccc2)nc2ccc(N)cc21] | 344 (M + H) | |

TABLE 1-continued

| No. | Structure | Mass Characterization | ¹H NMR Data |
|---|---|---|---|
| 335 | 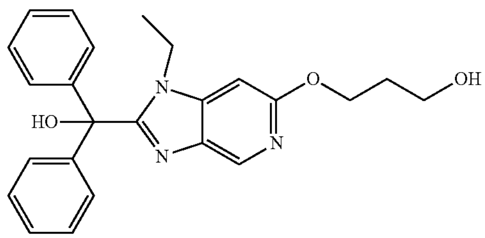 [SMILES: CCn1c(C(O)(c2ccccc2)c2ccccc2)nc2cnc(OCCCO)cc21] | 404 (M + H) | |
| 336 | 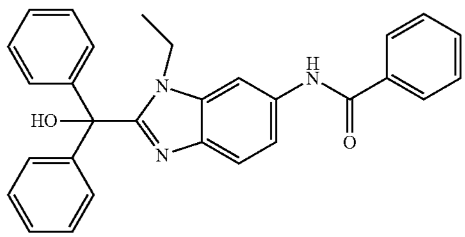 [SMILES: CCn1c(C(O)(c2ccccc2)c2ccccc2)nc2ccc(NC(=O)c3ccccc3)cc21] | 448 (M + H) | |
| 337 | 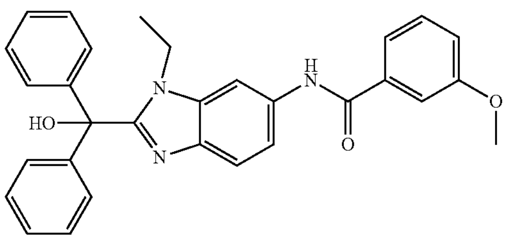 [SMILES: CCn1c(C(O)(c2ccccc2)c2ccccc2)nc2ccc(NC(=O)c3cccc(OC)c3)cc21] | 478 (M + H) | |
| 338 | 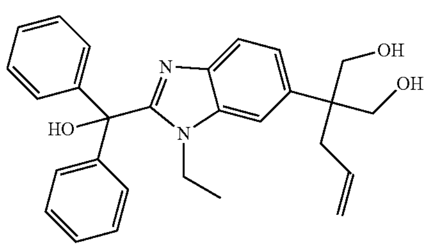 [SMILES: C=CCC(CO)(CO)c1ccc2nc(C(O)(c3ccccc3)c3ccccc3)n(CC)c2c1] | 443 (M + H) | |
| 339 | 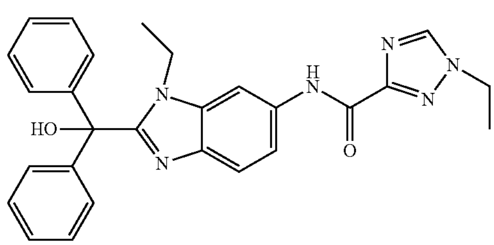 [SMILES: CCn1cnc(C(=O)Nc2ccc3nc(C(O)(c4ccccc4)c4ccccc4)n(CC)c3c2)n1] | 467 (M + H) | |
| 340 | 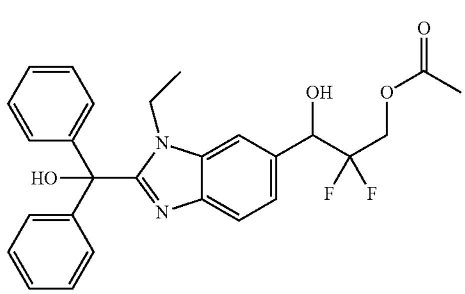 [SMILES: CCn1c(C(O)(c2ccccc2)c2ccccc2)nc2ccc(C(O)C(F)(F)COC(C)=O)cc21] | 481 (M + H) | |

TABLE 1-continued

| No. | Structure | Mass Characterization | $^1$H NMR Data |
|---|---|---|---|
| 341 | 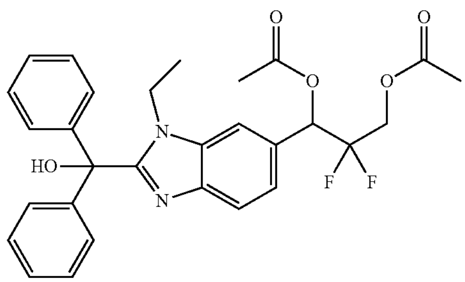 [SMILES: CCn1c(C(O)(c2ccccc2)c2ccccc2)nc2ccc(C(OC(C)=O)C(F)(F)COC(C)=O)cc21] | 523 (M + H) | |
| 342 | 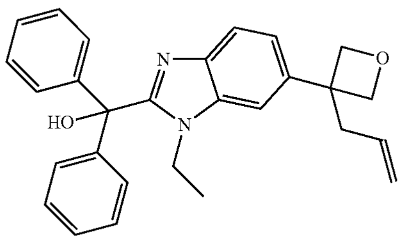 [SMILES: C=CCC1(c2ccc3nc(C(O)(c4ccccc4)c4ccccc4)n(CC)c3c2)COC1] | 425 (M + H) | |
| 343 | 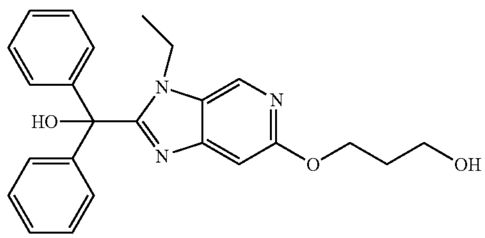 [SMILES: CCn1c(C(O)(c2ccccc2)c2ccccc2)nc2cc(OCCCO)ncc21] | 404 (M + H) | |
| 344 | 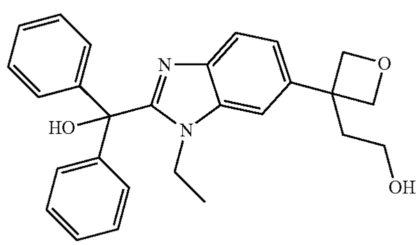 [SMILES: CCn1c(C(O)(c2ccccc2)c2ccccc2)nc2ccc(C3(CCO)COC3)cc21] | 429 (M + H) | |
| 345 | 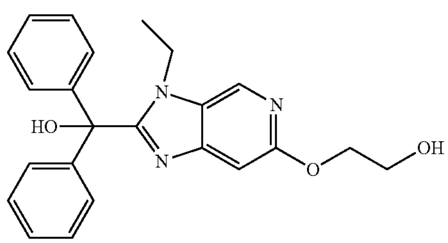 [SMILES: CCn1c(C(O)(c2ccccc2)c2ccccc2)nc2cc(OCCO)ncc21] | 390 (M + H) | |
| 346 | 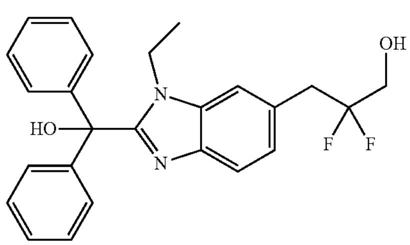 [SMILES: CCn1c(C(O)(c2ccccc2)c2ccccc2)nc2ccc(CC(F)(F)CO)cc21] | 423 (M + H) | |

TABLE 1-continued

| No. | Structure | Mass Characterization | ¹H NMR Data |
|---|---|---|---|
| 347 | 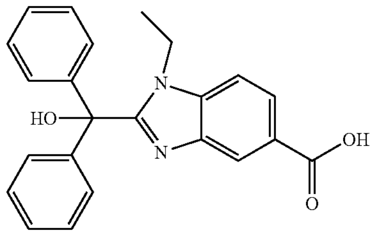 [SMILES: CCn1c(C(O)(c2ccccc2)c2ccccc2)nc2cc(C(=O)O)ccc21] | 373 (M + H) | |
| 348 | 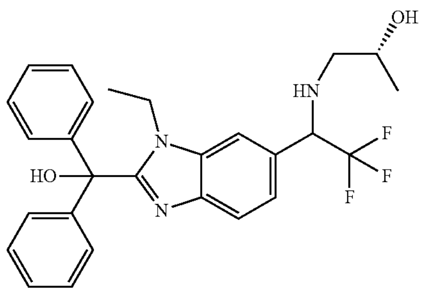 [SMILES: CCn1c(C(O)(c2ccccc2)c2ccccc2)nc2ccc(C(NC[C@@H](C)O)C(F)(F)F)cc21] | 484 (M + H) | |
| 349 | 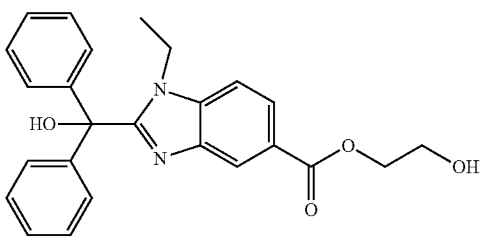 [SMILES: CCn1c(C(O)(c2ccccc2)c2ccccc2)nc2cc(C(=O)OCCO)ccc21] | | (400 MHz, CDCl₃): δ 8.55 (s, 1H), 8.03 (d, 1H), 7.27-7.38 (m, 11H), 4.70 (s, 1H), 4.28 (m, 2H), 4.08 (q, 2H), 3.94 (m, 2H), 2.15 (bs, 1H), 0.79 (t, 3H) |
| 350 | 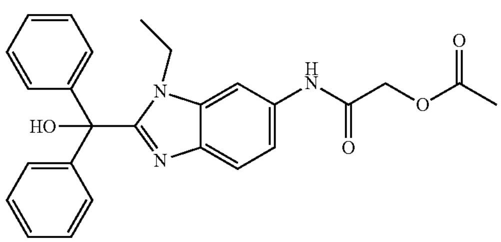 [SMILES: CCn1c(C(O)(c2ccccc2)c2ccccc2)nc2ccc(NC(=O)COC(C)=O)cc21] | 444 (M + H) | |
| 351 | 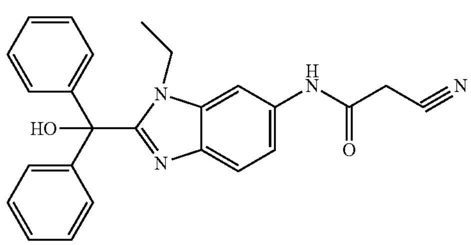 [SMILES: CCn1c(C(O)(c2ccccc2)c2ccccc2)nc2ccc(NC(=O)CC#N)cc21] | 411 (M + H) | |
| 352 | 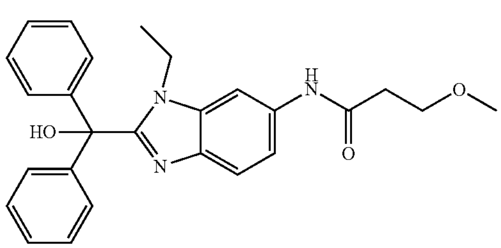 [SMILES: CCn1c(C(O)(c2ccccc2)c2ccccc2)nc2ccc(NC(=O)CCOC)cc21] | 430 (M + H) | |

TABLE 1-continued

| No. | Structure | Mass Characterization | ¹H NMR Data |
|---|---|---|---|
| 353 | 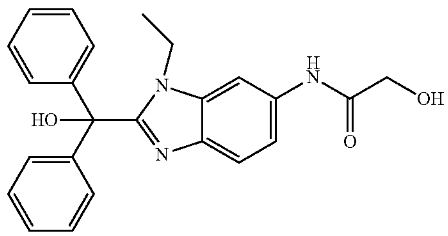 [SMILES: CCn1c(C(O)(c2ccccc2)c2ccccc2)nc2ccc(NC(=O)CO)cc21] | 402 (M + H) | |
| 354 | 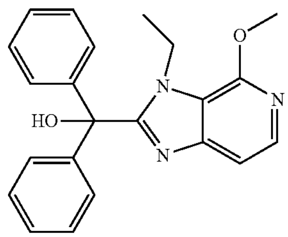 [SMILES: CCn1c(C(O)(c2ccccc2)c2ccccc2)nc2ccnc(OC)c21] | 360 (M + H) | |
| 355 | 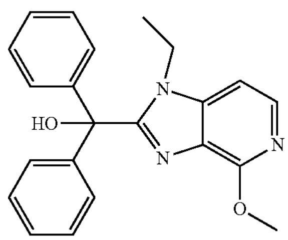 [SMILES: CCn1c(C(O)(c2ccccc2)c2ccccc2)nc2c(OC)nccc21] | 360 (M + H) | |
| 356 | 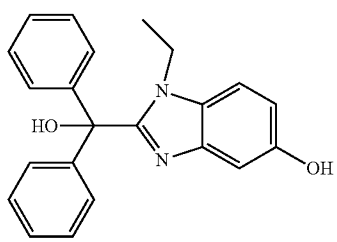 [SMILES: CCn1c(C(O)(c2ccccc2)c2ccccc2)nc2cc(O)ccc21] | 345 (M + H) | |
| 357 | 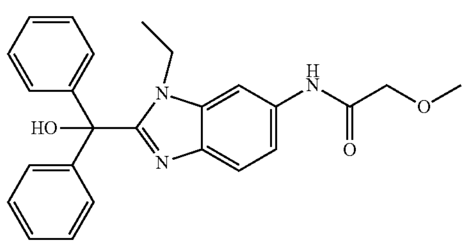 [SMILES: CCn1c(C(O)(c2ccccc2)c2ccccc2)nc2ccc(NC(=O)COC)cc21] | 416 (M + H) | |
| 358 | 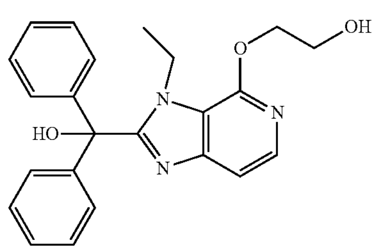 [SMILES: CCn1c(C(O)(c2ccccc2)c2ccccc2)nc2ccnc(OCCO)c21] | 390 (M + H) | |

TABLE 1-continued

| No. | Structure | Mass Characterization | ¹H NMR Data |
|---|---|---|---|
| 359 | 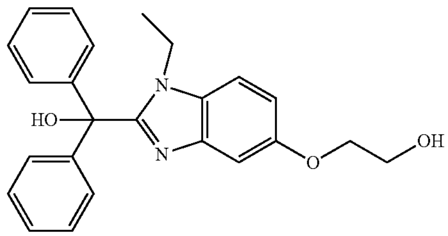 [SMILES: CCn1c(C(O)(c2ccccc2)c2ccccc2)nc2cc(OCCO)ccc21] | 389 (M + H) | |
| 360 | 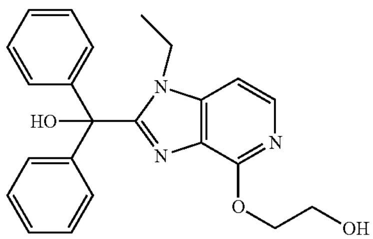 [SMILES: CCn1c(C(O)(c2ccccc2)c2ccccc2)nc2c(OCCO)nccc21] | 390 (M + H) | |
| 361 | 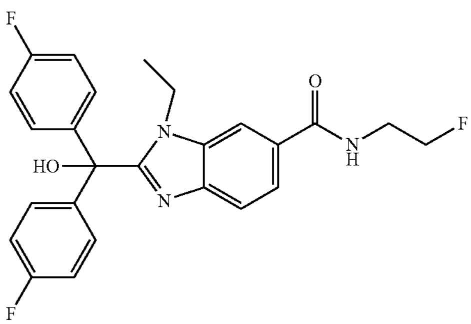 [SMILES: CCn1c(C(O)(c2ccc(F)cc2)c2ccc(F)cc2)nc2ccc(C(=O)NCCF)cc21] | 454 (M + H) | |
| 362 | 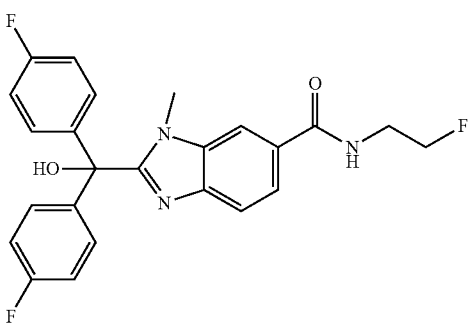 [SMILES: Cn1c(C(O)(c2ccc(F)cc2)c2ccc(F)cc2)nc2ccc(C(=O)NCCF)cc21] | 440 (M + H) | |
| 363 | 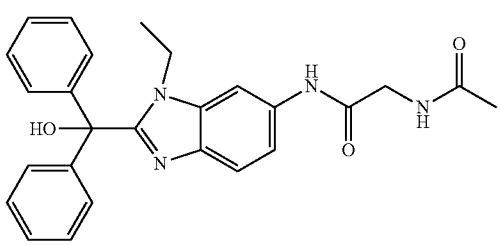 [SMILES: CCn1c(C(O)(c2ccccc2)c2ccccc2)nc2ccc(NC(=O)CNC(C)=O)cc21] | 443 (M + H) | |

TABLE 1-continued

| No. | Structure | Mass Characterization | $^1$H NMR Data |
|---|---|---|---|
| 364 | 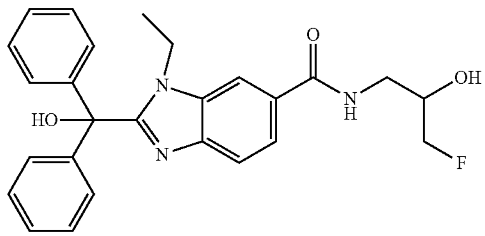 [SMILES: CCn1c(C(O)(c2ccccc2)c2ccccc2)nc2ccc(C(=O)NCC(O)CF)cc21] | 448 (M + H) | |
| 365 | 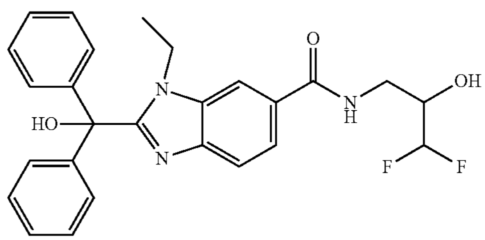 [SMILES: CCn1c(C(O)(c2ccccc2)c2ccccc2)nc2ccc(C(=O)NCC(O)C(F)F)cc21] | 466 (M + H) | |
| 366 | 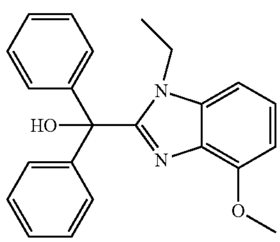 [SMILES: CCn1c(C(O)(c2ccccc2)c2ccccc2)nc2c(OC)cccc21] | 359 (M + H) | |
| 367 | 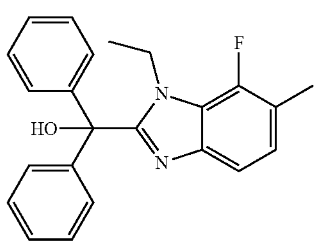 [SMILES: CCn1c(C(O)(c2ccccc2)c2ccccc2)nc2ccc(C)c(F)c21] | 361 (M + H) | |
| 368 | 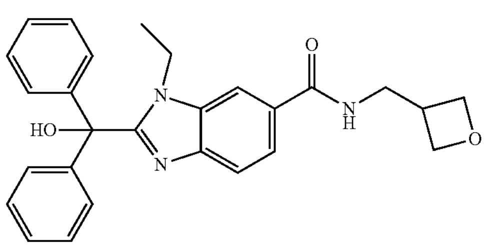 [SMILES: CCn1c(C(O)(c2ccccc2)c2ccccc2)nc2ccc(C(=O)NCC3COC3)cc21] | 442 (M + H) | |
| 369 | 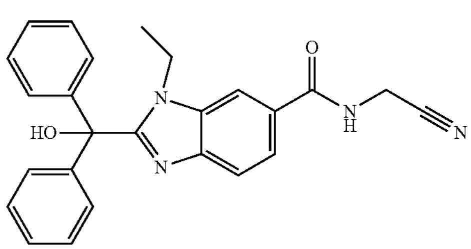 [SMILES: CCn1c(C(O)(c2ccccc2)c2ccccc2)nc2ccc(C(=O)NCC#N)cc21] | 411 (M + H) | |

TABLE 1-continued

| No. | Structure | Mass Characterization | ¹H NMR Data |
|---|---|---|---|
| 370 | 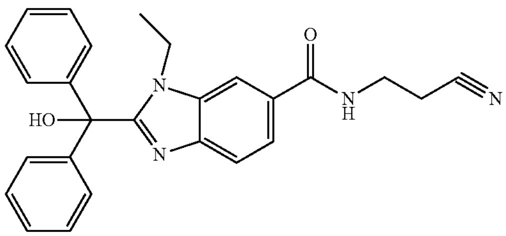 [SMILES: CCn1c(C(O)(c2ccccc2)c2ccccc2)nc2ccc(C(=O)NCCC#N)cc21] | 425 (M + H) | |
| 371 | 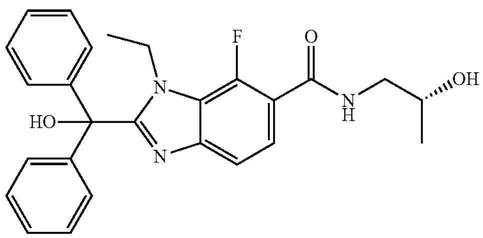 [SMILES: CCn1c(C(O)(c2ccccc2)c2ccccc2)nc2ccc(C(=O)NC[C@@H](C)O)c(F)c21] | 448 (M + H) | |
| 372 | 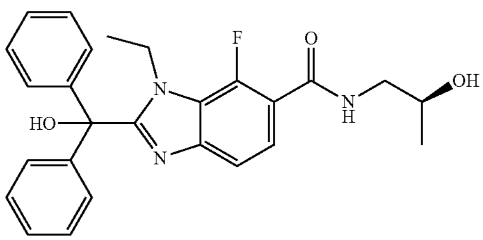 [SMILES: CCn1c(C(O)(c2ccccc2)c2ccccc2)nc2ccc(C(=O)NC[C@H](C)O)c(F)c21] | 448 (M + H) | |
| 373 | 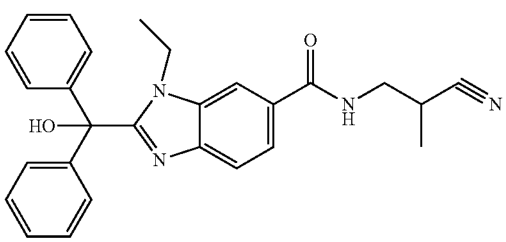 [SMILES: CCn1c(C(O)(c2ccccc2)c2ccccc2)nc2ccc(C(=O)NCC(C)C#N)cc21] | 439 (M + H) | |
| 374 | 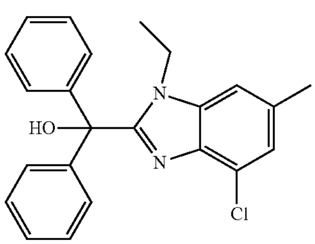 [SMILES: CCn1c(C(O)(c2ccccc2)c2ccccc2)nc2c(Cl)cc(C)cc21] | | (300 MHz, CDCl$_3$): δ 7.28-7.35 (m, 10H), 7.12 (s, 1H), 6.99 (s, 1H), 5.76 (s, 1H), 3.87 (q, 2H), 2.44 (s, 3H), 0.53 (t, 3H) |
| 375 | 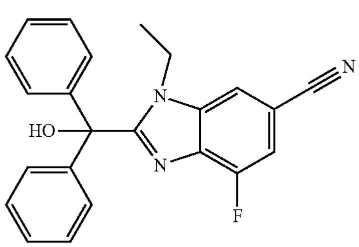 [SMILES: CCn1c(C(O)(c2ccccc2)c2ccccc2)nc2c(F)cc(C#N)cc21] | | (300 MHz, CDCl$_3$): δ 7.47 (s, 1H), 7.21-7.39 (m, 11H), 4.57 (s, 1H), 4.05 (q, 2H), 0.79 (t, 3H) |

TABLE 1-continued

| No. | Structure | Mass Characterization | ¹H NMR Data |
|---|---|---|---|
| 376 | 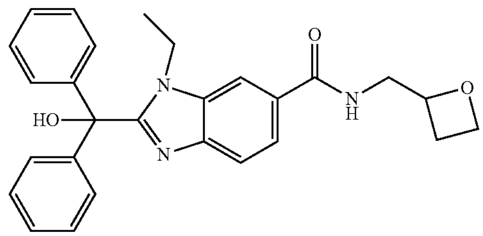 | 422 (M + H) | |
| 377 | 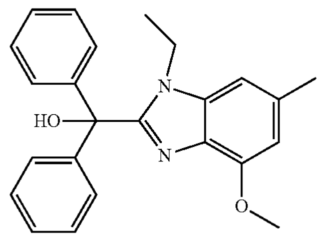 [SMILES: CCn1c(C(O)(c2ccccc2)c2ccccc2)nc2c(OC)cc(C)cc21] | | |
| 378 | 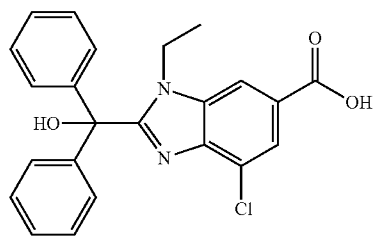 [SMILES: CCn1c(C(O)(c2ccccc2)c2ccccc2)nc2c(Cl)cc(C(=O)O)cc21] | | (300 MHz, CDCl₃): δ 8.07 (s, 1H), 8.02 (s, 1H), 7.27-7.36 (m, 10H), 5.40 (s, 1H), 3.98 (q, 2H), 0.62 (t, 3H) |
| 379 | 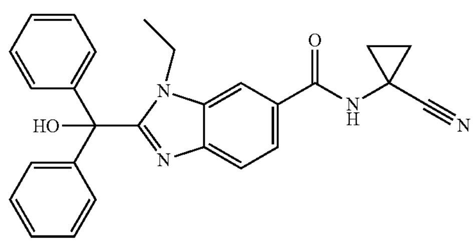 [SMILES: CCn1c(C(O)(c2ccccc2)c2ccccc2)nc2ccc(C(=O)NC3(C#N)CC3)cc21] | 437 (M + H) | |
| 380 | 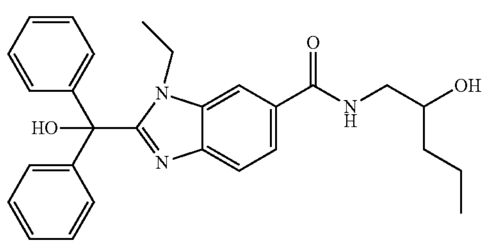 [SMILES: CCCC(O)CNC(=O)c1ccc2nc(C(O)(c3ccccc3)c3ccccc3)n(CC)c2c1] | 458 (M + H) | |
| 381 | 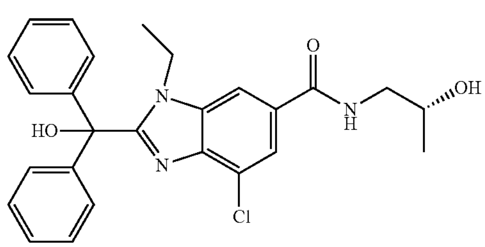 [SMILES: CCn1c(C(O)(c2ccccc2)c2ccccc2)nc2c(Cl)cc(C(=O)NC[C@@H](C)O)cc21] | 464 (M + H) | |

TABLE 1-continued

| No. | Structure | Mass Characterization | ¹H NMR Data |
|-----|-----------|----------------------|-------------|
| 382 | 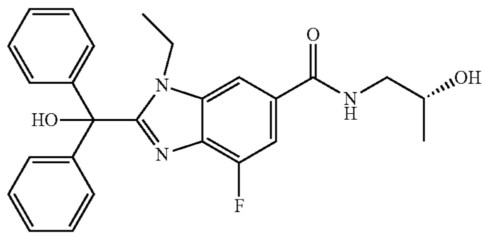 [SMILES: CCn1c(C(O)(c2ccccc2)c2ccccc2)nc2c(F)cc(C(=O)NC[C@@H](C)O)cc21] | 448 (M + H) | |
| 383 | 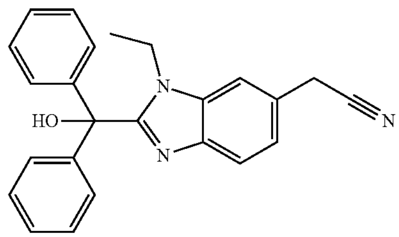 [SMILES: CCn1c(C(O)(c2ccccc2)c2ccccc2)nc2ccc(CC#N)cc21] | 368 (M + H) | |
| 384 | 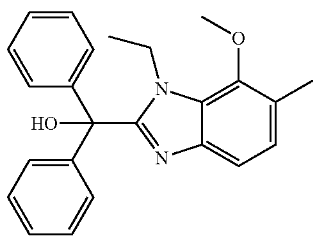 [SMILES: CCn1c(C(O)(c2ccccc2)c2ccccc2)nc2ccc(C)c(OC)c21] | 373 (M + H) | |
| 385 | 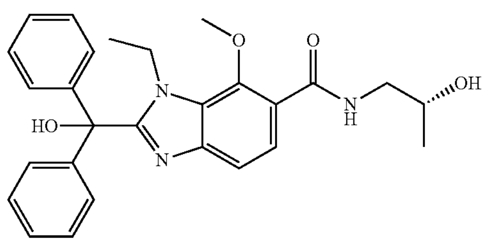 [SMILES: CCn1c(C(O)(c2ccccc2)c2ccccc2)nc2ccc(C(=O)NC[C@@H](C)O)c(OC)c21] | 460 (M + H) | |
| 386 | 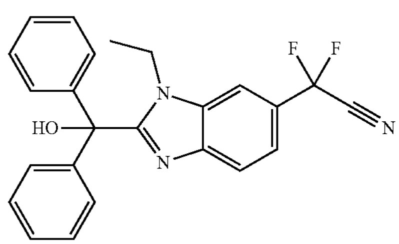 [SMILES: CCn1c(C(O)(c2ccccc2)c2ccccc2)nc2ccc(C(F)(F)C#N)cc21] | 404 (M + H) | |
| 387 | 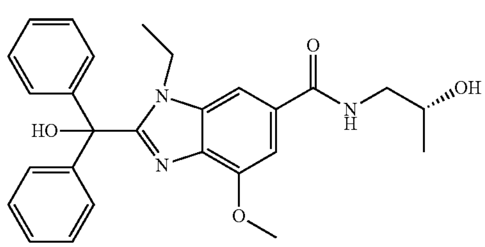 [SMILES: CCn1c(C(O)(c2ccccc2)c2ccccc2)nc2c(OC)cc(C(=O)NC[C@@H](C)O)cc21] | | (400 MHz, CDCl$_3$): δ 7.41 (s, 1H), 7.25-7.37 (m, 10H), 7.11 (s, 1H), 6.62 (m, 1H), 5.40 (s, 1H), 4.12 (s, 3H), 4.11 (m, 1H), 3.96 (q, 2H), 3.70 (m, 1H), 3.36 (m, 1H), 2.39 (bs, 1H), 1.24 (d, 3H), 0.58 (t, 3H) |

TABLE 1-continued

| No. | Structure | Mass Characterization | ¹H NMR Data |
|---|---|---|---|
| 388 | 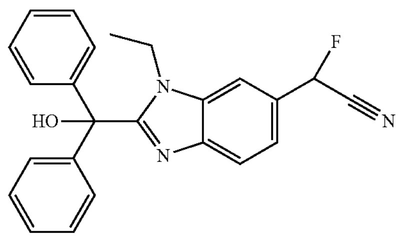 [SMILES: CCn1c(C(O)(c2ccccc2)c2ccccc2)nc2ccc(C(F)C#N)cc21] | 386 (M + H) | |
| 389 | 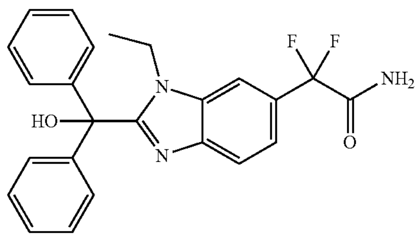 [SMILES: CCn1c(C(O)(c2ccccc2)c2ccccc2)nc2ccc(C(F)(F)C(N)=O)cc21] | 422 (M + H) | |
| 390 | 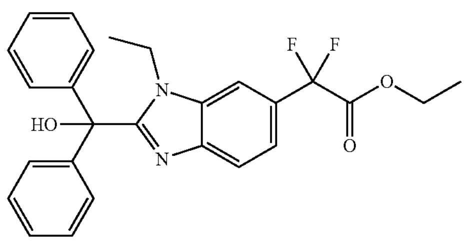 [SMILES: CCOC(=O)C(F)(F)c1ccc2nc(C(O)(c3ccccc3)c3ccccc3)n(CC)c2c1] | 451 (M + H) | |
| 391 | 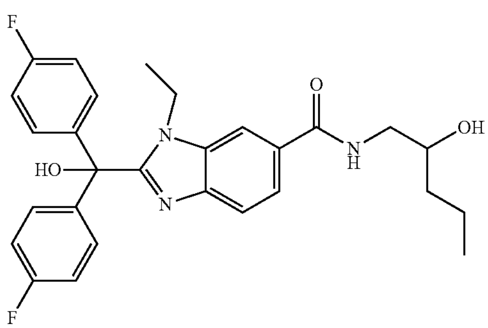 [SMILES: CCCC(O)CNC(=O)c1ccc2nc(C(O)(c3ccc(F)cc3)c3ccc(F)cc3)n(CC)c2c1] | 494 (M + H) | |
| 392 | 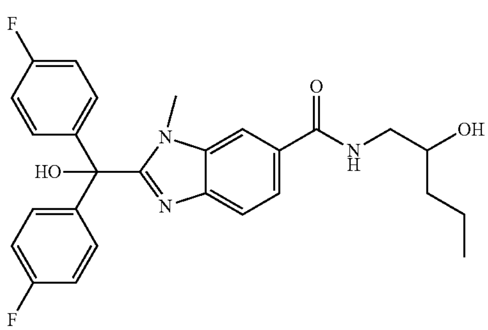 [SMILES: CCCC(O)CNC(=O)c1ccc2nc(C(O)(c3ccc(F)cc3)c3ccc(F)cc3)n(C)c2c1] | 480 (M + H) | |

TABLE 1-continued

| No. | Structure | Mass Characterization | ¹H NMR Data |
|---|---|---|---|
| 393 | 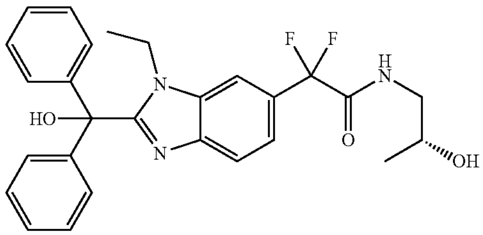 [SMILES: CCn1c(C(O)(c2ccccc2)c2ccccc2)nc2ccc(C(F)(F)C(=O)NC[C@@H](C)O)cc21] | 480 (M + H) | |
| 394 | 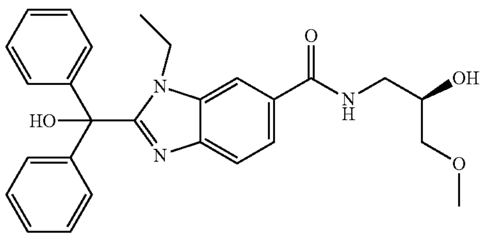 [SMILES: CCn1c(C(O)(c2ccccc2)c2ccccc2)nc2ccc(C(=O)NC[C@@H](O)COC)cc21] | 460 (M + H) | |
| 395 | 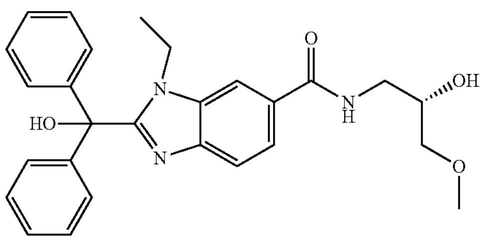 [SMILES: CCn1c(C(O)(c2ccccc2)c2ccccc2)nc2ccc(C(=O)NC[C@H](O)COC)cc21] | 460 (M + H) | |
| 396 | 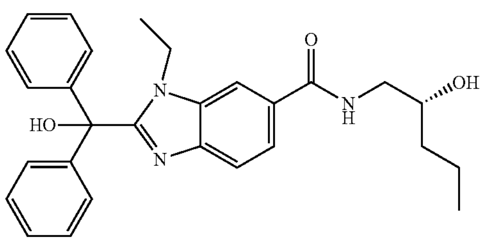 [SMILES: CCC[C@@H](O)CNC(=O)c1ccc2nc(C(O)(c3ccccc3)c3ccccc3)n(CC)c2c1] | 458 (M + H) | |
| 397 | 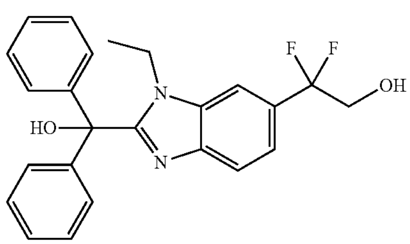 [SMILES: CCn1c(C(O)(c2ccccc2)c2ccccc2)nc2ccc(C(F)(F)CO)cc21] | 409 (M + H) | |
| 398 | 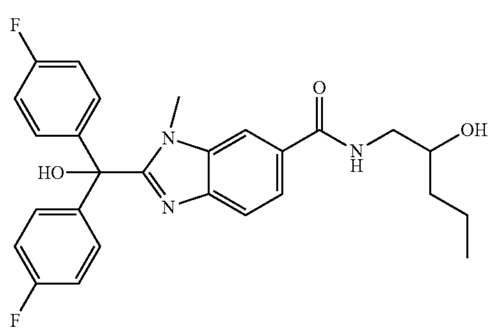 [SMILES: CCCC(O)CNC(=O)c1ccc2nc(C(O)(c3ccc(F)cc3)c3ccc(F)cc3)n(C)c2c1] | 480 (M + H) | |

TABLE 1-continued

| No. | Structure | Mass Characterization | $^1$H NMR Data |
|-----|-----------|----------------------|----------------|
| 399 | 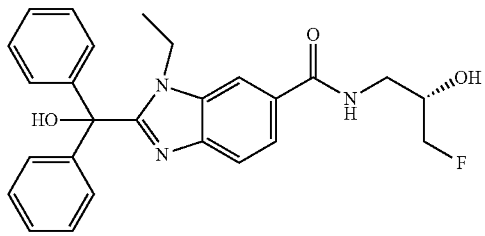 [SMILES: CCn1c(C(O)(c2ccccc2)c2ccccc2)nc2ccc(C(=O)NC[C@H](O)CF)cc21] | 448 (M + H) | |
| 400 | 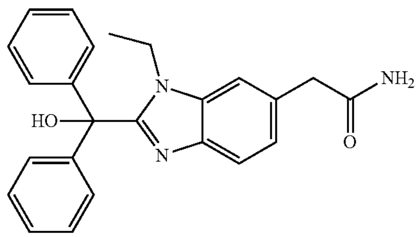 [SMILES: CCn1c(C(O)(c2ccccc2)c2ccccc2)nc2ccc(CC(N)=O)cc21] | 386 (M + H) | |
| 401 | 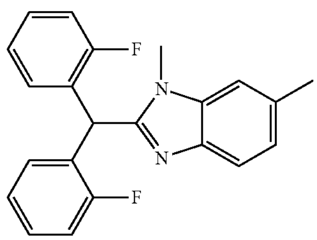 [SMILES: Cc1ccc2nc(C(c3ccccc3F)c3ccccc3F)n(C)c2c1] | 349 (M + H) | |
| 402 | 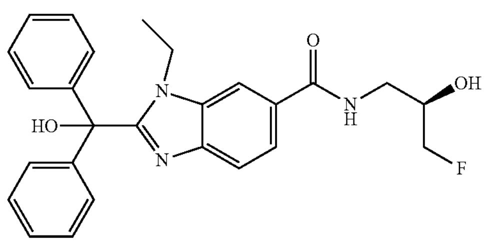 [SMILES: CCn1c(C(O)(c2ccccc2)c2ccccc2)nc2ccc(C(=O)NC[C@@H](O)CF)cc21] | 448 (M + H) | |
| 403 | 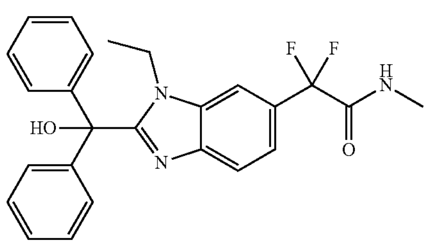 [SMILES: CCn1c(C(O)(c2ccccc2)c2ccccc2)nc2ccc(C(F)(F)C(=O)NC)cc21] | 436 (M + H) | |
| 404 | 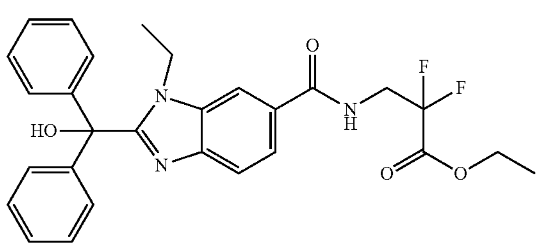 [SMILES: CCOC(=O)C(F)(F)CNC(=O)c1ccc2nc(C(O)(c3ccccc3)c3ccccc3)n(CC)c2c1] | 508 (M + H) | |

TABLE 1-continued

| No. | Structure | Mass Characterization | ¹H NMR Data |
|---|---|---|---|
| 405 | 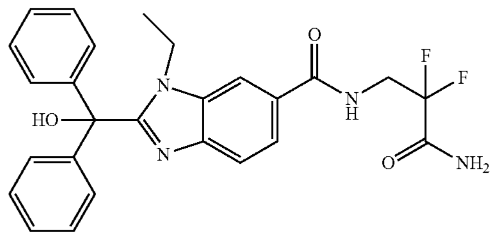 [SMILES: CCn1c(C(O)(c2ccccc2)c2ccccc2)nc2ccc(C(=O)NCC(F)(F)C(N)=O)cc21] | 479 (M + H) | |
| 406 | 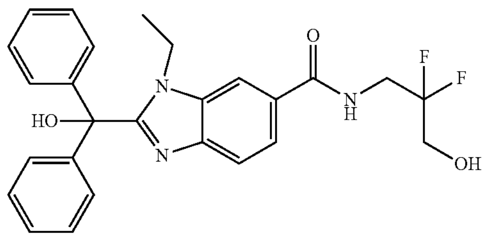 [SMILES: CCn1c(C(O)(c2ccccc2)c2ccccc2)nc2ccc(C(=O)NCC(F)(F)CO)cc21] | 466 (M + H) | |
| 407 | 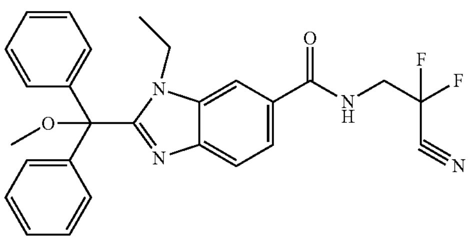 [SMILES: CCn1c(C(OC)(c2ccccc2)c2ccccc2)nc2ccc(C(=O)NCC(F)(F)C#N)cc21] | | (400 MHz, CDCl₃): δ8.02 (s, 1H), 7.87 (d, 1H), 7.61 (m, 5H), 7.27 (m, 4H), 7.23 (m, 2H), 6.54 (m, 1H), 4.23 (m, 4H), 3.18 (s, 3H), 0.84 (t, 3H) |
| 408 | 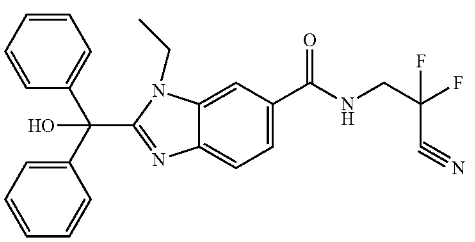 [SMILES: CCn1c(C(O)(c2ccccc2)c2ccccc2)nc2ccc(C(=O)NCC(F)(F)C#N)cc21] | 461 (M + H) | |
| 409 | 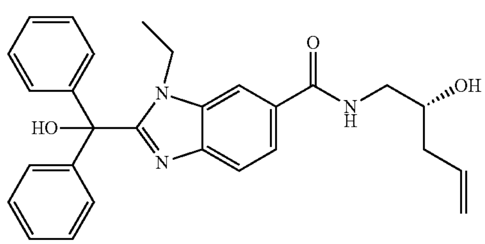 | 456 (M + H) | |
| 410 | 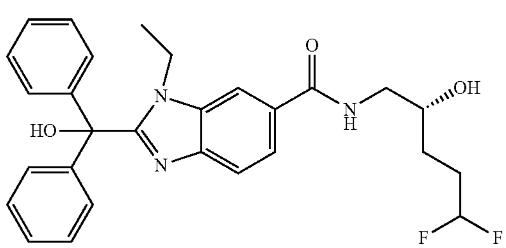 [SMILES: CCn1c(C(O)(c2ccccc2)c2ccccc2)nc2ccc(C(=O)NC[C@H](O)CCC(F)F)cc21] | 494 (M + H) | |

TABLE 1-continued

| No. | Structure | Mass Characterization | ¹H NMR Data |
|---|---|---|---|
| 411 | [structure] | 494 (M + H) | |
| 412 | [structure] | 333 (M + H) | |

Method of Use:

In one aspect, the present invention provides a method for treating a proliferative disorder in a subject in need thereof, comprising administering to said subject an ACSS2 inhibitor. In some embodiments, the proliferative disorder is a cancer condition. In some further embodiments, said cancer condition is a cancer selected from the group consisting of lung cancer, head and neck squamous cell carcinoma, pancreatic cancer, breast cancer, ovarian cancer, renal cell carcinoma, prostate cancer, neuroendocrine cancer, gastric cancer, bladder cancer and colon cancer.

In a further embodiment, the present invention provides a method of treating a cancer condition, wherein the ACSS2 inhibitor is effective in one or more of inhibiting proliferation of cancer cells, inhibiting metastasis of cancer cells, killing cancer cells and reducing severity or incidence of symptoms associated with the presence of cancer cells. In some other embodiments, said method comprises administering to the cancer cells a therapeutically effective amount of an ACSS2 inhibitor. In some embodiments, the administration takes place in vitro. In other embodiments, the administration takes place in vivo.

As used herein, a therapeutically effective amount of an ACSS2 inhibitor refers to an amount sufficient to effect the intended application, including but not limited to, disease treatment, as defined herein. Also contemplated in the subject methods is the use of a sub-therapeutic amount of an ACSS2 inhibitor for treating an intended disease condition.

The amount of the ACSS2 inhibitor administered may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

Measuring inhibition of biological effects of ACSS2 can comprise performing an assay on a biological sample, such as a sample from a subject. Any of a variety of samples may be selected, depending on the assay. Examples of samples include, but are not limited to blood samples (e.g. blood plasma or serum), exhaled breath condensate samples, bronchoalveolar lavage fluid, sputum samples, urine samples, and tissue samples.

A subject being treated with an ACSS2 inhibitor may be monitored to determine the effectiveness of treatment, and the treatment regimen may be adjusted based on the subject's physiological response to treatment. For example, if inhibition of a biological effect of ACSS2 inhibition is above or below a threshold, the dosing amount or frequency may be decreased or increased, respectively. The methods can further comprise continuing the therapy if the therapy is determined to be efficacious. The methods can comprise maintaining, tapering, reducing, or stopping the administered amount of a compound in the therapy if the therapy is determined to be efficacious. The methods can comprise increasing the administered amount of a compound in the therapy if it is determined not to be efficacious. Alternatively, the methods can comprise stopping therapy if it is determined not to be efficacious. In some embodiments, treatment with an ACSS2 inhibitor is discontinued if inhibition of the biological effect is above or below a threshold, such as in a lack of response or an adverse reaction. The biological effect may be a change in any of a variety of physiological indicators.

In general, an ACSS2 inhibitor is a compound that inhibits one or more biological effects of ACSS2. Examples of biological effects of ACSS2 include, but are not limited to, production of acetyl-CoA, acetate incorporation into lipids, acetate incorporation into histones, and utilization of acetate in tumor cells. Such biological effects may be inhibited by about or more than about 10%, 20%, 30%, 40%, 50%, 60%, 70%, 80%, 90%, 95%, or more.

In some other embodiments, the subject methods are useful for treating a disease condition associated with ACSS2. Any disease condition characterized by an abnormal activity or expression level of ACSS2 can be an intended disease condition. In some embodiments, the disease condition is a proliferative disorder, such as described herein, including but not limited to cancer. Many human cancers have an increased dependence on acetate, implicating a role of ACSS2 in tumorigenesis and tumor progression.

This dependence on acetate and ACSS2 activity is emerging as a common theme in diverse human cancers, consequently agents that target ACSS2 have therapeutic value.

The data presented in the Examples herein below demonstrate the anti-cancer effects of an ACSS2 inhibitor. As such, the subject method is particularly useful for treating a proliferative disorder, such as a neoplastic condition. Non-limiting examples of such conditions include but are not limited to acanthoma, acinic cell carcinoma, acoustic neuroma, acral lentiginous melanoma, acrospiroma, acute eosinophilic leukemia, acute lymphoblastic leukemia, acute megakaryoblastic leukemia, acute monocytic leukemia, acute myeloblastic leukemia with maturation, acute myeloid dendritic cell leukemia, acute myeloid leukemia, acute promyelocytic leukemia, adamantinoma, adenocarcinoma, adenoid cystic carcinoma, adenoma, adenomatoid odontogenic tumor, adrenocortical carcinoma, adult T-cell leukemia, aggressive NK-cell leukemia, AIDS-related cancers, AIDS-related lymphoma, alveolar soft part sarcoma, ameloblastic fibroma, anal cancer, anaplastic large cell lymphoma, anaplastic thyroid cancer, angioimmunoblastic T-cell lymphoma, angiomyolipoma, angiosarcoma, appendix cancer, astrocytoma, atypical teratoid rhabdoid tumor, basal cell carcinoma, basal-like carcinoma, B-cell leukemia, B-cell lymphoma, bellini duct carcinoma, biliary tract cancer, bladder cancer, blastoma, bone cancer, bone tumor, brain stem glioma, brain tumor, breast cancer, brenner tumor, bronchial tumor, bronchioloalveolar carcinoma, brown tumor, Burkitt's lymphoma, carcinoid tumor, carcinoma, carcinosarcoma, Castleman's disease, central nervous system embryonal tumor, cerebellar astrocytoma, cerebral astrocytoma, cervical cancer, cholangiocarcinoma, chondroma, chondrosarcoma, chordoma, choriocarcinoma, choroid plexus papilloma, chronic lymphocytic leukemia, chronic monocytic leukemia, chronic myelogenous leukemia, chronic myeloproliferative disorder, chronic neutrophilic leukemia, clear cell renal cell carcinoma, clear-cell tumor, colon cancer, colorectal cancer, craniopharyngioma, cutaneous T-cell lymphoma, dermatofibrosarcoma protuberans, dermoid cyst, desmoplastic small round cell tumor, diffuse large B cell lymphoma, dysembryoplastic neuroepithelial tumor, embryonal carcinoma, endodermal sinus tumor, endometrial cancer, endometrial uterine cancer, endometrioid tumor, enteropathy-associated T-cell lymphoma, ependymoblastoma, ependymoma, epithelioid sarcoma, erythroleukemia, esophageal cancer, esthesioneuroblastoma, Ewing's sarcoma, extracranial germ cell tumor, extragonadal germ cell tumor, extrahepatic bile duct cancer, extramammary Paget's disease, fallopian tube cancer, fibroma, fibrosarcoma, follicular lymphoma, follicular thyroid cancer, gallbladder cancer, ganglioglioma, ganglioneuroma, gastric cancer, gastric lymphoma, gastrointestinal cancer, gastrointestinal carcinoid tumor, gastrointestinal stromal tumor, germ cell tumor, germinoma, gestational choriocarcinoma, gestational trophoblastic tumor, giant cell tumor of bone, glioblastoma multiforme, glioma, gliomatosis cerebri, glomus tumor, glucagonoma, gonadoblastoma, granulosa cell tumor, hairy cell leukemia, head and neck cancer, heart cancer, hemangioblastoma, hemangiopericytoma, hemangiosarcoma, hematological malignancy, hepatocellular carcinoma, hepatosplenic T-cell lymphoma, Hodgkin lymphoma, hypopharyngeal cancer, hypothalamic glioma, inflammatory breast cancer, intraocular melanoma, islet cell carcinoma, juvenile myelomonocytic leukemia, Kaposi's sarcoma, kidney cancer, klatskin tumor, krukenberg tumor, laryngeal cancer, lentigo maligna melanoma, leukemia, lip and oral cavity cancer, liposarcoma, lung cancer, luteoma, lymphangioma, lymphangiosarcoma, lymphoepithelioma, lymphoid leukemia, lymphoma, macroglobulinemia, malignant fibrous histiocytoma, malignant glioma, malignant mesothelioma, malignant peripheral nerve sheath tumor, malignant rhabdoid tumor, malignant triton tumor, malt lymphoma, mantle cell lymphoma, mast cell leukemia, mediastinal germ cell tumor, mediastinal tumor, medullary thyroid cancer, medulloblastoma, medulloepithelioma, melanoma, meningioma, merkel cell carcinoma, mesothelioma, metastatic squamous neck cancer with occult primary, metastatic urothelial carcinoma, mixed mullerian tumor, monocytic leukemia, mouth cancer, mucinous tumor, multiple endocrine neoplasia syndrome, multiple myeloma, mycosis fungoides, myelodysplastic disease, myeloid leukemia, myeloid sarcoma, myeloproliferative disease, myxoma, nasal cavity cancer, nasopharyngeal cancer, neoplasm, neurinoma, neuroblastoma, neurofibroma, neuroma, nodular melanoma, non-Hodgkin lymphoma, non-melanoma skin cancer, non-small cell lung cancer, ocular oncology, oligoastrocytoma, oligodendroglioma, oncocytoma, optic nerve sheath meningioma, oral cancer, oropharyngeal cancer, osteosarcoma, ovarian cancer, ovarian epithelial cancer, ovarian germ cell tumor, ovarian low malignant potential tumor, pancoast tumor, pancreatic cancer, papillary thyroid cancer, papillomatosis, paraganglioma, paranasal sinus cancer, parathyroid cancer, penile cancer, perivascular epithelioid cell tumor, pharyngeal cancer, pheochromocytoma, pineal parenchymal tumor of intermediate differentiation, pineoblastoma, pituicytoma, pituitary adenoma, pituitary tumor, plasma cell neoplasm, pleuropulmonary blastoma, polyembryoma, precursor T-lymphoblastic lymphoma, primitive neuroectodermal tumor, prostate cancer, pseudomyxoma peritonei, rectal cancer, renal cell carcinoma, retinoblastoma, rhabdomyoma, rhabdomyosarcoma, Richter's transformation, sacrococcygeal teratoma, salivary gland cancer, sarcoma, schwannomatosis, sebaceous gland carcinoma, secondary neoplasm, seminoma, serous tumor, Sertoli-Leydig cell tumor, sex cord-stromal tumor, sezary syndrome, signet ring cell carcinoma, skin cancer, small blue round cell tumor, small cell carcinoma, small cell lung cancer, small cell lymphoma, small intestine cancer, soft tissue sarcoma, somatostatinoma, soot wart, spinal tumor, splenic marginal zone lymphoma, squamous cell carcinoma, stomach cancer, superficial spreading melanoma, supratentorial primitive neuroectodermal tumor, surface epithelial-stromal tumor, synovial sarcoma, T-cell acute lymphoblastic leukemia, T-cell large granular lymphocyte leukemia, T-cell leukemia, T-cell lymphoma, T-cell prolymphocytic leukemia, teratoma, terminal lymphatic cancer, testicular cancer, thecoma, throat cancer, thymic carcinoma, thymoma, thyroid cancer, transitional cell cancer of renal pelvis and ureter, transitional cell carcinoma, urachal cancer, urethral cancer, urogenital neoplasm, uterine sarcoma, uveal melanoma, vaginal cancer, verner morrison syndrome, verrucous carcinoma, visual pathway glioma, vulvar cancer, Waldenstrom's macroglobulinemia, Warthin's tumor, Wilms' tumor or any combination thereof.

In some embodiments, the methods of administering an ACSS2 inhibitor described herein are applied to the treatment of cancers of the adrenal glands, blood, bone marrow, brain, breast, cervix, colon, head and neck, kidney, liver, lung, ovary, pancreas, plasma cells, rectum, retina, skin, spine, throat or any combination thereof.

Certain embodiments contemplate a human subject such as a subject that has been diagnosed as having or being at risk for developing or acquiring a proliferative disorder condition. Certain other embodiments contemplate a non-human subject, for example a non-human primate such as a macaque, chimpanzee, gorilla, vervet, orangutan, baboon or other non-human primate, including such non-human subjects that can be known to the art as preclinical models. Certain other embodiments contemplate a non-human subject that is a mammal, for example, a mouse, rat, rabbit, pig, sheep, horse, bovine, goat, gerbil, hamster, guinea pig or other mammal. There are also contemplated other embodiments in which the subject or biological source can be a non-mammalian vertebrate, for example, another higher vertebrate, or an avian, amphibian or reptilian species, or another subject or biological source. In certain embodiments of the present invention, a transgenic animal is utilized. A transgenic animal is a non-human animal in which one or more of the cells of the animal includes a nucleic acid that is non-endogenous (i.e., heterologous) and is present as an extrachromosomal element in a portion of its cell or stably integrated into its germ line DNA (i.e., in the genomic sequence of most or all of its cells).

Therapuetic Efficacy:

In some embodiments, therapeutic efficacy is measured based on an effect of treating a proliferative disorder, such as cancer. In general, therapeutic efficacy of the methods and compositions of the invention, with regard to the treatment of a proliferative disorder (e.g. cancer, whether benign or malignant), may be measured by the degree to which the methods and compositions promote inhibition of tumor cell proliferation, the inhibition of tumor vascularization, the eradication of tumor cells, the reduction in the rate of growth of a tumor, and/or a reduction in the size of at least one tumor. Several parameters to be considered in the determination of therapeutic efficacy are discussed herein. The proper combination of parameters for a particular situation can be established by the clinician. The progress of the inventive method in treating cancer (e.g., reducing tumor size or eradicating cancerous cells) can be ascertained using any suitable method, such as those methods currently used in the clinic to track tumor size and cancer progress. The primary efficacy parameter used to evaluate the treatment of cancer by the inventive method and compositions preferably is a reduction in the size of a tumor. Tumor size can be figured using any suitable technique, such as measurement of dimensions, or estimation of tumor volume using available computer software, such as FreeFlight software developed at Wake Forest University that enables accurate estimation of tumor volume. Tumor size can be determined by tumor visualization using, for example, CT, ultrasound, SPECT, spiral CT, MRI, photographs, and the like. In embodiments where a tumor is surgically resected after completion of the therapeutic period, the presence of tumor tissue and tumor size can be determined by gross analysis of the tissue to be resected, and/or by pathological analysis of the resected tissue.

In some desirable embodiments, the growth of a tumor is stabilized (i.e., one or more tumors do not increase more than 1%, 5%, 10%, 15%, or 20% in size, and/or do not metastasize) as a result of the inventive method and compositions. In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. Preferably, the inventive method reduces the size of a tumor at least about 5% (e.g., at least about 10%, 15%, 20%, or 25%). More preferably, tumor size is reduced at least about 30% (e.g., at least about 35%, 40%, 45%, 50%, 55%, 60%, or 65%). Even more preferably, tumor size is reduced at least about 70% (e.g., at least about 75%, 80%, 85%, 90%, or 95%). Most preferably, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

In some embodiments, the efficacy of the inventive method in reducing tumor size can be determined by measuring the percentage of necrotic (i.e., dead) tissue of a surgically resected tumor following completion of the therapeutic period. In some further embodiments, a treatment is therapeutically effective if the necrosis percentage of the resected tissue is greater than about 20% (e.g., at least about 30%, 40%, 50%, 60%, 70%, 80%, 90%, or 100%), more preferably about 90% or greater (e.g., about 90%, 95%, or 100%). Most preferably, the necrosis percentage of the resected tissue is 100%, that is, no tumor tissue is present or detectable.

The efficacy of the inventive method can be determined by a number of secondary parameters. Examples of secondary parameters include, but are not limited to, detection of new tumors, detection of tumor antigens or markers (e.g., CEA, PSA, or CA-125), biopsy, surgical downstaging (i.e., conversion of the surgical stage of a tumor from unresectable to resectable), PET scans, survival, disease progression-free survival, time to disease progression, quality of life assessments such as the Clinical Benefit Response Assessment, and the like, all of which can point to the overall progression (or regression) of cancer in a human. Biopsy is particularly useful in detecting the eradication of cancerous cells within a tissue. Radioimmunodetection (RAID) is used to locate and stage tumors using serum levels of markers (antigens) produced by and/or associated with tumors ("tumor markers" or "tumor-associated antigens"), and can be useful as a pre-treatment diagnostic predicate, a post-treatment diagnostic indicator of recurrence, and a post-treatment indicator of therapeutic efficacy. Examples of tumor markers or tumor-associated antigens that can be evaluated as indicators of therapeutic efficacy include, but are not limited to, carcinembryonic antigen (CEA), prostate-specific antigen (PSA), CA-125, CA19-9, ganglioside molecules (e.g., GM2, GD2, and GD3), MART-1, heat shock proteins (e.g., gp96), sialyl Tn (STn), tyrosinase, MUC-1, HER-2/neu, c-erb-B2, KSA, PSMA, p53, RAS, EGF-R, VEGF, MAGE, and gp100. Other tumor-associated antigens are known in the art. RAID technology in combination with endoscopic detection systems also can efficiently distinguish small tumors from surrounding tissue (see, for example, U.S. Pat. No. 4,932,412).

In additional desirable embodiments, the treatment of cancer in a human patient in accordance with the inventive method is evidenced by one or more of the following results: (a) the complete disappearance of a tumor (i.e., a complete response), (b) about a 25% to about a 50% reduction in the size of a tumor for at least four weeks after completion of the therapeutic period as compared to the size of the tumor before treatment, (c) at least about a 50% reduction in the size of a tumor for at least four weeks after completion of the therapeutic period as compared to the size of the tumor before the therapeutic period, and (d) at least a 2% decrease (e.g., about a 5%, 10%, 20%, 30%, 40%, 50%, 60%, 70%, 80% or 90% decrease) in a specific tumor-associated antigen level at about 4-12 weeks after completion of the therapeutic period as compared to the tumor-associated antigen level before the therapeutic period. While at least a 2% decrease in a tumor-associated antigen level is preferred, any decrease in the tumor-associated antigen level is evidence of treatment of a cancer in a patient by the inventive method. For example, with respect to unresectable, locally advanced pancreatic cancer, treatment can be evidenced by at least a 10% decrease in the CA19-9 tumor-associated antigen level at 4-12 weeks after completion of the therapeutic period as compared to the CA19-9 level before the therapeutic period. Similarly, with respect to locally advanced rectal cancer, treatment can be evidenced by at least a 10% decrease in the CEA tumor-associated antigen level at 4-12 weeks after completion of the therapeutic period as compared to the CEA level before the therapeutic period.

With respect to quality of life assessments, such as the Clinical Benefit Response Criteria, the therapeutic benefit of the treatment in accordance with the invention can be evidenced in terms of pain intensity, analgesic consumption, and/or the Karnofsky Performance Scale score. The treatment of cancer in a human patient alternatively, or in addition, is evidenced by (a) at least a 50% decrease (e.g., at least a 60%, 70%, 80%, 90%, or 100% decrease) in pain intensity reported by a patient, such as for any consecutive four week period in the 12 weeks after completion of treatment, as compared to the pain intensity reported by the patient before treatment, (b) at least a 50% decrease (e.g., at least a 60%, 70%, 80%, 90%, or 100% decrease) in analgesic consumption reported by a patient, such as for any consecutive four week period in the 12 weeks after completion of treatment as compared to the analgesic consumption reported by the patient before treatment, and/or (c) at least a 20 point increase (e.g., at least a 30 point, 50 point, 70 point, or 90 point increase) in the Karnofsky Performance Scale score reported by a patient, such as for any consecutive four week period in the 12 weeks after completion of the therapeutic period as compared to the Karnofsky Performance Scale score reported by the patient before the therapeutic period.

The treatment of a proliferative disorder (e.g. cancer, whether benign or malignant) in a human patient desirably is evidenced by one or more (in any combination) of the foregoing results, although alternative or additional results of the referenced tests and/or other tests can evidence treatment efficacy.

In some embodiments, tumor size is reduced as a result of the inventive method preferably without significant adverse events in the subject. Adverse events are categorized or "graded" by the Cancer Therapy Evaluation Program (CTEP) of the National Cancer Institute (NCI), with Grade 0 representing minimal adverse side effects and Grade 4 representing the most severe adverse events. Desirably, the inventive method is associated with minimal adverse events, e.g. Grade 0, Grade 1, or Grade 2 adverse events, as graded by the CTEP/NCI. However, as discussed herein, reduction of tumor size, although preferred, is not required in that the actual size of tumor may not shrink despite the eradication of tumor cells. Eradication of cancerous cells is sufficient to realize a therapeutic effect. Likewise, any reduction in tumor size is sufficient to realize a therapeutic effect.

Detection, monitoring and rating of various cancers in a human are further described in Cancer Facts and Figures 2001, American Cancer Society, New York, N.Y., and International Patent Application WO 01/24684. Accordingly, a clinician can use standard tests to determine the efficacy of the various embodiments of the inventive method in treating cancer. However, in addition to tumor size and spread, the clinician also may consider quality of life and survival of the patient in evaluating efficacy of treatment.

In some embodiments, administration of an ACSS2 inhibitor provides improved therapeutic efficacy over treatment with either agent alone. Improved efficacy may be measured using any method known in the art, including but not limited to those described herein. In some embodiments, the improved therapeutic efficacy is an improvement of at least about 10%, 20%, 30%, 40%, 50%, 60%, 70%, 75%, 80%, 90%, 95%, 100%, 110%, 120%, 150%, 200%, 300%, 400%, 500%, 600%, 700%, 1000% or more, using an appropriate measure (e.g. tumor size reduction, duration of tumor size stability, duration of time free from metastatic events, duration of disease-free survival). Improved efficacy may also be expressed as fold improvement, such as at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold or more, using an appropriate measure (e.g. tumor size reduction, duration of tumor size stability, duration of time free from metastatic events, duration of disease-free survival).

Pharmaceutical Compositions:

A composition of the present disclosure may be formulated in any suitable pharmaceutical formulation. A pharmaceutical composition of the present disclosure typically contains an active ingredient (e.g., a compound of the present disclosure or a pharmaceutically acceptable salt and/or coordination complex thereof), and one or more pharmaceutically acceptable excipients, carriers, including but not limited to, inert solid diluents and fillers, diluents, sterile aqueous solution and various organic solvents, permeation enhancers, solubilizers and adjuvants. A composition of the present disclosure may be formulated in any suitable pharmaceutical formulation. In some embodiments, the pharmaceutical acceptable carriers, excipients are selected from the group consisting of water, alcohol, glycerol, chitosan, alginate, chondroitin, Vitamin E, mineral oil, and dimethyl sulfoxide (DMSO).

Pharmaceutical formulations may be provided in any suitable form, which may depend on the route of administration. In some embodiments, the pharmaceutical composition disclosed herein can be formulated in dosage form for administration to a subject. In some embodiments, the pharmaceutical composition is formulated for oral, intravenous, intraarterial, aerosol, parenteral, buccal, topical, transdermal, rectal, intramuscular, subcutaneous, intraosseous, intranasal, intrapulmonary, transmucosal, inhalation, and/or intraperitoneal administration. In some embodiments, the dosage form is formulated for oral intervention administration. For example, the pharmaceutical composition can be formulated in the form of a pill, a tablet, a capsule, an inhaler, a liquid suspension, a liquid emulsion, a gel, or a powder. In some embodiments, the pharmaceutical composition can be formulated as a unit dosage in liquid, gel, semi-liquid, semi-solid, or solid form.

The amount of each compound administered will be dependent on the mammal being treated, the severity of the disorder or condition, the rate of administration, the disposition of the compound and the discretion of the prescribing physician. However, an effective dosage may be in the range of about 0.001 to about 100 mg per kg body weight per day, in single or divided doses. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, the disclosure provides a pharmaceutical composition comprising an amount of an ACSS2 inhibitor formulated for administration to a subject in need thereof. In some embodiments, the pharmaceutical composition comprises a range of about 0.001 mg to about 10 mg per kilogram of body weight, about 0.001 mg to about 20 mg per kilogram of body weight, about 0.001 mg to about 50 mg per kilogram of body weight, about 0.001 mg to about 100 mg per kilogram of body weight, about 0.001 mg to about 200 mg per kilogram of body weight or about 0.001 mg to about 300 mg per kilogram of body weight, or more of an ACSS2 inhibitor. In some embodiments, the pharmaceutical composition comprises a range of about 0.1 mg to about 10 mg, or about 0.1 mg to about 20 mg, or about 0.1 mg to about 30 mg, or about 0.1 mg to about 40 mg, or about 0.1 mg to about 50 mg, or about 0.1 mg to about 60 mg, or about 0.1 mg to about 70 mg, or about 0.1 mg to about 80 mg, or about 0.1 mg to about 90 mg, or about 0.1 mg to about 100 mg, or about 0.1 mg to about 200 mg, or about 0.1 mg to about 300 mg, or about 0.1 mg to about 400 mg, or about 0.1 mg to about 500 mg, or about 0.1 mg to about 600 mg, or about 0.1 mg to about 700 mg, or about 0.1 mg to about 800 mg, or about 0.1 mg to about 900 mg, or about 0.1 mg to about 1 g of an ACSS2 inhibitor. Preferred fixed doses include about 1 mg, about 2 mg, about 3 mg, about 4 mg, about 5 mg, about 6 mg, about 7 mg, about 8 mg, about 9 mg, about 10 mg, about 12 mg, about 15 mg, about 18 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, or about 1 g, independently of body weight, of an ACSS2 inhibitor. However, it is understood that pediatric patients may require smaller dosages, and depending on the severity of the disease and condition of the patient, dosages may vary. The compound will preferably be administered once daily, but may be administered two, three or four times daily, or every other day, or once or twice per week.

In some embodiments, the effective amount is at least about 0.01 mg/kg body weight of an ACSS2 inhibitor. In some embodiments, the effective amount is an amount between about 0.01-30 mg/kg body weight of an ACSS2 inhibitor. In some embodiments, the therapeutic amount can be an amount between about 50-150 mg/kg body weight of an ACSS2 inhibitor.

In some embodiments, the composition is provided in one or more unit doses. For example, the composition can be administered in 1, 2, 3, 4, 5, 6, 7, 14, 30, 60, or more doses. Such amount can be administered each day, for example in individual doses administered once, twice, or three or more times a day. However, dosages stated herein on a per day basis should not be construed to require administration of the daily dose each and every day. For example, if one of the agents is provided in a suitably slow-release form, two or more daily dosage amounts can be administered at a lower frequency, e.g., as a depot every second day to once a month or even longer. Most typically and conveniently for the subject, an ACSS2 inhibitor can be administered once a day, for example in the morning, in the evening or during the day.

The unit doses can be administered simultaneously or sequentially. The composition can be administered for an extended treatment period. Illustratively, the treatment period can be at least about one month, for example at least about 3 months, at least about 6 months or at least about 1 year. In some cases, administration can continue for substantially the remainder of the life of the subject.

In some embodiments, the ACSS2 inhibitor can be administered as part of a therapeutic regimen that comprises administering one or more second agents (e.g. 1, 2, 3, 4, 5, or more second agents), either simultaneously or sequentially with the ACSS2 inhibitor. When administered sequentially, the ACSS2 inhibitor may be administered before or after the one or more second agents. When administered simultaneously, the ACSS2 inhibitor and the one or more second agents may be administered by the same route (e.g. injections to the same location; tablets taken orally at the same time), by a different route (e.g. a tablet taken orally while receiving an intravenous infusion), or as part of the same combination (e.g. a solution comprising an ACSS2 inhibitor and one or more second agents).

A combination treatment according to the invention may be effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. The exact dosage will depend upon the agent selected, the route of administration, the form in which the compound is administered, the subject to be treated, the body weight of the subject to be treated, and the preference and experience of the attending physician.

Pharmaceutical Composition for Oral Administration.

In some embodiments, the disclosure provides a pharmaceutical composition for oral administration containing at least one compound of the present disclosure and a pharmaceutical excipient suitable for oral administration. The composition may be in the form of a solid, liquid, gel, semi-liquid, or semi-solid. In some embodiments, the composition further comprises a second agent.

In some embodiments, the invention provides a solid pharmaceutical composition for oral administration containing: (i) an ACSS2 inhibitor; and (ii) a pharmaceutical excipient suitable for oral administration. In some embodiments, the composition further contains: (iii) a third agent or even a fourth agent. In some embodiments, each compound or agent is present in a therapeutically effective amount. In other embodiments, one or more compounds or agents is present in a sub-therapeutic amount, and the compounds or agents act synergistically to provide a therapeutically effective pharmaceutical composition.

Pharmaceutical compositions of the disclosure suitable for oral administration can be presented as discrete dosage forms, such as hard or soft capsules, cachets, troches, lozenges, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion, or dispersible powders or granules, or syrups or elixirs. Such dosage forms can be prepared by any of the methods of pharmacy, which typically include the step of bringing the active ingredient(s) into association with the carrier. In general, the composition are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient(s) in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This disclosure further encompasses anhydrous pharmaceutical composition and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time Anhydrous pharmaceutical compositions and dosage forms of the disclosure can be prepared using anhydrous or low moisture containing ingredients and low moisture or low humidity conditions. Pharmaceutical compositions and dosage forms of the disclosure which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the composition for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical composition and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical composition and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the composition of the disclosure to provide tablets that disintegrate when exposed to an aqueous environment. Too much of a disintegrant may produce tablets which may disintegrate in the bottle. Too little may be insufficient for disintegration to occur and may alter the rate and extent of release of the active ingredient(s) from the dosage form. A sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical composition and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical composition and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyllaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical composition and dosage forms of the disclosure include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present disclosure and to minimize precipitation of the compound of the present disclosure. This can be especially important for composition for non-oral use, e.g., composition for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, .epsilon.-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. If present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Composition for Topical (e.g., Transdermal) Delivery.

In some embodiments, the invention provides a pharmaceutical composition for transdermal delivery containing a compound of the present invention and a pharmaceutical excipient suitable for transdermal delivery. The composition may be in the form of a solid, liquid, gel, semi-liquid, or semi-solid. In some embodiments, the composition further comprises a second agent.

Composition of the present disclosure can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical composition also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Formulations for topical administration may include ointments, lotions, creams, gels (e.g., poloxamer gel), drops, suppositories, sprays, liquids and powders. Conventional pharmaceutical carriers, aqueous, powder or oily bases, thickeners and the like may be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or any bio-engineered materials.

Another exemplary formulation for use in the methods of the present disclosure employs transdermal delivery devices ("patches"). Such transdermal patches may be used to provide continuous or discontinuous infusion of a compound of the present disclosure in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Composition for Injection.

In some embodiments, the disclosure provides a pharmaceutical composition for injection containing a compound of the present disclosure and a pharmaceutical excipient suitable for injection. Components and amounts of agents in the composition are as described herein.

The forms in which the novel composition of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Composition for Inhalation.

Composition for inhalation or insufflation include solutions and suspensions in pharmaceutically acceptable, aqueous or organic solvents, or mixtures thereof, and powders. The liquid or solid composition may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Composition.

Pharmaceutical composition may also be prepared from composition described herein and one or more pharmaceutically acceptable excipients suitable for sublingual, buccal, rectal, intraosseous, intraocular, intranasal, epidural, or intraspinal administration. Preparations for such pharmaceutical composition are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., "Methods in Cell Biology", Volume XIV, ISBN: 978-0-12-564114-2, Academic Press, New York, N.W., p. 33 (1976) and Medina, Zhu, and Kairemo, "Targeted liposomal drug delivery in cancer", Current Pharm. Des. 10: 2981-2989, 2004. For additional information regarding drug formulation and administration, see "Remington: The Science and Practice of Pharmacy," Lippincott Williams & Wilkins, Philadelphia, ISBN-10: 0781746736, $21^{st}$ Edition (2005).

The invention also provides kits. The kits may include an ACSS2 inhibitor and one or more additional agents in suitable packaging with written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

Combination Therapies:

The present invention also provides methods for further combination therapies in which, in addition to an ACSS2 inhibitor, one or more second agents known to modulate other pathways, or other components of the same pathway, or even overlapping sets of target proteins is used, or a pharmaceutically acceptable salt, ester, prodrug, solvate, hydrate or derivative thereof. In one aspect, such therapy includes but is not limited to the combination of the composition comprising an ACSS2 inhibitor as described herein with one or more of other ACSS2 inhibitors as described herein, chemotherapeutic agents, therapeutic antibodies, and radiation treatment, to provide, where desired, a synergistic or additive therapeutic effect.

Second agents useful in the methods of the invention include any agent capable of modulating a target molecule, either directly or indirectly. Non-limiting examples of target molecules modulated by second agents include enzymes, enzyme substrates, products of transitions, antibodies, antigens, membrane proteins, nuclear proteins, cytosolic proteins, mitochondrial proteins, lysosomal proteins, scaffold proteins, lipid rafts, phosphoproteins, glycoproteins, membrane receptors, G-protein-coupled receptors, nuclear receptors, protein tyrosine kinases, protein serine/threonine kinases, phosphatases, proteases, hydrolases, lipases, phospholipases, ligases, reductases, oxidases, synthases, transcription factors, ion channels, RNA, DNA, RNAse, DNAse, phospholipids, sphingolipids, nuclear receptors, ion channel proteins, nucleotide-binding proteins, calcium-binding proteins, chaperones, DNA binding proteins, RNA binding proteins, scaffold proteins, tumor suppressors, cell cycle proteins, and histones.

Second agents may target one or more signaling molecules including but not limited to the following: 4EPB-1, 5-lipoxygenase, A1, Ab1, Acetyl-CoAa Carboxylase, actin, adaptor/scaffold proteins, adenylyl cyclase receptors, adhesion molecules, AFT, Akt1, Akt2, Akt3, ALK, AMPKs, APC/C, ARaf, Arf-GAPs, Arfs, ASK, ASK1, asparagine hydroxylase FIH transferases, ATF2, ATF-2, ATM, ATP citrate lyase, ATR, Auroras, B cell adaptor for PI3-kinase (BCAP), Bad, Bak, Bax, Bcl-2, Bcl-B, Bcl-w, Bcl-XL, Bid, Bik, Bim, BLNK, Bmf, BMP receptors, Bok, BRAF, Btk, Bub, cadherins, CaMKs, Casein kinases, Caspase 2, Caspase 3, Caspase 6, Caspase 7, Caspase 8, Caspase 9, caspases, catenins, cathepsins, caveolins, Cb1, CBP/P300 family, CD45, CDC25 phosphatases, Cdc42, Cdk 1, Cdk 2, Cdk 4, Cdk 6, Cdk 7, Cdks, CENPs, Chk1, Chk2, CLKs, Cot, cRaf, CREB, Crk, CrkL, Csk, Cyclin A, Cyclin B, Cyclin D, Cyclin E, Db1, deacetylases, DLK, DNA methyl transferases, DNA-PK, Dok, Dual Specificity phosphatases (DUSPs), E2Fs, eg5/KSP, Egr-1, eIF4E-binding protein, Elk, elongation factors, endosomal sorting complex required for transport (ESCRT) proteins, Eph receptors, Erks, esterases, Ets, Eyes absent (EYA) tyrosine phosphatases, FAK, Fas associated death domain (FADD), FGF receptors, Fgr, focal adhesion kinase, fodrin, Fos, FOXO, Fyn, GAD, Grb2, Grb2 associated binder (GAB), GSK3α, GSK3β, H-Ras, H3K27, Hdm, HER receptors, HIFs, histone acetylases, histone deacetylases, Histone H3K4 demethylases, HMGA, Hrk, Hsp27, Hsp70, Hsp90s, hydrolases, hydroxylases, IAPB, IGF receptors, IKKs, IL-2, IL-4, IL-6, IL-8, ILK, Immunoglobulin-like adhesion molecules, initiation factors, inositol phosphatases, Insulin receptor, integrins, interferon α, interferon β, IRAKs, Jak1, Jak2, Jak3, JHDM2A, Jnks, K-Ras, Kit receptor, KSR, LAR phosphatase, LAT, Lck, Lim kinase, LKB-1, Low molecular weight tyrosine phosphatase, Lyn, MAP kinase phosphatases (MKPs), MAPKAPKs, MARKs, Mcl-1, Mek 1, Mek 2, MEKKs, MELK, Met receptor, metabolic enzymes, metalloproteinases, MKK3/6, MKK4/7, MLKs, MNKs, molecular chaperones, Mos, mTOR, multi-drug resistance proteins, muscarinic receptors, Myc, MyD88, myosin, myosin binding proteins, myotubularins, MYST family, Myt 1, N-Ras, Nck, NFAT, NIK, nitric oxide synthase, Non receptor tyrosine phosphatases (NPRTPs), Noxa, nucleoside transporters, p130CAS, p14Arf, p16, p21CIP, p27KIP, p38s, p53, p70S6 Kinase, p90Rsks, PAKs, paxillin, PDGF receptors, PDK1, P-Glycoprotein, phopsholipases, phosphoinositide kinases, PI3-Kinase class 1, Pim1, Pim2, Pim3, Pin1 prolyl isomerase, PKAs, PKCs, PKR, potassium channels, PP1, PP2A, PP2B, PP2C, PP5, PRK, Prks, prolyl-hydroxylases PHD-1, prostaglandin synthases, pS6, PTEN, Puma, RABs, Rac, Ran, Ras-GAP, Rb, Receptor protein tyrosine phosphatases (RPTPs), Rel-A (p65-NFKB), Ret, RHEB, Rho, Rho-GAPs, RIP, RNA polymerase, ROCK 1, ROCK 2, SAPK/JNK1,2,3, SCF ubiquitination ligase complex, selectins, separase, serine phosphatases, SGK1, SGK2, SGK3, Shc, SHIPS, SHPs, sirtuins, SLAP, Slingshot phosphatases (SSH), Smac, SMADs, small molecular weight GTPases, sodium channels, Sos, Sp1, sphingomyelinases, sphingosine kinases, Src, SRFs, STAT1, STAT3, STAT4, STAT5, STATE, suppressors of cytokine signaling (SOCs), Syk, T-bet, T-Cell leukemia family, TCFs, TGFβ receptors, Tiam, TIE1, TIE2, topoisomerases, Tp1, TRADD, TRAF2, Trk receptors, TSC1,2, tubulin, Tyk2, ubiquitin proteases, urokinase-type plasminogen activator (uPA) and uPA receptor (uPAR) system, UTX, Vav, VEGF receptors, vesicular protein sorting (Vsps), VHL, Wee1, WT-1, WT-1, XIAP, Yes, ZAP70, β-adrenergic receptors and β-catenin.

In one aspect, this invention also relates to methods and pharmaceutical compositions for inhibiting abnormal cell growth in a mammal which comprises an amount of an ACSS2 inhibitor, or a pharmaceutically acceptable salt, ester, prodrug, solvate, hydrate or derivative thereof, in combination with an amount of an anti-cancer agent (e.g., a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, immunotherapeutic agents, proapoptotic agents, and anti-androgens. Non-limiting examples are chemotherapeutic agents, cytotoxic agents, and non-peptide small molecules such as Tykerb/Tyverb (lapatinib), Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include 2,2',2"-trichlorotriethylamine; 2-ethylhydrazide; aceglatone; aldophosphamide glycoside; alkyl sulfonates such as busulfan, improsulfan and piposulfan; alkylating agents such as thiotepa and cyclosphosphamide (CYTOXAN™); aminolevulinic acid; amsacrine; anti-adrenals such as aminoglutethimide, mitotane, trilostane; antibiotics such as anthracyclins, actinomycins and bleomycins including aclacinomysins, actinomycin, anthramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); arabinoside ("Ara-C"); aziridines such as benzodopa, carboquone, meturedopa, and uredopa; bestrabucil; bisantrene; capecitabine; cyclophosphamide; dacarbazine; defofamine; demecolcine; diaziquone; edatraxate; elfomithine; elliptinium acetate; esperamicins; ethylenimines and methylamelamines including altretamine, triethylenemelamine, trietylenephosphoramide, triethylenethiophosphaoramide and trimethylolomelamine; etoglucid; folic acid analogues such as denopterin, methotrexate, pteropterin, trimetrexate; folic acid replenisher such as frolinic acid; gacytosine; gallium nitrate; gemcitabine; hydroxyurea; lentinan; lonidamine; mannomustine; mitobronitol; mitoguazone; mitolactol; mitoxantrone; mopidamol; nitracrine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas; nitrosoureas such as carmustine, chlorozotocin, fotemustine, lomustine, nimustine, ranimustine; oxazaphosphorines; pentostatin; phenamet; pipobroman; pirarubicin; podophyllinic acid; procarbazine; PSK™; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; razoxane; retinoic acid; sizofiran; spirogermanium; taxanes, e.g., paclitaxel (TAXOL™, Bristol-Myers Squibb Oncology, Princeton, N.J.) and docetaxel (TAXOTERE™, Rhone-Poulenc Rorer, Antony, France); tenuazonic acid; thiotepa; triazenes; triaziquone; urethan; vindesine; and pharmaceutically acceptable salts, acids or derivatives of any of the above. Also included as suitable chemotherapeutic cell conditioners are antihormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum or platinum analogs and complexes such as cisplatin and carboplatin; anti-microtubule such as diterpenoids, including paclitaxel and docetaxel, or Vinca alkaloids including vinblastine, vincristine, vinflunine, vindesine, and vinorelbine; etoposide (VP-16); ifosfamide; mitomycin C; mitoxantrone; vincristine; vinorelbine; navelbine; novantrone; teniposide; daunomycin; aminopterin; xeloda; ibandronate; topoisomerase I and II inhibitors including camptothecins (e.g., camptothecin-11), topotecan, irinotecan, and epipodophyllotoxins; topoisomerase inhibitor RFS 2000; epothilone A or B; difluoromethylornithine (DMFO); histone deacetylase inhibitors; compounds which induce cell differentiation processes; gonadorelin agonists; methionine aminopeptidase inhibitors; compounds targeting/decreasing a protein or lipid kinase activity; compounds which target, decrease or inhibit the activity of a protein or lipid phosphatase; anti-androgens; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors; temozolomide (TEMODAL®); Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array PioPharma, AZD6244 from AstraZeneca, PD181461 or PD0325901 from Pfizer, leucovorin, EDG binders, antileukemia compounds, ribonucleotide reductase inhibitors, S-adenosylmethionine decarboxylase inhibitors, antiproliferative antibodies or other chemotherapeutic compounds. Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®.

This invention further relates to a method for using the compounds or pharmaceutical composition in combination with other tumor treatment approaches, including surgery, ionizing radiation, photodynamic therapy, or implants, e.g., with corticosteroids, hormones, or used as radiosensitizers.

One such approach may be, for example, radiation therapy in inhibiting abnormal cell growth or treating the proliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation, which comprises administering to the mammal an amount of an ACSS2 inhibitor or a pharmaceutically acceptable salt, ester, prodrug, solvate, hydrate or derivative thereof, which is effective in sensitizing abnormal cells to treatment with radiation. The amount of the compound in this method can be determined according to the means for ascertaining effective amounts of such compounds described herein.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

In some embodiments, the compositions and methods further comprise administering, separately or simultaneously one or more additional agents (e.g. 1, 2, 3, 4, 5, or more). Additional agents can include those useful in wound healing. Non-limiting examples of additional agents include antibiotics (e.g. Aminoglycosides, Cephalosporins, Chloramphenicol, Clindamycin, Erythromycins, Fluoroquinolones, Macrolides, Azolides, Metronidazole, Penicillin's, Tetracycline's, Trimethoprim-sulfamethoxazole, Vancomycin), steroids (e.g. Andranes (e.g. Testosterone), Cholestanes (e.g. Cholesterol), Cholic acids (e.g. Cholic acid), Corticosteroids (e.g. Dexamethasone), Estraenes (e.g. Estradiol), Pregnanes (e.g. Progesterone), narcotic and non-narcotic analgesics (e.g. Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine), chemotherapy (e.g. anti-cancer drugs such as but not limited to Altretamine, Asparaginase, Bleomycin, Busulfan, Carboplatin, Carmustine, Chlorambucil, Cisplatin, Cladribine, Cyclophosphamide, Cytarabine, Dacarbazine, Diethylstilbesterol, Ethinyl estradiol, Etoposide, Floxuridine, Fludarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine), anti-inflammatory agents (e.g. Alclofenac; Alclometasone Dipropionate; Algestone Acetonide; alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Ciclofrofen; Cintazone; Cliprofen; Clobetasol Propionate; Clobetasone Butyrate; Clopirac; Cloticasone Propionate; Cormethasone Acetate; Cortodoxone; Decanoate; Deflazacort; Delatestryl; Depo-Testosterone; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Lotepredonol Etabonate; Meclofenamate Sodium; Meclofenamic Acid; Meclorisone Dibutyrate; Mefenamic Acid; Mesalamine; Meseclazone; Mesterolone; Methandrostenolone; Methenolone; Methenolone Acetate; Methylprednisolone Suleptanate; Morniflumate; Nabumetone; Nandrolone; Naproxen; Naproxen Sodium; Naproxol; Nimazone; Olsalazine Sodium; Orgotein; Orpanoxin; Oxandrolane; Oxaprozin; Oxyphenbutazone; Oxymetholone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Stanozolol; Sudoxicam; Sulindac; Suprofen; Talmetacin; Talniflumate; Talosalate; Tebufelone; Tenidap; Tenidap Sodium; Tenoxicam; Tesicam; Tesimide; Testosterone; Testosterone Blends; Tetrydamine; Tiopinac; Tixocortol Pivalate; Tolmetin; Tolmetin Sodium; Triclonide; Triflumidate; Zidometacin; Zomepirac Sodium), or anti-histaminic agents (e.g. Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Bropheniramine, Clemastine, Acetaminophen, Pseudoephedrine, Triprolidine).

EXAMPLES

Example 1: Synthesis of (1-ethyl-6-fluoro-1H-benzo[d]imidazol-2-yl)diphenylmethanol (Compound 1)

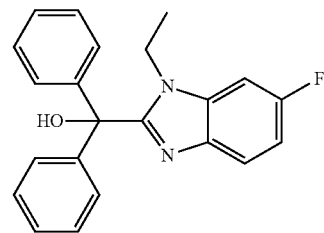 [SMILES: CCn1c(C(O)(c2ccccc2)c2ccccc2)nc2ccc(F)cc21]

Step A: Preparation of 5-fluoro-N-ethyl-2-nitroaniline: A suspension of 2,4-difluoro-1-nitrobenzene (0.32 g, 2 mmol), ethylamine hydrochloride (0.33 g, 4.0 mmol) and potassium carbonate (0.83 g, 6.0 mmol) in acetonitrile was stirred at ambient temperature for 16 hours. Acetonitrile was removed under reduced pressure. Water (20 mL) and ethyl acetate (50 mL) were added. The organic layer was separated, washed with brine, dried (sodium sulfate), filtered and concentrated under reduced pressure to give 5-fluoro-N-ethyl-2-nitroaniline (0.30 g, 82%) as solid.

Step B: Preparation of 1-ethyl-6-fluoro-1H-benzo[d]imidazole: To a mixture of 5-fluoro-N-ethyl-2-nitroaniline (0.32 g, 1.7 mmol), iron powder (0.96 g, 17.3 mmol), ammonium chloride (0.93 g, 17.3 mmol) in isopropyl alcohol (50 mL) was added formic acid (10 mL) at ambient temperature. The mixture was stirred at reflux for 12 hours and then cooled to ambient temperature. It was filtered through a pad of celite and washed with ethyl acetate. The filtrate was concentrated under reduce pressure and the residue was purified by flash chromatography on silica gel to give 1-ethyl-6-fluoro-1H-benzo[d]imidazole (0.24 g, 85%) as solid.

Step C: Preparation of (1-ethyl-6-fluoro-1H-benzo[d]imidazol-2-yl)diphenylmethanol: To a solution of 1-ethyl-6-fluoro-1H-benzo[d]imidazole (0.05 g, 0.30 mmol) in THF (20 mL) was added 2.5 M n-BuLi (0.15 mL, 0.36 mmol) at −78° C. The mixture was stirred at −78° C. for 1 hour. Benzophenone (0.055 g, 0.30 mmol) in THF (2 mL) was added. The reaction was warmed to ambient temperature and stirred at ambient temperature for 1 hour. Saturated aqueous ammonium chloride (10 mL) and ethyl acetate (40 mL) were added. The organic layer was separated, washed with brine, dried (sodium sulfate), filtered and concentrated under reduced pressure. The residue was purified by flash chromatography on silica gel to give (1-ethyl-6-fluoro-1H-benzo[d]imidazol-2-yl)diphenylmethanol (0.060 g, 57%) as solid. LCMS ESI (+) m/z 347 (M+H). $^1$HNMR (400 MHz, CDCl$_3$): δ 7.69 (dd, 1H), 7.29-7.37 (m, 10H), 6.96-7.03 (m, 2H), 4.83 (s, 1H), 3.96 (q, 2H), 0.71 (t, 3H).

Example 2: Synthesis of (1-ethyl-6-methoxy-1H-benzo[d]imidazol-2-yl)diphenylmethanol (Compound 2)

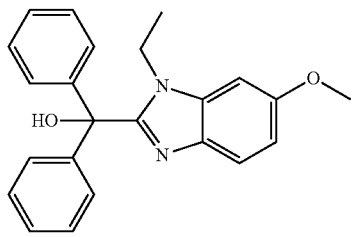 [SMILES: CCn1c(C(O)(c2ccccc2)c2ccccc2)nc2ccc(OC)cc21]

Step A: Preparation of 2-fluoro-4-methoxy-1-nitrobenzene: To a suspension of 3-fluoro-4-nitrophenol (0.16 g, 1 mmol) and potassium carbonate (0.42 g, 3 mmol) in DMF (10 mL) was added iodomethane (0.24 g, 2.0 mmol) at 0° C. The reaction was stirred at 0° C. for 1 hour and water (50 mL) was added. The solid formed was collected by filtration, washed with water and dried to give 2-fluoro-4-methoxy-1-nitrobenzene (0.15 g, 88%) as solid.

Step B: Preparation of (1-ethyl-6-methoxy-1H-benzo[d] imidazol-2-yl)diphenylmethanol: Prepared similarly as Example 1 using 2-fluoro-4-methoxy-1-nitrobenzene in place of 2,4-difluoro-1-nitrobenzene in Step A. LCMS ESI (+) m/z 359 (M+H). $^1$HNMR (400 MHz, CDCl$_3$): δ 7.67 (d, 1H), 7.30-7.38 (m, 10H), 6.92 (dd, 1H), 6.76 (d, 1H), 5.09 (s, 1H), 3.95 (q, 2H), 3.87 (s, 3H), 0.68 (t, 3H).

Example 3: Synthesis of 2-(hydroxydiphenylmethyl)-1-methyl-1H-benzo[d]imidazole-6-carboxylic acid (Compound 10)

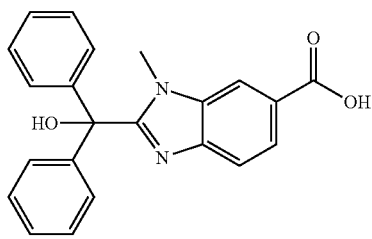 [SMILES: Cn1c(C(O)(c2ccccc2)c2ccccc2)nc2ccc(C(=O)O)cc21]

Step A: Preparation of N,5-dimethyl-2-nitroaniline: To a solution of 2-fluoro-4-methyl-1-nitro-benzene (30 g, 193 mmol) in 1-methyl-2-pyrrolidone (50 mL) was added 40% methylamine in water (50 mL, 580 mmol). The reaction mixture was stirred at ambient temperature for 5 hours. Water (300 mL) was added and the mixture was stirred at ambient temperature for 30 minutes. N,5-Dimethyl-2-nitroaniline (31.3 g, 97%) was obtained as solid by filtration, washed with water and dried under vacuum.

Step B: Preparation of 1,6-dimethyl-1H-benzo[d]imidazole: N,5-dimethyl-2-nitro-aniline (20.2 g, 122 mmol), trimethyl orthoformate (133 mL, 1216 mmol), 10% palladium on carbon (6.47 g, 6.1 mmol) and p-toluenesulfonic acid monohydrate (2.31 g, 12.2 mmol) in methanol (240 mL) was placed under 1 atmosphere of hydrogen with balloon and stirred at ambient temperature for 5 hours. Catalyst was removed by filtration and washed with methanol (200 mL). The filtrate was concentrated under reduced pressure. The residue was treated with saturated sodium bicarbonate (50 mL) and ethyl acetate (300 mL). The organic layer was separated, washed with brine, dried (sodium sulfate), filtered and concentrated under reduced pressure to give 1,6-dimethylbenzimidazole (17.7 g, quantitative) as solid.

Step C: Preparation of (1,6-dimethylbenzimidazol-2-yl)-diphenyl-methanol: To a solution of 1,6-dimethylbenzimidazole (5.0 g, 34.2 mmol) and benzophenone (7.79 g, 42.8 mmol) in THF (75 mL) was added 1.0 M lithium bis(trimethylsilyl)amide (1.0 M in THF, 41 mL, 41 mmol) at 0° C. The reaction mixture was stirred at 0° C. for 1 hour. Saturated ammonium chloride solution (50 mL) and ethyl acetate (100 mL) were added. The organic layer was separated, washed with brine, dried (sodium sulfate), filtered and concentrated under reduced pressure to give (1,6-dimethylbenzimidazol-2-yl)-diphenyl-methanol (10.7 g, 95%) as solid.

Step D: Preparation of 2-(hydroxydiphenylmethyl)-1-methyl-1H-benzo[d]imidazole-6-carboxylic acid: A solution of (1,6-dimethylbenzimidazol-2-yl)-diphenyl-methanol (6.6 g, 20.1 mmol) and potassium permanganate (12.7 g, 80 mmol) in tert-butanol (150 mL) and water (50 mL) was stirred at reflux for 3 hours. Additional potassium permanganate (3.2 g, 20.1 mmol) was added. The reaction was stirred at reflux for additional 3 hours. After cooling to ambient temperature, the reaction mixture was filtered through a pad of celite and washed with water (200 mL). MTBE (300 mL) was added to the filtrate. The aqueous layer was separated, acidified with saturated potassium hydrogen sulfate to pH~4 and extracted with ethyl acetate (300 mL). The organic layer was separated, washed with brine, dried (sodium sulfate), filtered through a pad of silica gel, washed with ethyl acetate (50 mL) and concentrated under reduced pressure to give 2-[hydroxy(diphenyl)methyl]-3-methyl-benzimidazole-5-carboxylic acid (4.4 g, 61%) as solid. LCMS ESI (+) m/z 359 (M+H).

Example 4: Synthesis of 2-(hydroxydiphenylmethyl)-1-ethyl-1H-benzo[d]imidazole-6-carboxylic acid (Compound 11)

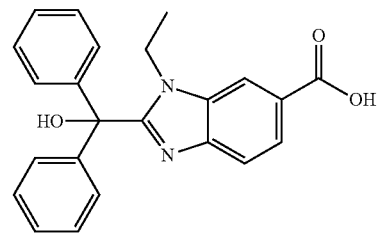 [SMILES: CCn1c(C(O)(c2ccccc2)c2ccccc2)nc2ccc(C(=O)O)cc21]

Prepared similarly as Example 3 substituting (1,6-dimethylbenzimidazol-2-yl)-diphenyl-methanol with (1-ethyl-6-methyl-1H-benzo[d]imidazol-2-yl)diphenylmethanol in Step D. LCMS ESI (+) m/z 373 (M+H). $^{1}$HNMR (400 MHz, d$^{6}$-DMSO): δ 8.07 (s, 1H), 7.79 (d, 1H), 7.64 (d, 1H), 7.24-7.34 (m, 10H), 7.22 (s, 1H), 4.25 (q, 2H), 1.01 (t, 3H).

Example 5: Synthesis of 2-(bis(2-fluorophenyl)(hydroxymethyl)-1-ethyl-1H-benzo[d]imidazole-6-carboxylic acid (Compound 13)

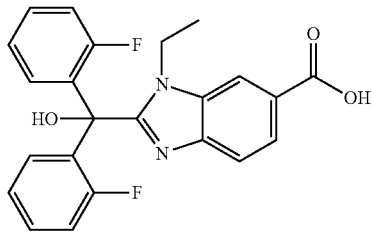 [SMILES: CCn1c(C(O)(c2ccccc2F)c2ccccc2F)nc2ccc(C(=O)O)cc21]

Step A: Preparation of methyl 3-(ethylamino)-4-nitrobenzoate: To a solution of methyl 3-fluoro-4-nitro-benzoate (5.0 g, 25 mmol) in 1-methyl-2-pyrrolidone (24 mL) was added 2.0 M ethylamine in THF (16.3 mL, 32.6 mmol). The reaction mixture was stirred at ambient temperature for 5 hours. Water (200 mL) was added and the mixture was stirred at ambient temperature for 30 minutes. Solid was collected by filtration. Ethyl acetate (75 ml) was added to the filtrate. The organic layer was separated, washed with brine, dried (sodium sulfate), filtered and concentrated under reduced pressure. The residue was combined with solid previously collected and dried to give methyl 3-(ethylamino)-4-nitro-benzoate (5.6 g, 99.5%) as solid.

Step B: Preparation of methyl-1-ethyl-1H-benzo[d]imidazole-6-carboxylate: A suspension of methyl 3-(ethylamino)-4-nitro-benzoate (5.6 g, 25.0 mmol), trimethyl orthoformate (27.3 mL, 249.8 mmol), 10% palladium on carbon (1.33 g, 1.25 mmol) and p-toluenesulfonic acid monohydrate (0.48 g, 2.5 mmol) in methanol (40 mL) was placed under 1 atmosphere of hydrogen and stirred at ambient temperature for 5 hours. Catalyst was removed by filtration and washed with methanol (30 mL). The filtrate was concentrated under reduced pressure. The residue was added dissolved in saturated aqueous sodium bicarbonate (20 mL) and ethyl acetate (50 mL). The organic layer was separated, washed with brine, dried (sodium sulfate), filtered and concentrated under reduced pressure to give a solid. The solid was suspended in 10:1 hexane/MTBE (30 mL) and stirred at ambient temperature for 30 minutes. The solid was collected by filtration and dried to give methyl 3-ethylbenzimidazole-5-carboxylate (5.0 g, 98%) as solid.

Step C: Preparation of methyl 2-(bis(2-fluorophenyl)(hydroxy)methyl)-1-ethyl-1H-benzo[d]imidazole-6-carboxylate: To a solution of bis(2-fluorophenyl)methanone (8.0 g, 36.7 mmol) and lithium bis(trimethylsilyl)amide (29.4 mL, 29.4 mmol) in THF (50 mL) was added methyl 3-ethylbenzimidazole-5-carboxylate (5.0 g, 24.5 mmol) in THF (40 mL) dropwise at −45° C. After the addition, the mixture was stirred at −45° C. for 1 hour. Saturated aqueous ammonium chloride solution (50 mL) and ethyl acetate (50 mL) were added. The organic layer was separated, washed with brine, dried (sodium sulfate), filtered and concentrated under reduced pressure. The residue was purified by flash chromatography on silica gel 2:1 hexane/ethyl acetate to give methyl 2-[bis(2-fluorophenyl)-hydroxy-methyl]-3-ethyl-benzimidazole-5-carboxylate (6.0 g, 58%) as solid.

Step D: Preparation of 2-(bis(2-fluorophenyl)(hydroxy)methyl)-1-ethyl-1H-benzo[d]imidazole-6-carboxylic acid: A solution of methyl 2-[bis(2-fluorophenyl)-hydroxymethyl]-3-ethyl-benzimidazole-5-carboxylate (6.0 g, 14.2 mmol) and lithium hydroxide monohydrate (2.39 g, 56.8 mmol) in 2:1 THF/H$_{2}$O (30 mL) was stirred at ambient temperature for 18 hours. THF was removed under reduced pressure. The resulting aqueous solution was extracted with MTBE (2×50 mL). The aqueous layer was separated, acidified with saturated potassium hydrogen sulfate to pH~3-4. The solid formed was collected by filtration, washed with water and dried to give 2-[bis(2-fluorophenyl)-hydroxymethyl]-3-ethyl-benzimidazole-5-carboxylic acid (5.75 g, 99%) as solid. LCMS ESI (+) m/z 409 (M+H).

Example 6: Synthesis of N-(1-ethyl-2-(hydroxydiphenylmethyl)-1H-benzo[d]imidazol-6-yl)acetamide (Compound 14)

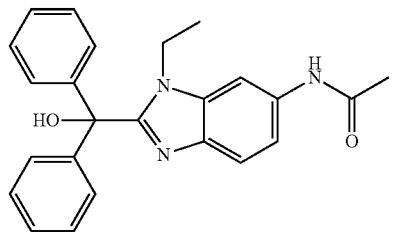 [SMILES: CCn1c(C(O)(c2ccccc2)c2ccccc2)nc2ccc(NC(C)=O)cc21]

Step A: Preparation of (6-amino-1-ethyl-1H-benzo[d]imidazol-2-yl)diphenylmethanol: To a solution of 2-[hydroxy(diphenyl)methyl]-3-ethyl-benzimidazole-5-carboxylic acid (0.35 g, 0.94 mmol) (Example 4) and triethylamine (0.19 g, 1.88 mmol) in DMF (50 mL) was added diphenylphosphoryl azide (0.39 g, 1.41 mmol) at ambient temperature. The reaction mixture was stirred for 30 minutes at ambient temperature. Water (2 mL) was added and the resulting mixture was stirred at 80° C. for 1 hour. After cooling to ambient temperature, water (100 mL) and ethyl acetate (30 mL) were added. The organic layer was separated, washed with brine, dried (sodium sulfate) and concentrated under reduced pressure. The residue obtained was purified by flash chromatography on silica gel to give (6-amino-1-ethyl-1H-benzo[d]imidazol-2-yl)diphenylmethanol (0.15 g, 46%) as solid.

Step B: Preparation of N-(1-ethyl-2-(hydroxydiphenylmethyl)-1H-benzo[d]imidazol-6-yl)acetamide: To a solution of (6-amino-1-ethyl-1H-benzo[d]imidazol-2-yl)diphenylmethanol (0.05 g, 0.15 mmol) and triethylamine (0.022 g, 0.22 mmol) in DCM (10 mL) was added acetyl chloride (0.013 g, 0.16 mmol) at 0° C. and the reaction mixture was stirred at 0° C. for 30 minutes. Water (10 mL) was added. The organic layer was separated, washed with brine, dried (sodium sulfate), filtered and concentrated under reduced pressure. The residue was purified by flash chromatography on silica gel to give N-(1-ethyl-2-(hydroxydiphenylmethyl)-1H-benzo[d]imidazol-6-yl)acetamide (0.05 g, 89%) as solid. LCMS ESI (+) m/z 386 (M+H). $^{1}$HNMR (400 MHz, d$^{6}$-DMSO): δ 9.97 (s, 1H), 7.92 (s, 1H), 7.47 (d, 1H), 7.23-7.33 (m, 10H), 7.16 (dd, 1H), 7.10 (s, 1H), 4.19 (q, 2H), 2.03 (s, 3H), 0.97 (t, 3H).

Example 7: Synthesis of 1-ethyl-2-(hydroxydiphenylmethyl)-N-methyl-1H-benzo[d]imidazole-6-carboxamide (Compound 15)

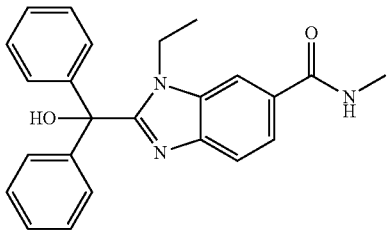

To a solution of methyl 1-ethyl-2-(hydroxydiphenylmethyl)-1H-benzo[d]imidazole-6-carboxylate (0.05 g, 0.13 mmol) in methanol (5 mL) was added 23% methyl amine in methanol (5 mL) at ambient temperature. The resulting solution was stirred at 100° C. in a sealed tube for 3 hours. After cooling to ambient temperature, methanol was removed under reduced pressure. The residue was purified by flash chromatography on silica gel to give 1-ethyl-2-(hydroxydiphenylmethyl)-N-methyl-1H-benzo[d]imidazole-6-carboxamide (0.025 g, 50%) as solid. LCMS ESI (+) m/z 386 (M+H). $^1$HNMR (400 MHz, CDCl$_3$): δ 7.98 (s, 1H), 7.79 (d, 1H), 7.55 (dd, 1H), 7.32-7.40 (m, 10H), 6.15-6.31 (brs, 1H), 4.93 (s, 1H), 4.08 (q, 2H), 3.06 (d, 3H), 0.78 (t, 3H).

Example 8: Synthesis of (7-ethoxy-1-ethyl-1H-benzo[d]imidazol-2-yl)diphenylmethanol (Compound 17)

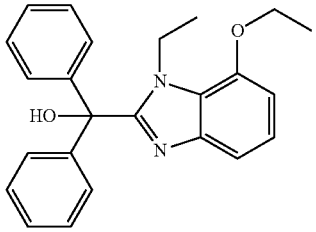 [SMILES: CCOc1cccc2nc(C(O)(c3ccccc3)c3ccccc3)n(CC)c12]

Step A: Preparation of 2-ethoxy-6-nitroaniline: To a solution of 2-amino-3-nitrophenol (1.0 g, 6.5 mmol) in DMSO (50 mL) was added potassium carbonate (1.79 g, 13 mmol) and ethyl bromide (0.77 g, 7.14 mmol) at ambient temperature. The reaction mixture was stirred at 60° C. in a sealed tube for 1 hour. After cooling to ambient temperature, the reaction mixture was poured into water (100 mL). The solid formed was collected by filtration, washed with water and dried to give 2-ethoxy-6-nitroaniline (0.9 g, 76%).

Step B: Preparation of N-(2-ethoxy-6-nitrophenyl)acetamide: To a solution of 2-ethoxy-6-nitroaniline (0.88 g, 4.8 mmol) in toluene (50 mL) was added acetyl chloride (0.75 g, 9.6 mmol) dropwise. Then the reaction mixture was stirred at 80° C. overnight. After cooling to ambient temperature, toluene was removed under reduced pressure. Water (100 mL) and DCM (50 mL) were added. The organic layer was separated, washed with brine, dried (sodium sulfate), filtered and concentrated under reduced pressure. The residue was purified by flash chromatography on silica gel to give N-(2-ethoxy-6-nitrophenyl)acetamide (0.76 g, 70%) as solid.

Step C: Preparation of 2-ethoxy-N-ethyl-6-nitroaniline: To a solution of N-(2-ethoxy-6-nitrophenyl)acetamide (0.76 g, 3.4 mmol) in THF (50 mL) was added borane dimethylsulfide complex (0.52 g, 6.8 mmol) at 0° C. The reaction mixture was warmed to ambient and stirred at ambient temperature for 2 days. Methanol (20 mL) was added dropwise. Solvent was removed under reduced pressure. The residue was purified by flash chromatography on silica gel to give 2-ethoxy-N-ethyl-6-nitroaniline (0.36 g, 51%) as solid.

Step D: Preparation of (7-ethoxy-1-ethyl-1H-benzo[d]imidazol-2-yl)diphenylmethanol: Prepared similarly as Example 1 substituting 5-fluoro-N-ethyl-2-nitroaniline with 2-ethoxy-N-ethyl-6-nitroaniline in Step B. LCMS ESI (+) m/z 373 (M+H). $^1$HNMR (400 MHz, CDCl$_3$): δ 7.36 (d, 1H), 7.26-7.35 (m, 10H), 7.14 (t, 1H), 6.68 (d, 1H), 5.52 (s, 1H), 4.13 (q, 4H), 1.41 (t, 3H), 0.59 (t, 3H).

Example 9: Synthesis of (1-ethyl-6-(2-methoxyethoxy)-1H-benzo[d]imidazol-2-yl)diphenylmethanol (Compound 21)

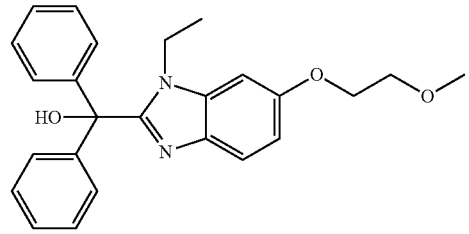 [SMILES: CCn1c(C(O)(c2ccccc2)c2ccccc2)nc2ccc(OCCOC)cc21]

Step A: Preparation of 1-ethyl-1H-benzo[d]imidazole-6-ol: Prepared similarly as Example 1 substituting 2,4-difluoro-1-nitrobenzene with 3-fluoro-4-nitrophenol in Step A.

Step B: Preparation of 6-((tert-butyldimethylsilyl)oxy)-1-ethyl-1H-benzo[d]imidazole: To a solution of 1-ethyl-1H-benzo[d]imidazole-6-ol (4.5 g, 27.2 mmol) and 1H-imidazole (3.78 g, 55.5 mmol) in DCM (200 mL) was added tert-butylchlorodimethylsilane (8.3 g, 55.5 mmol) at ambient temperature. The reaction mixture was stirred at ambient temperature for 2 hours. Water (100 mL) was added. The organic layer was separated, washed with brine, dried (sodium sulfate), filtered and concentrated under reduced pressure. The residue was purified by flash chromatography on silica gel to give 6-((tert-butyldimethylsilyl)oxy)-1-ethyl-1H-benzo[d]imidazole (6.1 g, 80%) as solid.

Step C: Preparation of (6-((tert-butyldimethylsilyl)oxy)-1-ethyl-1H-benzo[d]imidazol-2-yl)diphenylmethanol: Prepared similarly as Example 1 substituting 1-ethyl-6-fluoro-1H-benzo[d]imidazole with 6-((tert-butyldimethylsilyl)oxy)-1-ethyl-1H-benzo[d]imidazole in Step C.

Step D: Preparation of 1-ethyl-2-(hydroxydiphenylmethyl)-1H-benzo[d]imidazol-6-ol: To a solution of (6-((tert-butyldimethylsilyl)oxy)-1-ethyl-1H-benzo[d]imidazol-2-yl)diphenylmethanol (6.6 g, 14.4 mmol) in DCM (200 mL) was added tetrabutylammonium fluoride (7.5 g, 28.8 mmol) at ambient temperature. The reaction mixture was stirred at ambient temperature for 30 minutes. Water was added. The organic layer was separated, washed with brine, dried (sodium sulfate), filtered and concentrated under reduced pressure. The residue was purified by flash chromatography on silica gel to give 1-ethyl-2-(hydroxydiphenylmethyl)-1H-benzo[d]imidazol-6-ol (4.0 g, 80%) as solid.

Step E: Preparation of (1-ethyl-6-(2-methoxyethoxy)-1H-benzo[d]imidazol-2-yl)diphenylmethanol: A suspension of 1-ethyl-2-(hydroxydiphenylmethyl)-1H-benzo[d]imidazol-6-ol (0.1 g, 0.29 mmol), 1-bromo-2-methoxyethane (0.06 g, 0.44 mmol) and potassium carbonate (0.08 g, 0.58 mmol) in DMF (5 mL) was stirred at ambient temperature for 6 hours. Water was added and extracted with DCM. The organic layer was separated, washed with brine, dried (sodium sulfate), filtered and concentrated under reduced pressure. The residue was purified by flash chromatography on silica gel to give (1-ethyl-6-(2-methoxyethoxy)-1H-benzo[d]imidazol-2-yl)diphenylmethanol (0.04 g, 35%) as solid. LCMS ESI (+) m/z 403 (M+H). $^1$HNMR (400 MHz, CDCl$_3$): δ 7.67 (d, 1H), 7.30-7.37 (m, 10H), 6.95 (d, 1H), 6.82 (s, 1H), 5.08 (s, 1H), 4.18 (t, 2H), 3.94 (q, 2H), 3.79 (t, 2H), 3.47 (s, 3H), 0.68 (t, 3H).

Example 10: Synthesis of 2-((1-ethyl-2-(hydroxydiphenylmethyl)-1H-benzo[d]imidazol-6-yl)oxy)acetic acid (Compound 23)

0.14 mmol) in methanol (20 mL) was added calcium chloride (0.08 g, 0.72 mmol) and sodium borohydride (0.028 g, 0.72 mmol) at ambient temperature. The reaction mixture was stirred at ambient temperature for 2 hours. Water was added and the mixture was extracted with DCM. The organic layer was separated, washed with brine, dried (sodium sulfate), filtered and concentrated under reduced pressure. The residue was purified by flash chromatography on silica gel to give 2-((1-ethyl-2-(hydroxydiphenylmethyl)-1H-benzo[d]imidazol-6-yl)oxy)ethan-1-ol (0.03 g, 54%) as solid. LCMS ESI (+) m/z 389 (M+H). $^1$HNMR (400 MHz, CDCl$_3$): δ 7.68 (d, 1H), 7.30-7.37 (m, 10H), 6.94 (dd, 1H), 6.80 (d, 1H), 5.02 (s, 1H), 4.15 (t, 2H), 4.00 (t, 2H), 3.95 (q, 2H), 2.04 (t, 1H), 0.70 (t, 3H).

Example 12: Synthesis of (1-ethyl-6-(2-(methylamino)ethoxy)-1H-benzo[d]imidazol-2-yl)diphenylmethanol (Compound 27)

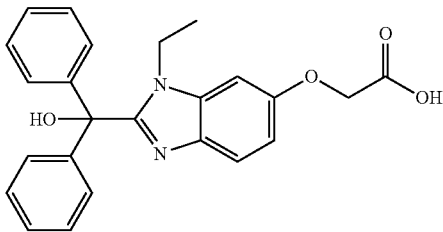 [SMILES: CCn1c(C(O)(c2ccccc2)c2ccccc2)nc2ccc(OCC(=O)O)cc21]

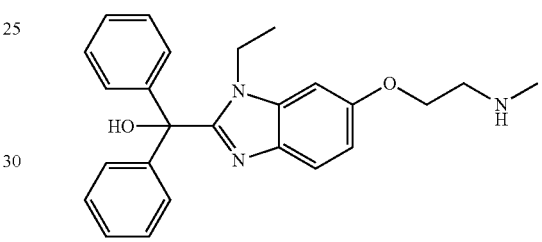

A solution of methyl 2-((1-ethyl-2-(hydroxydiphenylmethyl)-1H-benzo[d]imidazol-6-yl)oxy)acetate (0.40 g, 0.96 mmol) and sodium hydroxide (0.077 g, 1.92 mmol) in 1:1 MeOH/H2O was stirred at ambient temperature for 1 hour. Methanol was removed under reduced pressure and the resulting mixture was acidified with 2N HCl to pH~4. The solid formed was collected by filtration, washed with water and dried to give 2-((1-ethyl-2-(hydroxydiphenylmethyl)-1H-benzo[d]imidazol-6-yl)oxy)acetic acid (0.30 g, 78%). LCMS ESI (+) m/z 403 (M+H). $^1$HNMR (400 MHz, d$_6$-DMSO): δ 7.45 (d, 1H), 7.21-7.33 (m, 10H), 7.06 (s, 1H), 6.96 (s, 1H), 6.78 (d, 1H), 4.70 (s, 2H), 4.10 (q, 2H), 0.96 (t, 3H).

Example 11: Synthesis of 2-((1-ethyl-2-(hydroxydiphenylmethyl)-1H-benzo[d]imidazol-6-yl)oxy)ethan-1-ol (Compound 26)

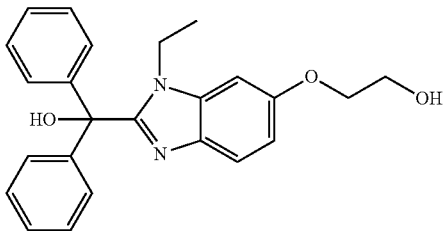 [SMILES: CCn1c(C(O)(c2ccccc2)c2ccccc2)nc2ccc(OCCO)cc21]

To a solution of methyl 2-((1-ethyl-2-(hydroxydiphenylmethyl)-1H-benzo[d]imidazol-6-yl)oxy)acetate (0.06 g, Step A: Preparation of 2-((1-ethyl-2-(hydroxydiphenylmethyl)-1H-benzo[d]imidazol-6-yl)oxy)ethyl methanesulfonate: To a solution of 2-((1-ethyl-2-(hydroxydiphenylmethyl)-1H-benzo[d]imidazol-6-yl)oxy)ethan-1-ol (0.12 g, 0.3 mmol) (Example 11) and triethylamine (0.065 g, 0.6 mmol) in DCM (30 mL) was added methanesulfonyl chloride (0.043 g, 0.37 mmol) at ambient temperature. The reaction mixture was stirred at ambient temperature for 1 hour. Water was added. The organic layer was separated, washed with brine, dried (sodium sulfate), filtered and concentrated under reduced pressure. The residue was purified by flash chromatography on silica gel to give 2-((1-ethyl-2-(hydroxydiphenylmethyl)-1H-benzo[d]imidazol-6-yl)oxy)ethyl methanesulfonate (0.13 g, 90%) as solid.

Step B: Preparation of (1-ethyl-6-(2-(methylamino)ethoxy)-1H-benzo[d]imidazol-2-yl)diphenylmethanol: To a solution of 2-((1-ethyl-2-(hydroxydiphenylmethyl)-1H-benzo[d]imidazol-6-yl)oxy)ethyl methanesulfonate (0.12 g, 0.26 mmol) in methanol (30 mL) was added 2 N methyl amine in THF (5 mL, 10 mmol) at ambient temperature. The reaction mixture was stirred at 60° C. in a sealed tube for 6 hours. After cooling to ambient temperature, the residue obtained was purified by flash chromatography on silica gel to give (1-ethyl-6-(2-(methylamino)ethoxy)-1H-benzo[d]imidazol-2-yl)diphenylmethanol (0.082 g, 80%) as solid. LCMS ESI (+) m/z 402 (M+H). $^1$HNMR (400 MHz, CDCl$_3$): δ 7.64 (d, 1H), 7.27-7.38 (m, 10H), 6.91 (d, 1H), 6.81 (s, 1H), 4.20 (t, 2H), 3.94 (q, 2H), 3.34-3.57 (brs, 2H), 3.09 (t, 2H), 2.57 (s, 3H), 0.69 (t, 3H).

Example 13: Synthesis of N-(2-((1-ethyl-2-(hydroxydiphenylmethyl)-1H-benzo[d]imidazol-6-yl)oxy)ethyl)-N-methylacetamide (Compound 28)

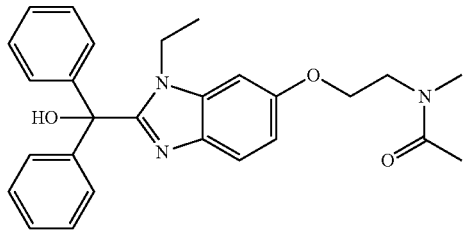 [SMILES: CCn1c(C(O)(c2ccccc2)c2ccccc2)nc2ccc(OCCN(C)C(C)=O)cc21]

To a solution of methyl 1-ethyl-6-(2-(methylamino)ethoxy)-1H-benzo[d]imidazol-2-yl)diphenylmethanol (0.05 g, 0.13 mmol) (Example 12) and triethylamine (0.025 g, 0.25 mmol) in DCM (20 mL) was added acetyl chloride (0.015 g, 0.19 mmol) at ambient temperature. The reaction mixture was stirred at ambient temperature for 2 hours. Water was added. The organic layer was separated, washed with brine, dried (sodium sulfate), filtered and concentrated under reduced pressure. The residue was purified by flash chromatography on silica gel to give N-(2-((1-ethyl-2-(hydroxydiphenylmethyl)-1H-benzo[d]imidazol-6-yl)oxy)ethyl)-N-methylacetamide (0.03 g, 55%) as solid. LCMS ESI (+) m/z 444 (M+H). $^1$HNMR (400 MHz, d$^6$-DMSO): δ 7.44 (dd, 1H), 7.23-7.32 (m, 10H), 7.05 (d, 1H), 7.02 (s, 1H), 6.77 (d, 1H), 4.07-4.18 (m, 4H), 3.69 (t, 1H), 3.63 (t, 1H), 3.06 (s, 1.5H), 2.86 (s, 1.5H), 2.06 (s, 1.5H), 1.98 (s, 1.5H), 0.95-1.00 (m, 3H).

Example 14: Synthesis of 1-((1-ethyl-2-(hydroxydiphenylmethyl)-1H-benzo[d]imidazol-6-yl)oxy)propan-2-ol (Compound 33)

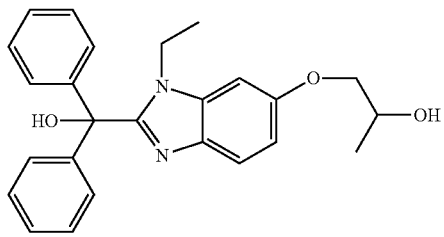 [SMILES: CCn1c(C(O)(c2ccccc2)c2ccccc2)nc2ccc(OCC(C)O)cc21]

Step A: Preparation of 1-((1-ethyl-2-(hydroxydiphenylmethyl)-1H-benzo[d]imidazol-6-yl)oxy)propan-2-one: Prepared similarly as Example 9 substituting 1-bromo-2-methoxyethane with 1-bromopropan-2-one in Step E.

Step B: Preparation of 1-((1-ethyl-2-(hydroxydiphenylmethyl)-1H-benzo[d]imidazol-6-yl)oxy)propan-2-ol: To a solution 1-((1-ethyl-2-(hydroxydiphenylmethyl)-1H-benzo[d]imidazol-6-yl)oxy)propan-2-one (0.05 g, 0.13 mmol) in methanol (10 mL) was added sodium borohydride (0.024 g, 0.63 mmol) at ambient temperature. The reaction mixture was stirred at ambient temperature for 30 minutes. Water (20 mL) and ethyl acetate (100 mL) were added. The organic layer was separated, washed with brine, dried (sodium sulfate), filtered and concentrated under reduced pressure. The residue was purified by flash chromatography on silica gel to give 1-((1-ethyl-2-(hydroxydiphenylmethyl)-1H-benzo[d]imidazol-6-yl)oxy)propan-2-ol (0.04 g, 80%) as solid. LCMS ESI (+) m/z 403 (M+H). $^1$HNMR (400 MHz, CDCl$_3$): δ 7.66 (d, 1H), 7.30-7.37 (m, 10H), 6.92 (dd, 1H), 6.78 (d, 1H), 5.02 (s, 1H), 4.16-4.27 (m, 1H), 3.98 (dd, 1H), 3.95 (q, 2H), 3.85 (dd, 1H), 2.37 (s, 1H), 1.30 (d, 3H), 0.39 (t, 3H).

Example 15: Synthesis of (6-(2-(dimethylamino)ethoxy)-1-ethyl-1H-benzo[d]imidazol-2-yl)diphenylmethanol (Compound 34)

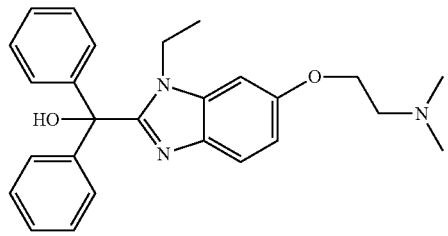 [SMILES: CCn1c(C(O)(c2ccccc2)c2ccccc2)nc2ccc(OCCN(C)C)cc21]

To a solution 1-ethyl-2-(hydroxydiphenylmethyl)-1H-benzo[d]imidazol-6-ol (0.10 g, 0.29 mmol) (Example 9, step D), 2-(dimethylamino)ethan-1-ol (0.052 g, 0.58 mmol) and triphenyl phosphine (0.15 g, 0.58 mmol) in THF (10 mL) was added diisopropyl azodicarboxylate (0.18 g, 0.58 mmol) at ambient temperature. After the addition, the reaction mixture was stirred at reflux overnight. After cooling to ambient temperature, the solvent was removed under reduced pressure. The residue was purified by flash chromatography on silica gel to give (6-(2-(dimethylamino)ethoxy)-1-ethyl-1H-benzo[d]imidazol-2-yl)diphenylmethanol (0.04 g, 33%) as solid. LCMS ESI (+) m/z 416 (M+H). $^1$HNMR (400 MHz, d$^6$-DMSO): δ 7.43 (d, 1H), 7.22-7.32 (m, 10H), 7.05 (s, 1H), 7.00 (d, 1H), 6.77 (dd, 1H), 4.08-4.13 (m, 4H), 2.72 (t, 2H), 2.28 (s, 6H), 0.97 (t, 3H).

Example 16: Synthesis of 3-((1-ethyl-2-(hydroxydiphenylmethyl)-1H-benzo[d]imidazol-6-yl)oxy)propane-1,2-diol (Compound 35)

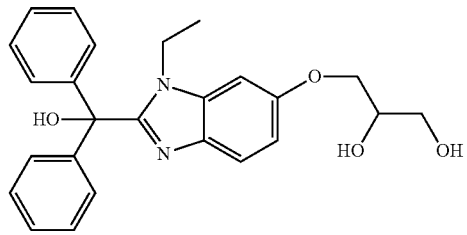 [SMILES: CCn1c(C(O)(c2ccccc2)c2ccccc2)nc2ccc(OCC(O)CO)cc21]

Step A: Preparation of (6-((2,2-dimethyl-1,3-dioxolan-4-yl)methoxy)-1-ethyl-1H-benzo[d]imidazol-2-yl)diphenylmethanol: Prepared similarly as Example 15 substituting 2-(dimethylamino)ethan-1-ol with (2,2-dimethyl-1,3-dioxolan-4-yl)methanol.

Step B: Preparation of 3-((1-ethyl-2-(hydroxydiphenylmethyl)-1H-benzo[d]imidazol-6-yl)oxy)propane-1,2-diol: To a solution (6-((2,2-dimethyl-1,3-dioxolan-4-yl)methoxy)-1-ethyl-1H-benzo[d]imidazol-2-yl)diphenylmethanol (0.06 g, 0.13 mmol) in methanol (5 mL) was added concentrated HCl (37%, 0.1 mL) at ambient temperature. The reaction mixture was stirred at ambient temperature for 1 hour. Water (20 mL) was added. The solid was collected by filtration, washed with water and dried to give 3-((1-ethyl-2-(hydroxydiphenylmethyl)-1H-benzo[d]imidazol-6-yl)oxy)propane-1,2-diol (0.04 g, 73%). LCMS ESI (+) m/z 419 (M+H). ¹HNMR (400 MHz, d⁶-DMSO): δ 7.43 (d, 1H), 7.21-7.35 (m, 10H), 7.01-7.07 (brs, 1H), 6.97 (d, 1H), 6.77 (dd, 1H), 4.91 (d, 1H), 4.64 (t, 1H), 4.10 (q, 2H), 4.01 (dd, 1H), 3.89 (dd, 1H), 3.77-3.83 (m, 1H), 3.44 (t, 2H), 0.97 (t, 3H).

Example 17: Synthesis of N,1-diethyl-2-(hydroxydiphenylmethyl)-1H-benzo[d]imidazole-6-carboxamide (Compound 37)

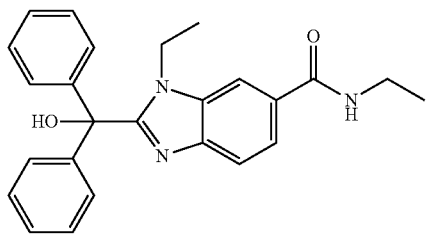 [SMILES: CCNC(=O)c1ccc2nc(C(O)(c3ccccc3)c3ccccc3)n(CC)c2c1]

To a solution 1-ethyl-2-(hydroxydiphenylmethyl)-1H-benzo[d]imidazole-6-carboxylic acid (0.06 g, 0.16 mmol) (Example 4), ethylamine hydrochloride (0.02 g, 0.24 mmol), N,N-diisopropylethylamine (0.039 g, 0.32 mmol) in DMF (5 mL) was added HATU (0.12 g, 0.32 mmol) at ambient temperature. The reaction mixture was stirred at ambient temperature for 6 hours. Water (20 mL) and ethyl acetate (20 mL) were added. The organic layer was separated, washed with brine, dried (sodium sulfate), filtered and concentrated under reduced pressure. The residue was purified by flash chromatography on silica gel to give N,1-diethyl-2-(hydroxydiphenylmethyl)-1H-benzo[d]imidazole-6-carboxamide (0.045 g, 70%) as solid. LCMS ESI (+) m/z 400 (M+H). ¹HNMR (400 MHz, d⁶-DMSO): δ 8.45 (t, 1H), 7.99 (s, 1H), 7.69 (dd, 1H), 7.25-7.35 (m, 10H), 7.20 (s, 1H), 4.22 (q, 2H), 3.27-3.34 (m, 2H), 1.31 (t, 3H), 1.04 (t, 3H).

Example 18: Synthesis of (1-ethyl-2-(hydroxydiphenylmethyl)-1H-benzo[d]imidazol-6-yl)(piperazin-1-yl)methanone (Compound 51)

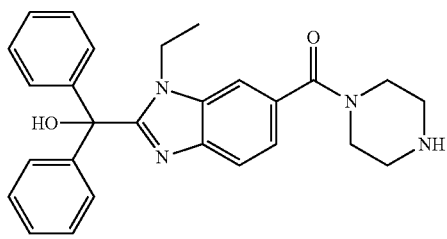 [SMILES: CCn1c(C(O)(c2ccccc2)c2ccccc2)nc2ccc(C(=O)N3CCNCC3)cc21]

Step A: Preparation of tert-butyl 4-(1-ethyl-2-(hydroxydiphenylmethyl)-1H-benzo[d]imidazole-6-carbonyl)piperazine-1-carboxylate: Prepared similarly as Example 17 substituting ethyl amine hydrochloride with tert-butyl piperazine-1-carboxylate.

Step B: Preparation of (1-ethyl-2-(hydroxydiphenylmethyl)-1H-benzo[d]imidazol-6-yl)(piperazin-1-yl)methanone: To a solution of tert-butyl 4-(1-ethyl-2-(hydroxydiphenylmethyl)-1H-benzo[d]imidazole-6-carbonyl)piperazine-1-carboxylate (0.06 g, 0.11 mmol) in DCM (5 mL) was added TFA (1 ml) at ambient temperature and stirred at ambient temperature for 1 hour. Water was added. The resulting mixture was neutralized with ammonium hydroxide to pH~10 and extracted with DCM. The organic layer was dried (sodium sulfate), filtered and concentrated under reduced pressure. The residue obtained was purified by flash chromatography on silica gel to give (1-ethyl-2-(hydroxydiphenylmethyl)-1H-benzo[d]imidazol-6-yl)(piperazin-1-yl)methanone (0.040 g, 82%) as solid. LCMS ESI (+) m/z 442 (M+H). ¹HNMR (400 MHz, d⁶-DMSO): δ 7.61 (d, 1H), 7.52 (s, 1H), 7.26-7.34 (m, 10H), 7.16 (d, 1H), 7.15 (s, 1H), 4.21 (q, 2H), 3.01-3.49 (m, 4H), 2.58-2.85 (m, 4H), 0.98 (t, 3H).

Example 19: Synthesis of 3-((6-chloro-1-methyl-1H-benzo[d]imidazol-2-yl)(hydroxy)(phenyl)methyl)-N-ethylbenzamide (Compound 64)

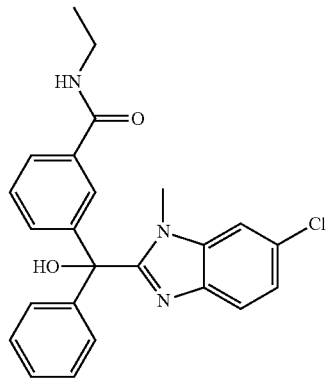 [SMILES: CCNC(=O)c1cccc(C(O)(c2ccccc2)c2nc3ccc(Cl)cc3n2C)c1]

Step A: Preparation (6-chloro-1-methyl-1H-benzo[d]imidazol-2-yl)(phenyl)(m-tolyl)methanol: Prepared similarly as Example 1 substituting 2,4-difluoro-1-nitrobenzene and ethyl amine hydrochloride with 4-chloro-2-fluoro-1-nitrobenzene and methyl amine in water in Step A and benzophone with phenyl(m-tolyl)methanone in Step C.

Step B: Preparation of 3-((6-chloro-1-methyl-1H-benzo[d]imidazol-2-yl)(hydroxy)(phenyl)methyl)benzoic acid: Prepared similarly as Example 3 substituting (1,6-dimethylbenzimidazol-2-yl)-diphenyl-methanol with (6-chloro-1-methyl-1H-benzo[d]imidazol-2-yl)(phenyl)(m-tolyl)methanol.

Step C: Preparation of 3-((6-chloro-1-methyl-1H-benzo[d]imidazol-2-yl)(hydroxy)(phenyl)methyl)-N-ethylbenzamide: Prepared similarly as Example 17 substituting 1-ethyl-2-(hydroxydiphenylmethyl)-1H-benzo[d]imidazole-6-carboxylic acid with 3-((6-chloro-1-methyl-1H-benzo[d]imidazol-2-yl)(hydroxy)(phenyl)methyl)benzoic acid. LCMS ESI (+) m/z 420 (M+H). ¹HNMR (400 MHz, d6-DMSO): δ 8.42 (t, 1H), 7.83 (s, 1H), 7.71 (d, 1H), 7.64 (d, 1H), 7.57 (d, 1H), 7.23-7.38 (m, 8H), 7.17 (dd, 1H), 3.51 (s, 3H), 3.18-3.25 (m, 2H), 1.06 (t, 3H).

Example 20: Synthesis of 2-benzhydryl-1-ethyl-N-methyl-1H-benzo[d]imidazole-6-carboxamide (Compound 76)

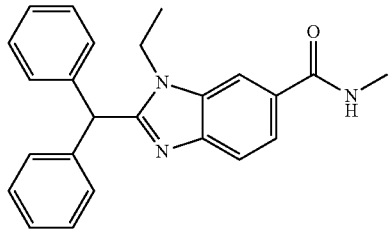 [SMILES: CCn1c(C(c2ccccc2)c2ccccc2)nc2ccc(C(=O)NC)cc21]

A solution of 1-ethyl-2-(hydroxydiphenylmethyl)-N-methyl-1H-benzo[d]imidazole-6-carboxamide (0.10 g, 0.26 mmol) in acetic acid (15 mL) was added phosphinic acid (0.034 g, 0.52 mmol) and iodine (0.007 g, 0.026 mmol). The mixture was stirred at 80° C. for 2 days. The solvent was evaporated and saturated sodium bicarbonate solution was added. The resulting mixture was extracted with ethyl acetate. The organic phase was separated and dried (sodium sulfate), filtered and concentrated under reduced pressure. The residue was purified by flash chromatography on silica gel to give 2-benzhydryl-1-ethyl-N-methyl-1H-benzo[d]imidazole-6-carboxamide (0.03 g, 32%) as solid. LCMS ESI (+) m/z 370 (M+H). $^1$HNMR (400 MHz, CDCl$_3$): δ 7.96 (d, 1H), 7.76 (d, 1H), 7.48 (dd, 1H), 7.26-7.35 (m, 10H), 6.16-6.23 (brs, 1H), 5.71 (s, 1H), 4.19 (q, 2H), 3.05 (d, 3H), 1.19 (t, 3H).

Example 21: Synthesis of (1,6-dimethyl-1H-benzo[d]imidazol-2-yl)(3-methylpyridin-2-yl)(phenyl)methanol (Compound 77)

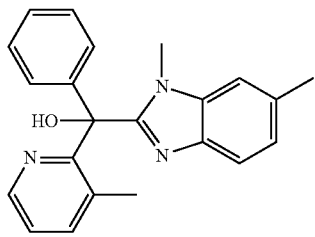

Step A: Preparation of (1,6-dimethyl-1H-benzo[d]imidazol-2-yl)(phenyl)methanone: Prepared similarly as Example 1 substituting ethyl amine with methyl amine in Step A and benzophone with N-methoxy-N-methylbenzamide in Step C.

Step B: Preparation of (1,6-dimethyl-1H-benzo[d]imidazol-2-yl)(3-methylpyridin-2-yl)(phenyl)methanol: To a solution of (1,6-dimethyl-1H-benzo[d]imidazole-2-yl)(phenyl)methanone (0.050 g, 0.20 mmol) and 2-bromo-3-methylpyridine (0.086 g, 0.50 mmol) in THF (3 mL) was added 1.7 M t-BuLi (0.47 mL, 0.80 mmol) in pentane at −78° C. The reaction mixture was stirred at −78° C. for 3 hours. Water (10 mL) and ethyl acetate (20 mL) were added. The organic layer was separated, washed with brine, dried (sodium sulfate), filtered and concentrated under reduced pressure. The residue was purified by flash chromatography on silica gel with 2:1 hexane/ethyl acetate to give (1,6-dimethyl-1H-benzo[d]imidazol-2-yl)(3-methylpyridin-2-yl)(phenyl)methanol (0.033 g, 48%). LCMS ESI (+) m/z 344 (M+H).

Example 22: Synthesis of (R)-1-ethyl-2-(hydroxydiphenylmethyl)-N-(2-hydroxypropyl)-1H-benzo[d]imidazole-6-carboxamide (Compound 79)

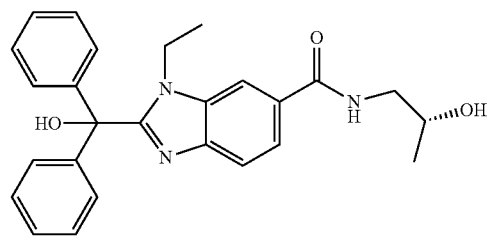 [SMILES: CCn1c(C(O)(c2ccccc2)c2ccccc2)nc2ccc(C(=O)NC[C@@H](C)O)cc21]

To a solution of 1-ethyl-2-(hydroxydiphenylmethyl)-1H-benzo[d]imidazole-6-carboxylic acid (3.00 g, 8.1 mmol), (R)-1-aminopropan-2-ol (0.91 g, 12.1 mmol) and DIEA (2.81 mL, 16.1 mmol) in DMF (5 mL) was added HATU (6.13 g, 16.1 mmol). The mixture was stirred at ambient temperature for 18 hours. The reaction mixture was directly purified by C18 reverse phase flash chromatography (Biotage Isolera One unit, C18 Flash 40+M column, 0-100% CH$_3$CN/water) to give Compound 79 (3.40 g, 98%) as solid. LCMS ESI (+) m/z 430 (M+H). $^1$HNMR (400 MHz, CDCl$_3$): δ 7.96 (s, 1H), 7.79 (d, 1H), 7.59 (d, 1H), 7.26-7.38 (m, 10H), 6.67 (bs, 1H), 4.86 (s, 1H), 4.08 (m, 3H), 3.69 (m, 1H), 3.37 (m, 1H), 2.59 (bs, 1H), 1.27 (d, 3H), 0.78 (t, 3H).

Example 23: Synthesis of 3-(1-ethyl-2-(hydroxydiphenylmethyl)-1H-benzo[d]imidazol-6-yl)-N-methylpropanamide (Compound 87)

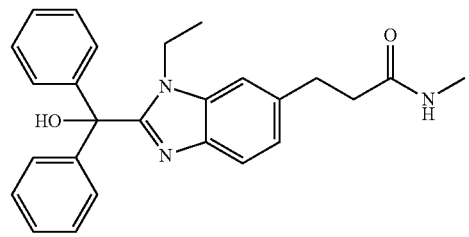 [SMILES: CCn1c(C(O)(c2ccccc2)c2ccccc2)nc2ccc(CCC(=O)NC)cc21]

Step A: Preparation of 1-ethyl-2-(hydroxydiphenylmethyl)-1H-benzo[d]imidazol-6-yl trifluoromethanesulfonate: To a solution of 1-ethyl-2-(hydroxydiphenylmethyl)-1H-benzo[d]imidazol-6-ol (0.3 g, 0.87 mmol) (Example 9, Step A) in DCM (25 mL) was added triflic anhydride (0.49 g, 1.74 mmol) and then followed by triethylamine (0.26 g, 2.61 mmol) at ambient temperature. The reaction mixture was stirred at ambient temperature for 4 hours. Solvent was removed under reduced pressure. The residue was purified by flash chromatography on silica gel to give 1-ethyl-2-(hydroxydiphenylmethyl)-1H-benzo[d]imidazol-6-yl trifluoromethanesulfonate (0.2 g, 42%) as solid.

Step B: Preparation of methyl (E)-3-(1-ethyl-2-(hydroxydiphenylmethyl)-1H-benzo[d]imidazol-6-yl)acrylate: A solution of 1-ethyl-2-(hydroxydiphenylmethyl)-1H-benzo[d]imidazol-6-yl trifluoromethanesulfonate (1.4 g, 2.9 mmol), methyl acrylate (0.30 g, 3.5 mmol), {1,1'-bis(diphenylphosphino)ferrocene]dichloropalladium(II) (0.043 g, 0.059 mmol) and triethylamine (0.36 g, 3.53 mmol) in DMF (50 mL) was stirred at 110° C. overnight. After cooling to ambient temperature, DMF was removed under reduced pressure. Ethyl acetate was added to the residue and the mixture was stirred at ambient temperature for 30 minutes. Solid was removed by filtration and washed with ethyl acetate. The filtrate was concentrated under reduced pressure. The residue was purified by flash chromatography on silica gel to give (E)-3-(1-ethyl-2-(hydroxydiphenylmethyl)-1H-benzo[d]imidazol-6-yl)acrylate (0.36 g, 30%) as solid.

Step C: Preparation of methyl 3-(1-ethyl-2-(hydroxydiphenylmethyl)-1H-benzo[d]imidazol-6-yl)propanoate: A mixture of methyl (E)-3-(1-ethyl-2-(hydroxydiphenylmethyl)-1H-benzo[d]imidazol-6-yl)acrylate (0.36 g, 0.86 mmol) and 10% Pd/C (0.15 g) in methanol was charged with 1 atmosphere hydrogen and stirred at ambient temperature for 1 hour. The catalyst was removed by filtration and washed with methanol. The filtrate was concentrated under reduced pressure to give methyl 3-(1-ethyl-2-(hydroxydiphenylmethyl)-1H-benzo[d]imidazol-6-yl)propanoate (0.29 g, 80%) as solid.

Step D: Preparation of 3-(1-ethyl-2-(hydroxydiphenylmethyl)-1H-benzo[d]imidazol-6-yl)-N-methylpropanamide: Prepared similarly as Example 7 substituting methyl 1-ethyl-2-(hydroxydiphenylmethyl)-1H-benzo[d]imidazole-6-carboxylate with methyl 3-(1-ethyl-2-(hydroxydiphenylmethyl)-1H-benzo[d]imidazol-6-yl)propanoate. LCMS ESI (+) m/z 414 (M+H). $^1$HNMR (400 MHz, d$^6$-DMSO): δ 7.72 (d, 1H), 7.45 (d, 1H), 7.26-7.32 (m, 10H), 7.08 (s, 1H), 6.99 (d, 1H), 4.12 (q, 2H), 2.91 (t, 2H), 2.53 (d, 3H), 2.39 (t, 2H), 0.97 (t, 3H).

Example 24: Synthesis of 3-(1-ethyl-2-(hydroxydiphenylmethyl)-1H-benzo[d]imidazol-6-yl)propan-1-ol (Compound 88)

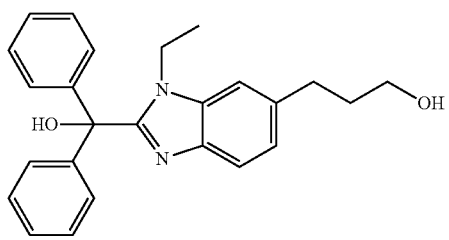

To a solution of methyl 3-(1-ethyl-2-(hydroxydiphenylmethyl)-1H-benzo[d]imidazol-6-yl)propanoate (0.15 g, 0.36 mmol) (Example 23, Step C) in methanol (20 mL) were added sodium borohydride (0.068 g, 0.18 mmol) and calcium chloride (0.2 g, 1.8 mmol) at ambient temperature. The reaction mixture was stirred at ambient temperature for 3 hours. Water was added and extracted with DCM. The organic layer was separated, washed with brine, dried (sodium sulfate), filtered and concentrated under reduced pressure. The residue was purified by flash chromatography on silica gel to give 3-(1-ethyl-2-(hydroxydiphenylmethyl)-1H-benzo[d]imidazol-6-yl)propan-1-ol (0.03 g, 21%) as solid. LCMS ESI (+) m/z 387 (M+H). $^1$HNMR (400 MHz, CDCl$_3$): δ 7.70 (d, 1H), 7.31-7.37 (m, 10H), 7.13-7.15 (m, 2H), 5.21 (s, 1H), 3.97 (q, 2H), 3.72 (t, 2H), 2.84 (t, 2H), 1.93-2.00 (m, 2H), 0.68 (t, 3H).

Example 25: Synthesis of 1-(1-ethyl-2-(hydroxydiphenylmethyl)-1H-benzo[d]imidazol-6-yl)ethane-1,2-diol (Compound 91)

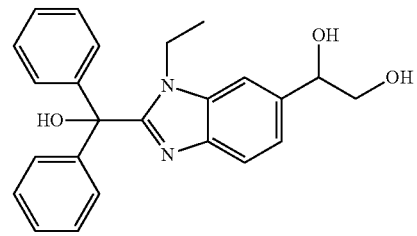 [SMILES: CCn1c(C(O)(c2ccccc2)c2ccccc2)nc2ccc(C(O)CO)cc21]

Step A: Preparation of (1-ethyl-6-vinyl-1H-benzo[d]imidazol-2-yl)diphenylmethanol: A mixture of 1-ethyl-2-(hydroxydiphenylmethyl)-1H-benzo[d]imidazol-6-yl trifluoromethanesulfonate (1.0 g, 2.1 mmol) (Example 23, Step A), tributyl(vinyl)stannane (0.79 g, 2.52 mmol), tetrakis(triphenylphosphine)palladium(0) (0.049 g, 0.042 mmol) and lithium chloride (0.27 g, 6.3 mmol) in DMF (20 mL) was stirred at 100° C. overnight. After cooling to ambient temperature, water and ethyl acetate were added. The organic layer was separated, washed with brine, dried (sodium sulfate), filtered and concentrated under reduced pressure. The residue was purified by flash chromatography on silica gel to give (1-ethyl-6-vinyl-1H-benzo[d]imidazol-2-yl)diphenylmethanol (0.74 g, 62%) as solid.

Step B: Preparation of 1-(1-ethyl-2-(hydroxydiphenylmethyl)-1H-benzo[d]imidazol-6-yl)ethane-1,2-diol: To a solution of (1-ethyl-6-vinyl-1H-benzo[d]imidazol-2-yl)diphenylmethanol (0.1 g, 0.28 mmol) in 8:1 acetone/water (10 mL) was added N-methylmorpholine N-oxide (0.040 g, 0.34 mmol), followed by osmium tetraoxide (0.021 g, 0.084 mmol) at ambient temperature. The reaction mixture was stirred at ambient temperature for 4 hours. Saturated aqueous sodium sulfite and ethyl acetate were added. The organic layer was separated, washed with brine, dried (sodium sulfate), filtered and concentrated under reduced pressure. The residue was purified by flash chromatography on silica gel to give 1-(1-ethyl-2-(hydroxydiphenylmethyl)-1H-benzo[d]imidazol-6-yl)ethane-1,2-diol. LCMS ESI (+) m/z 389 (M+H). $^1$HNMR (400 MHz, d$^6$-DMSO): δ 7.47 (d, 1H), 7.40 (s, 1H), 7.23-7.33 (m, 10H), 7.12 (d, 1H), 7.08 (s, 1H), 5.20 (d, 1H), 4.61-4.68 (m, 2H), 4.14 (q, 2H), 3.43-3.46 (m, 2H), 0.96 (t, 3H).

Example 26: Synthesis of (1,6-dimethyl-1H-benzo[d]imidazol-2-yl)(6-methoxypyridin-3-yl)(phenyl)methanol (Compound 93)

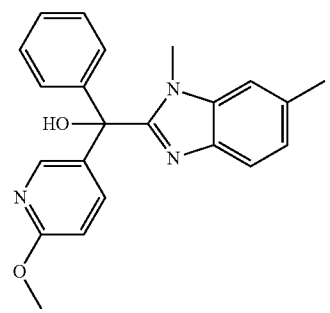 [SMILES: COc1ccc(C(O)(c2ccccc2)c2nc3ccc(C)cc3n2C)cn1]

Prepared similarly as Example 21 substituting 2-bromo-3-methylpyridine with 5-bromo-2-methoxypyridine in Step B. LCMS ESI (+) m/z 360 (M+H).

Example 27: Synthesis of N-((1-ethyl-2-(hydroxydiphenylmethyl)-1H-benzo[d]imidazol-6-yl)methyl)acetamide (Compound 94)

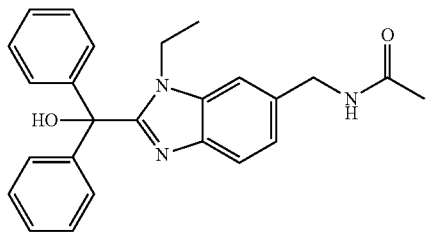 [SMILES: CCn1c(C(O)(c2ccccc2)c2ccccc2)nc2ccc(CNC(C)=O)cc21]

Step A: Preparation of (6-(aminomethyl)-1-ethyl-1H-benzo[d]imidazol-2-yl)diphenylmethanol: A suspension of 1-ethyl-2-(hydroxydiphenylmethyl)-1H-benzo[d]imidazole-6-carbonitrile (1.2 g, 3.4 mmol) and 10% Pd/C (0.2 g, 0.19 mmol) in methanol (50 mL) was charged with 1 atmosphere hydrogen and stirred at ambient temperature for 2 hours. The catalyst was removed by filtration. The solid was washed with methanol. The filtrate was concentrated under reduce pressure to give (6-(aminomethyl)-1-ethyl-1H-benzo[d]imidazol-2-yl)diphenylmethanol (0.6 g, 50%) as solid.

Step B: Preparation of N-((1-ethyl-2-(hydroxydiphenylmethyl)-1H-benzo[d]imidazol-6-yl)methyl)acetamide: To a solution of (6-(aminomethyl)-1-ethyl-1H-benzo[d]imidazol-2-yl)diphenylmethanol (0.1 g, 0.28 mmol) in DCM (20 mL) was added acetyl chloride (0.033 g, 0.42 mmol), followed by DIEA (0.057 g, 0.56 mmol) at ambient temperature. The reaction mixture was stirred at ambient temperature for 2 hours. Solvent was removed under reduced pressure. The residue was purified by flash chromatography on silica gel to give N-((1-ethyl-2-(hydroxydiphenylmethyl)-1H-benzo[d]imidazol-6-yl)methyl)acetamide (0.030 g, 27%) as solid. LCMS ESI (+) m/z 400 (M+H). $^1$HNMR (400 MHz, CDCl$_3$): δ 7.75 (d, 1H), 7.32-7.41 (m, 10H), 7.28 (s, 1H), 7.21 (d, 1H), 5.72-5.83 (brs, 1H), 5.07 (s, 1H), 4.56 (d, 2H), 4.01 (q, 2H), 2.03 (s, 3H), 0.72 (t, 3H).

Example 28: Synthesis of 1-((1-ethyl-2-(hydroxydiphenylmethyl)-1H-benzo[d]imidazol-6-yl)methyl)-3-methylurea (Compound 95)

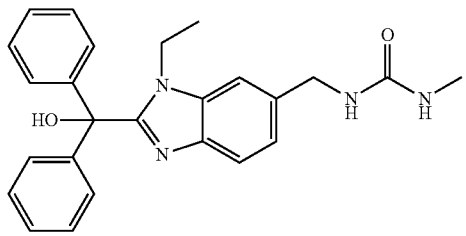

To a solution of (6-(aminomethyl)-1-ethyl-1H-benzo[d]imidazol-2-yl)diphenylmethanol (0.1 g, 0.28 mmol) (Example 27, Step A) in DCM (20 mL) was added carbonyldiimidazole (0.068 g, 0.42 mmol) at ambient temperature. The reaction mixture was stirred at ambient temperature for 1 hour. Methylamine hydrochloride (0.038 g, 0.56 mmol) and DIEA (0.11 g, 0.84 mmol) were added at ambient temperature. The reaction mixture was stirred at ambient temperature overnight. Solvent was removed under reduced pressure. The residue was purified by flash chromatography on silica gel to give 1-41-ethyl-2-(hydroxydiphenylmethyl)-1H-benzo[d]imidazol-6-yl)methyl)-3-methylurea (0.032 g, 28%) as solid. LCMS ESI (+) m/z 415 (M+H). $^1$HNMR (400 MHz, CDCl$_3$): δ 7.71 (d, 1H), 7.30-7.37 (m, 10H), 7.28 (s, 1H), 7.18 (dd, 1H), 5.08 (t, 1H), 4.69 (t, 1H), 4.48 (d, 2H), 4.26-4.35 (brs, 1H), 3.99 (q, 2H), 2.76 (d, 3H), 0.70 (t, 3H).

Example 29: Synthesis of 2-(1-ethyl-2-(hydroxydiphenylmethyl)-1H-benzo[d]imidazol-6-yl)ethan-1-ol (Compound 100)

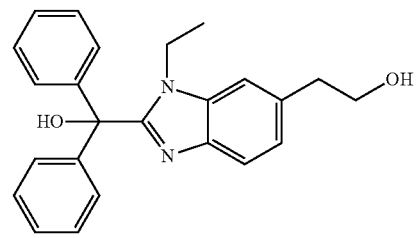 [SMILES: CCn1c(C(O)(c2ccccc2)c2ccccc2)nc2ccc(CCO)cc21]

To a solution of (1-ethyl-6-vinyl-1H-benzo[d]imidazol-2-yl)diphenylmethanol (0.3 g, 0.85 mmol) in THF was added borane dimethyl sulfide complex (0.064 g, 0.85 mmol) at ambient temperature. The reaction mixture was stirred at ambient temperature for 1 hour. Sodium hydroxide (0.034 g, 0.85 mmol) and hydrogen peroxide (30%, 1 mL) were added at ambient temperature. The resulting mixture was stirred at ambient temperature for 2 hours. Saturated aqueous sodium sulfite and ethyl acetate were added. The organic layer was separated, washed with brine, dried (sodium sulfate), filtered and concentrated under reduced pressure. The residue was purified by flash chromatography on silica gel to give 2-(1-ethyl-2-(hydroxydiphenylmethyl)-1H-benzo[d]imidazol-6-yl)ethan-1-ol (0.029 g, 9%) as solid. LCMS ESI (+) m/z 373 (M+H). $^1$HNMR (400 MHz, CDCl$_3$): δ 7.74 (d, 1H), 7.30-7.37 (m, 10H), 7.18 (s, 1H), 7.16 (dd, 1H), 5.17 (s, 1H), 3.98 (q, 2H), 3.92 (q, 2H), 3.00 (t, 2H), 1.40 (t, 1H), 0.69 (t, 3H).

Example 30: Synthesis of 6-((1,6-dimethyl-1H-benzo[d]imidazol-2-yl)(hydroxy)(phenyl)methyl)-1-methylpyridin-2(1H)-one (Compound 101)

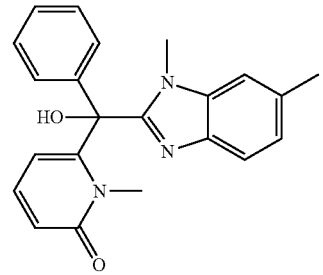 [SMILES: Cc1ccc2nc(C(O)(c3ccccc3)c3cccc(=O)n3C)n(C)c2c1]

Step A: Preparation of (1,6-dimethyl-1H-benzo[d]imidazol-2-yl)(6-methoxypyridin-2-yl)(phenyl)methanol: To a solution of 2-bromo-6-methoxypyridine (0.11 g, 0.6 mmol) in THF (10 mL) was added n-BuLi (2.4 M, 0.5 mL, 1.2 mmol) in hexane at −78° C. The reaction mixture was stirred at −78° C. for 1 hour. (1,6-Dimethyl-1H-benzo[d]imidazol-2-yl)(phenyl)methanone (0.10 g, 0.4 mmol) was added at −78° C. The reaction mixture was stirred at −78° C. for 1 hour. Saturated aqueous ammonium chloride solution and ethyl acetate were added. The organic layer was separated, washed with brine, dried (sodium sulfate), filtered and concentrated under reduced pressure. The residue was purified by flash chromatography on silica gel to give (1,6-dimethyl-1H-benzo[d]imidazol-2-yl)(6-methoxypyridin-2-yl)(phenyl)methanol (0.1 g, 69%) as solid.

Step B: Preparation of 6-((1,6-dimethyl-1H-benzo[d]imidazol-2-yl)(hydroxy)(phenyl)methyl)pyridin-2(1H)-one: A solution of (1,6-dimethyl-1H-benzo[d]imidazol-2-yl)(6-methoxypyridin-2-yl)(phenyl)methanol (0.10 g, 0.28 mmol) in 47% HBr (5 mL) was stirred at 120° C. in a sealed tube for 1 hour. After cooling to ambient temperature, pH of the reaction mixture was adjusted with saturated aqueous sodium bicarbonate to pH~8 and the resulting mixture was extracted with ethyl acetate. The organic layer was dried (sodium sulfate), filtered and concentrated under reduced pressure to give 6-((1,6-dimethyl-1H-benzo[d]imidazol-2-yl)(hydroxy)(phenyl)methyl)pyridin-2(1H)-one (0.060 g, 62%) as solid.

Step C: Preparation of 6-((1,6-dimethyl-1H-benzo[d]imidazol-2-yl)(hydroxy)(phenyl)methyl)-1-methylpyridin-2(1H)-one: To a suspension of 6-((1,6-dimethyl-1H-benzo[d]imidazol-2-yl)(hydroxy)(phenyl)methyl)pyridin-2(1H)-one (0.06 g, 0.17 mmol) and potassium carbonate (0.070 g, 0.51 mmol) in DMF (5 mL) was added iodomethane (0.049 g, 0.34 mmol) at ambient temperature. The reaction mixture was stirred at ambient temperature for 1 hour. Water and ethyl acetate were added. The organic layer was separated, washed with brine, dried (sodium sulfate), filtered and concentrated under reduced pressure. The residue was purified by flash chromatography on silica gel to give 6-((1,6-dimethyl-1H-benzo[d]imidazol-2-yl)(hydroxy)(phenyl)methyl)-1-methylpyridin-2(1H)-one (0.040 g, 65%) as solid. LCMS ESI (+) m/z 360 (M+H). $^1$HNMR (400 MHz, CDCl$_3$): δ 7.62 (d, 1H), 7.61 (t, 1H), 7.29-7.32 (m, 5H), 7.11 (s, 1H), 7.06 (d, 1H), 6.97 (d, 1H), 6.71 (d, 1H), 6.70 (s, 1H), 3.95 (s, 3H), 3.59 (s, 3H), 2.50 (s, 3H).

Example 31: Synthesis of 2-((4-chlorophenyl)(hydroxy)(phenyl)methyl)-1-methyl-1H-benzo[d]imidazole-6-carbonitrile (Compound 102)

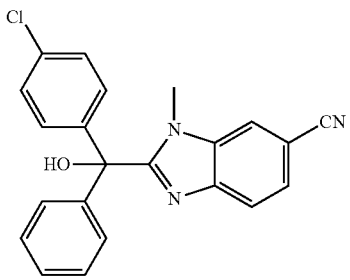 [SMILES: Cn1c(C(O)(c2ccccc2)c2ccc(Cl)cc2)nc2ccc(C#N)cc21]

To a solution of 2-benzoyl-1-methyl-1H-benzo[d]imidazole-6-carbonitrile (0.05 g, 0.19 mmol) in diethyl ether (2 mL) was added 1M 4-chlorophenylmagnesium bromide in ether (0.19 mL, 0.19 mmol) dropwise at 0° C. The mixture was allowed to warm to ambient temperature and stirred overnight. The reaction mixture was treated with saturated aqueous NH$_4$Cl and partitioned between water and ethyl acetate. The organic layer was washed with brine, dried over MgSO$_4$, filtered, and evaporated under reduced pressure. The residue was chromatographed on a 10 g Biotage SNAP column with a 0% to 60% EtOAc/hexane gradient to afford 2-((4-chlorophenyl)(hydroxy)(phenyl)methyl)-1-methyl-1H-benzo[d]imidazole-6-carbonitrile (0.059 g, 82%) as a colorless glass. LCMS ESI (+) m/z 374 (M+H).

Example 32: Synthesis of (1-ethyl-6-propyl-1H-benzo[d]imidazol-2-yl)diphenylmethanol (Compound 106)

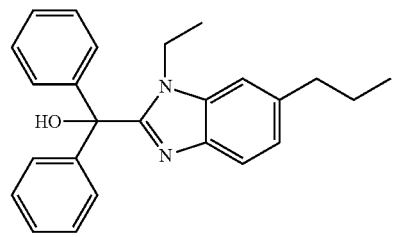 [SMILES: CCCc1ccc2nc(C(O)(c3ccccc3)c3ccccc3)n(CC)c2c1]

A mixture of methyl (6-allyl-1-ethyl-1H-benzo[d]imidazol-2-yl)diphenylmethanol (0.060 g, 0.16 mmol) and 10% Pd/C (0.020 g) in ethanol was charged with 1 atmosphere hydrogen and stirred at ambient temperature for 1 hour. The catalyst was removed by filtration and washed with ethanol. The filtrate was concentrated under reduced pressure. The residue was purified by flash chromatography on silica gel to give (1-ethyl-6-propyl-1H-benzo[d]imidazol-2-yl)diphenylmethanol (0.04 g, 67%) as solid. LCMS ESI (+) m/z 371 (M+H). $^1$HNMR (400 MHz, CDCl$_3$): δ 7.70 (d, 1H), 7.31-7.38 (m, 10H), 7.11-7.14 (m, 2H), 5.20-5.40 (brs, 1H), 3.97 (q, 2H), 2.73 (t, 2H), 1.67-1.76 (m, 2H), 0.99 (t, 3H), 0.68 (t, 3H).

Example 33: Synthesis of 2-(bis(2-fluorophenyl)(hydroxy)methyl)-N,1-dimethyl-1H-benzo[d]imidazole-6-carboxamide (Compound 114)

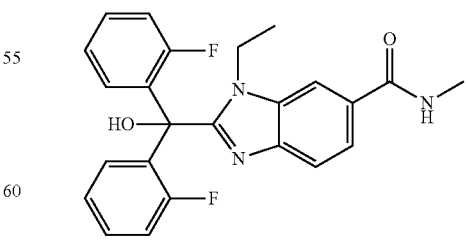

Step A: Preparation of N,5-dimethyl-2-nitro-aniline: A solution of 2-fluoro-4-methyl-1-nitro-benzene (30.0 g, 193 mmol) in NMP (50 mL) was added 40% methylamine in water (50.2 mL, 580.2 mmol). The reaction mixture was stirred at ambient temperature for 5 hours. Water (300 mL) was added and the mixture was stirred at ambient temperature for 30 minutes. The solid was collected by filtration, washed with water and dried to give N,5-dimethyl-2-nitroaniline (31.3 g, 97% yield).

Step B: Preparation of 1,6-dimethylbenzimidazole: N,5-dimethyl-2-nitro-aniline (20.2 g, 122 mmol), trimethyl orthoforamte (133 mL, 1216 mmol), 10% palladium on carbon (6.47 g, 6.1 mmol) and p-toluenesulfonic acid monohydrate (2.31 g, 12.2 mmol) in methanol (240 mL) was charged with 1 atmosphere of hydrogen and the reaction mixture was stirred at ambient temperature for 5 hours. Catalyst was removed by filtration and washed with methanol (200 mL). The filtrated was concentrated under reduced pressure. The residue was added saturated aqueous sodium bicarbonate (50 mL) and ethyl acetate (300 mL). The organic layer was separated, washed with brine, dried (sodium sulfate), filtered and concentrated under reduced pressure to give 1,6-dimethylbenzimidazole (17.7 g, 99.8%) as solid.

Step C: Preparation of (1,6-dimethylbenzimidazol-2-yl)-bis(2-fluorophenyl)methanol: To a solution of 1,6-dimethylbenzimidazole (7.7 g, 52.7 mmol) and bis(2-fluorophenyl) methanone (12.1 g, 55.3 mmol) in THF was added 1.0 M lithium bis(trimethylsilyl)amide in THF (68.5 mL, 68.5 mmol) at 0° C. The reaction mixture was stirred at 0° C. for 1 hour. Saturated aqueous ammonium chloride solution (50 ml) was added. THF was removed under reduced pressure. Water (100 mL) and ethyl acetate (200 mL) were added. The organic layer was separated, washed with brine, dried (sodium sulfate), filtered and concentrated under reduced pressure. The residue was purified by flash chromatography on silica gel with 2:1 hexane/ethyl acetate to give (1,6-dimethylbenzimidazol-2-yl)-bis(2-fluorophenyl)methanol (17.7 g, 92%) as foam.

Step D: Preparation of 2-(bis(2-fluorophenyl)(hydroxy) methyl)-1-methyl-1H-benzo[d]imidazole-6-carboxylic acid: A solution of (1,6-dimethylbenzimidazol-2-yl)-bis(2-fluorophenyl)methanol (17.6 g, 48.3 mmol) and potassium permanganate (30.5 g, 193.2 mmol) in tert-butanol (360 mL) and water (120 mL) was stirred at reflux for 3 hours. Additional potassium permanganate (3.2 g, 20.1 mmol) was added. The reaction was stirred at reflux for another 2 hours. After cooling to ambient temperature, the reaction mixture was filtered through a pad of celite and washed with water (200 mL). MTBE (300 mL) was added to the filtrate. The aqueous layer was separated, acidified with saturated potassium hydrogen sulfate to pH~4 and extracted with ethyl acetate (300 mL). The organic layer was separated, washed with brine, dried (sodium sulfate), filtered through a pad of silica gel, washed with ethyl acetate (50 mL) and concentrated under reduced pressure to give 2-(bis(2-fluorophenyl) (hydroxy)methyl)-1-methyl-1H-benzo[d]imidazole-6-carboxylic acid (12.6 g, 66%) as solid.

Step E: Preparation of 2-(bis(2-fluorophenyl)(hydroxy) methyl)-N,1-dimethyl-1H-benzo[d]imidazole-6-carboxamide: Prepared similarly as Example 17 substituting 1-ethyl-2-(hydroxydiphenylmethyl)-1H-benzo[d]imidazole-6-carboxylic acid and ethyl amine with 2-(bis(2-fluorophenyl) (hydroxy)methyl)-1-methyl-1H-benzo[d]imidazole-6-carboxylic acid and methyl amine. LCMS ESI (+) m/z 408 (M+H).

Example 34: Synthesis of (6-cyclopropyl-1-ethyl-1H-benzo[d]imidazol-2-yl)diphenylmethanol (Compound 121)

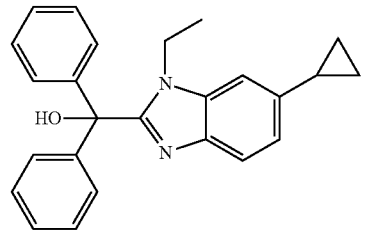 [SMILES: CCn1c(C(O)(c2ccccc2)c2ccccc2)nc2ccc(C3CC3)cc21]

Step A: Preparation of 5-bromo-N-ethyl-2-nitroaniline: Prepared similarly as Example 1 substituting 2,4-difluoro-1-nitrobenzene with 4-bromo-2-fluoro-1-nitrobenzene in Step A.

Step B: Preparation of 5-cyclopropyl-N-ethyl-2-nitroaniline: A solution of 5-bromo-N-ethyl-2-nitroaniline (0.30 g, 1.22 mmol), cyclopropyl boronic acid (0.13 g, 1.4 mmol), cesium carbonate (0.60 g, 1.84 mmol) and tetrakis(triphenylphosphine)palladium(0) (0.071 g, 0.06 mmol) in DMF (10 mL) was stirred at 80° C. for 4 hours. After cooling to ambient temperature, water (20 mL) and ethyl acetate (30 mL) were added. The organic layer was separated, washed with brine, dried (sodium sulfate), filtered and concentrated under reduced pressure. The residue was purified by flash chromatography on silica gel to give 5-cyclopropyl-N-ethyl-2-nitroaniline (0.17 g, 68%) as solid.

Step C: Preparation of (6-cyclopropyl-1-ethyl-1H-benzo [d]imidazol-2-yl)diphenylmethanol: Prepared similarly as Example 1 substituting 5-fluoro-N-ethyl-2-nitroaniline with 5-cyclopropyl-N-ethyl-2-nitroaniline in Step B. LCMS ESI (+) m/z 369 (M+H).

Example 35: Synthesis of 3-(1-ethyl-2-((3-fluoropyridin-2-yl)(hydroxy)(phenyl)methyl)-1H-benzo[d] imidazol-6-yl)propan-1-ol (Compound 125)

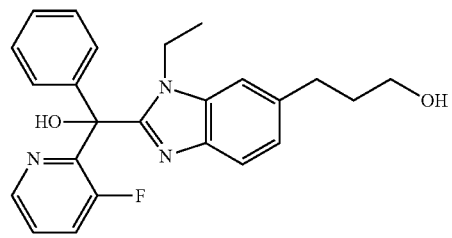

Step A: Preparation of methyl (E)-3-(1-ethyl-1H-benzo [d]imidazol-6-yl)acrylate: A solution of 6-bromo-1-ethyl-1H-benzo[d]imidazole (9.3 g, 41.3 mmol), methyl acrylate (4.27 g, 49.6 mmol), {1,1'-bis(diphenylphosphino)ferrocene]dichloropalladium(II) (1.51 g, 2.06 mmol) and TEA (8.36 g, 82.6 mmol) in DMF (200 mL) was stirred at 110° C. overnight. After cooling to ambient temperature, DMF was removed under reduced pressure. Ethyl acetate (100 mL) was added. The resulting mixture was stirred at ambient temperature for 30 minutes. Solid was removed by filtration and washed with ethyl acetate. The filtrate was concentrated under reduced pressure. The residue was purified by flash chromatography on silica gel to give methyl (E)-3-(1-ethyl-1H-benzo[d]imidazol-6-yl)acrylate (7.1 g, 75%) as solid.

Step B: Preparation of methyl 3-(1-ethyl-1H-benzo[d]imidazol-6-yl)propanoate: A solution of (E)-3-(1-ethyl-1H-benzo[d]imidazol-6-yl)acrylate (7.1 g, 30.8 mmol) and 10% Pd/C (2.0 g) was charged with 1 atmosphere of hydrogen and the reaction mixture was stirred at ambient temperature for 6 hours. The reaction mixture was filtered and the residue was washed with methanol. The filtrate was concentrated under reduced pressure to give 3-(1-ethyl-1H-benzo[d]imidazol-6-yl)propanoate (7.1 g, 100%) as solid.

Step C: Preparation of 3-(1-ethyl-1H-benzo[d]imidazol-6-yl)propan-1-ol: To a mixture of sodium borohydride (12.2 g, 323 mmol), calcium chloride (17.9 g, 162 mmol) in MeOH (200 mL) was added a solution of 3-(1-ethyl-1H-benzo[d]imidazol-6-yl)propanoate (7.5 g, 32.3 mmol) in methanol (200 mL). After the addition, the mixture was stirred at ambient temperature overnight. Solid was removed by filtration. The filtrate was concentrated under reduced pressure. The residue was purified by flash chromatography on silica gel to give 3-(1-ethyl-1H-benzo[c]imidazol-6-yl)propan-1-ol (4.9 g, 74%) as solid.

Step D: Preparation of 6-(3-((tert-butyldimethylsilyl)oxy)propyl)-1-ethyl-1H-benzo[d]imidazole: To a solution of 3-(1-ethyl-1H-benzo[c]imidazol-6-yl)propan-1-ol (4.9 g, 24 mmol) and imidazole (2.45 g, 36 mmol) in DCM was added tert-butylchlorodimethylsilane (5.4 g, 36 mmol). The reaction mixture was stirred at ambient temperature for 4 hours. Solvent was removed under reduced pressure. The residue was purified by flash chromatography on silica gel to give 6-(3-((tert-butyldimethylsilyl)oxy)propyl)-1-ethyl-1H-benzo[d]imidazole (7.1 g, 93%) as solid.

Step D: Preparation of 6-(3-((tert-butyldimethylsilyl)oxy)propyl)-1-ethyl-1H-benzo[d]imidazole: To a solution of 3-(1-ethyl-1H-benzo[d]imidazol-6-yl)propan-1-ol (4.9 g, 24.0 mmol) and imidazole (2.45 g, 36 mmol) in DCM was added tert-butylchlorodimethylsilane (5.4 g, 36 mmol). The reaction mixture was stirred at ambient temperature for 4 hours. Solvent was removed under reduced pressure. The residue was purified by flash chromatography on silica gel to give 6-(3-((tert-butyldimethylsilyl)oxy)propyl)-1-ethyl-1H-benzo[d]imidazole (7.1 g, 93%) as solid.

Step E: Preparation of (6-(3-((tert-butyldimethylsilyl)oxy)propyl)-1-ethyl-1H-benzo[d]imidazol-2-yl)(phenyl)methanone: Prepared similarly as Example 1 substituting 1-ethyl-6-fluoro-1H-benzo[d]imidazole and benzophone with 6-(3-((tert-butyldimethylsilyl)oxy)propyl)-1-ethyl-1H-benzo[d]imidazole and N-methoxy-N-methylbenzamide in Step C.

Step F: Preparation of (6-(3-((tert-butyldimethylsilyl)oxy)propyl)-1-ethyl-1H-benzo[d]imidazol-2-yl)(3-fluoropyridin-2-yl)(phenyl)methanol: Prepared similarly as Example 21 substituting 1,6-dimethyl-1H-benzo[d]imidazole-2-yl)(phenyl)methanone and 2-bromo-3-methylpyridine with (6-(3-((tert-butyldimethylsilyl)oxy)propyl)-1-ethyl-1H-benzo[d]imidazol-2-yl)(phenyl)methanone and 2-bromo-3-fluoropyridine in Step B.

Step G: Preparation of 3-(1-ethyl-2-((3-fluoropyridin-2-yl)(hydroxy)(phenyl)methyl)-1H-benzo[d]imidazol-6-yl)propan-1-ol: To a solution of (6-(3-((tert-butyldimethylsilyl)oxy)propyl)-1-ethyl-1H-benzo[d]imidazol-2-yl)(3-fluoropyridin-2-yl)(phenyl)methanol (0.15 g, 0.29 mmol) in DCM (10 mL) was added TBAF (0.15 g, 0.58 mmol) and the reaction mixture was stirred at ambient temperature overnight. Water was added. The organic layer was separated, washed with brine, dried (sodium sulfate), filtered and concentrated under reduced pressure. The residue was purified by flash chromatography on silica gel to give 3-(1-ethyl-2-((3-fluoropyridin-2-yl)(hydroxy)(phenyl)methyl)-1H-benzo[d]imidazol-6-yl)propan-1-ol (0.08 g, 70%) as solid. LCMS ESI (+) m/z 406 (M+H).

Example 36: Synthesis of 3-(1-ethyl-2-(hydroxy(3-methylpyridin-2-yl)(phenyl)methyl)-1H-benzo[d]imidazol-6-yl)propan-1-ol (Compound 126)

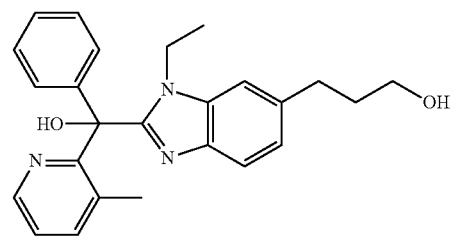 [SMILES: CCn1c(C(O)(c2ccccc2)c2ncccc2C)nc2ccc(CCCO)cc21]

Step A: Preparation of (6-(3-((tert-butyldimethylsilyl)oxy)propyl)-1-ethyl-1H-benzo[d]imidazol-2-yl)(3-methylpyridin-2-yl)(phenyl)methanol: To a solution of 2-bromo-3-methylpyridine (0.096 g, 0.56 mmol) in THF (10 mL) was added n-BuLi (2.4 M, 0.24 mL, 0.56 mmol) in hexane at −78° C. After 30 minutes at −78° C., (6-(3-((tert-butyldimethylsilyl)oxy)propyl)-1-ethyl-1H-benzo[d]imidazol-2-yl)(phenyl)methanone (0.2 g, 0.47 mmol) in THF (5 mL) was added. The mixture was warmed to ambient temperature and stirred for 1 hour. Saturated aqueous ammonium chloride and ethyl acetate was added. The organic layer was separated, washed with brine, dried (sodium sulfate), filtered and concentrated under reduced pressure. The residue was purified by flash chromatography on silica gel to give (6-(3-((tert-butyldimethylsilyl)oxy)propyl)-1-ethyl-1H-benzo[d]imidazol-2-yl)(3-methylpyridin-2-yl)(phenyl)methanol (0.16 g, 65%) as solid.

Step B: Preparation of 3-(1-ethyl-2-(hydroxy(3-methylpyridin-2-yl)(phenyl)methyl)-1H-benzo[d]imidazol-6-yl)propan-1-ol: Prepared similarly as in Example 35 substituting (6-(3-((tert-butyldimethylsilyl)oxy)propyl)-1-ethyl-1H-benzo[d]imidazol-2-yl)(phenyl)methanone with (6-(3-((tert-butyldimethylsilyl)oxy)propyl)-1-ethyl-1H-benzo[d]imidazol-2-yl)(3-methylpyridin-2-yl)(phenyl)methanol in Step G. LCMS ESI (+) m/z 402 (M+H).

Example 37: Synthesis of ((R)-2-benzhydryl-N-(2-hydroxypropyl)-1H-benzo[d]imidazole-6-carboxamide (Compound 131)

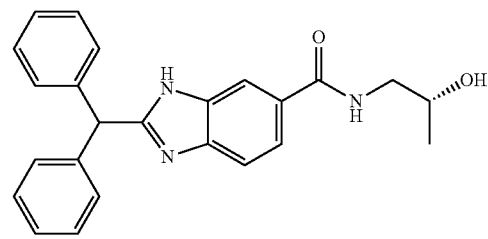 [SMILES: C[C@@H](O)CNC(=O)c1ccc2nc(C(c3ccccc3)c3ccccc3)[nH]c2c1]

Step A: Preparation of methyl 3,4-diaminobenzoate: To a solution of 3,4-diaminobenzoic acid (2.2 g, 14.5 mmol) in MeOH (50 ml) was added concentrated sulfuric acid (1 mL) and the mixture was stirred at reflux for 3 hours. After cooling to ambient temperature, the solvent removed under reduced pressure. Saturated sodium bicarbonate and ethyl acetate were added. The organic layer was separated, washed with brine, dried (sodium sulfate), filtered and concentrated under reduced pressure to give methyl 3,4-diaminobenzoate (1.8 g, 75%) as solid.

Step B: Preparation of methyl 2-(hydroxydiphenylmethyl)-1H-benzo[d]imidazole-6-carboxylate: DIEA (2.09 g, 16.2 mmol) was added to a solution of methyl 3,4-diaminobenzoate (1.8 g, 10.8 mmol) and 2-hydroxy-2,2-diphenylacetic acid (2.7 g,11.9 mmol) in DMF (50 ml) at 0° C. After stirring at 0° C. for 20 minutes, HATU (4.9 g, 13.0 mmol) was added. The reaction mixture was warmed to ambient temperature and stirred for 12 hours. Water and ethyl acetate were added. The organic layer was separated, washed with brine, dried (sodium sulfate), filtered and concentrated under reduced pressure. The residue was dissolved in acetic acid (100 ml) and stirred at 140° C. for 1 hour. After cooling to ambient temperature, solvent was removed under reduced pressure. Saturated sodium bicarbonate and ethyl acetate were added. The organic phase was separated, dried (sodium sulfate), filtered and concentrated under reduced pressure to give 2-(hydroxydiphenylmethyl)-1H-benzo[d]imidazole-6-carboxylate (1.16 g, 30%) as solid.

Step C: Preparation of 2-benzhydryl-1H-benzo[d]imidazole-6-carboxylic acid: A solution of 2-(hydroxydiphenylmethyl)-1H-benzo[d]imidazole-6-carboxylate (1.3 g, 3.6 mmol) in AcOH (50 ml) was added phosphinic acid (0.48 g, 7.24 mmol) and iodine (0.091 g, 0.36 mmol). The mixture was stirred at 110° C. for 2 days. After cooling to ambient temperature, solvent was removed under reduced pressure. Water and ethyl acetate were added. The organic phase was separated, dried (sodium sulfate), filtered and concentrated under reduced pressure. Water and ethyl acetate were added. The organic phase was separated, dried (sodium sulfate), filtered and concentrated under reduced pressure to give 2-benzhydryl-1H-benzo[d]imidazole-6-carboxylic acid (0.85 g, 72%) as solid.

Step D: Preparation of (R)-2-benzhydryl-N-(2-hydroxypropyl)-1H-benzo[d]imidazole-6-carboxamide: Prepared similarly as Example 17 substituting 1-ethyl-2-(hydroxydiphenylmethyl)-1H-benzo[d]imidazole-6-carboxylic acid and ethyl amine with 2-benzhydryl-1H-benzo[d]imidazole-6-carboxylic acid and (R)-1-aminopropan-2-ol. LCMS ESI (+) m/z 386 (M+H).

Example 38: Synthesis of 2-((1-ethyl-2-(hydroxydiphenylmethyl)-1H-benzo[d]imidazol-6-yl)methyl)propane-1,3-diol (Compound 136)

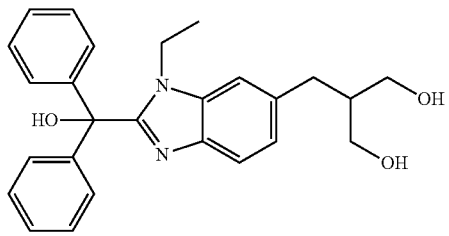 [SMILES: CCn1c(C(O)(c2ccccc2)c2ccccc2)nc2ccc(CC(CO)CO)cc21]

Step A: Preparation of (1-ethyl-6-(hydroxymethyl)-1H-benzo[d]imidazol-2-yl)diphenylmethanol: To a solution methyl 1-ethyl-2-(hydroxydiphenylmethyl)-1H-benzo[d]imidazole-6-carboxylate (0.93 g, 2.5 mmol) in THF (50 mL) was added lithiumaluminum hydride (0.19 g, 5.0 mmol) at ambient temperature and stirred overnight. Water was carefully added to the reaction mixture. The resulting mixture was extracted with ethyl acetate. The organic layer was separated, washed with brine, dried (sodium sulfate), filtered and concentrated under reduced pressure. The residue was purified by flash chromatography on silica gel to give (1-ethyl-6-(hydroxymethyl)-1H-benzo[d]imidazol-2-yl)diphenylmethanol (0.72 g, 83%) as solid.

Step B: Preparation of (6-(chloromethyl)-1-ethyl-1H-benzo[d]imidazol-2-yl)diphenylmethanol: To a solution of (1-ethyl-6-(hydroxymethyl)-1H-benzo[d]imidazol-2-yl)diphenylmethanol (0.72 g, 2.0 mmol) in DCM (20 mL) was added sulfurous dichloride (0.48 g, 4.0 mmol) at ambient temperature and stirred at ambient temperature for 3 hours. Water was added and the organic layer was separated, washed with brine, dried (sodium sulfate), filtered and concentrated under reduced pressure. The residue was purified by flash chromatography on silica gel to give (6-(chloromethyl)-1-ethyl-1H-benzo[d]imidazol-2-yl)diphenylmethanol (0.53 g, 90%) as solid.

Step C: Preparation of diethyl 2-((1-ethyl-2-(hydroxydiphenylmethyl)-1H-benzo[d]imidazol-6-yl)methyl)malonate: A solution of 46-(chloromethyl)-1-ethyl-1H-benzo[d]imidazol-2-yl)diphenylmethanol (0.30 g, 0.80 mmol), potassium carbonate (0.22 g, 1.6 mmol) and diethyl malonate (0.26 g, 1.6 mmol) in DMF (10 mL) was stirred at 100° C. for 3 hours. After cooling to ambient temperature, water and ethyl acetate were added. The organic layer was separated, washed with brine, dried (sodium sulfate), filtered and concentrated under reduced pressure. The residue was purified by flash chromatography on silica gel to give diethyl 2-((1-ethyl-2-(hydroxydiphenylmethyl)-1H-benzo[d]imidazol-6-yl)methyl)malonate (0.15 g, 38%) as solid.

Step D: Preparation of 2-((1-ethyl-2-(hydroxydiphenylmethyl)-1H-benzo[d]imidazol-6-yl)methyl)propane-1,3-diol: Prepared similarly as Example 24 substituting methyl 3-(1-ethyl-2-(hydroxydiphenylmethyl)-1H-benzo[d]imidazol-6-yl)propanoate with diethyl 2-((1-ethyl-2-(hydroxydiphenylmethyl)-1H-benzo[d]imidazol-6-yl)methyl)malonate. LCMS ESI (+) m/z 417 (M+H).

Example 39: Synthesis of 1-(1-ethyl-2-(hydroxydiphenylmethyl)-1H-benzo[d]imidazol-6-yl)propane-1,3-diol (Compound 141)

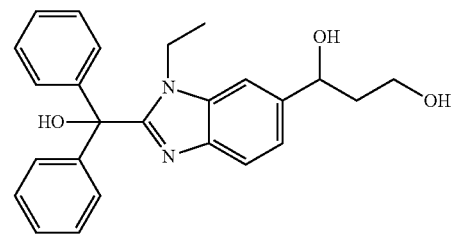 [SMILES: CCn1c(C(O)(c2ccccc2)c2ccccc2)nc2ccc(C(O)CCO)cc21]

Step A: Preparation of methyl 3-(1-ethyl-2-(hydroxydiphenylmethyl)-1H-benzo[d]imidazol-6-yl)-3-oxopropanoate: A solution of 2-(hydroxydiphenylmethyl)-1-ethyl-1H-benzo[d]imidazole-6-carboxylic acid (0.15 g, 0.4 mmol) and CDI (0.078 g, 0.48 mmol) in THF (15 mL) was stirred at ambient temperature for 2 hours. Potassium 3-methoxy-3-oxopropanoate (0.075 g, 0.48 mmol) and magnesium chloride (0.046 g, 0.48 mmoL) were added. The reaction mixture was stirred at 70° C. overnight. After cooling to ambient temperature, the solid was removed by filtration. Water was added to the filtrate and acidified with 2 N HCl to pH~6-7. The resulting mixture was extracted with ethyl acetate. The organic layer was separated, washed with brine, dried (sodium sulfate), filtered and concentrated under reduced pressure. The residue was purified by flash chromatography on silica gel to give methyl 3-(1-ethyl-2-(hydroxydiphenylmethyl)-1H-benzo[d]imidazol-6-yl)-3-oxopropanoate (0.14 g, 82%) as solid.

Step B: Preparation of 1-(1-ethyl-2-(hydroxydiphenylmethyl)-1H-benzo[d]imidazol-6-yl)propane-1,3-diol: Prepared similarly as Example 24 substituting methyl 3-(1-ethyl-2-(hydroxydiphenylmethyl)-1H-benzo[d]imidazol-6-yl)propanoate with methyl 3-(1-ethyl-2-(hydroxydiphenylmethyl)-1H-benzo[d]imidazol-6-yl)-3-oxopropanoate. LCMS ESI (+) m/z 403 (M+H).

Example 40: Synthesis of 4-(1-ethyl-2-(hydroxydiphenylmethyl)-1H-benzo[d]imidazol-6-yl)butan-2-ol (Compound 142)

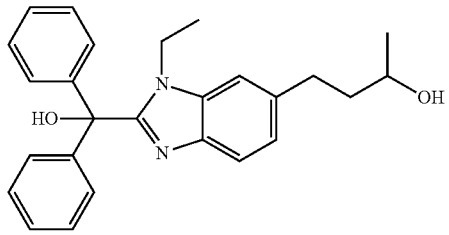

A solution of (6-(chloromethyl)-1-ethyl-1H-benzo[d]imidazol-2-yl)diphenylmethanol (0.10 g, 0.27 mmol), pentane-2,4-dione (0.027 g, 0.27 mmol) and potassium carbonate (0.044 g, 0.32 mmol) in ethanol (10 mL) was stirred at reflux for 6 hours. After cooling to ambient temperature, the solid was removed by filtration. Sodium boron hydride (0.020 g, 0.54 mmol) was added to the filtrate at ambient temperature. The resulting mixture was stirred at ambient temperature for 1 hour. Ethanol was removed under reduced pressure. Water and ethyl acetate were added. The organic layer was separated, washed with brine, dried (sodium sulfate), filtered and concentrated under reduced pressure. The residue was purified by flash chromatography on silica gel to give 4-(1-ethyl-2-(hydroxydiphenylmethyl)-1H-benzo[d]imidazol-6-yl)butan-2-ol (0.021 g, 20%) as solid. LCMS ESI (+) m/z 401 (M+H).

Example 41: Synthesis of 1-ethyl-2-(hydroxydiphenylmethyl)-1H-benzo[d]imidazole-6-sulfonamide (Compound 146)

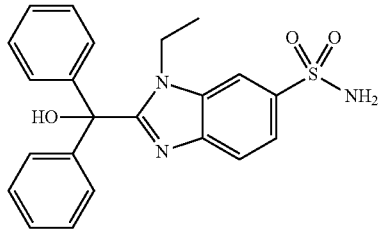 [SMILES: CCn1c(C(O)(c2ccccc2)c2ccccc2)nc2ccc(S(N)(=O)=O)cc21]

Step A: Preparation of tert-butyl (1-ethyl-2-(hydroxydiphenylmethyl)-1H-benzo[d]imidazol-6-yl)carbamate: A solution of 2-(hydroxydiphenylmethyl)-1-ethyl-1H-benzo[d]imidazole-6-carboxylic acid (1.0 g, 2.68 mmol), DPPA (1.1 g, 4.02 mmol) and TEA (0.54 g, 5.36 mmol) in tert-butanol was stirred at 100° C. for 2 hours. After cooling to ambient temperature, tert-butanol was removed under reduced pressure. Water and ethyl acetate were added. The organic layer was separated, washed with brine, dried (sodium sulfate), filtered and concentrated under reduced pressure. The residue was purified by flash chromatography on silica gel to give tert-butyl (1-ethyl-2-(hydroxydiphenylmethyl)-1H-benzo[d]imidazol-6-yl)carbamate (0.53 g, 45%) as solid.

Step B: Preparation of (6-amino-1-ethyl-1H-benzo[d]imidazol-2-yl)diphenylmethanol: To a solution of tert-butyl (1-ethyl-2-(hydroxydiphenylmethyl)-1H-benzo[d]imidazol-6-yl)carbamate (0.53 g, 1.2 mmol) in DCM (40 mL) was added TFA (20 mL) at ambient temperature. The reaction mixture was stirred at ambient temperature for 6 hours. Solvent was removed under reduced pressure. Saturated sodium bicarbonate and DCM were added. The organic layer was separated, washed with brine, dried (sodium sulfate), filtered and concentrated under reduced pressure. The residue was purified by flash chromatography on silica gel to give (6-amino-1-ethyl-1H-benzo[d]imidazol-2-yl)diphenylmethanol (0.35 g, 85%) as solid.

Step C: Preparation of 1-ethyl-2-(hydroxydiphenylmethyl)-1H-benzo[d]imidazole-6-sulfonic acid: In the first flask, (6-amino-1-ethyl-1H-benzo[d]imidazol-2-yl)diphenylmethanol (0.35 g, 1.0 mmol) was dissolved in concentrated HCl (37%, 1.1 mL), and the resulting solution was cooled to −5° C. A solution of sodium nitrite (0.079 g, 1.14 mmol) in water (1 mL) was added slowly with stirring while maintaining the temperature below 0° C. The mixture was stirred for 10 minutes at this temperature. In the second flask, thionyl chloride (0.33 mL, 4.6 mmol) was added drop wise to water (2 mL) at −5° C. The resulting solution was allowed to warm to ambient temperature, and then Cu(I)Cl (0.005 g, 0.05 mmol) was added, and then the reaction mixture was cooled to −5° C. The solution of the first flask was added slowly to the second flask, and the mixture was stirred for 30 minutes at 0° C. The solid formed was collected by filtration, washed with water and dried to give 1-ethyl-2-(hydroxydiphenylmethyl)-1H-benzo[d]imidazole-6-sulfonic acid (0.15 g, 35%) as solid.

Step D: Preparation of 1-ethyl-2-(hydroxydiphenylmethyl)-1H-benzo[d]imidazole-6-sulfonyl chloride: A solution of 1-ethyl-2-(hydroxydiphenylmethyl)-1H-benzo[d]imidazole-6-sulfonic acid (0.64 g, 1.57 mmol) in thionyl chloride (20 mL) was added a drop of DMF. The resulting mixture was stirred at 80° C. for 2 hours. After cooling to ambient temperature, solvent was removed under reduced pressure to give 1-ethyl-2-(hydroxydiphenylmethyl)-1H-benzo[d]imidazole-6-sulfonyl chloride (0.6 g, 90%) as solid.

Step E: Preparation of 1-ethyl-2-(hydroxydiphenylmethyl)-1H-benzo[d]imidazole-6-sulfonamide: A solution of 1-ethyl-2-(hydroxydiphenylmethyl)-1H-benzo[d]imidazole-6-sulfonyl chloride (0.08 g, 0.19 mmol) in DCM (20 mL) was bubble through ammonia for 30 minutes and then stirred at ambient temperature for 30 minutes. Solvent was removed under reduced under pressure. The residue was purified by flash chromatography on silica gel to give 1-ethyl-2-(hydroxydiphenylmethyl)-1H-benzo[d]imidazole-6-sulfonamide (0.022 g, 32%) as solid. LCMS ESI (+) m/z 408 (M+H).

Example 42: Synthesis of 2-((1-ethyl-2-(hydroxydiphenylmethyl)-1H-benzo[d]imidazol-6-yl)sulfonyl)ethan-1-ol (Compound 161)

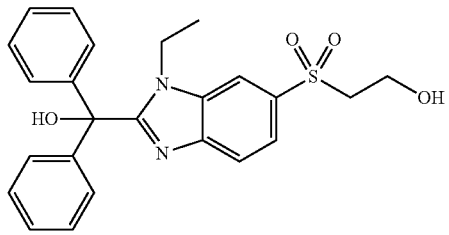 [SMILES: CCn1c(C(O)(c2ccccc2)c2ccccc2)nc2ccc(S(=O)(=O)CCO)cc21]

To a solution of sodium sulfite (0.030 g, 0.46 mmol) and sodium bicarbonate (0.020 g, 0.46 mmol) in water (5 mL) was added a solution of 1-ethyl-2-(hydroxydiphenylmethyl)-1H-benzo[d]imidazole-6-sulfonyl chloride (0.10 g, 0.23 mmol) in THF (5 mL) at ambient temperature. After the addition, the reaction mixture was stirred at 75° C. for 2 hours, and then cooled to ambient temperature. 2-Bromoethan-1-ol (0.059 g, 0.92 mmol) was added. The resulting mixture was stirred at 50° C. overnight. After cooling to ambient temperature, water and ethyl acetate were added. The organic layer was separated, washed with brine, dried (sodium sulfate), filtered and concentrated under reduced pressure. The residue was purified by flash chromatography on silica gel to give 2-((1-ethyl-2-(hydroxydiphenylmethyl)-1H-benzo[d]imidazol-6-yl)sulfonyl)ethan-1-ol (0.066 g, 65%) as solid. LCMS ESI (+) m/z 437 (M+H).

Example 43: Synthesis of 1-(1-ethyl-2-(hydroxydiphenylmethyl)-1H-benzo[d]imidazol-6-yl)cyclohexan-1-ol (Compound 162)

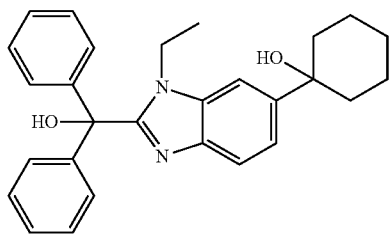 [SMILES: CCn1c(C(O)(c2ccccc2)c2ccccc2)nc2ccc(C3(O)CCCCC3)cc21]

Step A: Preparation of (6-bromo-1-ethyl-1H-benzo[d]imidazol-2-yl)diphenylmethanol: Prepared similarly as in Example 33 substituting 1,6-dimethylbenzimidazole and bis(2-fluorophenyl)methanone with 6-bromo-1-ethyl-1H-benzo[d]imidazole and benzophenone in Step C.

Step B: Preparation of 2-((1-ethyl-2-(hydroxydiphenylmethyl)-1H-benzo[d]imidazol-6-yl)sulfonyl)ethan-1-ol: To a solution of (6-bromo-1-ethyl-1H-benzo[d]imidazol-2-yl)diphenylmethanol (0.10 g, 0.25 mmol) in THF (20 mL) was added n-BuLi (2.4 M, 0.41 mL, 0.98 mmol) at −78° C. The mixture was stirred at −78° C. for 30 minutes. Cyclohexanone (0.096 g, 0.98 mmol) was added at −78° C. The reaction mixture was slowly warmed to ambient temperature and stirred at ambient temperature for 30 minutes. Saturated ammonium chloride and ethyl acetate were added. The organic layer was separated, washed with brine, dried (sodium sulfate), filtered and concentrated under reduced pressure. The residue was purified by flash chromatography on silica gel to give 1-(1-ethyl-2-(hydroxydiphenylmethyl)-1H-benzo[d]imidazol-6-yl)cyclohexan-1-ol (0.079 g, 75%) as solid. LCMS ESI (+) m/z 427 (M+H).

Example 44: Synthesis of (1-ethyl-6-(methylsulfonyl)-1H-benzo[d]imidazol-2-yl)diphenylmethanol (Compound 173)

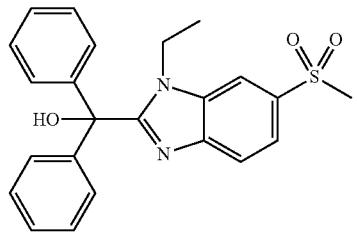 [SMILES: CCn1c(C(O)(c2ccccc2)c2ccccc2)nc2ccc(S(C)(=O)=O)cc21]

To a solution of sodium sulfite (0.044 g, 0.35 mmol) and sodium bicarbonate (0.029 g, 0.35 mmol) in water (20 mL) was added 1-ethyl-2-(hydroxydiphenylmethyl)-1H-benzo[d]imidazole-6-sulfonyl chloride (0.10 g, 0.23 mmol) at ambient temperature. The reaction mixture was stirred at 75° C. for 2 hours, then it was cooled to 30° C. Iodomethane (0.5 mL) was added and the resulting mixture was stirred at 70° C. for 2 hours. After cooling to ambient temperature, water and ethyl acetate were added. The organic layer was separated, washed with brine, dried (sodium sulfate), filtered and concentrated under reduced pressure. The residue was purified by flash chromatography on silica gel to give (1-ethyl-6-(methylsulfonyl)-1H-benzo[c]imidazol-2-yl)diphenylmethanol (0.040 g, 42%) as solid. LCMS ESI (+) m/z 389 (M+H).

Example 45: Synthesis of 2-(bis(2-fluorophenyl)(hydroxy)methyl)-1-methyl-1H-benzo[d]imidazole-6-sulfonamide (Compound 202)

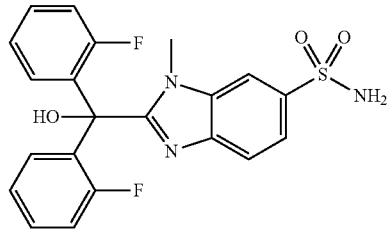 [SMILES: Cn1c(C(O)(c2ccccc2F)c2ccccc2F)nc2ccc(S(N)(=O)=O)cc21]

Step A: Preparation of 5-bromo-N-methyl-2-nitro-aniline: A suspension of 4-bromo-2-fluoro-1-nitro-benzene (5.0 g, 22.7 mmol) in 95% ethanol (20 mL) was treated with 40% methylamine in water (5.9 mL, 68 mmol) at ambient temperature. The mixture was stirred at ambient temperature for 2 days. Water (200 mL) was added. The resulting mixture was stirred at ambient temperature for 10 minutes. Ethyl acetate (100 mL) was added. The organic layer was separated, washed with brine, dried (sodium sulfate), filtered and concentrated under reduced pressure to give 5-bromo-N-methyl-2-nitro-aniline (5.2 g, 99%) as solid.

Step B: Preparation of 6-bromo-1-methyl-benzimidazole: A mixture of 5-bromo-N-methyl-2-nitro-aniline (6.0 g, 26 mmol), iron powder (14.5 g, 260 mmol), ammonium chloride (13.9 g, 260 mmol) and formic acid (49.0 mL, 1298 mmol) in 2-propanol (75 mL) was stirred under reflux for 24 hours. After cooling to ambient temperature, ethyl acetate (50 mL) was added. The solid was removed by filtering through a pad of celite. The filtrate was concentrated. Saturated sodium bicarbonate (20 mL) and ethyl acetate (50 mL) were added. The organic layer was separated, washed with brine, dried (sodium sulfate), filtered and concentrated. The residue was purified by flash chromatography on silica gel 10:1 ethyl acetate/MeOH to give 6-bromo-1-methyl-benzimidazole (5.35 g, 98%) as solid.

Step C: Preparation of (6-bromo-1-methyl-benzimidazol-2-yl)-bis(2-fluorophenyl)methanol: To a solution of bis(2-fluorophenyl)methanone (3.98 g, 18.2 mmol) and lithium bis(trimethylsilyl)amide (20.7 mL, 20.7 mmol) in THF (50 ml) was added 6-bromo-1-methyl-benzimidazole (3.5 g, 16.6 mmol) in THF (40 mL) dropwise at −45° C. After the addition, the mixture was stirred at −45° C. for 1 hour. Aqueous saturated ammonium chloride solution (50 mL) and ethyl acetate (50 mL) were added. The organic layer was separated, washed with brine, dried (sodium sulfate), filtered and concentrated. The residue was purified by flash chromatography on silica gel using 2:1 hexane/ethyl acetate to give (6-bromo-1-methyl-benzimidazol-2-yl)-bis(2-fluorophenyl)methanol (6.32 g, 89%) as solid.

Step D: Preparation of S-[2-[bis(2-fluorophenyl)-hydroxy-methyl]-3-methyl-benzimidazol-5-yl] ethanethioate: A solution of (6-bromo-1-methyl-benzimidazol-2-yl)-bis(2-fluorophenyl)methanol (6.3 g, 14.7 mmol), S-potassium thioacetate (2.18 g, 19.1 mmol), tris(dibenzylideneacetone)dipalladium(0) (0.67 g, 0.73 mmol) and (5-diphenylphosphanyl-9,9-dimethyl-xanthen-4-yl)-diphenyl-phosphane (0.93 g, 1.6 mmol) in 1,4-dioxane (50 mL) was stirred at 100° C. (bath) for 18 hours. After cooling to ambient temperature, water (50 mL) and ethyl acetate (100 mL) were added. The organic layer was separated, washed with brine, dried (sodium sulfate), filtered and concentrated. The residue was purified by flash chromatography on silica gel 2:1 hexane/ethyl acetate to give S-[2-[bis(2-fluorophenyl)-hydroxy-methyl]-3-methyl-benzimidazol-5-yl] ethanethioate (4.66 g, 75%) as solid.

Step E: Preparation of 2-[bis(2-fluorophenyl)-hydroxy-methyl]-3-methyl-benzimidazole-5-sulfonyl chloride: 1-Chloropyrrolidine-2,5-dione (5.79 g, 43.4 mmol) was added to a mixture of 2 M HCl (2.9 mL) and acetonitrile (14.5 mL) and then cooled to 10° C. Solid S-[2-[bis(2-fluorophenyl)-hydroxy-methyl]-3-methyl-benzimidazol-5-yl] ethanethioate (4.6 g, 10.8 mmol) was added slowly to control the internal temperature below 20° C. After the addition, the mixture was stirred at 10~20° C. for 20 minutes. Aqueous saturated sodium bicarbonate was added to adjust the pH of the reaction mixture to about 8. Ethyl acetate (40 mL) was added. The organic layer was separated, washed with brine, dried (sodium sulfate), filtered and concentrated to give 2-[bis(2-fluorophenyl)-hydroxy-methyl]-3-methyl-benzimidazole-5-sulfonyl chloride (4.8 g, 99%) as solid.

Step F: Preparation of 2-[bis(2-fluorophenyl)-hydroxy-methyl]-3-methyl-benzimidazole-5-sulfonamide: To a solution of 2-[bis(2-fluorophenyl)-hydroxy-methyl]-3-methyl-benzimidazole-5-sulfonyl chloride (4.8 g, 10.7 mmol) in ACN (20 mL) was added 7 N ammonium (15.3 mL, 107 mmol) in methanol at 0° C. After the addition, the mixture was stirred at 0° C. for 1 hour. Solvent was removed under reduced pressure. Water (80 mL) was added and stirred at ambient temperature for 10 minutes. The solid was collected by filtration, washed with water and dried. The resulting solid was suspended in 1:1 hexane/ethyl acetate (50 mL) and stirred at ambient temperature for 30 minutes. The solid was collected by filtration and dried to give 2-[bis(2-fluorophenyl)-hydroxy-methyl]-3-methyl-benzimidazole-5-sulfonamide (4.13 g, 90%) as solid. LCMS ESI (+) m/z 430 (M+H).

Example 46: Synthesis of (R)-2-(hydroxydiphenyl-methyl)-N-(2-hydroxypropyl)-1-(2,2,2-trifluoroethyl)-1H-benzo[d]imidazole-6-carboxamide (Compound 203)

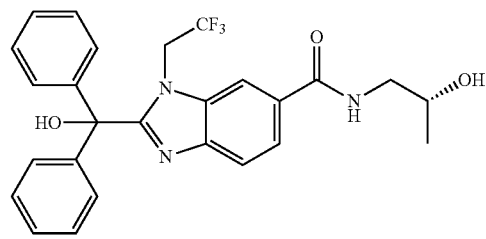 [SMILES: C[C@@H](O)CNC(=O)c1ccc2nc(C(O)(c3ccccc3)c3ccccc3)n(CC(F)(F)F)c2c1]

Step A: Preparation of 5-methyl-2-nitro-N-(2,2,2-trifluoroethyl)aniline: A mixture of 2-fluoro-4-methyl-1-nitro-benzene (3.0 g, 19.3 mmol), 2,2,2-trifluoroethylamine (4.55 mL, 58 mmol) and potassium carbonate (4.0 g, 29 mmol) in 1-methyl-2-pyrrolidone (10 mL) was stirred at 120° C. (bath) in a sealed tube for 20 hours. After cooling to ambient temperature, water (40 mL) and 1:1 MTBE/ethyl acetate (40 mL) were added. The organic layer was separated, washed with brine, dried (sodium sulfate), filtered and concentrated under reduced pressure. The residue obtained was purified by flash chromatography on silica gel to give 5-methyl-2-nitro-N-(2,2,2-trifluoroethyl)aniline (4.0 g, 88%) as yellow solid.

Step B: Preparation of 6-methyl-1-(2,2,2-trifluoroethyl)benzimidazole: A mixture of 5-methyl-2-nitro-N-(2,2,2-trifluoroethyl)aniline (4.0 g, 17 mmol), iron powder (9.5 g, 171 mmol), ammonium chloride (9.14 g, 171 mmol) and formic acid (32.2 mL, 854 mmol) in 2-propanol (30 mL) was stirred under reflux for 24 hours. After cooling to ambient temperature, ethyl acetate (100 mL) was added. The solid was removed by filtering through a pad of celite. Water (50 mL) was added to the filtrate. The organic layer was separated, washed with brine, dried (sodium sulfate), filtered and concentrated under reduced pressure. The residue obtained was purified by flash chromatography on silica gel using 2:1 hexane/ethyl acetate to give 6-methyl-1-(2,2,2-trifluoroethyl)benzimidazole (3.0 g, 82%) as solid.

Step C: Preparation of [6-methyl-1-(2,2,2-trifluoroethyl)benzimidazol-2-yl]-diphenyl-methanol: To a solution of 6-methyl-1-(2,2,2-trifluoroethyl)benzimidazole (1.0 g, 4.67 mmol) and benzophenone (1.28 g, 7 mmol) in THF (20 mL) was added 1.7 M tert-butyl lithium solution (4.12 mL, 7 mmol) slowly at −78° C. The reaction mixture was stirred at −78° C. for 1 hour. Additional tert-butyl lithium solution (4.12 mL, 7 mmol) was added slowly at −78° C. The reaction mixture was stirred at −78° C. for 30 minutes, and then 30 mL of saturated ammonium chloride was added. The mixture was warmed to ambient temperature, ethyl acetate (40 mL) was added. The organic layer was separated, washed with brine, dried (sodium sulfate), filtered and concentrated. The residue obtained was purified by flash chromatography on silica gel with 5:1 hexane/ethyl acetate to give [6-methyl-1-(2,2,2-trifluoroethyl)benzimidazol-2-yl]-diphenyl-methanol (0.30 g, 16%) as foam solid. LCMS ESI (+) m/z 397 (M+H).

Step D: Preparation of 2-[hydroxy(diphenyl)methyl]-3-(2,2,2-trifluoroethyl)benzimidazole-5-carboxylic acid: A solution of [6-methyl-1-(2,2,2-trifluoroethyl)benzimidazol-2-yl]-diphenyl-methanol (0.3 g, 0.76 mmol) and potassium permanganate (0.48 g, 3.03 mmol) in tert-butanol (7.5 mL) and water (7.5 mL) was stirred at reflux for 2 hours. Additional potassium permanganate (0.48 g, 3.03 mmol) was added and reaction mixture was stirred at reflux for additional 1 hour. After cooling to ambient temperature, the solid was removed by filtration and the filtrate was washed with water (10 mL) and ethyl acetate (20 mL). The aqueous layer was separated and acidified with saturated potassium hydrogen sulfate to pH~4. The mixture was extracted with ethyl acetate (20 mL). The organic layer was separated, washed with brine, dried (sodium sulfate), filtered and concentrated to give 2-[hydroxy(diphenyl)methyl]-3-(2,2,2-trifluoroethyl)benzimidazole-5-carboxylic acid (0.085 g, 26%) as solid.

Step E: Preparation of (R)-2-(hydroxydiphenylmethyl)-N-(2-hydroxypropyl)-1-(2,2,2-trifluoroethyl)-1H-benzo[d]imidazole-6-carboxamide: Prepared similarly as Example 17 substituting 1-ethyl-2-(hydroxydiphenylmethyl)-1H-benzo[d]imidazole-6-carboxylic acid and ethyl amine with 2-[hydroxy(diphenyl)methyl]-3-(2,2,2-trifluoroethyl)benzimidazole-5-carboxylic acid and (R)-1-aminopropan-2-ol. LCMS ESI (+) m/z 484 (M+H).

Example 47: Synthesis of 2-((3-methylpyridin-2-yl)(hydroxy)(phenyl)methyl)-N—((R)-2-hydroxypropyl)-1-methyl-1H-benzo[d]imidazole-6-carboxamide (Compound 204)

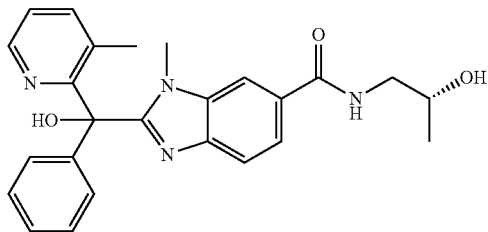 [SMILES: Cc1cccnc1C(O)(c1ccccc1)c1nc2ccc(C(=O)NC[C@@H](C)O)cc2n1C]

Step A: Preparation of (6-bromo-1-methyl-1H-benzo[d]imidazol-2-yl)(3-methylpyridin-2-yl)(phenyl)methanol: Prepared similarly as Example 3 substituting 1,6-dimethyl-benzimidazole and benzophenone with 6-bromo-1-methyl-1H-benzo[d]imidazole and (3-methylpyridin-2-yl)(phenyl)methanone in Step C.

Step B: Preparation of methyl 2-(hydroxy(3-methylpyridin-2-yl)(phenyl)methyl)-1-methyl-1H-benzo[d]imidazole-6-carboxylate: Carbon monoxide was bubbled through a solution of (6-bromo-1-methyl-1H-benzo[d]imidazol-2-yl)(3-methylpyridin-2-yl)(phenyl)methanol (2.1 g, 5.3 mmol), 1,1'-bis(diphenylphosphino)ferrocene]dichloropalladium (II) (0.19 g, 0.26 mmol) and TEA (1.06 g, 10.5 mmol) in DMF (30 mL) and methanol (30 mL) for 5 minutes. The reaction mixture was then stirred at 120° C. in an autoclave overnight. After cooling to ambient temperature, solvent was removed under reduced pressure. Ethyl acetate (100 mL) was added and the resulting mixture was stirred at ambient temperature for 30 minutes. Solid was removed by filtration and washed with ethyl acetate. The filtrate was concentrated under reduced pressure. The residue was purified by flash chromatography on silica gel to give methyl 2-(hydroxy(3-methylpyridin-2-yl)(phenyl)methyl)-1-methyl-1H-benzo[d]imidazole-6-carboxylate (1.0 g, 50%) as solid.

Step C: Preparation of 2-(hydroxy(3-methylpyridin-2-yl)(phenyl)methyl)-1-methyl-1H-benzo[d]imidazole-6-carboxylic acid: A solution of methyl 2-(hydroxy(3-methylpyridin-2-yl)(phenyl)methyl)-1-methyl-1H-benzo[d]imidazole-6-carboxylate (0.92 g, 2.4 mmol) and sodium hydroxide (0.19 g, 4.8 mmol) in methanol (50 mL) and water (50 mL) was stirred at 50° C. for 2 hours. After cooling to ambient temperature, methanol was removed under reduced pressure. The resulting aqueous solution was acidified with 2 N HCl to pH~4. Solid formed was collected by filtration, washed with water and dried to give 2-(hydroxy(3-methylpyridin-2-yl)(phenyl)methyl)-1-methyl-1H-benzo[d]imidazole-6-carboxylic acid (0.80 g, 90%).

Step D: Preparation of 2-((3-methylpyridin-2-yl)(hydroxy)(phenyl)methyl)-N—((R)-2-hydroxypropyl)-1-methyl-1H-benzo[d]imidazole-6-carboxamide: Prepared similarly as Example 17 substituting 1-ethyl-2-(hydroxydiphenylmethyl)-1H-benzo[d]imidazole-6-carboxylic acid and ethyl amine with 2-((3-methylpyridin-2-yl)(hydroxy)(phenyl)methyl)-1-methyl-1H-benzo[d]imidazole-6-carboxylic acid and (R)-1-aminopropan-2-ol. LCMS ESI (+) m/z 431 (M+H).

Example 48: Synthesis of (R)-2-(hydroxydiphenylmethyl)-1-(2-hydroxyethyl)-N-(2-hydroxypropyl)-1H-benzo[d]imidazole-6-carboxamide (Compound 209)

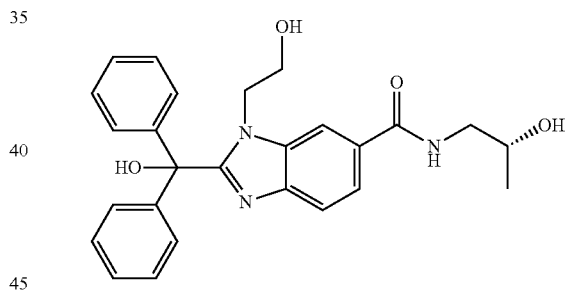

Step A: Preparation of (1-(2,2-dimethoxyethyl)-6-methyl-1H-benzo[d]imidazol-2-yl)diphenylmethanol: Prepared similarly as Example 3 substituting methyl amine with 2,2-dimethoxyethan-1-amine in Step A. LCMS ESI (+) m/z 403 (M+H).

Step B: Preparation of 2-[2-[hydroxy(diphenyl)methyl]-6-methyl-benzimidazol-1-yl]acetaldehyde: To a solution of [1-(2,2-dimethoxyethyl)-6-methyl-benzimidazol-2-yl]-diphenyl-methanol (0.66 g, 1.64 mmol) in 1,2-dichloroethane (2 mL) and water (3.7 mL) was added trifluoroacetic acid (3.8 mL, 49.2 mmol). The reaction mixture was stirred at 70° C. for 18 hours and then at 102° C. (bath) in a seal tube for 2 days. After cooling to ambient temperature, solvent was removed under reduced pressure. Saturated aqueous sodium bicarbonate (20 mL) and ethyl acetate (20 mL) were added. The organic layer was separated, washed with brine, dried (sodium sulfate), filtered and concentrated under reduced pressure to give 2-[2-[hydroxy(diphenyl)methyl]-6-methyl-benzimidazol-1-yl]acetaldehyde (0.58 g, 99%) as oil.

Step C: Preparation of 2-[2-[hydroxy(diphenyl)methyl]-6-methyl-benzimidazol-1-yl]ethanol: To a solution of 2-[2-

[hydroxy(diphenyl)methyl]-6-methyl-benzimidazol-1-yl] acetaldehyde (0.58 g, 1.63 mmol) in methanol (10 mL) was added sodium borohydride (0.31 g, 8.1 mmol). The reaction mixture was stirred at ambient temperature for 24 hours. Solvent was removed under reduced pressure. Saturated aqueous sodium bicarbonate (20 mL) and ethyl acetate (20 mL) were added. The organic layer was separated, washed with brine, dried (sodium sulfate), filtered and concentrated under reduced pressure to give 2-[2-[hydroxy(diphenyl) methyl]-6-methyl-benzimidazol-1-yl]ethanol (0.57 g, 97%) as oil.

Step D: Preparation of [1-[2-[tert-butyl(dimethyl)silyl] oxyethyl]-6-methyl-benzimidazol-2-yl]-diphenyl-methanol: A solution of 2-[2-[hydroxy(diphenyl)methyl]-6-methyl-benzimidazol-1-yl]ethanol (0.3 g, 0.84 mmol), imidazole (0.17 g, 2.51 mmol) and tert-butyldimethylsilyl chloride (0.19 g, 1.26 mmol) in DMF (2 mL) was stirred at ambient temperature for 18 hours. Water (10 mL) and MTBE (20 mL) were added. The organic layer were separated, washed with brine, dried (sodium sulfate), filtered and concentrated to give [1-[2-[tert-butyl(dimethyl)silyl]oxyethyl]-6-methyl-benzimidazol-2-yl]-diphenyl-methanol (0.39 g, 99%) as oil.

Step E: Preparation of 3-[2-[tert-butyl(dimethyl)silyl] oxyethyl]-2-[hydroxy(diphenyl)methyl]benzimidazole-5-carboxylic acid: A solution of [1-[2-[tert-butyl(dimethyl) silyl]oxyethyl]-6-methyl-benzimidazol-2-yl]-diphenyl-methanol (0.39 g, 0.83 mmol) and potassium permanganate (0.52 g, 3.3 mmol) in tert-butanol (5 mL) and water (5 mL) was stirred at reflux for 5 hours. After cooling to ambient temperature, the reaction mixture was filtered through a pad of celite and washed with water (10 mL). Hexane/MTBE (1:1, 20 mL) was added to the filtrate. The aqueous layer was separated, acidified with saturated potassium hydrogen sulfate to pH~4 and extracted with ethyl acetate (20 mL). The organic layer was separated, washed with brine, dried (sodium sulfate), filtered and concentrated to give 3-[2-[tert-butyl(dimethyl)silyl]oxyethyl]-2-[hydroxy(diphenyl) methyl]benzimidazole-5-carboxylic acid (0.40 g, 96%) as solid.

Step F: Preparation of 3-[2-[tert-butyl(dimethyl)silyl] oxyethyl]-2-[hydroxy(diphenyl)methyl]-N-[(2R)-2-hydroxypropyl]benzimidazole-5-carboxamide: To a solution of 3-[2-[tert-butyl(dimethyl)silyl]oxyethyl]-2-[hydroxy(diphenyl)methyl]benzimidazole-5-carboxylic acid (0.2 g, 0.40 mmol), (R)-isopropanolamine (0.04 g, 0.48 mmol) and N,N-diisopropylethylamine (0.21 mL, 1.19 mmol) in DMF (1 mL) was added HATU (0.23 g, 0.60 mmol). The reaction mixture was stirred at ambient temperature for 10 minutes and then directly purified by C18 reverse phase flash chromatography (Biotage Isolera One unit, C18 Flash 25+M column, 10-100% CH3CN/water, 15 CV) to give 3-[2-[tert-butyl(dimethyl)silyl]oxyethyl]-2-[hydroxy(diphenyl) methyl]-N-[(2R)-2-hydroxypropyl]benzimidazole-5-carboxamide (0.11 g, 49%) as solid.

Step G: Preparation of 2-[hydroxy(diphenyl)methyl]-3-(2-hydroxyethyl)-N-[(2R)-2-hydroxypropyl]benzimidazole-5-carboxamide: To a solution of 3-[2-[tert-butyl(dimethyl) silyl]oxyethyl]-2-[hydroxy(diphenyl)methyl]-N-[(2R)-2-hydroxypropyl]benzimidazole-5-carboxamide (0.11 g, 0.20 mmol) in THF was added tetrabutyl ammonium fluoride (1.0 M, 0.29 mL, 0.29 mmol). The reaction mixture was stirred at ambient temperature for 30 minutes and then directly purified by C18 reverse phase flash chromatography (Biotage Isolera One unit, C18 Flash 25+M column, 10-100% CH3CN/water, 15 CV) to give 2-[hydroxy(diphenyl) methyl]-3-(2-hydroxyethyl)-N-[(2R)-2-hydroxypropyl]benzimidazole-5-carboxamide (0.074 g, 84%) as solid. LCMS ESI (+) m/z 446 (M+H).

Example 49: Synthesis of N-(2-acetamidoethyl)-1-ethyl-2-(hydroxydiphenylmethyl)-1H-benzo[d]imidazole-6-carboxamide (Compound 211)

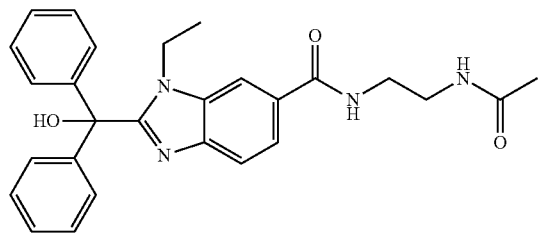 [SMILES: CCn1c(C(O)(c2ccccc2)c2ccccc2)nc2ccc(C(=O)NCCNC(C)=O)cc21]

To a solution of N-(2-aminoethyl)-3-ethyl-2-[hydroxy(diphenyl)methyl]benzimidazole-5-carboxamide (0.02 g, 0.04 mmol), N,N-diisopropylethylamine (0.02 mL, 0.11 mmol) and HATU (0.02 g, 0.05 mmol) in DMF (5 mL) was added acetic acid (0.01 g, 0.20 mmol). The reaction mixture was stirred at ambient temperature for 18 hours and then directly purified by C18 reverse phase flash chromatography (Biotage Isolera One unit, C18 Flash 25+M column, 0-100% CH₃CN/water, 15 CV) to give N-(2-acetamidoethyl)-3-ethyl-2-[hydroxy(diphenyl)methyl]benzimidazole-5-carboxamide (0.011 g, 67%) as solid. LCMS ESI (+) m/z 457 (M+H).

Example 50: Synthesis of (R)-2-(hydroxydiphenyl-methyl)-N-(2-hydroxypropyl)-1-phenyl-1H-benzo[d] imidazole-6-carboxamide (Compound 217)

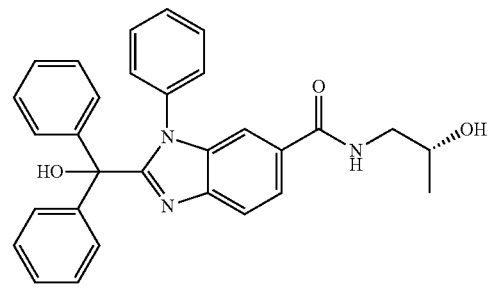 [SMILES: C[C@@H](O)CNC(=O)c1ccc2nc(C(O)(c3ccccc3)c3ccccc3)n(-c3ccccc3)c2c1]

Step A: Preparation of 5-methyl-2-nitro-N-phenylaniline: To a solution of aniline (0.72 g, 7.8 mmol) in THF (10 mL) was added 1.0 M LHMDS (7.74 mL, 7.74 mmol) at 0° C. The reaction mixture was stirred at 0° C. for 20 minutes. 2-Fluoro-4-methyl-1-nitrobenzene (1.0 g, 6.45 mmol) was added. The reaction mixture was warmed to ambient temperature and stirred at ambient temperature for 2 hours. Saturated aqueous ammonium chloride solution and ethyl acetate were added. The organic layer was separated, washed with brine, dried (sodium sulfate), filtered and concentrated. The residue was purified by flash chromatography on silica gel to give 5-methyl-2-nitro-N-phenylaniline (0.88 g, 60%) as solid.

Step B: Preparation of 5-methyl-N¹-phenylbenzene-1,2-diamine: A mixture of 5-methyl-2-nitro-N-phenylaniline (0.88 g, 3.86 mmol) and Raney Nickel (0.5 g) in THF was stirred under 1 atmosphere of hydrogen at ambient temperature for 2 hours. The catalyst was removed by filtration and washed with THF. The filtrate was concentrated under reduced pressure to give 5-methyl-N[1]-phenylbenzene-1,2-diamine (0.65 g, 85%) as oil.

Step C: Preparation of 6-methyl-1-phenyl-1H-benzo[d]imidazole: A solution of 5-methyl-N[1]-phenylbenzene-1,2-diamine (0.65 g, 3.28 mmol) and trimethyl orthoformate (0.52 g, 4.92 mmol) in DMF (20 mL) was stirred at 120° C. overnight. Water and ethyl acetate were added. The organic layer was separated, washed with brine, dried (sodium sulfate), filtered and concentrated under reduced pressure. The residue obtained was purified by flash chromatography on silica gel with 2:1 hexane/ethyl acetate to give 6-methyl-1-phenyl-1H-benzo[d]imidazole (0.48 g, 71%) as solid.

Step D: Preparation of 2-(hydroxydiphenylmethyl)-1-phenyl-1H-benzo[d]imidazole-6-carboxylic acid: Prepared similarly as Example 3 substituting 1,6-dimethylbenzimidazole with 6-methyl-1-phenyl-1H-benzo[d]imidazole in Step C.

Step E: Preparation of (R)-2-(hydroxydiphenylmethyl)-N-(2-hydroxypropyl)-1-phenyl-1H-benzo[d]imidazole-6-carboxamide: Prepared similarly as Example 17 substituting 1-ethyl-2-(hydroxydiphenylmethyl)-1H-benzo[d]imidazole-6-carboxylic acid and ethyl amine with 2-(hydroxydiphenylmethyl)-1-phenyl-1H-benzo[d]imidazole-6-carboxylic acid and (R)-1-aminopropan-2-ol. LCMS ESI (+) m/z 478 (M+H).

Example 51: Synthesis of 2-(hydroxydiphenylmethyl)-1-(2-hydroxyethyl)-1H-benzo[d]imidazole-6-sulfonamide (Compound 224)

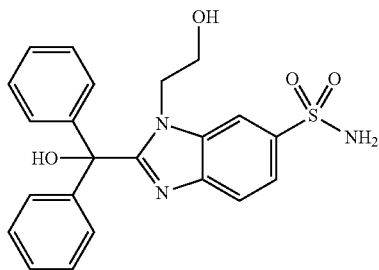 [SMILES: NS(=O)(=O)c1ccc2nc(C(O)(c3ccccc3)c3ccccc3)n(CCO)c2c1]

Step A: Preparation of 2-(6-bromo-1H-benzo[d]imidazol-1-yl)ethan-1-ol: Prepared similarly as Example 1 substituting 2,4-difluoro-1-nitrobenzene and ethyl amine with 4-bromo-2-fluoro-1-nitrobenzene and 2-amino-ethan-1-ol in Step A.

Step B: Preparation of 2-(6-bromo-2-(hydroxydiphenylmethyl)-1H-benzo[d]imidazol-1-yl)ethan-1-ol: Prepared similarly as Example 3 substituting 1,6-dimethylbenzimidazole with 2-(6-bromo-1H-benzo[d]imidazol-1-yl)ethan-1-ol in Step C.

Step C: Preparation of 2-(6-((diphenylmethylene)amino)-2-(hydroxydiphenylmethyl)-1H-benzo[d]imidazol-1-yl)ethan-1-ol: A mixture of 2-(6-bromo-2-(hydroxydiphenylmethyl)-1H-benzo[d]imidazol-1-yl)ethan-1-ol (1.0 g, 2.4 mmol), diphenylmethanimine (0.66 g, 3.6 mmol), palladium acetate (0.054 g, 0.24 mmol), BINAP (0.24 g, 0.36 mmol) and potassium tert-butyloxide (0.54 g, 4.8 mmol) was stirred at 100° C. for 1 hour. After cooling to ambient temperature, solid was removed by filtration. The filtrate was concentrated under reduced pressure. The residue obtained was purified by flash chromatography on silica gel to give 2-(6-((diphenylmethylene)amino)-2-(hydroxydiphenylmethyl)-1H-benzo[d]imidazol-1-yl)ethan-1-ol (0.70 g, 56%) as solid.

Step D: Preparation of 2-(6-amino-2-(hydroxydiphenylmethyl)-1H-benzo[d]imidazol-1-yl)ethan-1-ol: To a solution of 2-(6-((diphenylmethylene)amino)-2-(hydroxydiphenylmethyl)-1H-benzo[d]imidazol-1-yl)ethan-1-ol (0.70 g, 1.34 mmol) in THF (20 mL) was added 2.0 M HCl in water (10 mL) at ambient temperature. The reaction mixture was stirred at ambient temperature for 1 hour. Ammonium hydroxide (5 mL) and ethyl acetate (20 mL) were added. The organic layer was separated, washed with brine, dried (sodium sulfate), filtered and concentrated under reduced pressure. The residue was purified by flash chromatography on silica gel to give 2-(6-amino-2-(hydroxydiphenylmethyl)-1H-benzo[d]imidazol-1-yl)ethan-1-ol (0.40 g, 83%) as solid.

Step E: Preparation of 2-(hydroxydiphenylmethyl)-1-(2-hydroxyethyl)-1H-benzo[d]imidazole-6-sulfonamide: Prepared similarly as Example 41 substituting (6-amino-1-ethyl-1H-benzo[d]imidazol-2-yl)diphenylmethanol with 2-(6-amino-2-(hydroxydiphenylmethyl)-1H-benzo[d]imidazol-1-yl)ethan-1-ol in Step C. LCMS ESI (+) m/z 424 (M+H).

Example 52: Synthesis of (R)-2-(hydroxydiphenylmethyl)-N-(2-hydroxypropyl)-1-(piperidin-4-yl)-1H-benzo[d]imidazole-6-carboxamide (Compound 227)

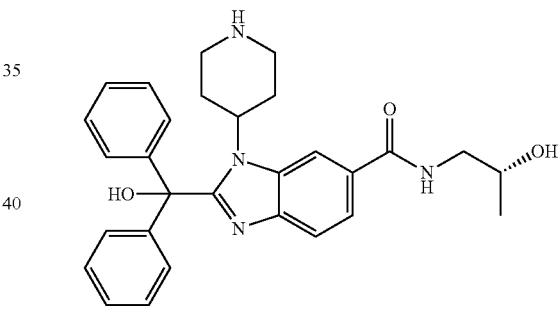

Step A: Preparation of 1-(1-(tert-butoxycarbonyl)piperidin-4-yl)-2-(hydroxydiphenylmethyl)-1H-benzo[d]imidazole-6-carboxylic acid: Prepared similarly as Example 5 substituting ethyl amine with tert-butyl 4-aminopiperidine-1-carboxylate in Step A and bis(2-fluorophenyl)methanone with benzophenone in Step C.

Step B: Preparation of tert-butyl (R)-4-(2-(hydroxydiphenylmethyl)-6-((2-hydroxypropyl)carbamoyl)-1H-benzo[d]imidazol-1-yl)piperidine-1-carboxylate: Prepared similarly as Example 17 substituting 1-ethyl-2-(hydroxydiphenylmethyl)-1H-benzo[d]imidazole-6-carboxylic acid and ethyl amine with 1-(1-(tert-butoxycarbonyl)piperidin-4-yl)-2-(hydroxydiphenylmethyl)-1H-benzo[d]imidazole-6-carboxylic acid and (R)-1-aminopropan-2-ol.

Step C: Preparation of (R)-2-(hydroxydiphenylmethyl)-N-(2-hydroxypropyl)-1-(piperidin-4-yl)-1H-benzo[d]imidazole-6-carboxamide: To a solution of tert-butyl (R)-4-(2-(hydroxydiphenylmethyl)-6-((2-hydroxypropyl)carbamoyl)-1H-benzo[d]imidazol-1-yl)piperidine-1-carboxylate (0.077 g, 0.13 mmol) in DCM (20 mL) was added TFA (10 mL) at ambient temperature. The mixture was stirred at ambient temperature for 2 hours. Solvent was removed under reduced pressure. Saturated aqueous sodium bicarbonate and DCM were added. The organic layer was separated, washed with brine, dried (sodium sulfate), filtered and concentrated. The residue was purified by flash chromatography on silica gel with 10:1 DCM/MeOH to give (R)-2-(hydroxydiphenylmethyl)-N-(2-hydroxypropyl)-1-(piperidin-4-yl)-1H-benzo[d]imidazole-6-carboxamide (0.050 g, 80%) as solid. LCMS ESI (+) m/z 485 (M+H).

Example 53: Synthesis of (S)—N-(2,3-dihydroxypropyl)-1-ethyl-2-(hydroxydiphenylmethyl)-1H-benzo[d]imidazole-6-carboxamide (Compound 237)

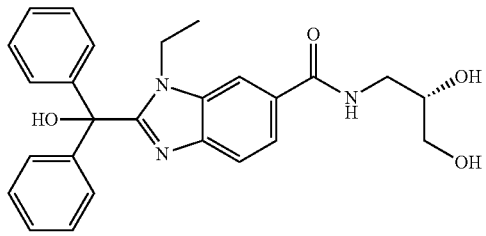 [SMILES: CCn1c(C(O)(c2ccccc2)c2ccccc2)nc2ccc(C(=O)NC[C@H](O)CO)cc21]

To a solution of 3-ethyl-2-[hydroxy(diphenyl)methyl] benzimidazole-5-carboxylic acid (0.1 g, 0.27 mmol), (2S)-3-aminopropane-1,2-diol (0.04 g, 0.40 mmol) and N,N-diisopropylethylamine (0.09 mL, 0.54 mmol) in DMF (1 mL) was added HATU (0.15 g, 0.40 mmol). The reaction mixture was stirred at ambient temperature for 30 minutes and then directly purified by C18 reverse phase flash chromatography (Biotage Isolera One unit, C18 Flash 25+M column, 0-80% CH₃CN/water, 15 CV) to give N-[(2S)-2,3-dihydroxypropyl]-3-ethyl-2-[hydroxy(diphenyl)methyl] benzimidazole-5-carboxamide (0.11 g, 92%) as solid. LCMS ESI (+) m/z 446 (M+H).

Example 54: Synthesis of 1-ethyl-N-(1-ethyl-1H-pyrazol-3-yl)-2-(hydroxydiphenylmethyl)-1H-benzo[d]imidazole-6-carboxamide (Compound 238)

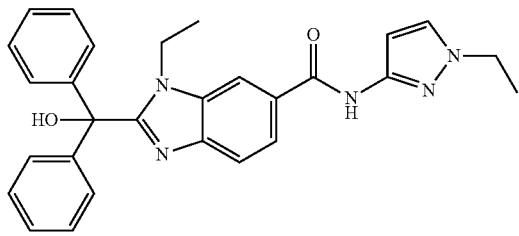

To a solution of 3-ethyl-2-[hydroxy(diphenyl)methyl] benzimidazole-5-carboxylic acid (0.1 g, 0.27 mmol), 1-ethyl-1H-pyrazol-3-amine (0.04 g, 0.40 mmol) and N,N-diisopropylethylamine (0.09 mL, 0.54 mmol) in DMF (1 mL) was added HATU (0.15 g, 0.40 mmol). The reaction mixture was stirred at ambient temperature overnight and directly purified by C18 reverse phase flash chromatography (Biotage Isolera One unit, C18 Flash 25+M column, 0-80% CH₃CN/water, 15 CV) to give 1-ethyl-N-(1-ethyl-1H-pyrazol-3-yl)-2-(hydroxydiphenylmethyl)-1H-benzo[d]imidazole-6-carboxamide (0.11 g, 92%) as solid. LCMS ESI (+) m/z 466 (M+H).

Example 55: Synthesis of 2-(bis(2-fluorophenyl)(hydroxy)methyl)-N-(1-ethyl-1H-pyrazol-3-yl)-1-methyl-1H-benzo[d]imidazole-6-carboxamide (Compound 239)

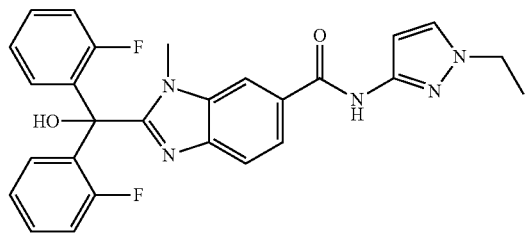 [SMILES: CCn1ccc(NC(=O)c2ccc3nc(C(O)(c4ccccc4F)c4ccccc4F)n(C)c3c2)n1]

To a solution of 2-[bis(2-fluorophenyl)-hydroxy-methyl]-3-methyl-benzimidazole-5-carboxylic acid (0.11 g, 0.28 mmol), 1-ethylpyrazol-3-amine (0.05 g, 0.42 mmol) and N,N-diisopropylethylamine (0.1 mL, 0.56 mmol) in DMF (1 mL) was added HATU (0.16 g, 0.42 mmol). The reaction mixture was stirred at ambient temperature overnight and then directly purified by C18 reverse phase flash chromatography (Biotage Isolera One unit, C18 Flash 25+M column, 0-80% CH₃CN/water, 15 CV) to give Compound 239 (0.060 g, 44%) as solid. LCMS ESI (+) m/z 466 (M+H).

Example 56: Synthesis of N-(1-ethyl-1H-pyrazol-3-yl)-2-(hydroxydiphenylmethyl)-1-(2-hydroxyethyl)-1H-benzo[d]imidazole-6-carboxamide (Compound 240)

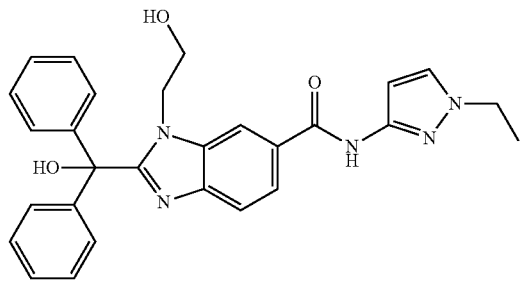 [SMILES: CCn1ccc(NC(=O)c2ccc3nc(C(O)(c4ccccc4)c4ccccc4)n(CCO)c3c2)n1]

Step A: Preparation of methyl 3-((2-hydroxyethyl)amino)-4-nitrobenzoate: A solution of methyl 3-fluoro-4-nitro-benzoate (3.3 g, 16.6 mmol) and triethylamine (3.0 mL, 21.5 mmol) in NMP (20 mL) was added ethanolamine (1.91 g, 21.5 mmol). The reaction mixture was stirred at ambient temperature for 18 hours. Water (100 mL) was added and the mixture was stirred at ambient temperature for 30 minutes. Methyl 3-(2-hydroxyethylamino)-4-nitro-benzoate was obtained as solid by filtration, washing with water and drying under vacuum (3.95 g, 99%).

Step B: Preparation of methyl 1-(2-hydroxyethyl)-1H-benzo[d]imidazole-6-carboxylate: A solution of methyl 3-(2-hydroxyethylamino)-4-nitro-benzoate (3.95 g, 16.4 mmol), trimethyl orthoformate (18.0 mL, 164 mmol), 10% palladium on carbon (0.44 g, 0.41 mmol) and p-toluenesulfonic acid monohydrate (0.16 g, 0.82 mmol) in methanol (30 mL) was charged with 1 atmosphere of hydrogen and stirred at ambient temperature for 5 hours. Catalyst was removed by filtration and washed with methanol (30 mL). The filtrate was concentrated under reduced pressure. The residue was added to saturated aqueous sodium bicarbonate (20 mL) and 4:1 DCM/isopropyl alcohol (100 mL). The organic layer was separated, washed with brine, dried (sodium sulfate), filtered and concentrated under reduced pressure. The residue was suspended in 5:1 hexane/ethyl acetate (60 mL) and stirred at ambient temperature for 30 minutes. Solid was collected by filtration to give methyl 3-(2-hydroxyethyl) benzimidazole-5-carboxylate (3.3 g, 91%) as solid.

Step C: Preparation of methyl 2-(hydroxydiphenylmethyl)-1-(2-hydroxyethyl)-1H-benzo[d]imidazole-6-carboxylate: To a solution of benzophenone (4.1 g, 22.5 mmol) and methyl 3-(2-hydroxyethyl)benzimidazole-5-carboxylate (3.3 g, 15.0 mmol) in THF (50 mL) was added 1.0 M lithium bis(trimethylsilyl)amide (34.5 mL, 34.5 mmol) at 0° C. After the addition, the reaction mixture was slowly warmed to ambient temperature and stirred at ambient temperature for 1 hour. Saturated aqueous ammonium chloride (20 mL) and ethyl acetate (50 mL) were added. The organic layer was separated, washed with brine, dried (sodium sulfate), filtered and concentrated under reduced pressure. The residue was purified by flash chromatography on silica gel with 2:1 hexane/ethyl acetate to give methyl 2-[hydroxy(diphenyl)methyl]-3-(2-hydroxyethyl)benzimidazole-5-carboxylate (3.03 g, 50%) as solid.

Step D: Preparation of N-(1-ethyl-1H-pyrazol-3-yl)-2-(hydroxydiphenylmethyl)-1-(2-hydroxyethyl)-1H-benzo[d]imidazole-6-carboxamide: A solution of methyl 2-[hydroxy(diphenyl)methyl]-3-(2-hydroxyethyl)benzimidazole-5-carboxylate (2.89 g, 7.2 mmol) and lithium hydroxide monohydrate (0.9 g, 21.5 mmol) in 2:1 THF/H2O (30 mL) was stirred at ambient temperature overnight. MTBE (40 ml) was added. The aqueous layer was separated and acidified with potassium hydrogen sulfate to pH~3-4. 2-[Hydroxy(diphenyl)methyl]-3-(2-hydroxyethyl)benzimidazole-5-carboxylic acid (2.6 g, 93%) was obtained as solid by filtration, washing with water and dried under vacuum.

Step E: Preparation of N-(1-ethyl-1H-pyrazol-3-yl)-2-(hydroxydiphenylmethyl)-1-(2-hydroxyethyl)-1H-benzo[d]imidazole-6-carboxamide: To a solution of 2-[hydroxy(diphenyl)methyl]-3-(2-hydroxyethyl)benzimidazole-5-carboxylic acid (0.1 g, 0.24 mmol), 1-ethylpyrazol-3-amine (0.04 g, 0.37 mmol) and DIEA (0.09 mL, 0.49 mmol) in DMF (1 mL) was added HATU (0.14 g, 0.37 mmol) at ambient temperature. The reaction mixture was stirred at ambient temperature overnight. It was directly purified by C18 reverse phase flash chromatography (Biotage Isolera One unit, C18 Flash 25+M column, 0-80% CH3CN/water, 15 CV) to give Compound 240 (0.09 g, 76%) as solid. LCMS ESI (+) m/z 482 (M+H).

Example 57: Synthesis of 2-(bis(2-fluorophenyl)(hydroxy)methyl)-1-ethyl-N-(1-ethyl-1H-pyrazol-3-yl)-1H-benzo[d]imidazole-6-carboxamide (Compound 261)

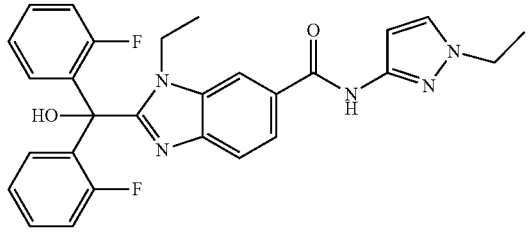 [SMILES: CCn1ccc(NC(=O)c2ccc3nc(C(O)(c4ccccc4F)c4ccccc4F)n(CC)c3c2)n1]

To a solution of 2-[bis(2-fluorophenyl)-hydroxy-methyl]-3-ethyl-benzimidazole-5-carboxylic acid (0.10 g, 0.24 mmol), 1-ethylpyrazol-3-amine (0.040 g, 0.37 mmol) and DIEA (0.090 mL, 0.49 mmol) in DMF (1 mL) was added HATU (0.14 g, 0.37 mmol) at ambient temperature. The reaction mixture was stirred at ambient temperature for 2 hours and then directly purified by C18 reverse phase flash chromatography (Biotage Isolera One unit, C18 Flash 25+M column, 0-80% CH3CN/water, 15 CV) to give 2-[bis(2-fluorophenyl)-hydroxy-methyl]-3-ethyl-N-(1-ethylpyrazol-3-yl)benzimidazole-5-carboxamide (0.081 g, 66%) as solid. LCMS ESI (+) m/z 502 (M+H). $^1$HNMR (400 MHz, CDCl$_3$): δ 8.51 (s, 1H), 8.03 (s, 1H), 7.79 (d, 1H), 7.70 (d, 1H), 7.37 (m, 2H), 7.26 (s, 1H), 7.14 (m, 4H), 7.03 (m, 2H), 6.83 (s, 1H), 4.63 (t, 1H), 4.23 (q, 2H), 4.05 (q, 2H), 1.47 (t, 3H), 1.10 (t, 3H).

Example 58: Synthesis of 2-(bis(4-fluorophenyl)(hydroxy)methyl)-1-ethyl-N-(1-ethyl-1H-pyrazol-3-yl)-1H-benzo[d]imidazole-6-carboxamide (Compound 262)

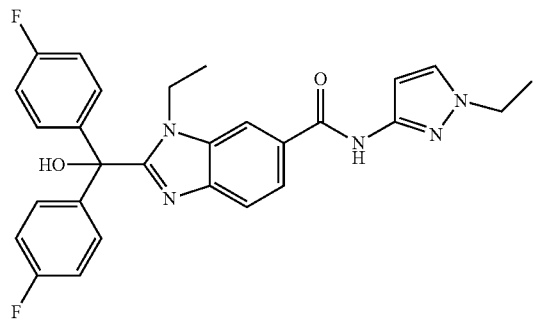 [SMILES: CCn1ccc(NC(=O)c2ccc3nc(C(O)(c4ccc(F)cc4)c4ccc(F)cc4)n(CC)c3c2)n1]

To a solution of 2-[bis(4-fluorophenyl)-hydroxy-methyl]-3-ethyl-benzimidazole-5-carboxylic acid (0.10 g, 0.24 mmol), 1-ethylpyrazol-3-amine (0.040 g, 0.37 mmol) and DIEA (0.090 mL, 0.49 mmol) in DMF (1 mL) was added HATU (0.14 g, 0.37 mmol) at ambient temperature. The reaction mixture was stirred at ambient temperature for 30 minutes and then directly purified by C18 reverse phase flash chromatography (Biotage Isolera One unit, C18 Flash 25+M column, 0-80% CH$_3$CN/water, 15 CV) to give 2-[bis(4-fluorophenyl)-hydroxy-methyl]-3-ethyl-N-(1-ethylpyrazol-3-yl)benzimidazole-5-carboxamide (0.082 g, 66%) as solid. LCMS ESI (+) m/z 502 (M+H). $^1$HNMR (400 MHz, CDCl$_3$): δ 8.51 (s, 1H), 8.02 (s, 1H), 7.84 (d, 1H), 7.77 (d, 1H), 7.28 (m, 5H), 7.06 (m, 4H), 6.80 (s, 1H), 4.65 (s, 1H), 4.08 (m, 4H), 1.47 (t, 3H), 0.88 (t, 3H).

Example 59: Synthesis of N-(1-ethyl-1H-pyrazol-3-yl)-1-(2-fluoroethyl)-2-(hydroxydiphenylmethyl)-1H-benzo[d]imidazole-6-carboxamide (Compound 264)

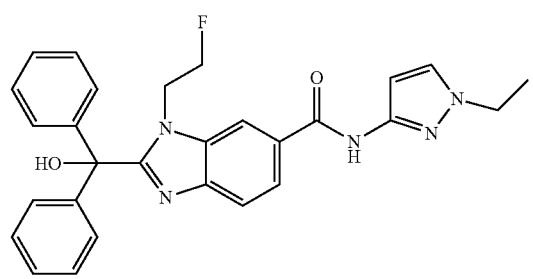 [SMILES: CCn1ccc(NC(=O)c2ccc3nc(C(O)(c4ccccc4)c4ccccc4)n(CCF)c3c2)n1]

To a solution of 3-(2-fluoroethyl)-2-[hydroxy(diphenyl) methyl]benzimidazole-5-carboxylic acid (0.060 g, 0.15 mmol), 1-ethylpyrazol-3-amine (0.020 g, 0.18 mmol) and DIEA (0.050 mL, 0.31 mmol) in DMF (1 mL) was added HATU (0.070 g, 0.19 mmol) at ambient temperature. The reaction mixture was stirred at ambient temperature overnight and then directly purified by C18 reverse phase flash chromatography (Biotage Isolera One unit, C18 Flash 25+M column, 0-80% CH$_3$CN/water, 15 CV) to give N-(1-ethyl-pyrazol-3-yl)-3-(2-fluoroethyl)-2-[hydroxy(diphenyl) methyl]benzimidazole-5-carboxamide (0.035 g, 47%) as solid. LCMS ESI (+) m/z 484 (M+H). $^1$HNMR (400 MHz, CDCl$_3$): δ 8.50 (s, 1H), 8.06 (s, 1H), 7.83 (d, 1H), 7.77 (d, 1H), 7.35 (m, 5H), 7.28 (m, 5H), 6.82 (s, 1H), 4.42 (m, 1H), 4.37 (m, 1H), 4.21 (m, 1H), 4.16 (m, 1H), 4.08 (m, 3H), 1.46 (t, 3H).

Example 60: Synthesis of 1-ethyl-N-(2-ethyl-2H-1,2,3-triazol-4-yl)-2-(hydroxydiphenylmethyl)-1H-benzo[d]imidazole-6-carboxamide (Compound 269)

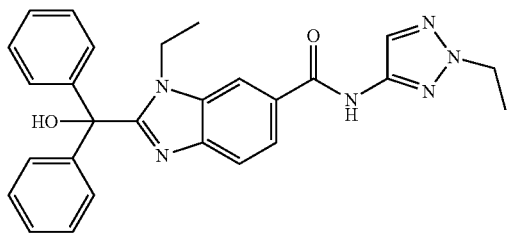 [SMILES: CCn1ncc(NC(=O)c2ccc3nc(C(O)(c4ccccc4)c4ccccc4)n(CC)c3c2)n1]

To a solution of 3-ethyl-2-[hydroxy(diphenyl)methyl] benzimidazole-5-carboxylic acid (0.060 g, 0.16 mmol), 2-ethyl triazol-4-amine hydrochloride (0.040 g, 0.24 mmol) and DIEA (0.050 mL, 0.31 mmol) in DMF (1 mL) was added HATU (0.090 g, 0.24 mmol) at ambient temperature. The reaction mixture was stirred at ambient temperature for 24 hours and then directly purified by C18 reverse phase flash chromatography (Biotage Isolera One unit, C18 Flash 25+M column, 10-100% CH$_3$CN/water, 15 CV) to give Compound 269 (0.052 g, 69%) as solid. LCMS ESI (+) m/z 467 (M+H). $^1$HNMR (400 MHz, CDCl$_3$): δ 8.58 (s, 1H), 8.15 (s, 1H), 8.02 (s, 1H), 7.83 (d, 1H), 7.71 (d, 1H), 7.31-7.37 (m, 10H), 4.79 (s, 1H), 4.40 (q, 2H), 4.12 (q, 2H), 1.47 (t, 3H), 0.8 (t, 3H).

Example 61: Synthesis of 1-ethyl-2-(hydroxydiphenylmethyl)-N-(4-methyl-1H-imidazol-2-yl)-1H-benzo[d]imidazole-6-carboxamide (Compound 281)

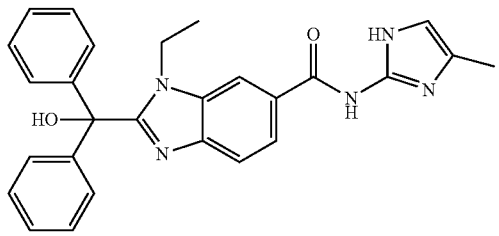 [SMILES: CCn1c(C(O)(c2ccccc2)c2ccccc2)nc2ccc(C(=O)Nc3nc(C)c[nH]3)cc21]

1-Ethyl-2-(hydroxydiphenylmethyl)-1H-benzo[d]imidazole-6-carboxylic acid (0.19 g, 0.5 mmol), 4-methyl-1H-imidazol-2-amine (0.048 g, 0.5 mmol) and HATU (038 g, 1 mmol) in DMF (10 mL) was treated with potassium tert-butyl oxide (0.28 g, 2.5 mmol) at ambient temperature. The reaction mixture was stirred at ambient temperature for 30 minutes and then poured into 50 mL of 10% sodium hydroxide solution. Solid was collected by filtration and purified by flash chromatography on silica gel to give 1-ethyl-2-(hydroxydiphenylmethyl)-N-(4-methyl-1H-imidazol-2-yl)-1H-benzo[d]imidazole-6-carboxamide (0.025 g, 11%). LCMS ESI (+) m/z 452 (M+H).

Example 62: Synthesis of (1-ethyl-6-(1-ethyl-1H-pyrazol-4-yl)-1H-benzo[d]imidazol-2-yl)diphenyl-methanol (Compound 282)

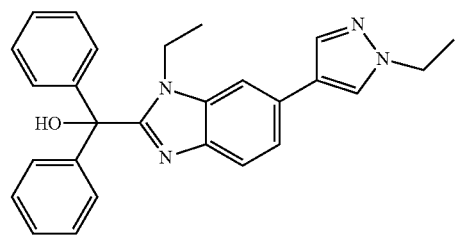 [SMILES: CCn1cc(-c2ccc3nc(C(O)(c4ccccc4)c4ccccc4)n(CC)c3c2)cn1]

A solution of (6-bromo-1-ethyl-1H-benzo[d]imidazol-2-yl)diphenylmethanol (0.29 g, 0.71 mmol), 1-ethyl-1H-pyrazol-4-yl)boronic acid (0.10 g, 0.71 mmol), tetrakis(triphenylphosphine)palladium (0) (0.08 g, 0.071 mmol) and cesium carbonate (0.46 g, 1.42 mmol) in 1,4-dioxane(20 mL) and water (5 mL) was stirred at 100° C. for 10 hours. After cooling to ambient temperature, ethyl acetate and water were added. The organic layer was separated, washed with brine, dried (sodium sulfate), filtered and concentrated under reduced pressure. The residue was purified by flash chromatography on silica gel to give (1-ethyl-6-(1-ethyl-1H-pyrazol-4-yl)-1H-benzo[d]imidazol-2-yl)diphenylmethanol (0.06 g, 32%) as solid. LCMS ESI (+) m/z 423 (M+H).

Example 63: Synthesis of (1-ethyl-6-(1-ethyl-1H-pyrazol-4-yl)-5-fluoro-1H-benzo[d]imidazol-2-yl) diphenylmethanol (Compound 283)

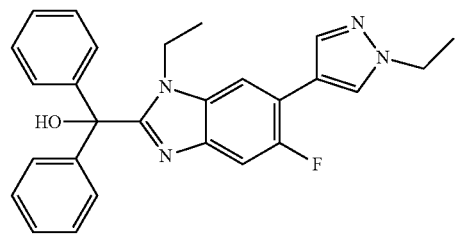 [SMILES: CCn1cc(-c2cc3c(cc2F)nc(C(O)(c2ccccc2)c2ccccc2)n3CC)cn1]

A solution of (6-bromo-1-ethyl-5-fluoro-1H-benzo[d]imidazol-2-yl)diphenylmethanol (0.21 g, 0.50 mmol), 4,4,4',4',5,5,5',5'-octamethyl-2,2'-bi(1,3,2-dioxaborolane) (0.25 g, 1.0 mmol), 1,1'-bis(diphenylphosphino)ferrocenepalladium (II) dichloride (0.035 g, 0.050 mmol) and potassium acetate (0.098 g, 1.0 mmol) in dioxane (10 mL) was stirred at reflux for 5 hours. After cooling to ambient temperature, 4-bromo-1-ethyl-1H-pyrazole (0.088 g, 0.5 mmol), tetrakis(triphenylphosphine)palladium (O) (0.055 g, 0.05 mmol), cesium carbonate (0.33 g, 1.0 mmol) and water (3 mL) were added. The reaction mixture was stirred at 100° C. for 12 hours.

After cooling to ambient temperature, ethyl acetate and water were added. The organic layer was separated, washed with brine, dried (sodium sulfate), filtered and concentrated under reduced pressure. The residue was purified by flash chromatography on silica gel to give (1-ethyl-6-(1-ethyl-1H-pyrazol-4-yl)-5-fluoro-1H-benzo[d]imidazol-2-yl)diphenylmethanol (0.10 g, 45%) as solid. LCMS ESI (+) m/z 441 (M+H).

Example 64: Synthesis of 1-ethyl-N-(1-ethyl-1H-1,2,4-triazol-3-yl)-2-(hydroxydiphenylmethyl)-1H-benzo[d]imidazole-6-carboxamide (Compound 284)

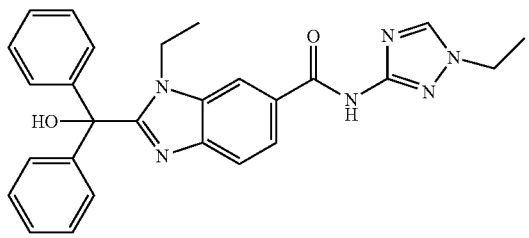 [SMILES: CCn1cnc(NC(=O)c2ccc3nc(C(O)(c4ccccc4)c4ccccc4)n(CC)c3c2)n1]

To a solution of 3-ethyl-2-[hydroxy(diphenyl)methyl]benzimidazole-5-carboxylic acid (0.07 g, 0.19 mmol), 1-ethyl-1,2,4-triazol-3-amine hydrochloride (0.04 g, 0.24 mmol) and DIEA (0.050 mL, 0.31 mmol) in DMF (1 mL) was added HATU (0.090 g, 0.23 mmol) at ambient temperature. The reaction mixture was stirred at ambient temperature for 2 hours and heated to 66° C. (bath) for 18 hours. After cooling to ambient temperature, the reaction mixture was directly purified by C18 reverse phase flash chromatography (Biotage Isolera One unit, C18 Flash 25+M column, 10-90% CH₃CN/water, 15 CV) to give 1-ethyl-N-(1-ethyl-1H-1,2,4-triazol-3-yl)-2-(hydroxydiphenylmethyl)-1H-benzo[d]imidazole-6-carboxamide (0.038 g, 43%) as solid. LCMS ESI (+) m/z 467 (M+H). ¹HNMR (400 MHz, CDCl₃): δ 8.59 (s, 1H), 8.04 (s, 1H), 7.90 (s, 1H), 7.83 (d, 1H), 7.78 (d, 1H), 7.31-7.39 (m, 10H), 4.85 (s, 1H), 4.68 (q, 2H), 4.10 (q, 2H), 1.58 (t, 3H), 0.78 (t, 3H).

Example 65: Synthesis of 1-ethyl-N-(2-ethyl-2H-tetrazol-5-yl)-2-(hydroxydiphenylmethyl)-1H-benzo[d]imidazole-6-carboxamide (Compound 285)

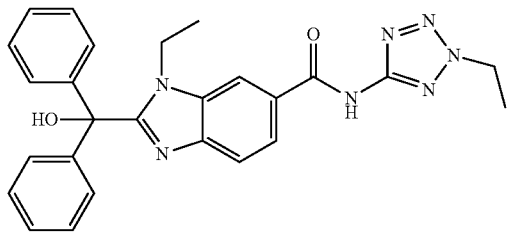

Step A: Preparation of 1-ethyl-N-(2-ethyl-2H-tetrazol-5-yl)-1H-benzo[d]imidazole-6-carboxamide: To a suspension of 3-ethylbenzimidazole-5-carboxylic acid (0.15 g, 0.76 mmol) in DCM (5 mL) was added a drop of DMF, followed by oxalic chloride (0.10 mL, 1.14 mmol) at ambient temperature. The reaction mixture was stirred at ambient temperature for 1 hour. Solvent was removed under reduced pressure. 2-Ethyltetrazol-5-amine (0.10 g, 0.91 mmol) in pyridine (2 mL) were added. The mixture was stirred at ambient temperature for 30 minutes. Solvent was removed under reduced pressure. The residue was purified by C18 reverse phase flash chromatography (Biotage Isolera One unit, C18 Flash 25+M column, 5-60% CH₃CN/water, 15 CV) to give 3-ethyl-N-(2-ethyltetrazol-5-yl)benzimidazole-5-carboxamide (0.17 g, 76%) as solid.

Step B: Preparation of 1-ethyl-N-(2-ethyl-2H-tetrazol-5-yl)-2-chydroxydiphenylmethyl)-1H-benzo[d]imidazole-6-carboxamide: To a solution of 3-ethyl-N-(2-ethyltetrazol-5-yl)benzimidazole-5-carboxamide (0.16 g, 0.56 mmol) and benzophenone (0.12 g, 0.67 mmol) in THF was added 1.0 M LHMDS in THF (1.26 mL, 1.26 mmol) at 0° C. The reaction mixture was stirred at 0° C. for 1 hour. Saturated aqueous ammonium chloride solution (10 mL) and ethyl acetate (20 mL) were added. The organic layer was separated, washed with brine, dried (sodium sulfate), filtered and concentrated under reduced pressure. The residue was purified by C18 reverse phase flash chromatography (Biotage Isolera One unit, C18 Flash 25+M column, 15-90% CH₃CN/water, 15 CV) to give 3-ethyl-N-(2-ethyltetrazol-5-yl)-2-[hydroxy(diphenyl)methyl]benzimidazole-5-carboxamide (0.19 g, 72%) as solid. LCMS ESI (+) m/z 468 (M+H). ¹HNMR (400 MHz, CDCl₃): δ 8.89 (s, 1H), 8.06 (s, 1H), 7.86 (d, 1H), 7.79 (d, 1H), 7.32-7.40 (m, 10H), 4.79 (s, 1H), 4.68 (q, 2H), 4.17 (q, 2H), 1.70 (t, 3H), 0.81 (t, 3H).

Example 66: Synthesis of 1-(1,6-dimethyl-1H-benzo[d]imidazol-2-yl)-1-phenylethane-1,2-diol (Compound 286)

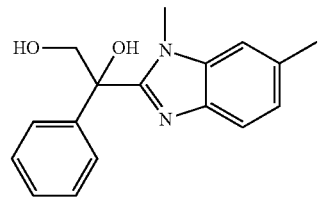 [SMILES: Cc1ccc2nc(C(O)(CO)c3ccccc3)n(C)c2c1]

Step A: Preparation of 2-((tert-butyldimethylsilyl)oxy)-1-(1,6-dimethyl-1H-benzo[d]imidazol-2-yl)-1-phenylethan-1-ol: To a solution of 1,6-dimethylbenzimidazole (0.25 g, 1.71 mmol) in THF (5 mL) was added n-BuLi (2.5 M, 0.72 mL, 1.8 mmol) at −78° C. The reaction mixture was stirred at −78° C. for 30 minutes. 2-[tert-Butyl(dimethyl)silyl]oxy-1-phenyl-ethanone (0.47 g, 1.88 mmol) in THF (5 mL) was added at −78° C. After the addition, the reaction mixture was slowly warmed to ambient temperature and stirred at ambient temperature for 1 hour. Saturated aqueous ammonium chloride solution (10 mL) and ethyl acetate (20 mL) were added. The organic layer was separated, washed with brine, dried (sodium sulfate), filtered and concentrated under reduced pressure. The residue was purified by flash chromatography on silica gel using 10:1 hexane/ethyl acetate to give 2-[tert-butyl(dimethyl)silyl]oxy-1-(1,6-dimethylbenzimidazol-2-yl)-1-phenyl-ethanol (0.43 g, 62%) as oil.

Step B: Preparation of 1-(1,6-dimethyl-1H-benzo[d]imidazol-2-yl)-1-phenylethane-1,2-diol: To a solution of 2-[tert-butyl(dimethyl)silyl]oxy-1-(1,6-dimethylbenzimidazol-2-yl)-1-phenyl-ethanol (0.31 g, 0.78 mmol) in THF (5 mL) was added tetrabutylammonium fluoride (1.0 M in THF, 0.78 mL, 0.78 mmol) at ambient temperature. The mixture was stirred at ambient temperature for 1 hour. Solvent was removed under reduced pressure. Methanol (5 mL) was added. Solid was collected by filtration and dried to give 1-(1,6-dimethylbenzimidazol-2-yl)-1-phenyl-ethane-1,2-diol (0.14 g, 64%). LCMS ESI (+) m/z 283 (M+H). $^1$HNMR (400 MHz, CDCl$_3$): δ 7.64 (d, 1H), 7.37 (m, 5H), 7.14 (d, 1H), 7.12 (s, 1H), 4.63 (m, 1H), 4.41 (m, 1H), 3.85 (s, 1H), 3.58 (t, 1H), 3.39 (s, 3H), 2.48 (s, 3H).

Example 67: Synthesis of 2-(1,6-dimethyl-1H-benzo[d]imidazol-2-yl)-2,2-diphenylethan-1-ol (Compound 287)

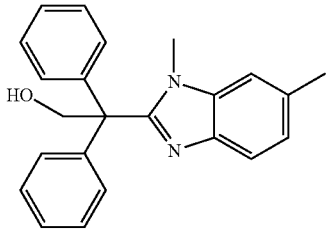 [SMILES: Cc1ccc2nc(C(CO)(c3ccccc3)c3ccccc3)n(C)c2c1]

Step A: Preparation of ethyl 2-(1,6-dimethyl-1H-benzo[d]imidazol-2-yl)-2-hydroxy-2-phenylacetate: To a solution of 1,6-dimethylbenzimidazole (0.35 g, 2.39 mmol) in THF (5 mL) was added n-BuLi (2.5 M in hexane, 1.0 mL, 2.5 mmol) at −78° C. The reaction mixture was stirred at −78° C. for 30 minutes. Ethyl 2-oxo-2-phenyl-acetate (0.47 g, 2.63 mmol) in THF (5 mL) was added at −78° C. After the addition, the reaction mixture was warmed to ambient temperature and stirred at ambient temperature for 1 hour. Saturated aqueous ammonium chloride solution (10 mL) and ethyl acetate (20 mL) were added. The organic layer was separated, washed with brine, dried (sodium sulfate), filtered and concentrated under reduced pressure. The residue obtained was purified by flash chromatography on silica gel with 3:1 hexane/ethyl acetate to give ethyl 2-(1,6-dimethylbenzimidazol-2-yl)-2-hydroxy-2-phenyl-acetate (0.10 g, 13%) as oil.

Step B: Preparation of ethyl 2-(1,6-dimethyl-1H-benzo[d]imidazol-2-yl)-2,2-diphenylacetate: To a solution of ethyl 2-(1,6-dimethylbenzimidazol-2-yl)-2-hydroxy-2-phenyl-acetate (0.10 g, 0.31 mmol) in benzene (1 mL) was added trifluoromethanesulfonic acid (0.82 mL, 9.25 mmol) at ambient temperature. The reaction mixture was stirred at ambient temperature for 1 hour. Saturated aqueous sodium bicarbonate (20 mL) and ethyl acetate (20 mL) were added. The organic layer was separated, washed with brine, dried (sodium sulfate), filtered and concentrated under reduced pressure. The residue was purified by flash chromatography on silica gel with 3:1 hexane/ethyl acetate to give ethyl 2-(1,6-dimethylbenzimidazol-2-yl)-2,2-diphenyl-acetate (0.045 g, 38%) as solid.

Step C: Preparation of 2-(1,6-dimethyl-1H-benzo[d]imidazol-2-yl)-2,2-diphenylethan-1-ol: To a solution of ethyl 2-(1,6-dimethylbenzimidazol-2-yl)-2,2-diphenyl-acetate (0.040 g, 0.11 mmol) in tetrahydrofuran (3 mL) was added lithium aluminum hydride (1.0 M, 0.23 mL, 0.23 mmol) at 0° C. After the addition, the reaction mixture was warmed to ambient temperature and stirred at ambient temperature for 30 minutes. Water (5 mL) was added and extracted with ethyl acetate. The organic layer was washed with brine, dried (sodium sulfate), filtered and concentrated under reduced pressure. The residue was purified by flash chromatography on silica gel to give 2-(1,6-dimethylbenzimidazol-2-yl)-2,2-diphenyl-ethanol (0.009 g, 23%) as solid.

LCMS ESI (+) m/z 343 (M+H). $^1$HNMR (400 MHz, CDCl$_3$): δ 7.67 (d, 1H), 7.52 (m, 4H), 7.41 (m, 2H), 7.33 (d, 1H), 7.22 (m, 3H), 7.13 (m, 2H), 4.37-4.44 (m, 2H), 4.18 (bs, 1H), 3.42 (s, 3H), 2.43 (s, 3H).

Example 68: Synthesis of N-(1-ethyl-1H-pyrazol-3-yl)-2-(hydroxydiphenylmethyl)-1-(2-methoxyethyl)-1H-benzo[d]imidazole-6-carboxamide (Compound 288)

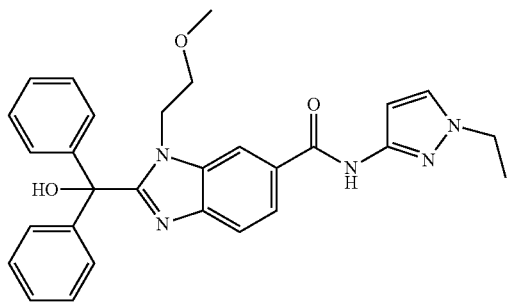 [SMILES: CCn1ccc(NC(=O)c2ccc3nc(C(O)(c4ccccc4)c4ccccc4)n(CCOC)c3c2)n1]

To a solution of 2-[hydroxy(diphenyl)methyl]-3-(2-methoxyethyl)benzimidazole-5-carboxylic acid (0.08 g, 0.19 mmol), 1-ethylpyrazol-3-amine (0.030 g, 0.24 mmol) and DIEA (0.060 mL, 0.37 mmol) in N,N-dimethylformamide (1 mL) was added HATU (0.090 g, 0.24 mmol). The reaction mixture was stirred at ambient temperature overnight and then directly purified by C18 reverse phase flash chromatography (Biotage Isolera One unit, C18 Flash 25+M column, 0-80% CH$_3$CN/water, 15 CV) to give N-(1-ethyl-pyrazol-3-yl)-2-[hydroxy(diphenyl)methyl]-3-(2-methoxy-ethyl)benzimidazole-5-carboxamide (0.075 g, 81%) as solid. LCMS ESI (+) m/z 496 (M+H). $^1$HNMR (400 MHz, CDCl$_3$): δ 8.53 (s, 1H), 8.02 (s, 1H), 7.81 (d, 1H), 7.73 (d, 1H), 7.31-7.40 (m, 10H), 6.83 (s, 1H), 5.53 (s, 1H), 4.25 (t, 2H), 4.08 (q, 2H), 3.45 (t, 2H), 3.20 (s, 3H), 1.47 (t, 3H).

Example 69: Synthesis of N-(1-ethyl-1H-1,2,4-triazol-3-yl)-2-(hydroxydiphenylmethyl)-1-(2-methoxyethyl)-1H-benzo[d]imidazole-6-carboxamide (Compound 289)

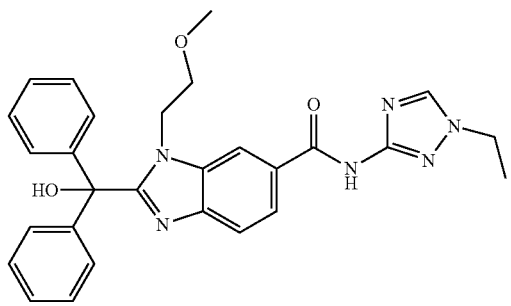 [SMILES: CCn1cnc(NC(=O)c2ccc3nc(C(O)(c4ccccc4)c4ccccc4)n(CCOC)c3c2)n1]

To a solution of 2-[hydroxy(diphenyl)methyl]-3-(2-methoxyethyl)benzimidazole-5-carboxylic acid (0.080 g, 0.19 mmol) and 1-ethyl-1,2,4-triazol-3-amine hydrochloride (0.040 g, 0.24 mmol) in pyridine (1 mL) was added HATU (0.090 g, 0.24 mmol) at ambient temperature. The reaction mixture was stirred at 66° C. (bath) for 18 hours. After cooling to ambient temperature, the reaction mixture was directly purified by C18 reverse phase flash chromatography (Biotage Isolera One unit, C18 Flash 25+M column, 10-90% CH₃CN/water, 15 CV) to give N-(1-ethyl-1,2,4-triazol-3-yl)-2-[hydroxy(diphenyl)methyl]-3-(2-methoxyethyl)benzimidazole-5-carboxamide (0.059 g, 63%) as solid. LCMS ESI (+) m/z 497 (M+H). ¹HNMR (400 MHz, CDCl₃): δ 8.67 (s, 1H), 8.06 (s, 1H), 7.87 (s, 1H), 7.83 (d, 1H), 7.78 (d, 1H), 7.32-7.40 (m, 10H), 4.50 (s, 1H), 4.35 (t, 2H), 4.20 (q, 2H), 3.22 (t, 2H), 3.21 (s, 3H), 1.57 (t, 3H).

Example 70: Synthesis of N-(2-ethyl-2H-tetrazol-5-yl)-2-(hydroxydiphenylmethyl)-1-(2-methoxyethyl)-1H-benzo[d]imidazole-6-carboxamide (Compound 290)

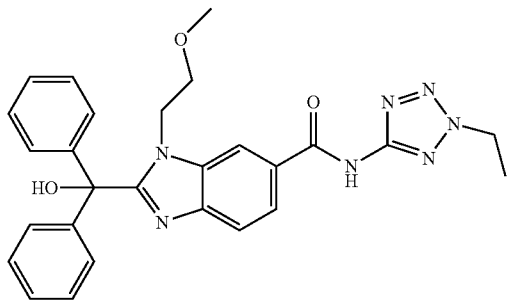 [SMILES: CCn1nnc(NC(=O)c2ccc3nc(C(O)(c4ccccc4)c4ccccc4)n(CCOC)c3c2)n1]

To a solution of 2-[hydroxy(diphenyl)methyl]-3-(2-methoxyethyl)benzimidazole-5-carboxylic acid (0.080 g, 0.19 mmol) and 2-ethyltetrazol-5-amine (0.030 g, 0.28 mmol) in pyridine (1 mL) was added HATU (0.11 g, 0.28 mmol) at ambient temperature. The reaction mixture was stirred at 100° C. (bath) for 24 hours. After cooling to ambient temperature, the reaction mixture was directly purified by C18 reverse phase flash chromatography (Biotage Isolera One unit, C18 Flash 25+M column, 10-90% CH₃CN/water, 15 CV) to give N-(2-ethyltetrazol-5-yl)-2-[hydroxy(diphenyl)methyl]-3-(2-methoxyethyl)benzimidazole-5-carboxamide (0.042 g, 45%). LCMS ESI (+) m/z 498 (M+H). ¹HNMR (400 MHz, CDCl₃): δ 8.98 (s, 1H), 8.14 (s, 1H), 7.85 (d, 1H), 7.79 (d, 1H), 7.32-7.38 (m, 10H), 5.19 (s, 1H), 4.65 (q, 2H), 4.37 (t, 2H), 3.40 (t, 2H), 3.22 (s, 3H), 1.65 (t, 3H).

Example 71: Synthesis of 2-(1,6-dimethyl-1H-benzo[d]imidazol-2-yl)-2-hydroxy-2-phenylethyl acetate (Compound 294)

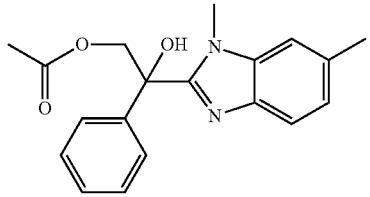 [SMILES: CC(=O)OCC(O)(c1ccccc1)c1nc2ccc(C)cc2n1C]

To a solution of 1-(1,6-dimethylbenzimidazol-2-yl)-1-phenyl-ethane-1,2-diol (0.14 g, 0.49 mmol) in pyridine (1 mL) was added acetic anhydride (0.060 mL, 0.59 mmol) at 0° C. After the addition, the reaction mixture was slowly warmed to ambient temperature and stirred at ambient temperature for 2 hours. After removing pyridine under reduced pressure, the residue was purified by C18 reverse phase flash chromatography (Biotage Isolera One unit, C18 Flash 25+M column, 10-80% CH₃CN/water, 15 CV) to give [2-(1,6-dimethylbenzimidazol-2-yl)-2-hydroxy-2-phenylethyl] acetate (0.15 g, 94%) as solid. LCMS ESI (+) m/z 325 (M+H). ¹HNMR (400 MHz, CDCl₃): δ 7.75 (d, 1H), 7.27-7.38 (m, 5H), 7.11 (d, 1H), 7.06 (s, 1H), 4.20 (d, 1H), 3.68 (d, 1H), 3.91 (s, 1H), 3.49 (s, 3H), 2.50 (s, 3H), 2.03 (s, 3H).

Example 72: Synthesis of N-(1-ethyl-1H-1,2,4-triazol-3-yl)-1-(2-fluoroethyl)-2-(hydroxydiphenylmethyl)-1H-benzo[d]imidazole-6-carboxamide (Compound 295)

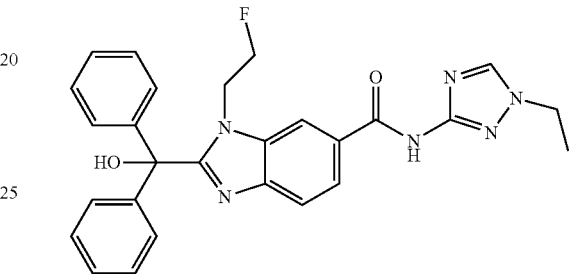

To a solution of 3-(2-fluoroethyl)-2-[hydroxy(diphenyl)methyl]benzimidazole-5-carboxylic acid (0.08 g, 0.19 mmol) and 1-ethyl-1,2,4-triazol-3-amine hydrochloride (0.04 g, 0.29 mmol) in pyridine (1 mL) was added HATU (0.11 g, 0.29 mmol) at ambient temperature. The reaction mixture was stirred at 78° C. (bath) for 7 hours. After cooling to ambient temperature, the reaction mixture was directly purified by C18 reverse phase flash chromatography (Biotage Isolera One unit, C18 Flash 25+M column, 10-90% CH₃CN/water, 15 CV) to give N-(1-ethyl-1,2,4-triazol-3-yl)-3-(2-fluoroethyl)-2-[hydroxy(diphenyl)methyl]benzimidazole-5-carboxamide (0.035 g, 37%). LCMS ESI (+) m/z 485 (M+H). ¹HNMR (400 MHz, CDCl₃): δ 8.58 (s, 1H), 8.07 (s, 1H), 7.88 (s, 1H), 7.81 (d, 1H), 7.79 (d, 1H), 7.26-7.38 (m, 10H), 4.45 (m, 1H), 4.39 (m, 1H), 4.20 (m, 4H), 4.11 (m, 1H), 1.58 (t, 3H).

Example 73: Synthesis of N-(1-ethyl-1H-1,2,4-triazol-3-yl)-2-(hydroxydiphenylmethyl)-1-(2-hydroxyethyl)-1H-benzo[d]imidazole-6-carboxamide (Compound 296)

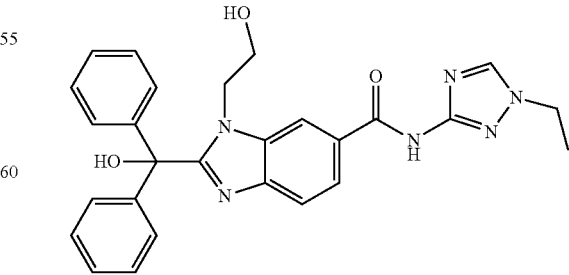

To a solution of 2-[hydroxy(diphenyl)methyl]-3-(2-hydroxyethyl)benzimidazole-5-carboxylic acid (0.080 g, 0.19 mmol) and 1-ethyl-1,2,4-triazol-3-amine hydrochloride (0.040 g, 0.29 mmol) in pyridine (1 mL) was added HATU (0.11 g, 0.29 mmol) at ambient temperature. The reaction mixture was stirred at 66° C. (bath) for 18 hours. After cooling to ambient temperature, the reaction mixture was directly purified by C18 reverse phase flash chromatography (Biotage Isolera One unit, C18 Flash 25+M column, 10-90% CH$_3$CN/water, 15 CV) to give N-(1-ethyl-1,2,4-triazol-3-yl)-2-[hydroxy(diphenyl)methyl]-3-(2-hydroxyethyl)benzimidazole-5-carboxamide (0.045 g, 48%). LCMS ESI (+) m/z 483 (M+H). $^1$HNMR (400 MHz, CDCl$_3$): δ 8.97 (s, 1H), 7.92 (s, 1H), 7.84 (s, 1H), 7.59 (m, 2H), 7.25-7.39 (m, 10H), 5.82 (s, 1H), 4.18 (m, 4H), 3.85 (bs, 1H), 3.69 (m, 2H), 1.48 (t, 3H).

Example 74: Synthesis of 2-(bis(2-fluorophenyl) (hydroxy)methyl)-1-ethyl-N-(1-ethyl-1H-1,2,4-triazol-3-yl)-1H-benzo[d]imidazole-6-carboxamide (Compound 297)

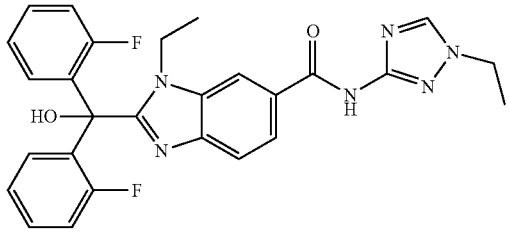 [SMILES: CCn1cnc(NC(=O)c2ccc3nc(C(O)(c4ccccc4F)c4ccccc4F)n(CC)c3c2)n1]

To a solution of 2-[bis(2-fluorophenyl)-hydroxy-methyl]-3-ethyl-benzimidazole-5-carboxylic acid (0.080 g, 0.18 mmol) and 1-ethyl-1,2,4-triazol-3-amine hydrochloride (0.040 g, 0.28 mmol) in pyridine (1 mL) was added HATU (0.10 g, 0.28 mmol) at ambient temperature. The reaction mixture was stirred at 96° C. (bath) for 18 hours. After cooling to ambient temperature, the reaction mixture was directly purified by C18 reverse phase flash chromatography (Biotage Isolera One unit, C18 Flash 25+M column, 10-90% CH$_3$CN/water, 15 CV) to give 2-[bis(2-fluorophenyl)-hydroxy-methyl]-3-ethyl-N-(1-ethyl-1,2,4-triazol-3-yl)benzimidazole-5-carboxamide (0.02 g, 21%). LCMS ESI (+) m/z 503 (M+H). $^1$HNMR (400 MHz, CDCl$_3$): δ 8.57 (s, 1H), 8.08 (s, 1H), 7.91 (s, 1H), 7.80 (d, 1H), 7.76 (d, 1H), 7.40 (m, 2H), 7.17 (m, 4H), 7.17 (m, 2H), 4.62 (m, 1H), 4.23 (m, 4H), 1.58 (t, 3H), 1.14 (t, 3H).

Example 75: Synthesis of 2-(bis(2-fluorophenyl) (hydroxy)methyl)-N-(1-ethyl-1H-1,2,4-triazol-3-yl)-1-methyl-1H-benzo[d]imidazole-6-carboxamide (Compound 298)

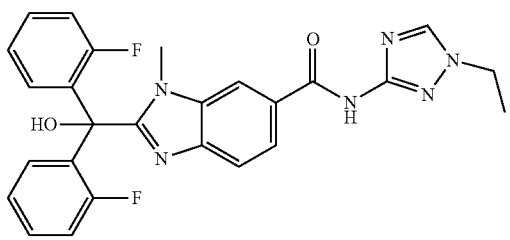 [SMILES: CCn1cnc(NC(=O)c2ccc3nc(C(O)(c4ccccc4F)c4ccccc4F)n(C)c3c2)n1]

To a solution of 2-[bis(2-fluorophenyl)-hydroxy-methyl]-3-methyl-benzimidazole-5-carboxylic acid (0.080 g, 0.19 mmol) and 1-ethyl-1,2,4-triazol-3-amine hydrochloride (0.040 g, 0.29 mmol) in pyridine (1 mL) was added HATU (0.11 g, 0.29 mmol) at ambient temperature. The reaction mixture was stirred at 88° C. (bath) for 18 hours. After cooling to ambient temperature, the reaction mixture was directly purified by C18 reverse phase flash chromatography (Biotage Isolera One unit, C18 Flash 25+M column, 10-90% CH$_3$CN/water, 15 CV) to give 2-[bis(2-fluorophenyl)-hydroxy-methyl]-N-(1-ethyl-1,2,4-triazol-3-yl)-3-methyl-benzimidazole-5-carboxamide (0.030 g, 32%). LCMS ESI (+) m/z 489 (M+H). $^1$HNMR (400 MHz, CDCl$_3$): δ 8.86 (s, 1H), 8.07 (s, 1H), 7.85 (s, 1H), 7.78 (d, 1H), 7.76 (d, 1H), 7.38 (m, 2H), 7.05-7.18 (m, 6H), 4.70 (m, 1H), 4.21 (q, 2H), 3.65 (s, 3H), 1.57 (t, 3H).

Example 76: Synthesis of N-(1-ethyl-1H-1,2,4-triazol-3-yl)-2-(hydroxydiphenylmethyl)-1-methyl-1H-benzo[d]imidazole-6-carboxamide (Compound 299)

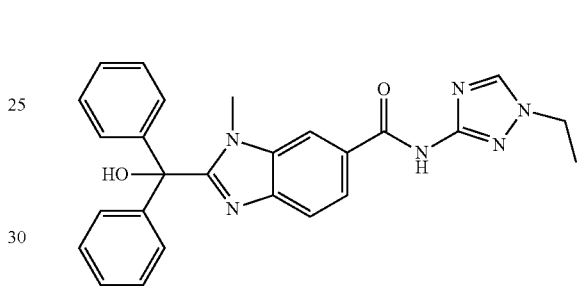

To a solution of 2-[hydroxy(diphenyl)methyl]-3-methyl-benzimidazole-5-carboxylic acid (0.080 g, 0.21 mmol) and 1-ethyl-1,2,4-triazol-3-amine hydrochloride (0.050 g, 0.31 mmol) in pyridine (1 mL) was added HATU (0.12 g, 0.31 mmol) at ambient temperature. The reaction mixture was stirred at 88° C. (bath) for 18 hours. After cooling to ambient temperature, the reaction mixture was directly purified by C18 reverse phase flash chromatography (Biotage Isolera One unit, C18 Flash 25+M column, 10-90% CH$_3$CN/water, 15 CV) to give N-(1-ethyl-1,2,4-triazol-3-yl)-2-[hydroxy (diphenyl)methyl]-3-methyl-benzimidazole-5-carboxamide (0.062 g, 65%). LCMS ESI (+) m/z 453 (M+H). $^1$HNMR (400 MHz, CDCl$_3$): δ 8.79 (s, 1H), 8.03 (s, 1H), 7.87 (s, 1H), 7.78 (d, 1H), 7.75 (d, 1H), 7.28-7.38 (m, 10H), 4.80 (s, 1H), 4.21 (q, 2H), 3.43 (s, 3H), 1.56 (t, 3H).

Example 77: Synthesis of (1-ethyl-6-(4-ethyl-1H-imidazol-2-yl)-1H-benzo[d]imidazol-2-yl)diphenylmethanol (Compound 300)

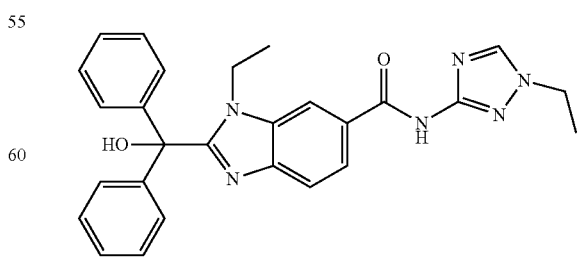

Step A: Preparation of 1-ethyl-2-(hydroxydiphenylmethyl)-1H-benzo[d]imidazole-6-carboximidamide: Hydrogen chloride gas was bubbled through a solution of 1-ethyl-2-(hydroxydiphenylmethyl)-1H-benzo[d]imidazole-6-carbonitrile (0.18 g, 0.5 mmol) in methanol (30 mL) at 0° C. for 2 hours. The mixture was warmed to ambient temperature and stirred at ambient temperature for 24 hours. Ammonium gas was bubbled through the solution for 1 hour at ambient temperature, then the reaction mixture was stirred at ambient temperature for additional 12 hours. Methanol was removed under reduced pressure. Ether was added. The resulting solid was collected by filtration and dried to give 1-ethyl-2-(hydroxydiphenylmethyl)-1H-benzo[d]imidazole-6-carboximidamide (0.05 g, 27%) as solid.

Step B: Preparation of (1-ethyl-6-(4-ethyl-1H-imidazol-2-yl)-1H-benzo[d]imidazol-2-yl)diphenylmethanol: A suspension of 1-ethyl-2-(hydroxydiphenylmethyl)-1H-benzo[d]imidazole-6-carboximidamide (0.050 g, 0.14 mmol), 1-bromobutan-2-one (0.020 g, 0.14 mmol) and potassium carbonate (0.037 g, 0.27 mmol) in acetonitrile (10 mL) was stirred at reflux for 12 hours. After cooling to ambient temperature, ethyl acetate and water were added. The organic layer was separated, washed with brine, dried (sodium sulfate), filtered and concentrated under reduced pressure. The residue was purified by flash chromatography on silica gel to give (1-ethyl-6-(4-ethyl-1H-imidazol-2-yl)-1H-benzo[d]imidazol-2-yl)diphenylmethanol (0.006 g, 11%) as solid. LCMS ESI (+) m/z 423 (M+H).

Example 78: Synthesis of 1-(1-ethyl-2-(hydroxydiphenylmethyl)-1H-benzo[d]imidazol-6-yl)-2,2-difluoropropane-1,3-diol (Compound 318)

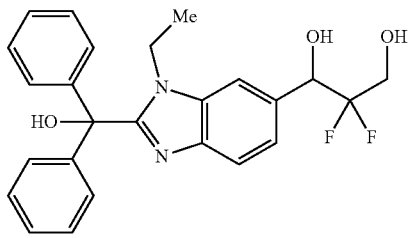 [SMILES: CCn1c(C(O)(c2ccccc2)c2ccccc2)nc2ccc(C(O)C(F)(F)CO)cc21]

Step A: Preparation of ethyl 3-[3-ethyl-2-[hydroxy(diphenyl)methyl]benzimidazol-5-yl]-3-oxo-propanoate: Oxalyl chloride (0.38 mL, 4.54 mmol) was added drop-wise to a solution of 3-ethyl-2-[hydroxy(diphenyl)methyl]benzimidazole-5-carboxylic acid (1.3 g, 3.49 mmol) in dichloromethane (5.0 mL) with a drop of DMF at room temperature (vented to a bubbler) and stirred for 2 h (checked by LC-MS with a methanol quench for ester formation). Concentrated in vacuo. During the acid chloride formation, dichloromagnesium (498.5 mg, 5.24 mmol) was added to an ice-cold mixture of ethyl malonate, potassium salt (742.6 mg, 4.36 mmol) and triethylamine (1.25 mL, 8.97 mmol) in acetonitrile (10.0 mL) and stirred for 3 h. The crude acid chloride was then added drop-wise to this mixture and stirred overnight. Cooled to 0° C. followed by the addition of 2 M HCl (10 mL) and stirred for 1 h gradually warming to room temperature. Diluted with water, extracted with ethyl acetate, washed with saturated sodium bicarbonate, brine then dried over sodium sulfate, filtered and concentrated in vacuo. Purified on silica gel (25 g SNAP Ultra, 14 CV, 10-100% ethyl acetate/hexanes) affording ethyl 3-[3-ethyl-2-[hydroxy(diphenyl)methyl]benzimidazol-5-yl]-3-oxo-propanoate (720 mg, 1.63 mmol, 47% yield).

Step B: Preparation of ethyl 3-[3-ethyl-2-[hydroxy(diphenyl)methyl]benzimidazol-5-yl]-2,2-difluoro-3-oxo-propanoate: 1-Chloromethyl-4-fluoro-1,4-diazoniabicyclo[2.2.2]octane bis(tetrafluoroborate) (200.1 mg, 0.56 mmol) was added all at once to ethyl 3-[3-ethyl-2-[hydroxy(diphenyl)methyl]benzimidazol-5-yl]-3-oxo-propanoate (100.0 mg, 0.23 mmol) and sodium carbonate (71.9 mg, 0.68 mmol) in acetonitrile (2.0 mL) at room temperature and stirred overnight (~25% starting material remained). Diluted with water, extracted with ethyl acetate, washed with brine, dried over sodium sulfate, filtered and concentrated in vacuo. Purified on silica gel (10 g SNAP Ultra, 14 CV, 10-80% ethyl acetate/hexanes) affording ethyl 3-[3-ethyl-2-[hydroxy(diphenyl)methyl]benzimidazol-5-yl]-2,2-difluoro-3-oxo-propanoate (66 mg, 0.14 mmol, 61% yield).

Step C: Preparation of 1-[3-ethyl-2-[hydroxy(diphenyl)methyl]benzimidazol-5-yl]-2,2-difluoro-propane-1,3-diol: Sodium borohydride (31.3 mg, 0.83 mmol) was added all at once to ethyl 3-[3-ethyl-2-[hydroxy(diphenyl)methyl]benzimidazol-5-yl]-2,2-difluoro-3-oxo-propanoate (66.0 mg, 0.14 mmol) in methanol (2.0 mL) at room temperature then stirred until complete as judged by LC-MS. Quenched with 1 N HCl, extracted with ethyl acetate, washed with brine, dried over sodium sulfate, filtered and concentrated in vacuo. Purified on silica gel (10 g SNAP Ultra, 12 CV, 60-100% ethyl acetate/hexanes) affording 1-[3-ethyl-2-[hydroxy(diphenyl)methyl]benzimidazol-5-yl]-2,2-difluoropropane-1,3-diol (33 mg, 0.075 mmol, 55% yield). LC-MS ESI (+) m/z [M+H]$^+$ 439.

Example 79: Synthesis of 1-(1-ethyl-2-(hydroxydiphenylmethyl)-1H-benzo[d]imidazol-6-yl)-2,2,2-trifluoroethan-1-ol (Compound 332)

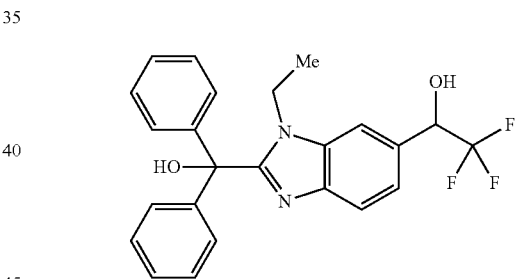

Step A: Preparation of 3-ethyl-2-[hydroxy(diphenyl)methyl]benzimidazole-5-carbaldehyde: Dess-Martin periodinane (566.7 mg, 1.51 mmol) added all at once to a suspension of [1-ethyl-6-(hydroxymethyl)benzimidazol-2-yl]-diphenyl-methanol (360.0 mg, 1.0 mmol) in dichloromethane (10.0 mL) at room temperature then stirred for 2 h. Diluted with 1:1 saturated sodium carbonate:sodium thiosulfate, extracted with dichloromethane, washed with brine, dried over sodium sulfate, filtered and concentrated in vacuo. Purified on silica gel (10 g SNAP Ultra, 12 CV, 25-100% ethyl acetate/hexanes) affording 3-ethyl-2-[hydroxy(diphenyl)methyl]benzimidazole-5-carbaldehyde (305 mg, 0.86 mmol, 85% yield).

Step B: Preparation of 1-(1-ethyl-2-(hydroxydiphenylmethyl)-1H-benzo[d]imidazol-6-yl)-2,2,2-trifluoroethan-1-ol: Cesium fluoride (10.0 mg, 0.07 mmol) was added to 3-ethyl-2-[hydroxy(diphenyl)methyl]benzimidazole-5-carbaldehyde (305.0 mg, 0.86 mmol) and placed under hi-vac overnight. Anhydrous THF (8.0 mL) was added to the reaction flask under nitrogen followed by trimethyl(trifluoromethyl)silane (0.51 mL, 3.42 mmol). The reaction mixture was stirred until complete as judged by LC-MS. Added 6 N HCl (5.0 mL) and stirred until complete as judged by LC-MS (TMS deprotection). Poured into saturated sodium carbonate, extracted with MTBE, washed with brine, dried over sodium sulfate, filtered and concentrated in vacuo. Purified on silica gel (10 g SNAP Ultra, 14 CV, 5-85% ethyl acetate/hexanes) affording 1-(1-ethyl-2-(hydroxydiphenylmethyl)-1H-benzo[d]imidazol-6-yl)-2,2,2-trifluoroethan-1-ol (360 mg, 0.84 mmol, 99% yield). LC-MS ESI (+) m/z [M+H]$^+$ 427.

Example 80: Synthesis of (2R)-1-((1-(1-ethyl-2-(hydroxydiphenylmethyl)-1H-benzo[d]imidazol-6-yl)-2,2,2-trifluoroethyl)amino)propan-2-ol (Compound 348)

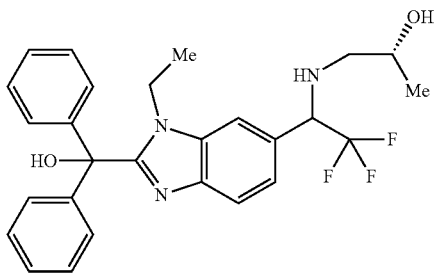 [SMILES: CCn1c(C(O)(c2ccccc2)c2ccccc2)nc2ccc(C(NC[C@@H](C)O)C(F)(F)F)cc21]

Step A: Preparation of [1-[3-ethyl-2-[hydroxy(diphenyl)methyl]benzimidazol-5-yl]-2,2,2-trifluoro-ethyl] 4-methylbenzenesulfonate:Lithium bis(trimethylsilyl)amide; 1.0 M in THF (273.4 µL, 0.27 mmol) was added all at once to a solution of 1-[3-ethyl-2-[hydroxy(diphenyl)methyl]benzimidazol-5-yl]-2,2,2-trifluoro-ethanol (53.0 mg, 0.12 mmol) in tetrahydrofuran (1.0 mL) at 0° C. then stirred for 30 min. p-Toluenesulfonyl chloride (24.9 mg, 0.13 mmol) was added all at once then stirred until complete as judged by LC-MS gradually warming to room temperature overnight. Diluted with saturated sodium bicarbonate, extracted with ethyl acetate, washed with brine, dried over sodium sulfate, filtered then concentrated in vacuo. Crude [1-[3-ethyl-2-[hydroxy(diphenyl)methyl]benzimidazol-5-yl]-2,2,2-trifluoro-ethyl] 4-methylbenzenesulfonate (72.0 mg) was used as is in the following reaction.

Step B: Preparation of (2R)-1-[[1-[3-ethyl-2-[hydroxy(diphenyl)methyl]benzimidazol-5-yl]-2,2,2-trifluoro-ethyl]amino]propan-2-ol: Crude [1-[3-ethyl-2-[hydroxy(diphenyl)methyl]benzimidazol-5-yl]-2,2,2-trifluoro-ethyl] 4-methylbenzenesulfonate (72.0 mg, 0.12 mmol) in tetrahydrofuran (1.0 mL) was added to a screw cap vial charged with a stir bar, (2R)-1-aminopropan-2-ol (13.0 mg, 0.17 mmol) and potassium carbonate (25.7 mg, 0.19 mmol) at room temperature. The vial was then sealed then warmed to reflux overnight. Very little product was observed and starting material largely remained. The THF was removed under a stream of nitrogen then acetonitrile (1.0 mL) was added, vial resealed then warmed to reflux overnight. Cooled to room temperature, filtered through a plug of celite, concentrated in vacuo then purified on silica gel (10 g SNAP Ultra, 14 CV, 12-100% ethyl acetate/hexanes) affording (2R)-1-[[1-[3-ethyl-2-[hydroxy(diphenyl)methyl]benzimidazol-5-yl]-2,2,2-trifluoro-ethyl]amino]propan-2-ol (24.0 mg, 0.05 mmol, 40% yield) as a mixture of diastereomers. LC-MS ESI (+) m/z [M+H]$^+$ 484.

Example 81: Synthesis of 2-(1-ethyl-7-fluoro-2-(hydroxydiphenylmethyl)-1H-benzo[d]imidazol-6-yl)acetonitrile (Compound 383)

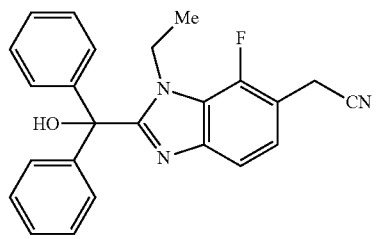 [SMILES: CCn1c(C(O)(c2ccccc2)c2ccccc2)nc2ccc(CC#N)c(F)c21]

Step A: Preparation of [6-(chloromethyl)-1-ethyl-benzimidazol-2-yl]-diphenyl-methanol: Thionyl chloride (0.97 mL, 13.39 mmol) was added all at once to [1-ethyl-6-(hydroxymethyl)benzimidazol-2-yl]-diphenyl-methanol (2.4 g, 6.7 mmol) and in dichloromethane (33.5 mL) at room temperature then stirred until complete as judged by LC-MS. Quenched with water, extracted with dichloromethane, washed with brine, dried over sodium sulfate, filtered and concentrated in vacuo. Purified on silica gel (25 g SNAP Ultra, 12 CV, 10-80% ethyl acetate/hexanes) affording [6-(chloromethyl)-1-ethyl-benzimidazol-2-yl]-diphenyl-methanol (2.04 g, 5.41 mmol, 81% yield).

Step B: Preparation of 2-(1-ethyl-7-fluoro-2-(hydroxydiphenylmethyl)-1H-benzo[d]imidazol-6-yl)acetonitrile: Sodium cyanide (109.9 mg, 2.24 mmol) added to a solution of [6-(chloromethyl)-1-ethyl-benzimidazol-2-yl]-diphenyl-methanol (650.0 mg, 1.72 mmol) in DMF (6.0 mL) at room temperature under nitrogen and stirred for 16 h. Diluted with water, extracted with ethyl acetate, washed with saturated sodium bicarbonate, brine, dried over sodium sulfate, filtered and dried in vacuo. Purified on silica gel (10 g SNAP Ultra, 12 CV, 15-100% ethyl acetate/hexanes) affording 2-(1-ethyl-7-fluoro-2-(hydroxydiphenylmethyl)-1H-benzo[d]imidazol-6-yl)acetonitrile (590.0 mg, 1.61 mmol, 93% yield). LC-MS ESI (+) m/z [M+H]$^+$ 368.

Example 82: Synthesis of (4-ethyl-1-methyl-1,4-dihydroimidazo[4,5-c]pyrazol-5-yl)diphenylmethanol (Compound 412)

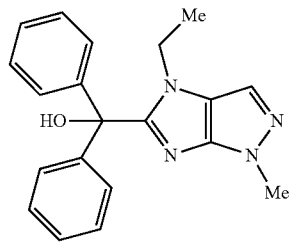 [SMILES: CCn1c(C(O)(c2ccccc2)c2ccccc2)nc2c1cnn2C]

Step A: Preparation of N-ethyl-2-oxo-2-phenylacetimidoyl chloride: Oxalyl chloride (0.25 mL, 2.93 mmol) added to N-ethyl-2-oxo-2-phenyl-acetamide (400.0 mg, 2.26 mmol) and one drop of DMF in dichloromethane (8.0 mL) under nitrogen and stirred for 2.5 h. Used immediately in the next reaction.

Step B: Preparation of N-ethyl-N-(2-methylpyrazol-3-yl)-2-oxo-2-phenyl-acetamidine: 2-Methylpyrazol-3-amine (327.6 mg, 3.37 mmol) and triethylamine (0.63 mL, 4.5 mmol) in dichloromethane (5.0 mL) under nitrogen was added by syringe to the crude N-ethyl-2-oxo-2-phenylacetimidoyl chloride solution (Step A) and stirred at room temperature over the weekend. Quenched with saturated sodium bicarbonate, extracted with dichloromethane, washed with brine, dried over sodium sulfate, filtered and concentrated in vacuo. Purified on silica gel (25 g SNAP Ultra, 14 CV, 15-100% ethyl acetate/hexanes) affording N-ethyl-N'-(2-methylpyrazol-3-yl)-2-oxo-2-phenyl-acetamidine (60.0 mg, 0.23 mmol, 10% yield).

Step C: Preparation of N'-(4-bromo-2-methyl-pyrazol-3-yl)-N-ethyl-2-oxo-2-phenyl-acetamidine: N-bromosuccinimide (43.8 mg, 0.25 mmol) was added all at once to a solution of N-ethyl-N'-(2-methylpyrazol-3-yl)-2-oxo-2-phenyl-acetamidine (60.0 mg, 0.23 mmol) in acetonitrile (1.5 mL) at room temperature then the reaction vial was sealed with a teflon lined threaded cap and warmed to reflux until complete as judged by LC-MS (1 h). Concentrated then purified on silica gel (10 g SNAP Ultra, 14 CV, 15-100% ethyl acetate/hexanes) affording N'-(4-bromo-2-methyl-pyrazol-3-yl)-N-ethyl-2-oxo-2-phenyl-acetamidine (57.0 mg, 0.17 mmol, 73% yield).

Step D: Preparation of (4-ethyl-1-methyl-imidazo[4,5-c]pyrazol-5-yl)-phenyl-methanone: N'-(4-bromo-2-methyl-pyrazol-3-yl)-N-ethyl-2-oxo-2-phenyl-acetamidine (57.0 mg, 0.17 mmol) in dry DMF (1.0 mL) was added to a microwave reaction vial charged with a stir bar, copper(I) iodide (3.2 mg, 0.02 mmol), N;N'-dimethylethylenediamine (18.3 µL, 0.17 mmol) and cesium carbonate (110.8 mg, 0.34 mmol) under argon. The reaction vial was then quickly sealed with a crimp cap under a blanket of argon then warmed to 150° C. under microwave irradiation for 15 min. Cooled to room temperature, filtered, diluted with water, extracted with ethyl acetate, washed with brine, dried over sodium sulfate, filtered and concentrated in vacuo. Purified on silica gel (10 g SNAP Ultra, 14 CV, 15-100% ethyl acetate/hexanes) affording (4-ethyl-1-methyl-imidazo[4,5-c]pyrazol-5-yl)-phenyl-methanone (27.5 mg, 0.11 mmol, 64% yield).

Step E: Preparation of (4-ethyl-1-methyl-imidazo[4,5-c]pyrazol-5-yl)-diphenyl-methanol: Phenylmagnesium bromide solution 3 M in diethyl ether (72.1 µL, 0.22 mmol) was added dropwise to a solution of (4-ethyl-1-methyl-imidazo[4,5-c]pyrazol-5-yl)-phenyl-methanone (27.5 mg, 0.11 mmol) in tetrahydrofuran (2.0 mL) at 0° C. under nitrogen then stirred for 30 min. Quenched with ethyl acetate and methanol, concentrated in vacuo then purified on silica gel (10 g SNAP Ultra, 14 CV, 20-100% ethyl acetate/hexanes) affording (4-ethyl-1-methyl-imidazo[4,5-c]pyrazol-5-yl)-diphenyl-methanol (32.0 mg, 0.096 mmol, 89% yield). LC-MS ESI (+) m/z [M+H]$^+$ 333.

Example 83: Measurement of ACSS2 Enzymatic Activity

Human ACSS2 enzyme was expressed in insect cells using the Invitrogene BactoBac® expression system. The enzyme had an N-terminal 6× histidine tag and was purified by Ni-affinity chromatography. Human ACSS2 activity was measured by quantifying pyrophosphate, a reaction product, in a coupled enzymatic assay. In addition to ACSS2 and its substrates, the assay included pyrophosphatase, which converts pyrophosphate to phosphate, and purine nucleotide phosphorylase (PNP). In a typical reaction, the reaction mixture included 50 µM CoA, 100 µM ATP, 5 mM sodium acetate, 0.2 mM MESG, 0.2% BSA, 20 nM ACSS2, 0.4 µM purine nucleotide phosphorylase (PNP), 1 unit/mL of yeast pyrophosphatase in a reaction buffer of 1 mM $MgCl_2$, 150 mM NaCl, and 50 mM HEPES at pH about 7.5. The assay was carried out at room temperature and the reaction was monitored at 360 nm for about 30 minutes. The rate of reaction was calculated by the software (Gens) of the plate reader (Synergy II made by Biotek).

Example 84: Measurement of $^{14}$C-Acetate Uptake Assay

HCT116 cells were grown in DMEM (Dulbecco's Modified Eagle Medium) in a 6-well plate to 80-90% confluence. The media was replaced with fresh DMEM (1 mL) and the cells were pretreated with compound(s) for 2 hours. About 0.2 µCi sodium acetate [1,2-$^{14}$C] (0.1 µCi/µL) was added to each well and the cells were incubated for 3 hours. The media was removed and the cells were washed twice with PBS (3 mL). SOLVABLE™ (Perkin Elmer order #6NE9100) was added to each well and the plate was shaken for 1 hour to lyse the cells. Lysate (0.2 mL) was mixed with 10 mL of scintillation cocktail overnight and radioactivity was counted. $EC_{50}$ values were calculated with Prism or Dotmatics program.

Table 2 shows biological activities of selected compounds in ACSS2 Human Enzyme and $^{14}$C-Acetate Cell Uptake assays. Compound numbers correspond to the numbers and structures provided in Table 1 and Examples 1-82.

TABLE 2

| | Less than 50 nM (++++) | 50 nM to 249 nM (+++) | 250 nM to 1000 nM (++) | Greater than 1000 nM (+) |
|---|---|---|---|---|
| ACSS2 Human Enzyme Assay $IC_{50}$ (nM) | 79, 82, 88, 99, 110, 111, 112, 117, 119, 120, 125, 126, 127, 135, 138, 141, 142, 146, 147, 148, 149, 150, 153, 154, 156, 167, 173, 181, 182, 184, 186, 187, 188, 192, 208, 210, 211, 213, 214, 223, 224, 226, 234, 243, 246, 249, 250, 252, 258, 260, 261, 262, 263, 265, 266, 271, 273, | 9, 11, 12, 14, 15, 16, 22, 23, 26, 32, 36, 37, 39, 42, 43, 53, 56, 59, 61, 62, 70, 78, 80, 81, 83, 85, 86, 87, 89, 91, 92, 94, 95, 96, 97, 98, 100, 104, 113, 114, 115, 116, 118, 122, 123, 128, 136, 137, 139, 140, 143, 151, 157, 160, 161, 164, 165, 166, 177, 178, 180, 183, 189, | 2, 5, 6, 24, 25, 31, 35, 38, 40, 41, 44, 47, 50, 52, 55, 57, 60, 66, 68, 71, 72, 90, 105, 107, 108, 109, 121, 124, 129, 130, 132, 133, 144, 145, 158, 159, 162, 168, 171, 172, 174, 176, 179, 194, 203, 204, 206, 207, 212, 216, 217, 220, 222, 225, 228, 259, 292, 293, 294, 307, 312, | 1, 3, 4, 7, 8, 17, 18, 21, 27, 28, 29, 30, 33, 34, 45, 46, 48, 49, 51, 54, 58, 63, 64, 65, 73, 74, 75, 76, 77, 84, 93, 101, 102, 103, 106, 131, 134, 152, 155, 163, 169, 170, 175, 219, 221, 227, 229, 230, 232, 233, 235, 236, 242, 278, 286, 287, 308, 311, 326, 343, 348, 349, 355, 356, |

TABLE 2-continued

| | Less than 50 nM (++++) | 50 nM to 249 nM (+++) | 250 nM to 1000 nM (++) | Greater than 1000 nM (+) |
|---|---|---|---|---|
| | 274, 275, 277, 279, 281, 284, 297, 301, 303, 304, 305, 306, 310, 313, 314, 315, 316, 318, 323, 324, 325, 328, 329, 336, 337, 339, 340, 346, 350, 351, 352, 353, 362, 363, 364, 365, 369, 370, 371, 373, 380, 383, 389, 391, 392, 394, 395, 396, 397, 398, 399, 400, 402, 403, 404, 406, 408, 409, 410, 411 | 190, 191, 193, 195, 196, 197, 198, 199, 200, 201, 209, 215, 231, 237, 241, 244, 251, 253, 254, 255, 256, 257, 267, 268, 270, 276, 282, 283, 300, 309, 317, 319, 321, 322, 332, 333, 334, 341, 342, 344, 345, 354, 357, 361, 368, 372, 376, 379, 382, 388, 390, 393, 405 | 320, 327, 330, 331, 335, 338, 358, 367, 381, 384, 385, 386, 387, 407, 412 | 359, 360, 366, 374, 375, 377, 378, 401 |
| $^{14}$C-Acetate Cell Uptake Assay $EC_{50}$ (nM) | 78, 79, 116, 119, 182, 183, 185, 186, 187, 188, 202, 205, 209, 211, 215, 223, 224, 226, 231, 237, 238, 239, 240, 245, 246, 247, 248, 249, 250, 252, 258, 260, 261, 262, 263, 264, 265, 267, 269, 270, 271, 272, 274, 275, 279, 280, 284, 285, 288, 289, 290, 291, 295, 296, 297, 303, 304, 305, 306, 312, 315, 316, 318, 324, 325, 328, 329, 337, 339, 340, 346, 350, 351, 353, 361, 362, 363, 364, 365, 368, 369, 370, 373, 376, 380, 382 | 61, 82, 108, 184, 189, 190, 191, 192, 199, 200, 201, 208, 210, 213, 214, 218, 234, 243, 266, 273, 277, 281, 283, 309, 313, 314, 336, 352, 354, 372 | 198, 310, 319, 344 | n/a |

Example 85: In Vivo Efficacy Study

Efficacy studies for Compounds 79, 116, 119 and 183: All compounds were formulated with 10% absolute ethanol, 30% PEG400, 60% water containing 0.5% methyl cellulose and 0.5% Tween80®. About 5×10$^6$ 786-O renal cell carcinoma cells (ATCC® CRL-1932™) in PBS and Matrigel (1:1 in volume) were inoculated subcutaneously in the right flank of SCID/Biege mice at 6-7 weeks of age for tumor development. When the xenografts reached about 200 mm$^3$ in size, the tumor-bearing mice were randomly grouped into six groups (n=8) and treated by oral gavage with Compound 79, Compound 116, Compound 119, Compound 183 (each at 200 mg/kg BID), and vehicle (BID) for 20 days. Tumor sizes were measured twice weekly in two dimensions using a caliper and the volume expressed in mm$^3$ using the formula V=0.5×a×b$^2$, wherein a and b were the long and short diameters of the tumor, respectively.

TABLE 3

786-O Xenograft Study: Tumor sizes after 20 days of dosing

| Treatment Groups | Vehicle | Compound 79 (200 mg/kg) | Compound 116 (200 mg/kg) | Compound 119 (200 mg/kg) | Compound 183 (200 mg/kg) |
|---|---|---|---|---|---|
| Tumor Size (mm$^3$) Mean ± SEM | 623.1 ± 95.1 | 281.1 ± 45.2 | 597.5 ± 72.5 | 475.2 ± 60.7 | 668.9 ± 62.5 |

What is claimed is:

1. A compound of Formula II:

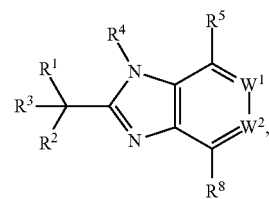

Formula II or a pharmaceutically acceptable salt thereof, wherein:

$R^1$ and $R^2$ are independently optionally substituted aryl or optionally substituted heteroaryl; or $R^1$ and $R^2$ together with the atom to which they are attached form a 13- to 16-membered tricyclic ring;

$R^3$ is $OR^{14}$, or —$CH_2OR^{14}$;

$R^4$ is selected from optionally substituted alkyl, optionally substituted cycloalkyl, optionally substituted heterocycloalkyl, and optionally substituted aryl;

$R^5$ and $R^8$ are independently selected from hydrogen, halo, cyano, optionally substituted alkoxy, and optionally substituted alkyl;

$W^1$ is $CR^6$;

$W^2$ is $CR^7$ or N;

$R^6$ is selected from substituted alkyl, optionally substituted cycloalkyl, optionally substituted heteroalkyl, optionally substituted heterocycloalkyl, optionally substituted alkoxy, optionally substituted aryl, optionally substituted heteroaryl, —$(CH_2)_tNR^9C(=O)R^{10}$, —$C(=O)OR^9$, —$C(=O)NR^{10}R^{11}$, —$S(=O)_2R^{12}$, and —$S(=O)_2NR^{10}R^{11}$;

$R^7$ is selected from hydrogen, halo, optionally substituted alkyl, optionally substituted cycloalkyl, optionally substituted heteroalkyl, optionally substituted heterocycloalkyl, optionally substituted alkoxy, optionally substituted aryl, optionally substituted heteroaryl, cyano, —$(CH_2)_tNR^9C(=O)R^{10}$, —$C(=O)OR^9$, —$C(=O)NR^{10}R^{11}$, —$S(=O)_2 R^{12}$, and —$S(=O)_2 NR^{10}R^{11}$;

t is 0, 1, or 2;

$R^9$ is selected from hydrogen, optionally substituted alkyl, optionally substituted cycloalkyl, optionally substituted alkenyl, optionally substituted alkynyl, optionally substituted aryl, optionally substituted heteroaryl, and optionally substituted heterocycloalkyl;

$R^{10}$ and $R^{11}$ are independently selected from hydrogen, optionally substituted alkyl, optionally substituted cycloalkyl, optionally substituted alkenyl, optionally substituted alkynyl, optionally substituted aryl, optionally substituted heteroaryl, and optionally substituted heterocycloalkyl, or $R^{10}$ and $R^{11}$ together with the atom to which they are attached form a 4- to 8-membered ring containing 0-2 heteroatoms;

$R^{12}$ is selected from optionally substituted alkyl, optionally substituted cycloalkyl, and optionally substituted heterocycloalkyl; and $R^{14}$ is selected from hydrogen, optionally substituted $C_1$-$C_4$ alkyl, and optionally substituted $C_1$-$C_4$ acyl.

2. The compound of claim 1, wherein $W^1$ is $CR^6$, $W^2$ is $CR^7$, $R^6$ is substituted alkyl, optionally substituted cycloalkyl, optionally substituted heteroalkyl, optionally substituted heterocycloalkyl, optionally substituted alkoxy, optionally substituted aryl, optionally substituted heteroaryl, —$(CH_2)_tNR^9C(=O)R^{10}$, —$C(=O)OR^9$, —$C(=O)NR^{10}R^{11}$, —$S(=O)_2R^{12}$, or —$S(=O)_2NR^{10}R^{11}$, and $R^7$ is hydrogen, halo, or optionally substituted alkyl.

3. The compound of claim 1, wherein $R^1$ and $R^2$ are independently selected from phenyl and pyridyl, and each of $R^1$ and $R^2$ is optionally substituted with one or more substituents selected from halo, optionally substituted alkyl, cyano, and optionally substituted alkoxy.

4. The compound of claim 1, wherein $R^3$ is hydroxy.

5. The compound of claim 1, wherein the compound has the structure of Formula II-A:

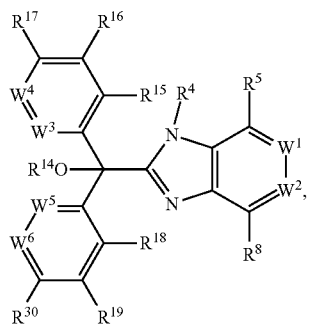

Formula II-A or a pharmaceutically acceptable salt thereof, wherein:

$R^4$ is selected from optionally substituted alkyl, optionally substituted cycloalkyl, optionally substituted heterocycloalkyl, and optionally substituted aryl;

$R^5$ and $R^8$ are independently selected from hydrogen, halo, cyano, optionally substituted alkoxy, and optionally substituted alkyl;

$W^1$ is $CR^6$;

$W^2$ is $CR^7$ or N;

$R^6$ is selected from substituted alkyl, optionally substituted cycloalkyl, optionally substituted heteroalkyl, optionally substituted heterocycloalkyl, optionally substituted alkoxy, optionally substituted aryl, optionally substituted heteroaryl, —$(CH_2)_tNR^9C(=O)R^{10}$, —$C(=O)OR^9$, —$C(=O)NR^{10}R^{11}$, —$S(=O)_2R^{12}$, and —$S(=O)_2NR^{10}R^{11}$;

$R^7$ is selected from hydrogen, halo, optionally substituted alkyl, optionally substituted cycloalkyl, optionally substituted heteroalkyl, optionally substituted heterocycloalkyl, optionally substituted alkoxy, optionally substituted aryl, optionally substituted heteroaryl, cyano, —$(CH_2)_tNR^9C(=O)R^{10}$, —$C(=O)OR^9$, —$C(=O)NR^{10}R^{11}$, —$S(=O)R^{12}$, and —$S(=O)_2NR^{10}R^{11}$;

t is 0, 1, or 2;

$R^9$ is selected from hydrogen, optionally substituted alkyl, optionally substituted cycloalkyl, optionally substituted alkenyl, optionally substituted alkynyl, optionally substituted aryl, optionally substituted heteroaryl, and optionally substituted heterocycloalkyl;

$R^{10}$ and $R^{11}$ are independently selected from hydrogen, optionally substituted alkyl, optionally substituted cycloalkyl, optionally substituted alkenyl, optionally substituted alkynyl, optionally substituted aryl, optionally substituted heteroaryl, and optionally substituted heterocycloalkyl, or $R^{10}$ and $R^{11}$ together with the atom to which they are attached form a 4- to 8-membered ring containing 0-2 heteroatoms;

$R^{12}$ is selected from optionally substituted alkyl, optionally substituted cycloalkyl, and optionally substituted heterocycloalkyl;

$W^3$ and $W^5$ are independently $CR^{31}$ or N;

$W^4$ and $W^6$ are independently $CR^{22}$ or N;

$R^{14}$ is selected from hydrogen, optionally substituted $C_1$-$C_4$ alkyl, and optionally substituted $C_1$-$C_4$ acyl;

each of $R^{15}$, $R^8$, $R^{19}$, $R^{30}$, $R^{31}$, and $R^{22}$ is independently selected from hydrogen, halo, hydroxy, optionally substituted alkyl, optionally substituted alkoxy, cyano, —$C(=O)NR^{23}R^{24}$, optionally substituted aryl, and optionally substituted heteroaryl;

$R^{16}$ and $R^{17}$ are independently selected from hydrogen, halo, hydroxy, optionally substituted alkyl, optionally substituted alkoxy, cyano, —C(═O)NR²³R²⁴, optionally substituted aryl, and optionally substituted heteroaryl, or R¹⁶ and R¹⁷ together with the atoms to which they are attached form a 5- to 8-membered ring containing 0-2 heteroatoms;

R²³ and R²⁴ are independently selected from hydrogen, optionally substituted C₁-C₆ alkyl, and —(CH₂)ₘOR²⁵;

m is 1, 2, 3, or 4; and

R²⁵ is selected from hydrogen, optionally substituted C₁-C₄ alkyl, and optionally substituted C₁-C₄ acyl.

6. The compound of claim 1, wherein R⁴ is optionally substituted C₁-C₆ alkyl.

7. The compound of claim 1, wherein R⁵ and R⁸ are each hydrogen.

8. The compound of claim 1, wherein W¹ is CR⁶, R⁶ is —C(═O)NR¹⁰R¹¹ or —S(═O)₂NR¹⁰R¹¹, W² is CR⁷, and R⁷ is hydrogen, halo, or optionally substituted alkyl.

9. The compound of claim 1, wherein R¹¹ is selected from:

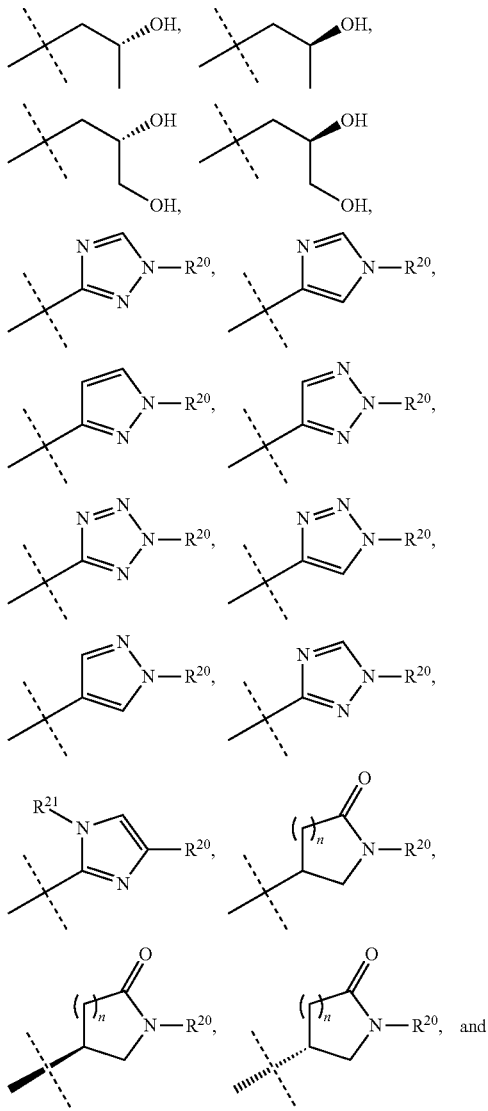

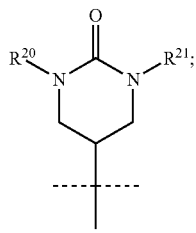

wherein n is 1, 2, 3, or 4, and R²⁰ and R²¹ are independently selected from hydrogen, optionally substituted alkyl, optionally substituted cycloalkyl, and optionally substituted heterocycloalkyl.

10. The compound of claim 1, wherein R¹¹ is optionally substituted aryl, optionally substituted heteroaryl, or optionally substituted C₁-C₆ alkyl.

11. The compound of claim 10, wherein R¹¹ is C₁-C₆ alkyl optionally substituted with 1, 2, or 3 groups independently selected from hydroxy and fluoro.

12. The compound of claim 1, wherein R⁹ is hydrogen.

13. The compound of claim 1, wherein R¹² is optionally substituted C₁-C₄ alkyl.

14. The compound of claim 1, wherein W¹ is CR⁶, R⁶ is —(CH₂)ₚOH and p is 1, 2, 3, or 4.

15. The compound of claim 1, wherein R⁷ is hydrogen or fluoro.

16. The compound of claim 1, wherein:

R¹ and R² are independently optionally substituted aryl or optionally substituted heteroaryl;

R³ is hydroxy, or —CH₂OH;

R⁴ is selected from the group consisting of optionally substituted alkyl, optionally substituted cycloalkyl, optionally substituted heterocycloalkyl, and optionally substituted aryl;

R⁵ and R⁸ are independently hydrogen, halo, cyano, optionally substituted alkoxy or optionally substituted alkyl;

W¹ is CR⁶;

W² is CR⁷;

R⁶ is substituted alkyl, optionally substituted cycloalkyl, optionally substituted alkoxy, optionally substituted aryl, optionally substituted heteroaryl, —NR⁹C(═O)R¹⁰, —C(═O)OR⁹, —C(═O)NR¹⁰R¹¹, —S(═O)₂R¹², or —S(═O)₂NR¹⁰R¹¹;

R⁷ is hydrogen, halo, optionally substituted alkyl, optionally substituted cycloalkyl, optionally substituted alkoxy, optionally substituted aryl, optionally substituted heteroaryl, —NR⁹C(═O)R¹⁰, —C(═O)OR⁹, —C(═O)NR¹⁰R¹¹, —S(═O)₂R¹², or —S(═O)₂NR¹⁰R¹¹;

each of said R⁹, R¹⁰, and R¹¹ is independently selected from the group consisting of hydrogen, optionally substituted alkyl, optionally substituted cycloalkyl, optionally substituted aryl, optionally substituted heteroaryl, and optionally substituted heterocycloalkyl;

R¹² is selected from the group consisting of optionally substituted alkyl, optionally substituted cycloalkyl, and optionally substituted heterocycloalkyl;

R¹⁰, R¹¹ and the atom(s) to which they are attached optionally form a 4-8 membered ring containing 0-2 heteroatoms selected from the group consisting of O, N and S; and at least one of R⁶ and R⁷ is not hydrogen.

17. The compound of claim 1, wherein the compound is selected from the group consisting of:

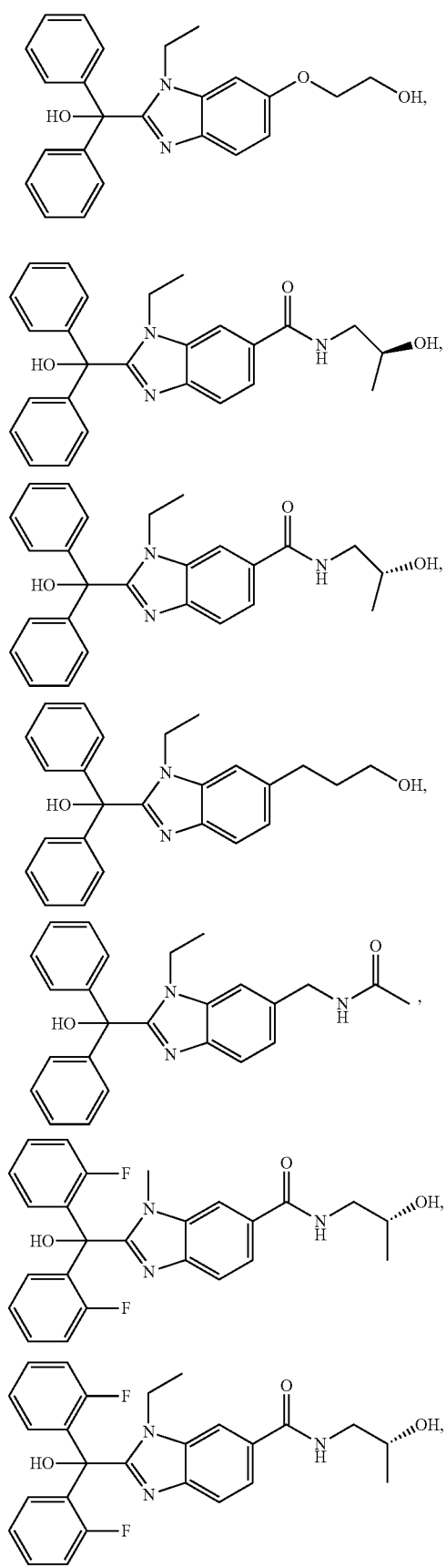
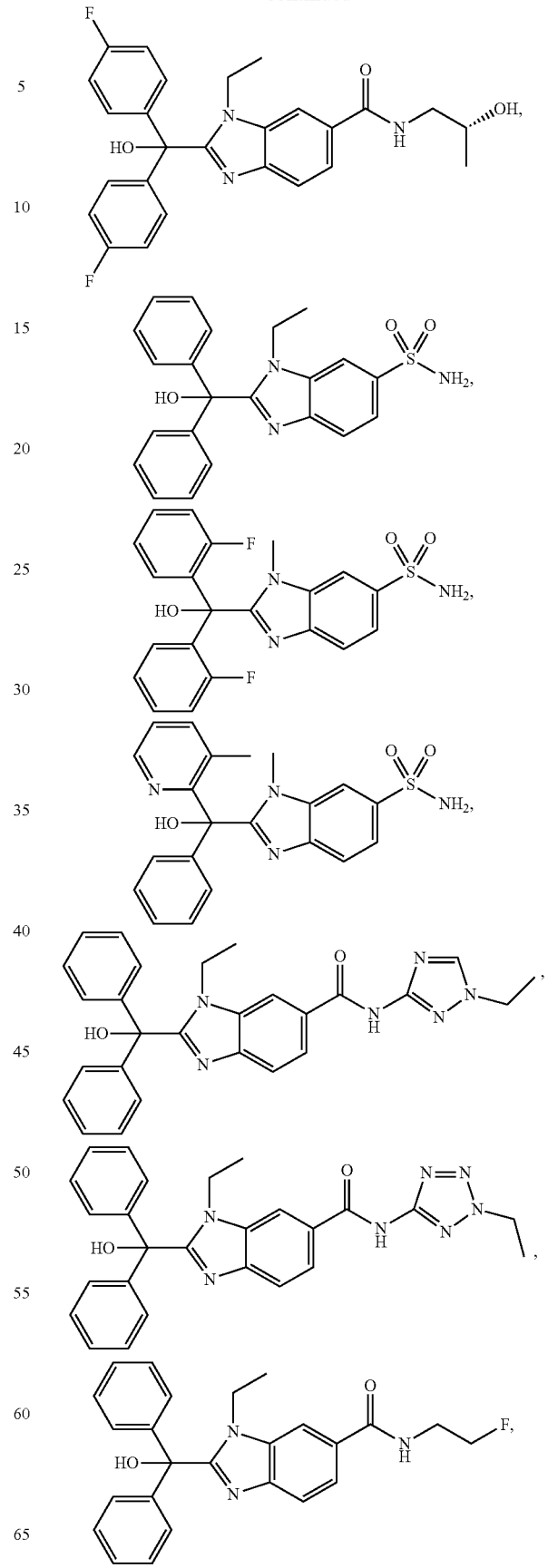

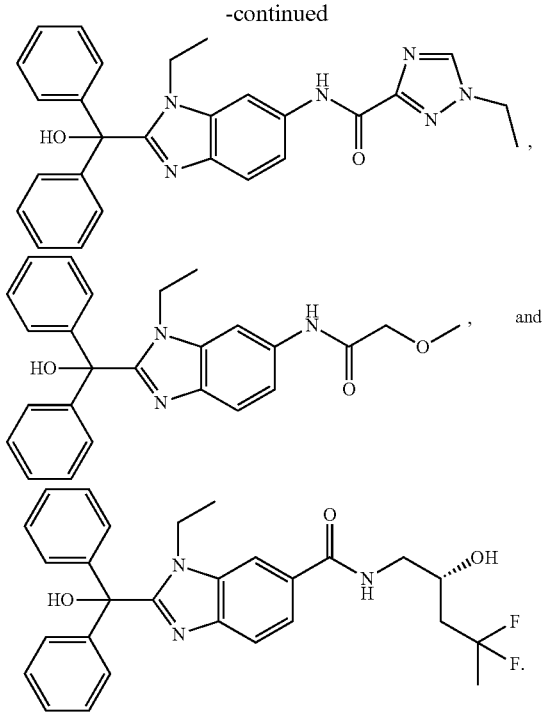

18. A pharmaceutical composition comprising the compound of claim 1 and a pharmaceutically acceptable carrier.

19. A method of inhibiting ACSS2 enzymatic activity, comprising contacting ACSS2 with an effective amount of the compound of claim 1.

20. The method of claim 19, comprising administering a second therapeutic agent to the cell.

21. A compound of Formula II:

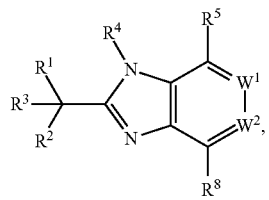

or a pharmaceutically acceptable salt thereof, wherein:

$R^1$ and $R^2$ are independently optionally substituted aryl or optionally substituted heteroaryl; or $R^1$ and $R^2$ together with the atom to which they are attached form a 13- to 16-membered tricyclic ring;

$R^3$ is hydrogen, $-OR^{14}$, or $-CH_2OR^{14}$;

$R^4$ is selected from hydrogen, optionally substituted alkyl, optionally substituted cycloalkyl, optionally substituted heterocycloalkyl, and optionally substituted aryl;

$R^5$ and $R^8$ are independently selected from hydrogen, halo, cyano, optionally substituted alkoxy, and optionally substituted alkyl;

$W^1$ is $CR^6$;

$W^2$ is $CR^7$;

$R^6$ is selected from $-C(=O)NR^{10}R^{11}$ and $-S(=O)_2NR^{10}R^{11}$;

$R^7$ is selected from hydrogen, halo and optionally substituted alkyl;

t is 0, 1, or 2;

$R^{10}$ and $R^{11}$ are independently selected from hydrogen, optionally substituted alkyl, optionally substituted cycloalkyl, optionally substituted alkenyl, optionally substituted alkynyl, optionally substituted aryl, optionally substituted heteroaryl, and optionally substituted heterocycloalkyl, or $R^{10}$ and $R^{11}$ together with the atom to which they are attached form a 4- to 8-membered ring containing 0-2 heteroatoms;

$R^{12}$ is selected from optionally substituted alkyl, optionally substituted cycloalkyl, and optionally substituted heterocycloalkyl; and $R^{14}$ is selected from hydrogen, optionally substituted $C_1$-$C_4$ alkyl, and optionally substituted $C_1$-$C_4$ acyl.

22. A method of treating a condition associated with ACSS2, comprising administering to a subject in need thereof a therapeutically effective amount of the compound of claim 1, wherein the condition is selected from prostate cancer, lung cancer, liver cancer, brain cancer, kidney cancer, breast cancer, ovarian cancer, colorectal cancer, colon cancer and renal cell carcinoma.

23. The method of claim 22, wherein the condition is selected from colorectal cancer, colon cancer and renal cell carcinoma.

* * * * *